US012089631B2

(12) United States Patent
Minami et al.

(10) Patent No.: US 12,089,631 B2
(45) Date of Patent: Sep. 17, 2024

(54) INHALER

(71) Applicant: JAPAN TOBACCO INC., Tokyo (JP)

(72) Inventors: Yuki Minami, Tokyo (JP); Takahisa Kudo, Tokyo (JP); Michihiro Inagaki, Tokyo (JP); Jumpei Inoue, Tokyo (JP); Yuki Abe, Tokyo (JP); Adam Geernaert, Cambridge (GB); Franck Rubiconi, Cambridge (GB); Simon Cox, Cambridge (GB); Rishi Jobanputra, Cambridge (GB)

(73) Assignee: JAPAN TOBACCO INC., Tokyo (JP)

( * ) Notice: Subject to any disclaimer, the term of this patent is extended or adjusted under 35 U.S.C. 154(b) by 1014 days.

(21) Appl. No.: 17/066,793

(22) Filed: Oct. 9, 2020

(65) Prior Publication Data

US 2021/0030069 A1    Feb. 4, 2021

Related U.S. Application Data

(63) Continuation of application No. PCT/JP2019/015384, filed on Apr. 9, 2019.

(30) Foreign Application Priority Data

Apr. 10, 2018  (WO) .................. PCT/JP2018/015128
Dec. 19, 2018  (WO) .................. PCT/JP2018/046712

(51) Int. Cl.
*A24F 40/05*  (2020.01)
*A24F 40/30*  (2020.01)
(Continued)

(52) U.S. Cl.
CPC ............. *A24F 40/05* (2020.01); *A24F 40/30* (2020.01); *A24F 40/40* (2020.01); *A24F 40/46* (2020.01);
(Continued)

(58) Field of Classification Search
CPC .......... A24F 40/05; A24F 40/30; A24F 40/40; A24F 40/46; A24F 40/48; A24F 40/50;
(Continued)

(56) References Cited

U.S. PATENT DOCUMENTS 4,659,014 A      4/1987  Soth et al.
5,996,903 A  *  12/1999  Asai .................... B05B 17/0676
                                                      239/102.1
(Continued)

FOREIGN PATENT DOCUMENTS

CA      3172016 A1  *  10/2021  ............. A24F 40/44
CA      3172027 A1  *  10/2021  ............. A24F 40/10
(Continued)

OTHER PUBLICATIONS

Extended European Search Report for European Application No. 19785759.2, dated Jun. 3, 2022.
(Continued)

*Primary Examiner* — Shawntina T Fuqua
(74) *Attorney, Agent, or Firm* — Birch, Stewart, Kolasch & Birch, LLP

(57) ABSTRACT

A controller for controlling an atomizing unit, wherein the atomizing unit includes a piezoelectric element substrate including an IDT including a pair of interlocking comb-shaped metallic electrodes, and a liquid supplier configured to supply liquid, which is to be atomized, to the piezoelectric element substrate; wherein the piezoelectric element substrate is configured to atomize the liquid by use of a surface acoustic wave generated by applying a high-frequency voltage to the pair of interlocking comb-shaped metallic electrodes; and the controller is configured to periodically change amplitude and/or a frequency of the high-frequency voltage applied to the pair of interlocking comb-shaped metallic electrodes.

20 Claims, 76 Drawing Sheets

(51) Int. Cl.
*A24F 40/40* (2020.01)
*A24F 40/46* (2020.01)
*A24F 40/48* (2020.01)
*A24F 40/50* (2020.01)
*A24F 40/51* (2020.01)
*A24F 40/53* (2020.01)
*A24F 40/57* (2020.01)
*A61M 15/06* (2006.01)
*B05B 17/06* (2006.01)
*F24H 15/10* (2022.01)
*F24H 15/219* (2022.01)
*A24F 40/10* (2020.01)
*A24F 47/00* (2020.01)

(52) U.S. Cl.
CPC .............. *A24F 40/48* (2020.01); *A24F 40/50* (2020.01); *A24F 40/51* (2020.01); *A24F 40/53* (2020.01); *A24F 40/57* (2020.01); *A61M 15/06* (2013.01); *B05B 17/0676* (2013.01); *F24H 15/10* (2022.01); *F24H 15/219* (2022.01); *A24F 40/10* (2020.01); *A24F 47/00* (2013.01)

(58) Field of Classification Search
CPC .......... A24F 40/51; A24F 40/53; A24F 40/57; A24F 40/10; A24F 47/00; A61M 15/06; B05B 17/0676; B05B 17/0607; B05B 17/06; F24H 15/10; F24H 15/219
See application file for complete search history.

(56) References Cited

U.S. PATENT DOCUMENTS

| | | | |
|---|---|---|---|
| 6,978,779 B2* | 12/2005 | Haveri | A61M 16/08 128/204.22 |
| 8,807,131 B1 | 8/2014 | Tunnell et al. | |
| 8,978,779 B2 | 3/2015 | Aposhian | |
| 2003/0196660 A1 | 10/2003 | Haveri | |
| 2004/0079360 A1* | 4/2004 | Coffee | B05B 5/1691 128/200.14 |
| 2010/0264234 A1 | 10/2010 | Marchetti et al. | |
| 2016/0001316 A1 | 1/2016 | Friend et al. | |
| 2017/0280771 A1 | 10/2017 | Courbat et al. | |
| 2021/0112882 A1* | 4/2021 | Hejazi | A24F 40/465 |
| 2021/0329971 A1* | 10/2021 | Li | A24F 40/60 |
| 2023/0356252 A1* | 11/2023 | Courbat | B05B 17/0607 |

FOREIGN PATENT DOCUMENTS

| | | | | |
|---|---|---|---|---|
| EP | 0844027 A1 | 5/1998 | | |
| EP | 1142600 A1 | 10/2001 | | |
| GB | 2548071 A | 9/2017 | | |
| JP | 11-207224 A | 8/1999 | | |
| JP | 2008-104966 A | 5/2008 | | |
| JP | 2012-24646 A | 2/2012 | | |
| JP | 2016-513992 A | 5/2016 | | |
| KR | 10-2016-0052845 A | 5/2016 | | |
| WO | WO 97/05960 A1 | 2/1997 | | |
| WO | WO-2021182274 A1 * | 9/2021 | ............... | A61L 9/14 |

OTHER PUBLICATIONS

International Search Report, issued in PCT/JP2019/015384, PCT/ISA/210, dated Jul. 16, 2019.
Chinese Ofice Action and Search Report dated Jul. 8, 2022 for Application No. 201980039492.6 with an English translation.
Russian Office Action and Search Report for Russian Application No. 2020136603, dated Apr. 16, 2021, with English translation.
Canadian Office Action for Canadian Application No. 3,097,416, dated Oct. 4, 2021.
Russian Office Action for Russian Application No. 2020136603, dated Sep. 3, 2021, with English translation.

* cited by examiner

Fig. 11

| N | Frequency (MHz) | NBW (MHz) |
|---|---|---|
| 20 | 50 | 5 |
| 40 | 50 | 2.5 |
| 80 | 50 | 1.25 |

Fig. 13
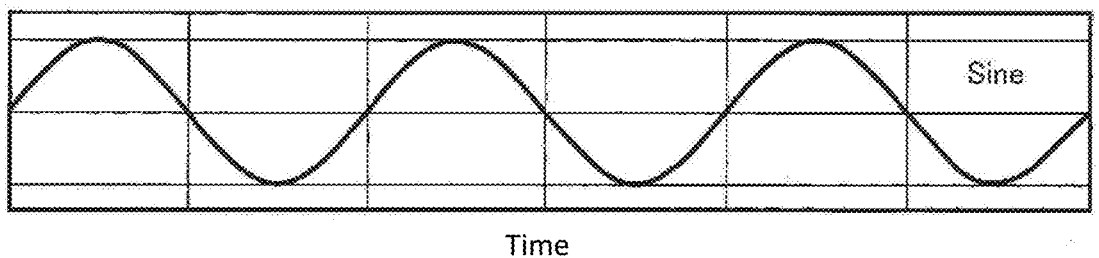
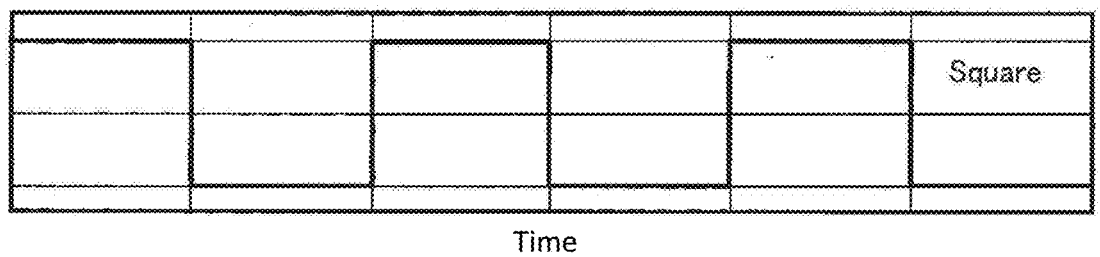
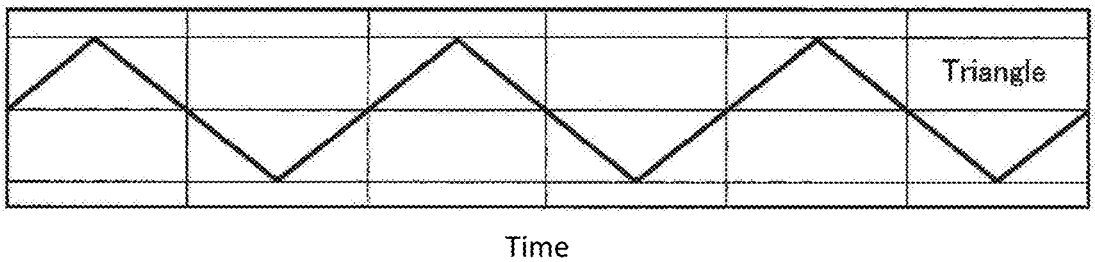
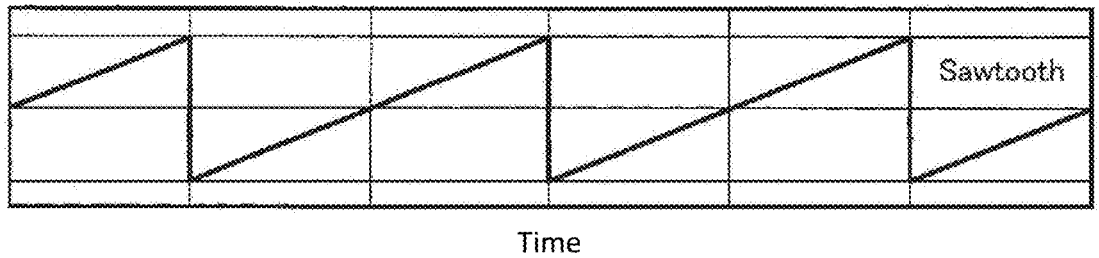

Fig. 25
(a)
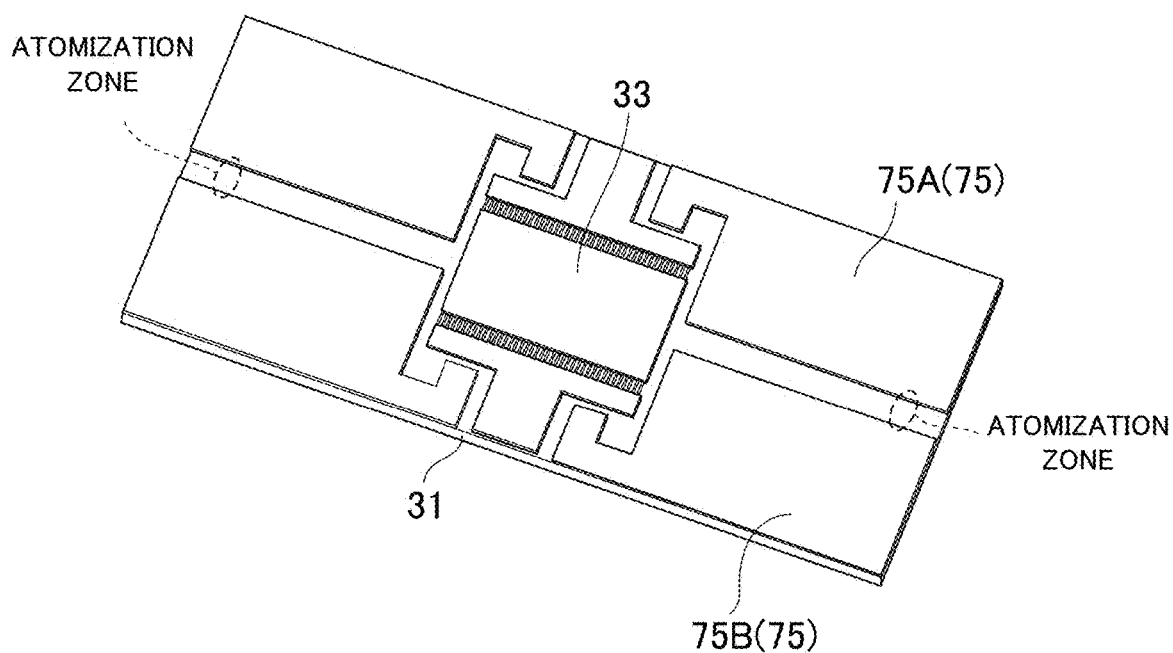
(b)
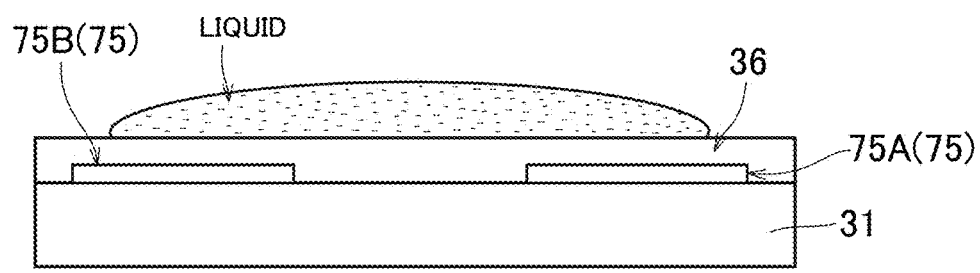

Fig. 63
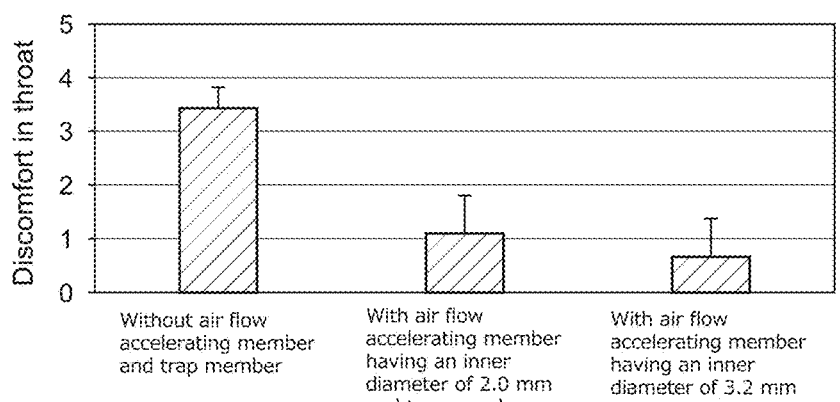
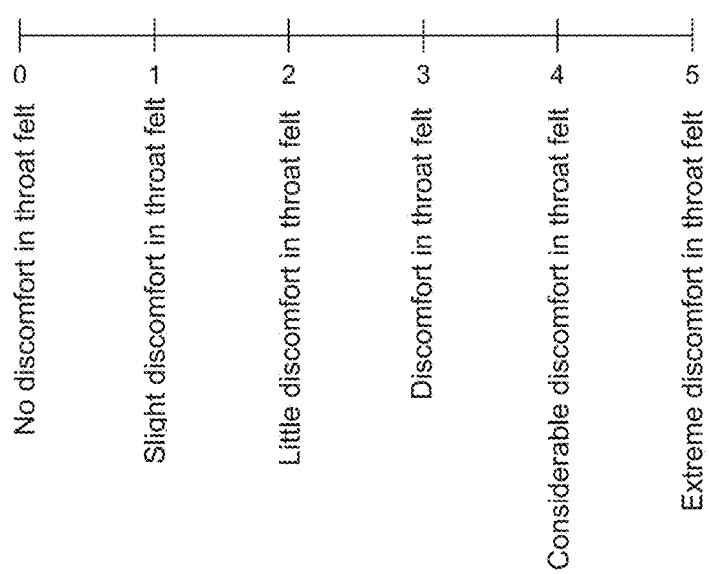

Fig. 68
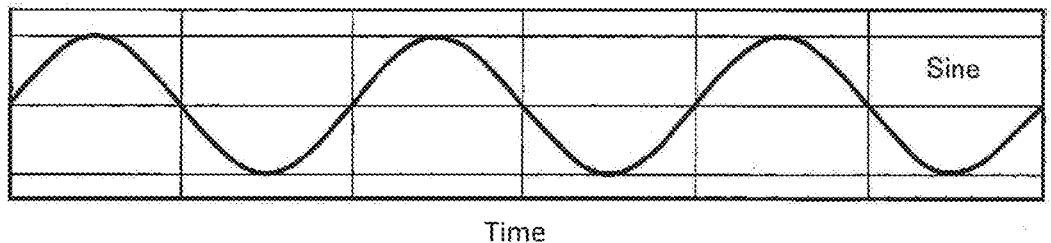
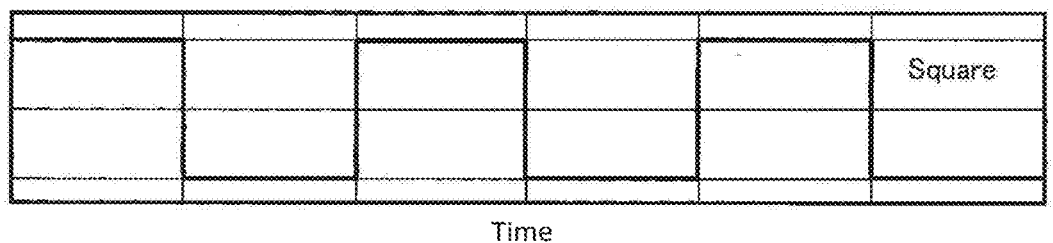
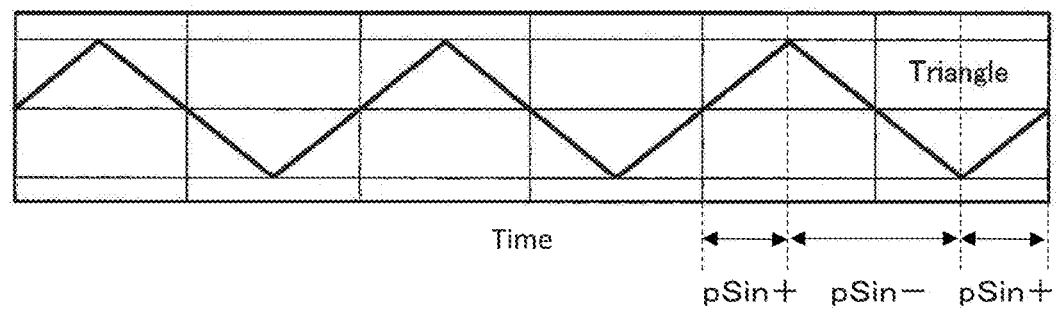
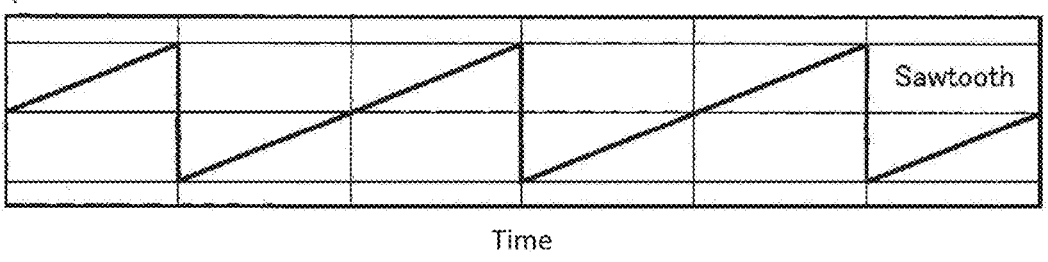

Fig. 80B

4601B Adjust a liquid surface level and monitor a resonant frequency of a pair of interlocking comb-shaped electrodes (standby mode)

4602B Detect a request to atomize liquid? N / Y

4604B Start atomization of liquid by an atomizing unit

4606B During atomization of liquid by an atomizing unit, apply a voltage to a pair of interlocking comb-shaped electrodes at a resonant frequency monitored in standby mode for the first inhalation and at a frequency based on a resonant frequency for immediately previous inhalation at the time of inhalation from the second time onward

4608B Monitor a resonant frequency of a pair of interlocking comb-shaped electrodes after completion of atomization of liquid by an atomizing unit

4604C Adjust a liquid surface level and monitor a resonant frequency of a pair of interlocking comb-shaped electrodes (standby mode)

4606C Determine a frequency range including a monitored resonant frequency

4607C Detect a request to atomize liquid? N

Y

4608C Start atomization of liquid by an atomizing unit

4610C During atomization of liquid by an atomizing unit, control a frequency of a voltage applied to a pair of interlocking comb-shaped electrodes so as to vary within a determined frequency range

4704B — Adjust a liquid surface level and monitor a resonant frequency of a pair of interlocking comb-shaped electrodes (standby mode)

4706B — Determine an initial value of a resonant frequency used at the time of the first inhalation

4707B — Detect a request to atomize liquid? N (loop back) / Y

4708B — Set an initial value of a frequency of a voltage applied to a pair of interlocking comb-shaped electrodes

4709B — Start atomization of liquid by an atomizing unit

4710B — Control a voltage applied to a pair of interlocking comb-shaped electrodes so as to vary within a predetermined range including a frequency determined based on the initial value

4712B — Monitor a resonant frequency of a pair of interlocking comb-shaped electrodes

4714B — Adjust the predetermined frequency range so as to include a monitored resonant frequency

4700B

INHALER

CROSS REFERENCE TO RELATED APPLICATIONS

This application is a Continuation of PCT International Application No. PCT/JP2019/015384 filed on Apr. 9, 2019, which claims priority under 35 U.S.C. § 119(a) to Patent Application Nos. PCT/JP2018/015128 and PCT/JP2018/046712 filed in Japan on Apr. 10, 2018 and Dec. 19, 2018, respectively, all of which are hereby expressly incorporated by reference into the present application.

TECHNICAL FIELD

The present invention relates to an inhaler.

BACKGROUND ART

Conventionally, known is an atomizing unit configured to atomize liquid by using a piezoelectric element substrate having an IDT (interdigital transducer) made of a pair of interlocking comb-shaped electrodes to generate a SAW (Surface Acoustic Wave) (for example, Patent Documents 1 and 2). Further, technology has been proposed in which such an atomizing unit is used for a flavor inhaler (for example, Patent Document 3).

CITATION LIST

Patent Literature

PTL 1: Japanese Patent Application Publication No. 2012-24646
PTL 2: Japanese Patent Application Publication (Translation of PCT Application) No. 2016-513992
PTL3: US Patent No. 2017/0280771

SUMMARY OF INVENTION

A first feature is an inhaler, and the gist thereof is that the inhaler comprises a first liquid storage unit; a second liquid storage unit; an atomizing unit which comprises a piezoelectric element substrate having an IDT constructed by use of a pair of interlocking comb-shaped metallic electrodes and is constructed to atomize liquid by a surface acoustic wave generated by applying a high-frequency voltage to the pair of interlocking comb-shaped metallic electrodes; and a mouthpiece for guiding aerosol which is generated by atomizing the liquid in the atomizing unit; wherein the atomizing unit is constructed to atomize first liquid supplied from the first liquid storage unit and second liquid supplied from the second liquid storage unit, respectively.

A second feature comprises the first feature, wherein the gist thereof is that the first liquid and the second liquid are different from each other.

A third feature comprises the first feature or the second feature, wherein the gist thereof is that the first liquid comprises at least nicotine.

A fourth feature comprises the third feature, wherein the gist thereof is that the first liquid further comprises at least one of an acid, a taste component, and a somatosensory component.

A fifth feature comprises one of the first feature to the fourth feature, wherein the gist thereof is that the second liquid comprises a flavor component.

A sixth feature comprises the fifth feature, wherein the gist thereof is that the flavor component comprises at least one of menthol, limonene, citral, linalool, vanillin, carvone, and glycosides of these.

A seventh feature comprises the fifth feature or the sixth feature, wherein the gist thereof is that the second liquid further comprises at least one of a taste component, a somatosensory component, an emulsifier, glycerin, propylene glycol, and ethanol.

A eighth feature comprises one of the first feature to the seventh feature, wherein the gist thereof is that the mouthpiece comprises a first flow path through which first aerosol generated by atomizing the first liquid passes mainly, and a second flow path through which second aerosol generated by atomizing the second liquid, passes.

A ninth feature comprises the eighth feature when it is dependent on the third feature or the fourth feature, wherein the gist thereof is that the first flow path is defined by a pipe line which comprises at least a part which is curved.

A tenth feature comprises the eighth feature when it is dependent on one of the fifth feature to the seventh feature, wherein the gist thereof is that the second flow path is defined by an approximately straight pipe line.

An eleventh feature comprises the eighth feature when it is dependent on the third feature or the fourth feature, wherein the gist thereof is that the first flow path is provided with an air flow accelerating member which is constructed to reduce the first flow path.

A twelfth feature comprises the first feature, wherein the gist thereof is that the first flow path is provided with a trap member which is arranged in such a manner that the aerosol passed through the air flow accelerating member collides the trap member.

A thirteenth feature comprises one of the first feature to the seventh feature, wherein the gist thereof is that the mouthpiece comprises a flow path in which the aerosol, which is generated by atomizing the first liquid, swirls while the aerosol passes through the flow path.

A fourteenth feature comprises one of the first feature to the thirteenth feature, wherein the gist thereof is that the piezoelectric element substrate comprises a front surface on which the pair of interlocking comb-shaped metallic electrodes is arranged; a rear surface positioned opposite to the front surface; and a pair of edges opposite to each other; and the inhaler further comprises a first liquid supplier constructed to supply the first liquid to one of the edges of the piezoelectric element substrate, and a second liquid supplier constructed to supply the second liquid to another of the edges of the piezoelectric element substrate.

A fifteenth feature comprises the fourteenth feature, wherein the gist thereof is that the inhaler comprises a cover which covers the front surface of the piezoelectric element substrate; wherein the cover comprises a first opening part which is positioned right above the one edge and through which the first aerosol, which is generated by atomizing the first liquid, passes, and a second opening part which is positioned right above the other edge and through which the second aerosol, which is generated by atomizing the second liquid, passes.

A sixteenth feature comprises the fifteenth feature, wherein the gist thereof is that the cover comprises an opening which is different from the first opening part and the second opening part; wherein air that flows into the inside side of the cover from the opening passes over the IDT and flows toward the outside side of the cover from the first opening part and the second opening part.

A seventeenth feature comprises the fifteenth feature or the sixteenth feature, wherein the gist thereof is that the piezoelectric element substrate comprises a disposition portion where the pair of interlocking comb-shaped metallic electrodes is positioned, and the cover is arranged in such a manner that it covers at least the part right above the disposition portion and is not to be in contact with the front surface of the piezoelectric element substrate.

An eighteenth feature comprises one of the fifteenth feature to the seventeenth feature, wherein the gist thereof is that the first flow path communicates with the first opening part, and the second flow path communicates with the second opening part.

A nineteenth feature comprises one of the first feature to the eighteenth feature, wherein the gist thereof is that the inhaler comprises a trap member constructed to trap at least a part of one of the first aerosol generated by atomizing the first liquid and the second aerosol generated by atomizing the second liquid.

A twentieth feature is an inhaler, and the gist thereof is that the inhaler comprises: a piezoelectric element substrate having an IDT constructed by use of a pair of interlocking comb-shaped metallic electrodes; a liquid supplier for supplying liquid, which is to be atomized, to a front surface of the piezoelectric element substrate on which the pair of interlocking comb-shaped metallic electrodes is positioned; a sensor, which comprises at least a pair of detection parts which are opposite to each other, for detecting liquid supplied to the front surface of the piezoelectric element substrate; and a controller for controlling, based on result of detection by the sensor, the liquid supplier in such a manner that the liquid supplier supplies a certain quantity of the liquid to the front surface of the piezoelectric element substrate.

A twenty-first feature comprises twentieth feature, wherein the gist thereof is that the detection parts are positioned apart from the front surface of the piezoelectric element substrate.

A twenty-second feature comprises twentieth feature or the twenty-first feature, wherein the gist thereof is that the piezoelectric element substrate comprises an edge to which the liquid from the liquid supplier is supplied; each of the detection parts comprises a convex part which projects toward an opposite detection part; and a distance between the edge and the convex part is 0.10 mm to 0.20 mm.

A twenty-third feature comprises the twenty-second feature, wherein the gist thereof is that the inhaler further comprises a guide wall positioned at an edge side of the piezoelectric element substrate; and a distance between the edge and an end surface, at the edge side, of the guide wall is equal to or longer than 0.25 mm.

A twenty-fourth feature comprises the twenty-second feature or the twenty-third feature, wherein the gist thereof is that a distance between the convex parts of the detection parts, which are opposite to each other, corresponds to an overlap length of the pair of interlocking comb-shaped metallic electrodes.

A twenty-fifth feature comprises one of the twentieth feature to the twenty-fourth feature, wherein the gist thereof is that the piezoelectric element substrate comprises edges that are opposite to each other across the pair of interlocking comb-shaped metallic electrodes, and the sensor is arranged on each of the edges that are opposite to each other.

A twenty-sixth feature comprises one of the twentieth feature to the twenty-fifth feature, wherein the gist thereof is that the sensor comprises one of an electric conductivity sensor, an emitter-receiver sensor, and a capacitive sensor.

A twenty-seventh feature is a controller for controlling an atomizing unit, wherein the gist thereof is that the atomizing unit comprises a piezoelectric element substrate comprising an IDT comprising a pair of interlocking comb-shaped metallic electrodes, and a liquid supplier configured to supply liquid, which is to be atomized, to the piezoelectric element substrate; wherein the piezoelectric element substrate is configured to atomize the liquid by use of a surface acoustic wave generated by applying a high-frequency voltage to the pair of interlocking comb-shaped metallic electrodes; and the controller is configured to periodically change amplitude and/or a frequency of the high-frequency voltage applied to the pair of interlocking comb-shaped metallic electrodes.

A twenty-eighth feature comprises the twenty-seventh feature, wherein the gist thereof is that the controller is configured to modulate the high-frequency voltage applied to the pair of interlocking comb-shaped metallic electrodes based on a sine wave, a rectangular wave, a triangular wave, or a saw tooth wave; and the modulation is amplitude modulation and/or frequency modulation.

A twenty-ninth feature comprises the twenty-seventh feature, wherein the gist thereof is that the controller is configured to modify the amplitude of the high-frequency voltage applied to the pair of interlocking comb-shaped metallic electrodes to have the form of a sine wave, a rectangular wave, a triangular wave, or a saw tooth wave.

A thirtieth comprises the twenty-ninth feature, wherein the gist thereof is that the controller is configured to modify the amplitude of the high-frequency voltage applied to the pair of interlocking comb-shaped metallic electrodes by providing with, in an alternating manner, a period during which the high-frequency voltage is applied and a period during which the high-frequency voltage is not applied.

A thirty-first feature comprises one of the twenty-eighth feature to the thirtieth feature, wherein the gist thereof is that a duty ratio of the rectangular wave is set in such a manner that damage to the piezoelectric element substrate due to high temperature is avoided, and/or in such a manner that generation, by atomization, of particles having particle sizes larger than a predetermined size is suppressed, when the high-frequency voltage is applied to the pair of interlocking comb-shaped metallic electrodes.

A thirty-second feature comprises the twenty-eighth feature or the twenty-ninth feature, wherein the gist thereof is that, in a single period of the triangular wave, a ratio between amplitude and a length of a period during which a change occurs in a first direction which is parallel to the amplitude and a ratio between amplitude and a length of a period during which a change occurs in a second direction which is opposite to the first direction are set in such a manner that damage to the piezoelectric element substrate due to high temperature is avoided, and/or in such a manner that generation, by atomization, of particles having particle sizes larger than a predetermined size is suppressed, when the high-frequency voltage is applied to the pair of interlocking comb-shaped metallic electrodes.

A thirty-third feature comprises the twenty-eighth feature or the twenty-ninth feature, wherein the gist thereof is that a ratio between a length of a single period and amplitude of the saw tooth wave is set in such a manner that damage to the piezoelectric element substrate due to high temperature is avoided, and/or in such a manner that generation, by atomization, of particles having particle sizes larger than a predetermined size is suppressed, when the high-frequency voltage is applied to the pair of interlocking comb-shaped metallic electrodes.

A thirty-fourth feature comprises one of the twenty-seventh feature to the thirty-third feature, wherein the gist thereof is that a frequency of the periodical changing is equal to or higher than 50 Hz and equal to or lower than 500 Hz.

A thirty fifth feature is a controller for controlling an atomizing unit, wherein the gist thereof is that the atomizing unit comprises a piezoelectric element substrate comprising an IDT comprising a pair of interlocking comb-shaped metallic electrodes, and a liquid supplier configured to supply liquid, which is to be atomized, to the piezoelectric element substrate; wherein the piezoelectric element substrate is configured to atomize the liquid by use of a surface acoustic wave generated by applying a high-frequency voltage to the pair of interlocking comb-shaped metallic electrodes; and the controller performs control to start supply of the liquid, which is to be atomized, to the piezoelectric element substrate after predetermined time has elapsed since application of the high-frequency voltage to the pair of interlocking comb-shaped metallic electrodes has started.

A thirty-sixth feature comprises the thirty-fifth feature, wherein the gist thereof is that a length of the predetermined time is set in such a manner that generation, by atomization, of particles having particle sizes larger than a predetermined size is suppressed.

A thirty-seventh feature comprises the thirty-fifth feature or the thirty-sixth feature, wherein the gist thereof is that the controller is configured to set a speed to supply the liquid, which is to be atomized, to the piezoelectric element substrate to a predetermined value, right after supplying is started.

A thirty-eighth feature comprises the thirty-fifth feature or the thirty-sixth feature, wherein the gist thereof is that the controller is configured to set a speed to supply the liquid, which is to be atomized, to the piezoelectric element substrate to zero right after supplying is started, and gradually increase the supply speed to a predetermined value.

A thirty-ninth feature comprises the thirty-eighth feature, wherein the gist thereof is that a length of time during which the supply speed increases from zero to the predetermined value is set in such a manner that generation, by atomization, of particles having particle sizes larger than a predetermined size is suppressed.

A fortieth feature is a controller for controlling an atomizing unit, wherein the gist thereof is that the atomizing unit comprises a piezoelectric element substrate comprising an IDT comprising a pair of interlocking comb-shaped metallic electrodes, a liquid supplier configured to supply liquid, which is to be atomized, to the piezoelectric element substrate, and a sensor for detecting a quantity of the liquid. which is to be atomized, which exists on the piezoelectric element substrate; wherein the piezoelectric element substrate is configured to atomize the liquid by use of a surface acoustic wave generated by applying a high-frequency voltage to the pair of interlocking comb-shaped metallic electrodes; and the controller is configured to control supply of the liquid, which is to be atomized, to the piezoelectric element substrate based on the quantity of the liquid existing on the piezoelectric element substrate.

A forty-first feature comprises the fortieth feature, wherein the gist thereof is that the controller is configured to start, at the same time, application of the high-frequency voltage to the pair of interlocking comb-shaped metallic electrodes, and supply of the liquid, which is to be atomized, to the piezoelectric element substrate.

A forty-second feature comprises the fortieth feature, wherein the gist thereof is that the controller is configured to start supply of the liquid, which is to be atomized, to the piezoelectric element substrate, after starting application of the high-frequency voltage to the pair of interlocking comb-shaped metallic electrodes.

A forty-third feature comprises one of the fortieth feature to the forty-second feature, wherein the gist thereof is that the controller is configured to control supply of the liquid, which is to be atomized, to the piezoelectric element substrate in such a manner that a quantity, that is in a first predetermined range of quantities, of the liquid, which is to be atomized, exists on the piezoelectric element substrate, before application of the high-frequency voltage to the pair of interlocking comb-shaped metallic electrodes is started.

A forty-fourth feature comprises the forty-third feature, wherein the gist thereof is that the first predetermined range of quantities is set in such a manner that generation, by atomization, of particles having particle sizes larger than a predetermined size is suppressed.

A forty-fifth feature comprises one of the fortieth feature to the forty-fourth feature, wherein the gist thereof is that controller is configured to control supply of the liquid, which is to be atomized, to the piezoelectric element substrate in such a manner that the speed of supply of the liquid, which is to be atomized, to the piezoelectric element substrate is made to have a predetermined value or predetermined change, after application of the high-frequency voltage to the pair of interlocking comb-shaped metallic electrodes is started.

A forty-sixth feature comprises one of the fortieth feature to the forty-fifth feature, wherein the gist thereof is that the controller is configured to stop supply of the liquid, which is to be atomized, to the piezoelectric element substrate, in the case that the quantity of the liquid, which is to be atomized, existing on the piezoelectric element substrate is equal to or above an upper limit in a second predetermined range of quantities, when supplying the liquid, which is to be atomized, to the piezoelectric element substrate; and the upper limit and a lower limit of the second predetermined range of quantities are equal to or larger than an upper limit and a lower limit of the first predetermined range of quantities, respectively.

A forty-seventh feature comprises the forty-sixth feature, wherein the gist thereof is that the controller is configured to restart supply of the liquid, which is to be atomized, to the piezoelectric element substrate, in the case that the quantity of the liquid, which is to be atomized, existing on the piezoelectric element substrate is less than the lower limit of the second predetermined range of quantities, when supply of the liquid, which is to be atomized, to the piezoelectric element substrate is being stopped.

A forty-eighth feature comprises the forty-sixth feature or the forty-seventh feature, wherein the gist thereof is that the second predetermined range of quantities is set in such a manner that generation, by atomization, of particles having particle sizes larger than a predetermined size is suppressed.

A forty-ninth feature comprises a program, wherein the gist thereof is that the program makes a processor to function as at least a part of the controller recited in one of the twenty-seventh feature to the forty-eighth feature.

A fiftieth feature is an inhaler, and the gist thereof is that the inhaler comprises an atomizing unit which comprises a piezoelectric element substrate having a first IDT consisting of a pair of interlocking comb-shaped electrodes and is configured to atomize liquid by a surface acoustic wave generated by applying a high-frequency voltage to the pair of interlocking comb-shaped electrodes, and a controller configured to monitor a resonant frequency of the pair of interlocking comb-shaped electrodes and apply a voltage to the pair of interlocking comb-shaped electrodes at a frequency determined based on the monitored resonant frequency.

A fifty first feature comprises the fiftieth feature, wherein the gist thereof is that the controller is configured to, when monitoring the resonant frequency, apply a voltage to the pair of interlocking comb-shaped electrodes at a frequency selected from multiple different frequencies and determine as the resonant frequency, a frequency of a voltage applied to the pair of interlocking comb-shaped electrodes when power reflected from the pair of interlocking comb-shaped electrodes is the lowest.

A fifty second feature comprises the fifty first feature, wherein the gist thereof is that the controller is configured to detect first power reflected from the pair of interlocking comb-shaped electrodes when a voltage is applied to the pair of interlocking comb-shaped electrodes at a first frequency, detect second power reflected from the pair of interlocking comb-shaped electrodes when a voltage is applied to the pair of interlocking comb-shaped electrodes at a second frequency separated from the first frequency by a first value, and apply a voltage to the pair of interlocking comb-shaped electrodes at a third frequency separated from the second frequency by a second value that is smaller than the first value when the second power is lower than the first power.

A fifty third feature comprises the fifty first feature, wherein the gist thereof is that the controller is configured to monitor reflected power from the pair of interlocking comb-shaped electrodes while discretely increasing or decreasing a frequency of a voltage applied to the pair of interlocking comb-shaped electrodes, end a scan when the trend of the value indicating reflected power shifts from a decreasing trend to an increasing trend, and determine as the resonant frequency, a frequency of a voltage applied to the pair of interlocking comb-shaped electrodes when the reflected power becomes the lowest.

A fifty fourth feature comprises the fifty first feature, wherein the gist thereof is that the controller is configured to monitor reflected power from the pair of interlocking comb-shaped electrodes while discretely increasing a frequency of a voltage applied to the pair of interlocking comb-shaped electrodes, reduce the range of variation in a frequency of a voltage applied to the pair of interlocking comb-shaped electrodes and discretely decrease the frequency when the trend of the value indicating the reflected power shifts from a decreasing trend to an increasing trend.

A fifty fifth feature comprises the fifty first feature, wherein the gist thereof is that the controller is configured to monitor reflected power from the pair of interlocking comb-shaped electrodes while discretely decreasing a frequency of a voltage applied to the pair of interlocking comb-shaped electrodes, reduce the range of variation in a frequency of a voltage applied to the pair of interlocking comb-shaped electrodes and discretely increase the frequency when the trend of the value indicating the reflected power shifts from a decreasing trend to an increasing trend.

A fifty sixth feature comprises the fifty first feature, wherein the gist thereof is that the controller is configured to determine a resonant frequency monitored before the start of atomization of liquid by the atomizing unit, a resonant frequency estimated from the temperature of the piezoelectric element substrate or a frequency closest to the resonant frequency at the time of the previous inhalation as a frequency to be selected first from the multiple different frequencies.

A fifty seventh feature comprises the fiftieth feature, wherein the gist thereof is that the inhaler further comprises a second IDT located on the piezoelectric element substrate and configured to generate a voltage in response to the surface acoustic wave and the controller is configured to, when monitoring the resonant frequency, apply a voltage to the pair of interlocking comb-shaped electrodes at a frequency selected from multiple different frequencies and determine as the resonant frequency, a frequency of a voltage applied to the pair of interlocking comb-shaped electrodes when a voltage arising at the second IDT is the highest.

A fifty eighth feature comprises the fifty seventh feature, wherein the gist thereof is that the controller is configured to detect a first voltage arising at the second IDT when a voltage is applied to the pair of interlocking comb-shaped electrodes at a first frequency, detect a second voltage arising at the second IDT when applying a voltage to the pair of interlocking comb-shaped electrodes at a second frequency separated from the first frequency by a first value, and apply a voltage to the pair of interlocking comb-shaped electrodes at a third frequency separated from the second frequency by a second value that is smaller than the first value when the second voltage is higher than the first voltage.

A fifty ninth feature comprises the fifty seventh feature, wherein the gist thereof is that the controller is configured to monitor a voltage arising at the second IDT while discretely increasing or decreasing a frequency of a voltage applied to the pair of interlocking comb-shaped electrodes, end a scan when the trend of the value of the voltage arising at the second IDT shifts from an increasing trend to a decreasing trend, and determine as the resonant frequency, a frequency of a voltage applied to the pair of interlocking comb-shaped electrodes when the voltage becomes the highest.

A sixtieth feature comprises the fifty seventh feature, wherein the gist thereof is that the controller is configured to monitor a voltage arising at the second IDT while discretely increasing a frequency of a voltage applied to the pair of interlocking comb-shaped electrodes, reduce the range of variation in a frequency of a voltage applied to the pair of interlocking comb-shaped electrodes and discretely decrease the frequency when the trend of the value of the voltage arising at the second IDT shifts from an increasing trend to a decreasing trend.

A sixty first feature comprises the fifty seventh feature, wherein the gist thereof is that the controller is configured to monitor a voltage arising at the second IDT while discretely decreasing a frequency of a voltage applied to the pair of interlocking comb-shaped electrodes, reduce the range of variation in a frequency of a voltage applied to the pair of interlocking comb-shaped electrodes and discretely increase the frequency when the trend of the value of the voltage arising at the second IDT shifts from an increasing trend to a decreasing trend.

A sixty second feature comprises the fifty seventh feature, wherein the gist thereof is that the controller is configured to determine a resonant frequency monitored before the start of atomization of the liquid by the atomizing unit, a resonant frequency estimated from the temperature of the piezoelectric element substrate or a frequency closest to the resonant frequency at the time of the previous inhalation as a frequency to be selected first from the multiple different frequencies.

A sixty third feature comprises any one of the fiftieth to sixty second features, wherein the gist thereof is that the controller is configured to monitor the resonant frequency before the start or after the end of atomization of the liquid by the atomizing unit.

A sixty fourth feature comprises any one of the fiftieth to sixty second features, wherein the gist thereof is that the controller is configured to monitor the resonant frequency after detecting a request to atomize the liquid.

A sixty fifth feature comprises any one of the fiftieth to sixty second features, wherein the gist thereof is that the controller is configured to apply a voltage to the pair of interlocking comb-shaped electrodes at a frequency determined based on the monitored resonant frequency during atomization of the liquid by the atomizing unit.

A sixty sixth feature comprises the sixty third feature, wherein the gist thereof is that the controller is configured to determine a range of frequencies including the monitored resonant frequency and control a frequency of a voltage applied to the pair of interlocking comb-shaped electrodes in such a manner as to vary within the determined range of frequencies during atomization of the liquid by the atomizing unit.

The sixty seventh feature comprises the sixty sixth feature, wherein the gist thereof is that the inhaler further comprises a memory unit for storing a correspondence between a resonant frequency and a frequency range and the controller is configured to determine the frequency range based on the monitored resonant frequency and the correspondence.

The sixty eighth feature comprises any one of the fiftieth to sixty second features, wherein the gist thereof is that the resonant frequency is monitored during atomization of the liquid by the atomizing unit.

The sixty ninth feature comprises the sixth eighth feature, wherein the gist thereof is that the controller is configured to control a frequency of a voltage applied to the pair of interlocking comb-shaped electrodes in such a manner as to vary within a predetermined range and adjust the predetermined range in such a manner as to include the monitored resonant frequency, during atomization of the liquid by the atomizing unit.

The seventieth feature comprises the sixty eighth feature, wherein the gist thereof is that the controller is configured to control a frequency of a voltage applied to the pair of interlocking comb-shaped electrodes and determine the monitored resonant frequency as a frequency of a voltage applied to the pair of interlocking comb-shaped electrodes at the time of the next inhalation, during atomization of the liquid by the atomizing unit.

The seventy first feature comprises any one of fiftieth to sixty second features, wherein the gist thereof is that the inhaler further comprises a temperature sensor for detecting a temperature of the piezoelectric element substrate, wherein the controller is configured to obtain the temperature detected by the temperature sensor and determine a frequency of a voltage applied to the pair of interlocking comb-shaped electrodes based on the detected temperature, during atomization of the liquid by the atomizing unit.

The seventy second feature comprises the seventy first feature, wherein the gist thereof is that the controller is configured to predict a variation in a resonant frequency during atomization of the liquid by the atomizing unit based on the detected temperature and determine a frequency of a voltage applied to the pair of interlocking comb-shaped electrodes based on the predicted variation in the resonant frequency.

The seventy third feature comprises the seventy second feature, wherein the gist thereof is that the inhaler further comprises a memory unit for storing a correspondence between a temperature and a resonant frequency of the pair of interlocking comb-shaped electrodes, wherein the controller is configured to predict a variation in the resonant frequency based on the detected temperature and the correspondence.

BRIEF DESCRIPTION OF DRAWINGS

FIG. 1 is a diagram illustrating a flavor inhaler 1 according to an embodiment.

FIG. 2 is a diagram illustrating an atomizing unit 100 according to the embodiment.

FIG. 3 is a diagram illustrating a planar view of a SAW module 30 viewed from a front surface side of a piezoelectric element substrate 31.

FIG. 4 is a diagram illustrating a cross-section of the SAW module 30.

FIG. 5 is a diagram for describing a mechanism of generating an aerosol.

FIG. 6 is a diagram for describing a penetrated aperture 34 according to a first modification.

FIG. 7 is a diagram for describing a separation wall 37 according to a second modification.

FIG. 8 is a diagram for describing the separation wall 37 according to the second modification.

FIG. 9 is a diagram for describing a hydrophilic layer 38 according to a third modification.

FIG. 10 shows photographs of a result of a first experiment.

FIG. 11 is a table showing a result of a second experiment.

FIG. 12 is a graph showing a result of a third experiment.

FIG. 13 is a diagram for describing a fifth modification.

FIG. 14 is a diagram for describing a sixth modification.

FIG. 15 is a diagram for describing the sixth modification.

FIG. 16 is a diagram for describing a seventh modification.

FIG. 17 is a diagram for describing the seventh modification.

FIG. 18 is a diagram for describing an eighth modification.

FIG. 19 is a diagram for describing the eighth modification.

FIG. 20 is a diagram for describing the eighth modification.

FIG. 21 is a diagram for describing a ninth modification.

FIG. 22 is a diagram for describing the ninth modification.

FIG. 23 is a diagram for describing the ninth modification.

FIG. 24 is a diagram for describing the ninth modification.

FIG. 25 is a diagram for describing the ninth modification.

FIG. 26 is a diagram for describing a tenth modification.

FIG. 27 is a diagram for describing an eleventh modification.

FIG. 28 is a diagram for describing a twelfth modification.

FIG. 29 is a diagram for describing a thirteenth modification.

FIG. 30 is a diagram for describing a fourteenth modification.

FIG. 31 is a diagram for describing the fourteenth modification.

FIG. 32 is a diagram for describing the fourteenth modification.

FIG. 33 is a diagram for describing the fourteenth modification.

FIG. 34 is a diagram for describing a fifteenth modification.

FIG. 35 is a diagram for describing a sixteenth modification.

FIG. 36 is a diagram for describing the sixteenth modification.

FIG. 37 is a diagram for describing a seventeenth modification.

FIG. 63 is a graph showing discomfort in a throat.

FIG. 68 is figure for explaining twenty-sixth modification A.

FIG. 80B is a flow chart illustrating a method of operating the inhaler according to the twenty seventh modification.

FIG. 80C is a flow chart illustrating a method of operating the inhaler according to the twenty seventh modification.

FIG. 81B is a flow chart illustrating a method of operating the inhaler according to the twenty seventh modification

DESCRIPTION OF EMBODIMENTS

Figure 1:
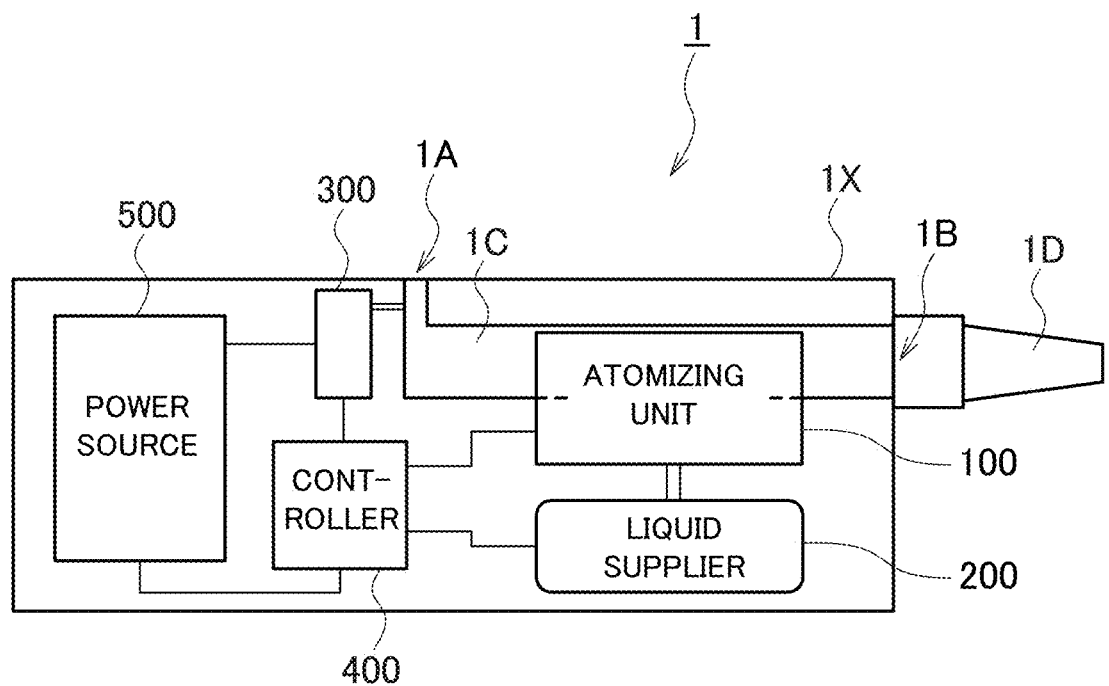

Hereinafter, embodiments of the present invention will be described. In the following description of the drawings, the same or similar parts are denoted by the same or similar reference numerals. It is noted that the drawings are schematic, and the ratios of dimensions and the like may be different from the actual ones.

Therefore, specific dimensions and the like should be determined by referring to the following description. Of course, the drawings may include the parts with different dimensions and ratios.

Overview of Disclosure

As described in the background art, technology has been proposed in which an atomizing unit using a piezoelectric element substrate is used for a flavor inhaler. As a result of extensive studies, the inventors found that various means need to be devised if using a piezoelectric element substrate in an atomizing unit to be used for the flavor inhaler.

An atomizing unit according to the overview of disclosure comprises: a piezoelectric element substrate having an interdigital transducer made of a pair of interlocking comb-shaped metallic electrodes; and a liquid supplier configured to supply liquid to be aerosolized to the piezoelectric element substrate. The piezoelectric element substrate is configured to atomize the liquid by use of a surface acoustic wave generated by applying a voltage to the pair of interlocking comb-shaped metallic electrodes at a high frequency (resonant frequency). The piezoelectric element substrate has a certain number of the pair of interlocking comb-shaped metallic electrodes, the certain number being determined based on a desired aerosol atomized by use of the surface acoustic wave.

According to the overview of the disclosure, the number of pair of interlocking comb-shaped metallic electrodes is determined based on a desired aerosol. Therefore, as the atomizing unit having the limited power that can be supplied to the pair of interlocking comb-shaped metallic electrodes, it is possible to provide an appropriate atomizing unit by improving atomizing efficiency of the liquid.

Embodiment (Flavor Inhaler)

A flavor inhaler according to an embodiment will be described below. FIG. 1 is a diagram illustrating a flavor inhaler 1 according to the embodiment.

As illustrated in FIG. 1, the flavor inhaler 1 has an atomizing unit 100, a liquid storage unit 200, a sensor 300, a controller 400, and a power source 500. The flavor inhaler 1 has a housing 1X configured to house the atomizing unit 100, the liquid storage unit 200, the sensor 300, the controller 400, and the power source 500. The housing 1X may have a rectangular box shape as illustrated in FIG. 1, or may have a cylindrical shape. The flavor inhaler 1 has a chamber 1C communicating from an inlet 1A to an outlet 1B. The outlet 1B may be provided with a mouthpiece 1D. The mouthpiece 1D may be a continuous body with the housing 1X, or may be a separate body from the housing 1X. The mouthpiece 1D may have a filter.

The atomizing unit 100 atomizes a liquid to be aerosolized supplied from the liquid storage unit 200. The atomizing unit 100 uses a surface acoustic wave (SAW) to atomize the liquid. The atomizing unit 100 may be a cartridge configured to be detachable. Details of the atomizing unit 100 will be given later.

The liquid storage unit 200 houses the liquid. The liquid storage unit 200 may be a cartridge configured to be detachable. The liquid storage unit 200 may be integrally formed with the atomizing unit 100. The liquid may include solvents such as water, glycerin, propylene glycol, and ethanol. The liquid may include solutes (flavor components) contributing to at least any one of a fragrance and a taste. The flavor component may include a volatile component and a non-volatile component. It may be sufficient that the volatile component is a component generally used as a flavor. The volatile component may be a plant-derived component or a synthetic component. Examples of the volatile component include menthol, limonene, linalool, vanillin, tobacco extracts, and the like. The non-volatile component may be a component contributing to the sense of taste. Examples of the non-volatile component include sugars such as glucose, fructose, sucrose and lactose; bitter substance such as tannin, catechin, and naringin, acids such as malic acid and citric acid, and salts. The liquid may be in an emulsified state by an emulsifier, or may be in a suspended state by a dispersant. The liquid may include an ionic substance and a water-soluble flavor that is insoluble in glycerin and propylene glycol and soluble in water.

If the liquid storage unit 200 is a cartridge and a SAW module described below has two or more penetrated apertures, the liquid may be supplied to the two or more penetrated apertures from one cartridge, or the liquid may be supplied to the two or more penetrated apertures individually from two or more cartridges. If two or more cartridges are provided, each cartridge may store liquid of a different kind. For example, a first cartridge may store a volatile component and a second cartridge may store a non-volatile component.

If the liquid storage unit 200 is a cartridge, the cartridge may include the above-described mouthpiece 1D as a continuous body. According to such a configuration, the mouthpiece 1D is also replaced when the cartridge is replaced, and thus, the mouthpiece 1D is hygienically maintained.

If the liquid storage unit 200 is a cartridge, the cartridge may be a disposable type, or may be a refillable type. The refillable type is a type that a user refills the cartridge with liquid of choice.

The sensor 300 detects a puff action of a user. For example, the sensor 300 detects a flow of gas passing through the chamber 1C. For example, the sensor 300 is a flow rate sensor. The flow rate sensor includes an orifice disposed within the chamber 1C. The flow rate sensor monitors a pressure difference between an upstream of the orifice and a downstream of the orifice, and detects an air flow by the monitored pressure difference.

The controller 400 is configured of a processor, a memory, and the like, and controls each configuration provided to the flavor inhaler 1. The controller 400 may be an article configured to be detachable. For example, the controller 400 specifies a start of a puff action by a detection result of the sensor 300. The controller 400 may start an atomization action of the atomizing unit 100, in response to the start of the puff action. The controller 400 may specify a stop of the puff action by the detection result of the sensor 300. The controller 400 may stop the atomization action of the atomizing unit 100, in response to the stop of the puff action. If a certain period has passed from the start of the puff action, the controller 400 may stop the atomization action of the atomizing unit 100.

In the embodiment, the controller 400 may include a voltage and frequency control circuit configured to control the SAW module described below. A voltage and frequency adjustment circuit controls, as the atomization action of the atomizing unit 100, a frequency and magnitude of power (for example, AC voltage) supplied to a SAW module 30. However, as described below, the voltage and frequency adjustment circuit may be provided to a drive circuit board 20.

The power source 500 supplies power for driving the flavor inhaler 1. The power source 500 may be a primary battery such as a manganese battery, an alkaline battery, an oxyride battery, a nickel battery, a nickel manganese battery, and a lithium battery, or may be a secondary battery such as a nickel-cadmium battery, a nickel-metal hydride battery, and a lithium battery. The power source 500 may be an article configured to be detachable.

(Atomizing Unit)

Figure 2:
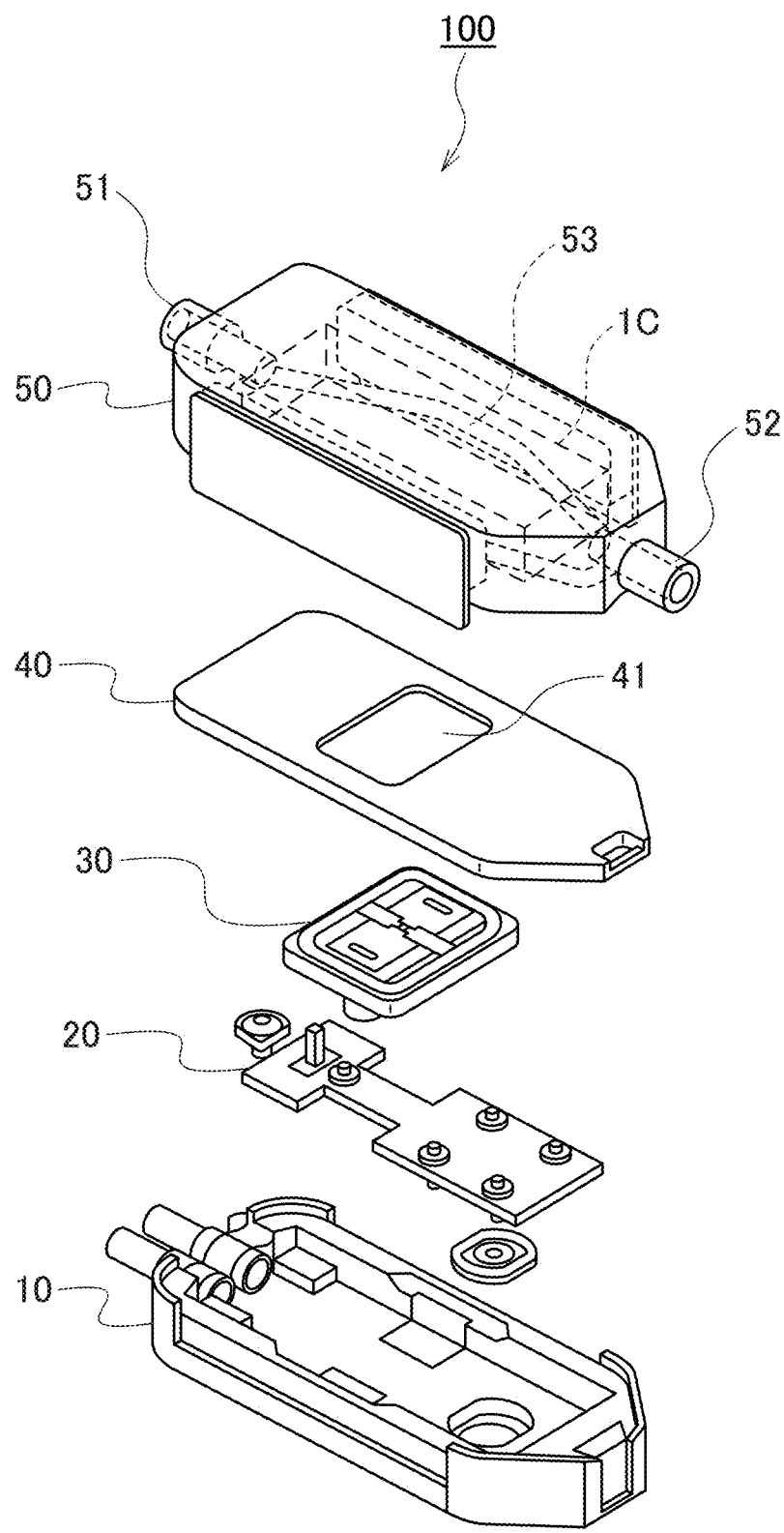

An atomizing unit according to the embodiment will be described below. FIG. 2 is a diagram illustrating the atomizing unit 100 according to the embodiment.

As illustrated in FIG. 2, the atomizing unit 100 has a housing 10, the drive circuit board 20, the SAW module 30, a ceiling plate 40, and a top cover 50.

The housing 10 houses the drive circuit board 20, the SAW module 30, and the ceiling plate 40. The housing 10 may house a housing body configured to house the liquid to be aerosolized, or may house a liquid supplier (for example, a syringe pump) configured to supply the liquid to the SAW module 30.

The drive circuit board 20 has a drive circuit configured to drive the SAW module 30. The drive circuit board 20 may be considered to include a part of the above-described controller 400 (for example, the voltage and frequency control circuit). Alternatively, the drive circuit board 20 may be considered to be a part of the controller 400. For example, the drive circuit uses the power supplied from the power source 500 to drive the SAW module 30. The drive circuit controls the frequency and the magnitude of the power (for example, AC voltage) supplied to the SAW module 30. The drive circuit may control an amount of the liquid supplied to the SAW module 30.

As described below, the SAW module 30 has a piezoelectric element substrate having interdigital transducer made of at least one pair of interlocking comb-shaped metallic electrodes. Details of the SAW module 30 will be described later (see FIG. 3 and FIG. 4).

The ceiling plate 40 is a plate-like member disposed on the drive circuit board 20 and the SAW module 30. The drive circuit board 20 and the SAW module 30 are disposed between the housing 10 and the ceiling plate 40. The ceiling plate 40 has an opening 41 exposing at least the piezoelectric element substrate. For example, the ceiling plate 40 is configured by stainless steel.

The top cover 50 is disposed on the ceiling plate 40. The top cover 50 has an inlet 51 and an outlet 52 and has an air flow path extending from the inlet 51 to the outlet 52. The aerosol is led out from the SAW module 30 to the outlet 52 by an airstream from inlet 51 to outlet 52. The top cover 50 may have an O ring 53 configured to improve airtightness of the air flow path. For example, the top cover 50 is configured by resins having heat resistance such as polycarbonates, and the O ring 53 may be configured by resins having elasticity such as silicon. A position of the outlet 52 may be any position and the outlet 52 may be provided immediately above the opening 41 of the ceiling plate 40. According to such a configuration, it is possible to efficiently lead the aerosol generated toward a direction immediately above the SAW module 30 and an aerosol flow path can be shortened. The outlet 52 may have a filter.

(Saw Module)

A SAW module according to the embodiment will be described below. FIG. 3 is a diagram illustrating a planar view of the SAW module 30 viewed from the front surface side of a piezoelectric element substrate 31. FIG. 4 is a diagram illustrating a cross-section of the SAW module 30.

As illustrated in FIG. 3 and FIG. 4, the SAW module 30 has the piezoelectric element substrate 31, an electrode (a main body portion 32 and an interdigital transducer made of the pairs of interlocking comb-shaped metallic electrodes 33), a penetrated aperture 34, and a heat sink structure 35. The piezoelectric element substrate 31 is configured to atomize the liquid by use of a SAW generated by applying a voltage to the pairs of interlocking comb-shaped metallic electrodes 33 at a high frequency (resonant frequency).

The piezoelectric element substrate 31 includes a front surface 31F on which the main body portion 32 and the pairs of interlocking comb-shaped metallic electrodes 33 are disposed and a rear surface 31B provided on an opposite side of the front surface 31F. The piezoelectric element substrate 31 includes a piezoelectric body configured to expand and contract as a result of applying the voltage thereto. A portion of the piezoelectric element substrate 31 where the pairs of interlocking comb-shaped metallic electrodes 33 are disposed may be referred to as a disposition portion 30A. It may be sufficient that the piezoelectric body configures at least the front surface 31F. As the piezoelectric body, a known piezoelectric body configured by ceramics such as quartz, barium titanate, and lithium niobate can be used.

The main body portion 32 is electrically connected to the power source 500. The main body portion 32 includes a first main body portion 32A integrally formed with a first electrode 33A that is one of the pairs of interlocking comb-shaped metallic electrodes 33, and a second main body portion 32B integrally formed with a second electrode 33B that is the other one of the pairs of interlocking comb-shaped metallic electrodes 33. The first main body portion 32A and the second main body portion 32B are disposed, with the disposition portion 30A being sandwiched therebetween, in an orthogonal direction B to a travel direction A of the SAW. The power output from a battery is supplied to the pairs of interlocking comb-shaped metallic electrodes 33 through the main body portion 32.

The pairs of interlocking comb-shaped metallic electrodes 33 include the first electrode 33A and the second electrode 33B. The first electrode 33A and the second electrode 33B are alternately disposed in the travel direction A of the SAW. The first electrode 33A has a shape extending along the orthogonal direction B from the first main body portion 32A. The second electrode 33B has a shape extending along the orthogonal direction B from the second main body portion 32B. For example, the pairs of interlocking comb-shaped metallic electrodes 33 are configured by gold plated metal and the like.

The penetrated aperture 34 is an aperture penetrating the piezoelectric element substrate 31 from the rear surface 31B to the front surface 31F. The penetrated aperture 34 forms a flow path leading the liquid from the rear surface 31B to the front surface 31F. The penetrated aperture 34 has, in a planar view viewed from a side of the front surface 31F, a maximum width $W_{MAX}$ in the travel direction A of the SAW and a maximum length $L_{MAX}$ in the orthogonal direction B. The maximum length $L_{MAX}$ is greater than the maximum width $W_{MAX}$. In other words, the penetrated aperture 34 has a shape longer in the orthogonal direction B (for example, an elliptical shape or a rectangular shape). If the penetrated aperture 34 is an elliptical shape or a rectangular shape, it may be sufficient that a longitudinal axis of the penetrated aperture 34 extends along the orthogonal direction B. "Extending along the orthogonal direction B" may mean to have an inclination in which the longitudinal axis of the penetrated aperture 34 is equal to or less than 45° with respect to the orthogonal direction B. It is preferable that the maximum length $L_{MAX}$ is greater than a length of the disposition portion 30A in the orthogonal direction B (for example, overlapping portion of the first electrode 33A and the second electrode 33B). As illustrated in FIG. 3, it is preferable that the penetrated aperture 34 includes at least two penetrated apertures that sandwich the pairs of interlocking comb-shaped metallic electrodes 33. According to such a configuration, it increases an interaction of SAW and liquid and increases the amount of liquid atomized for the same power.

The heat sink structure 35 is a structure configured to conduct away the heat generated by a reflection of the surface acoustic wave on an edge of the piezoelectric element substrate 31. The heat sink structure 35 includes at least any one of a heat conductive layer and a Peltier element, the heat conductive layer being configured by a material having a thermal conductivity higher than a thermal conductivity of the piezoelectric element substrate 31. The heat sink structure 35 has a penetrated aperture 35A continuous to the penetrated aperture 34. The penetrated aperture 35A is an aperture through which the liquid is led to the front surface 31F of the piezoelectric element substrate 31. In an example illustrated in FIG. 4, the heat sink structure 35 is a heat conductive layer disposed on the rear surface 31B of the piezoelectric element substrate 31. However, the embodiment is not limited thereto. For example, the heat sink structure 35 may only need to be in contact with the piezoelectric element substrate 31 and may be disposed on the front surface 31F of the piezoelectric element substrate 31. The heat sink structure 35 may be a Peltier element. The heat sink structure 35 may include both the heat conductive layer and the Peltier element. For example, as the heat conductive layer, metals such as aluminum, copper, and iron may be used, and carbon, Aluminum nitride, and ceramics may also be used. For example, the Peltier element may be stuck to the piezoelectric element substrate 31 by an adhesive (a grease, an epoxy resin, a metal paste). It is preferable that the thermal conductivity of the adhesive is higher than 0.1 W/m/K. Further, it is preferable that the thermal conductivity of the adhesive is higher than 0.5 W/m/K. The thinner adhesive would be preferable, and the thin adhesive may be available by a screen printing.

Figure 4:
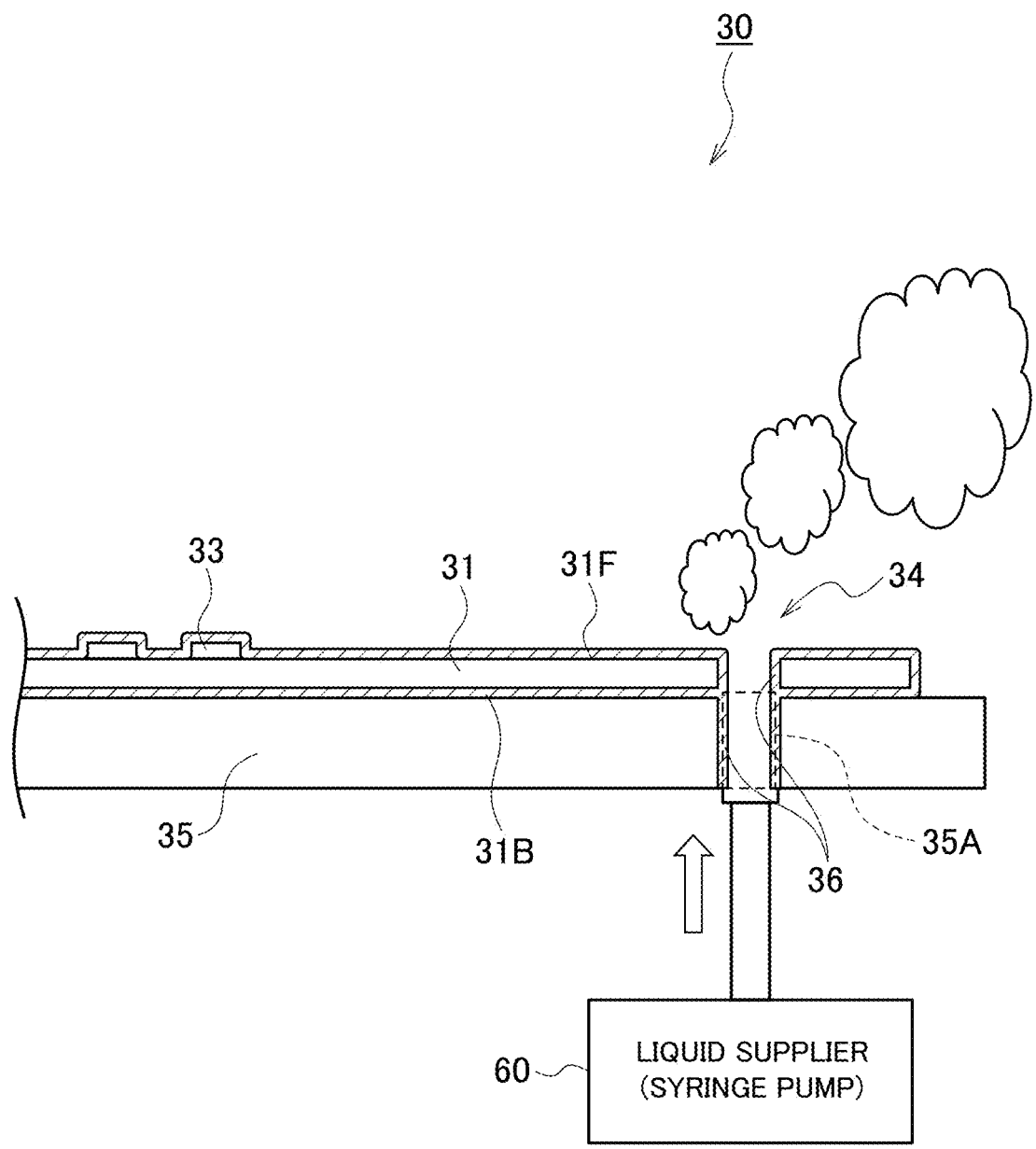

As illustrated in FIG. 4, a liquid supplier 60 is provided on a side of the rear surface 31B of the piezoelectric element substrate 31, the liquid supplier 60 is configured to supply the liquid to the piezoelectric element substrate 31. The liquid supplier 60 supplies the liquid to the front surface 31F of the piezoelectric element substrate 31 through the penetrated aperture 34 and the penetrated aperture 35A.

For example, the liquid supplier 60 is a syringe pump. In such a case, the penetrated aperture 34 and the penetrated aperture 35A configure a flow path of the liquid. The syringe pump may be manually operated or electrically operated.

Figure 3:
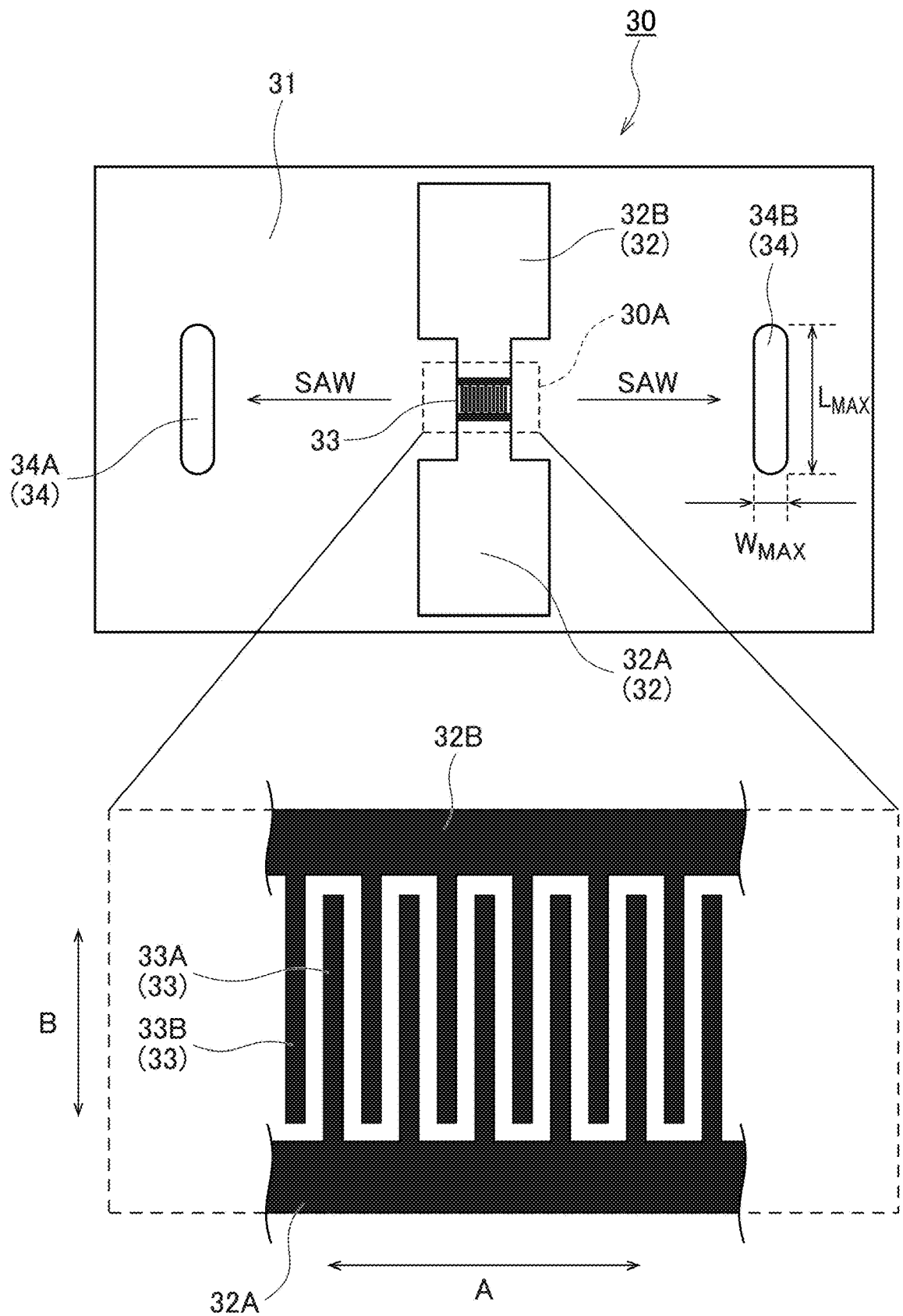

In FIG. 3, a case is exemplified where the liquid supplier 60 is a syringe pump; however, the embodiment is not limited to this. For example, the liquid supplier 60 may be a member configured to supply the liquid by a capillary phenomenon. In such a case, the liquid supplier 60 includes a capillary member through which the liquid is suctioned up and the penetrated aperture 34 and the penetrated aperture 35A configure an aperture through which the capillary member is passed. A first end of the capillary member at least reaches the liquid storage unit 200 and a second end of the capillary member reaches the SAW module 30. In a cross-section of the penetrated aperture 34 and the penetrated aperture 35A, the capillary member is disposed on at least a part of the cross-section. The capillary member may be configured by at least any one of a naturally derived fiber material, a plant-derived fiber material, and a synthetic fiber material. For example, the naturally derived fiber material may be at least any one of a dried plant, a cut-up dried plant, cut-up leaf tobacco, a dried fruit, a cut-up dried fruit, a dried vegetable, and a cut-up dried vegetable. For example, the plant-derived fiber material may be at least any one of an absorbent cotton and a linen fiber. The capillary member may be a cut-up dried plant formed in a sheet shape, such as a cut-up filter paper and a cut-up tobacco sheet.

Further, the liquid supplier 60 may be a combination of the syringe pump and the capillary member. If a remaining amount of the liquid stored in the liquid storage unit 200 is equal to or more than a threshold value, the liquid may be supplied by the capillary member and if the remaining amount of the liquid is less than the threshold value, the liquid may be supplied by the syringe pump. The controller 400 may determine, based on a predetermined reference, whether to use either the syringe pump or the capillary member.

If the liquid storage unit 200 is a cartridge, the liquid supplier 60 may automatically supply the liquid to the SAW module 30 in response to an attachment of the cartridge. If a power source switch configured to drive the flavor inhaler 1 is provided, the liquid supplier 60 may automatically supply the liquid to the SAW module 30 in response to the turning on of the power source.

As illustrated in FIG. 4, the SAW module 30 may include a coating layer 36. The coating layer 36 may entirely cover the piezoelectric element substrate 31, or may partially cover the piezoelectric element substrate 31. The coating layer 36 may be provided on an inner surface of the penetrated aperture 34. According to such a configuration, it is possible to prevent the liquid from coming in contact with the piezoelectric element substrate 31. Further, by conformably depositing the coating material, the coating layer 36 may be provided on an inner surface of the penetrated aperture 35A, in addition to the inner surface of the penetrated aperture 34. According to such a configuration, it is possible to further prevent the liquid from coming in contact with the piezoelectric element substrate 31.

It may be sufficient that the coating layer 36 is configured by a material suppressing denaturation of the piezoelectric element substrate 31 caused due to adherence or the like of the liquid. For example, the coating layer 36 may be configured by polymeric materials such as polypropylene and polyethylene. The coating layer 36 may be configured by a material such as metal, carbon, Teflon (trademark), glass, Parylene, Silicon dioxide, and Titanium dioxide, or a ceramic material such as Silicon nitride, Silicon oxynitride, and Alumina oxide.

Under such premise, the piezoelectric element substrate 31 has a certain number of pairs of interlocking comb-shaped metallic electrodes 33, the certain number being determined based on a desired aerosol atomized by use of the SAW. Specifically, the number of pairs of interlocking comb-shaped metallic electrodes 33 is determined based on atomizing efficiency of the aerosol atomized by use of the SAW. The interval of electrodes adjacent to each other included in the pairs of interlocking comb-shaped metallic electrodes 33 and the width of the electrodes in the travel direction are determined in accordance with a frequency set based on a desired particle size of the aerosol atomized by use of the SAW.

Here, the desired aerosol is an aerosol including an aerosol having the desired particle size as a peak of the number concentration. The atomizing efficiency is a degree of the number concentration of the aerosol in a case where the power supplied to the pairs of interlocking comb-shaped metallic electrodes 33 is constant. The number concentration is the number of aerosol particles included per unit volume. For example, the number concentration of sub-micron droplets is equal to or more than $10^8/cm^3$.

In the embodiment, the power supplied to the pairs of interlocking comb-shaped metallic electrodes 33 is provided by a battery included in the flavor inhaler having the atomizing unit 100. Under such an environment, it is preferable that the power supplied to the pairs of interlocking comb-shaped metallic electrodes 33 is equal to or more than 3 W. When the power is equal to or more than 3 W, the atomization of the liquid appropriately occurs. On the other hand, it is preferable that the power supplied to the pairs of interlocking comb-shaped metallic electrodes 33 is equal to or less than 10 W. When the power is equal to or less than 10 W, the power supplied to the pairs of interlocking comb-shaped metallic electrodes 33 can be appropriately controlled while suppressing an overheating or the like of the pairs of interlocking comb-shaped metallic electrodes 33, the piezoelectric element substrate, and the liquid under restrictions such as the power that can be supplied and the capacity of the battery.

Generally, the decrease of the amount of power supplied to the pairs of interlocking comb-shaped metallic electrodes 33 would suppress the overheating of the SAW module 30, however, it also causes the decrease of the aerosol amount. Under such a premise, the amount of power supplied to the pairs of interlocking comb-shaped metallic electrodes 33 may be controlled by PWM (Pulse Width Modulation) in view of suppressing the overheating of the SAW module 30. According to such a configuration, the overheating of the SAW module 30 can be suppressed by PWM while suppressing the decrease of the aerosol amount generated by SAW.

Under such power restrictions, it is preferable that the number of pairs of interlocking comb-shaped metallic electrodes 33 is equal to or more than 10. According to such a configuration, it is possible to atomize the liquid at a high atomizing efficiency. On the other hand, it is preferable that the number of pairs of interlocking comb-shaped metallic electrodes 33 is equal to or less than 80. According to such a configuration, the frequency bandwidth does not become too narrow, and thus, it is possible to achieve appropriate atomization even in consideration of the manufacturing variation of the atomizing unit 100 and variations of the resonant frequency under different operating conditions (temperature, pressure, humidity, etc. . . . ).

The interval of the electrodes adjacent to each other and the width of the electrodes in the travel direction are inevitably determined in accordance with the frequency of the power supplied to the pairs of interlocking comb-shaped metallic electrodes 33. The higher the frequency, the narrower the interval of the electrodes adjacent to each other, and the smaller the particle size of the aerosol. Under such a relationship, the desired particle size having the peak number concentration may be between 0.2 μm and 1.0 μm, for example. In such a case, it is preferable that the frequency is equal to or more than 20 MHz. According to such a configuration, it is possible to keep the particle size having the peak number concentration within a range of the desired particle size. On the other hand, it is preferable that the frequency is equal to or less than 200 MHz. Such a configuration may ensure that the interval of the electrodes do not become too narrow so that it is less likely to cause short-circuiting of electrode at powers higher than the required minimum power (3 W, for example).

As described above, it should be noted that as a result of extensive studies, the inventors obtained a new finding that, under the condition where the power that can be supplied to the pairs of interlocking comb-shaped metallic electrodes 33 is limited, the number of pairs of interlocking comb-shaped metallic electrodes 33 is determined based on the atomizing efficiency of the aerosol. It also should be noted that the inventors obtained a new finding that the interval (that is, the frequencies) of the electrodes are determined in accordance with the frequency set based on the desired particle size of the aerosol. Further, it should be noted that the inventors obtained, based on the finding that the atomizing efficiency may change depending on the interval (that is, the frequencies or the desired particle sizes) of the electrodes, a new finding that the number of pairs of interlocking comb-shaped metallic electrodes 33 is determined based on the desired aerosol. The desired aerosol is an aerosol in which the aerosol having the desired particle size is included in a desired distribution.

Further, as a result of extensive studies, the inventors obtained a new finding that the atomizing efficiency of the aerosol is high when a ratio (hereinafter, "R") of a length (hereinafter, "H") of the overlapping portion of the pairs of interlocking comb-shaped metallic electrodes 33 to a wavelength (hereinafter, "$\lambda_0$") of the SAW is within a predetermined range. It is preferable that R ($=H/\lambda_0$) is equal to or more than 10 and equal to or less than 150. Further, it is preferable that R is less than 70, preferably equal to or less than 50. Here, $\lambda_0$ is represented by a ratio (v/f) of a frequency (hereinafter, "f") for the power supplied to the pairs of interlocking comb-shaped metallic electrodes 33 to a propagation velocity (hereinafter, "v") of the SAW. Where f has a correlation with the interval of the electrodes and the width of the electrodes in the travel direction, and v has a correlation with the type (characteristic) of the piezoelectric element substrate on which the pairs of interlocking comb-shaped metallic electrodes 33 are provided. In other words, it is preferable that the length of the overlapping portion of the pairs of interlocking comb-shaped metallic electrodes 33, the interval of the electrodes, and the type of the piezoelectric element substrate are determined so that a relationship of $10 \leq R \leq 150$ is satisfied. According to such a configuration, it is possible to provide the atomizing unit 100 having a high atomizing efficiency of the aerosol.

(Shape of Penetrated Aperture)

Figure 5:
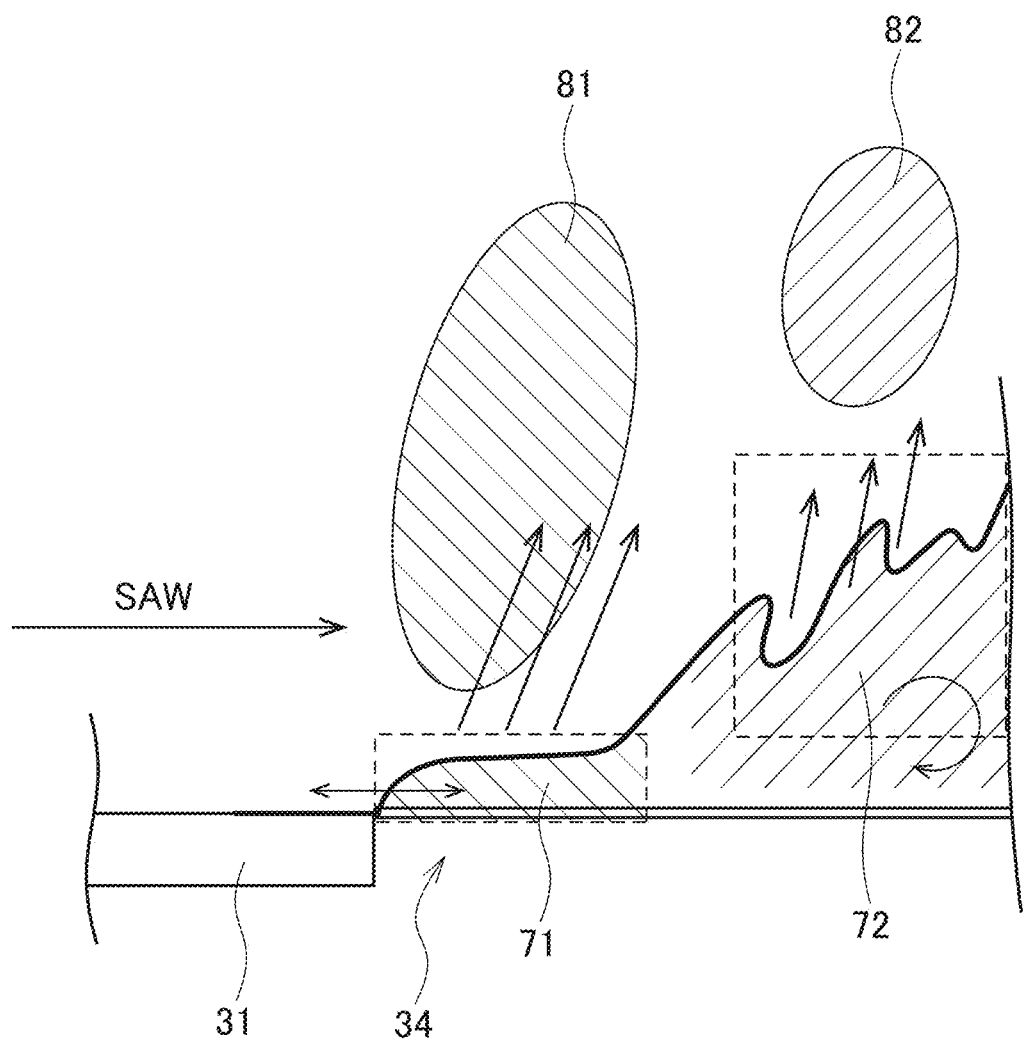

A shape of a penetrated aperture according to the embodiment will be described below. FIG. 5 is a diagram for describing a mechanism of generating an aerosol.

As illustrated in FIG. 5, of the liquid exposed from the penetrated aperture 34, a portion relatively close to a portion coming in contact with the SAW configures a thin film portion 71. Of the liquid exposed from the penetrated aperture 34, a portion relatively far from the portion coming in contact with the SAW configures a thick film portion 72. The particle size of an aerosol 81 atomized from the thin film portion 71 is smaller than the particle size of an aerosol 82 atomized from the thick film portion 72. Therefore, if the desired particle size is comparatively small particle size (for example, 0.2 μm to 1.0 μm), it is effective to increase the area of the thin film portion 71 in the planar view of the piezoelectric element substrate 31 viewed from the side of the front surface 31F. From such a perspective, it is preferable that the penetrated aperture 34 has a shape in which the maximum length $L_{MAX}$ is greater than the maximum width $W_{MAX}$.

Further, if assuming that the penetrated aperture has a circular shape having a diameter corresponding to the maximum length $L_{MAX}$, the area of the liquid exposed from the penetrated aperture becomes too large, and thus, the liquid is likely to flow out above the piezoelectric element substrate 31 when a user diagonally tilts the flavor inhaler 1. From such a perspective also, it is preferable that the penetrated aperture 34 has a shape in which the maximum length $L_{MAX}$ is greater than the maximum width $W_{MAX}$.

(Operation and Effect)

According to the embodiment, the number of pairs of interlocking comb-shaped metallic electrodes 33 is determined based on the desired aerosol. Therefore, in the atomizing unit 100 where the power that can be supplied to the pairs of interlocking comb-shaped metallic electrodes 33 is limited, it is possible to provide an appropriate atomizing unit by improving the atomizing efficiency of the liquid.

First Modification

A first modification of the embodiment will be described below. A difference from the embodiment will be mainly described below.

Figure 6:
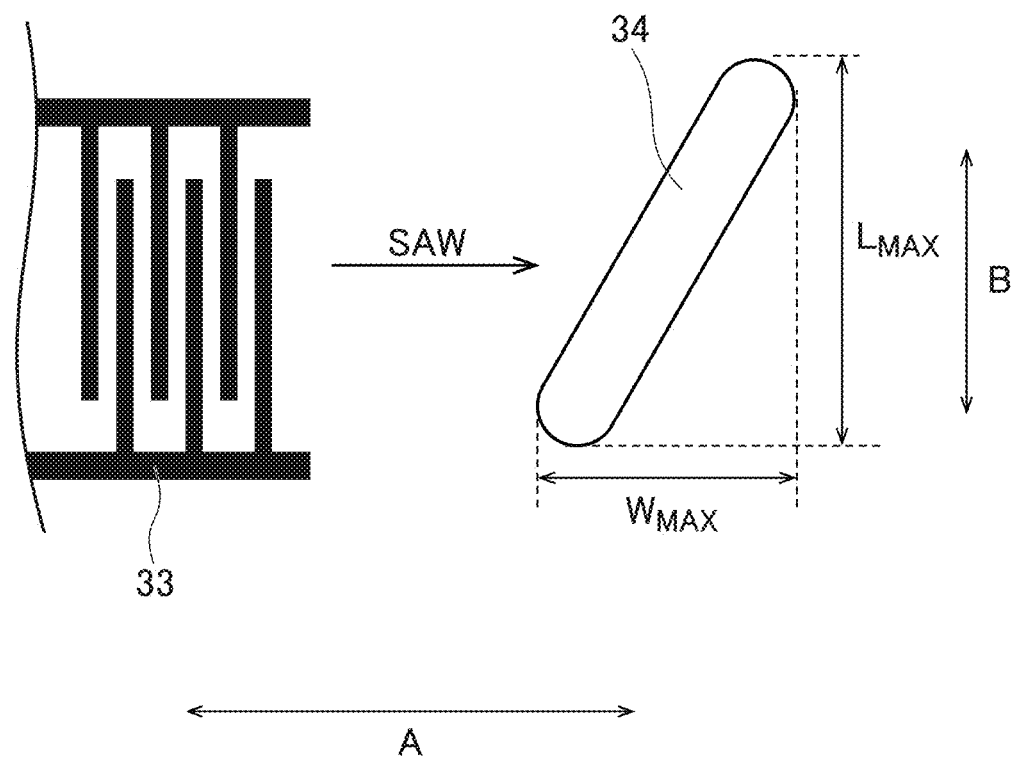
Figure 7:
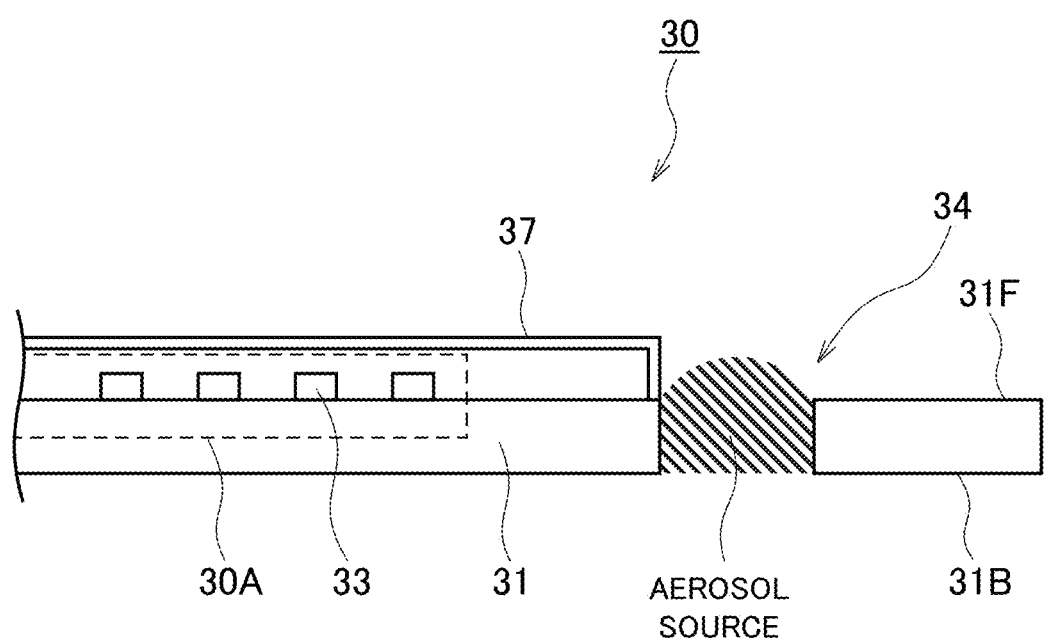
Figure 8:
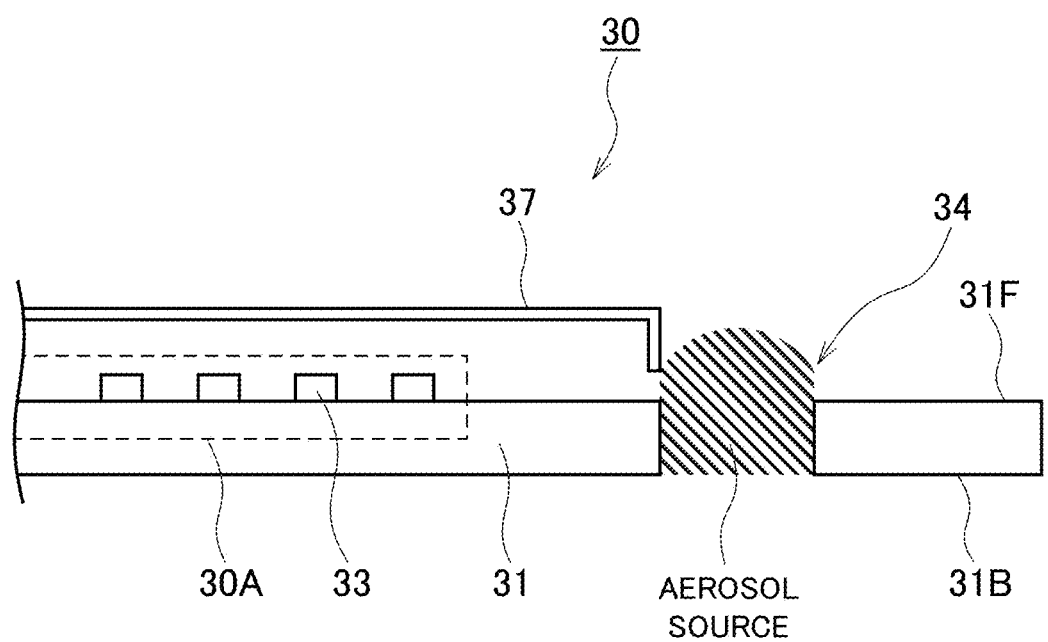
Figure 9:
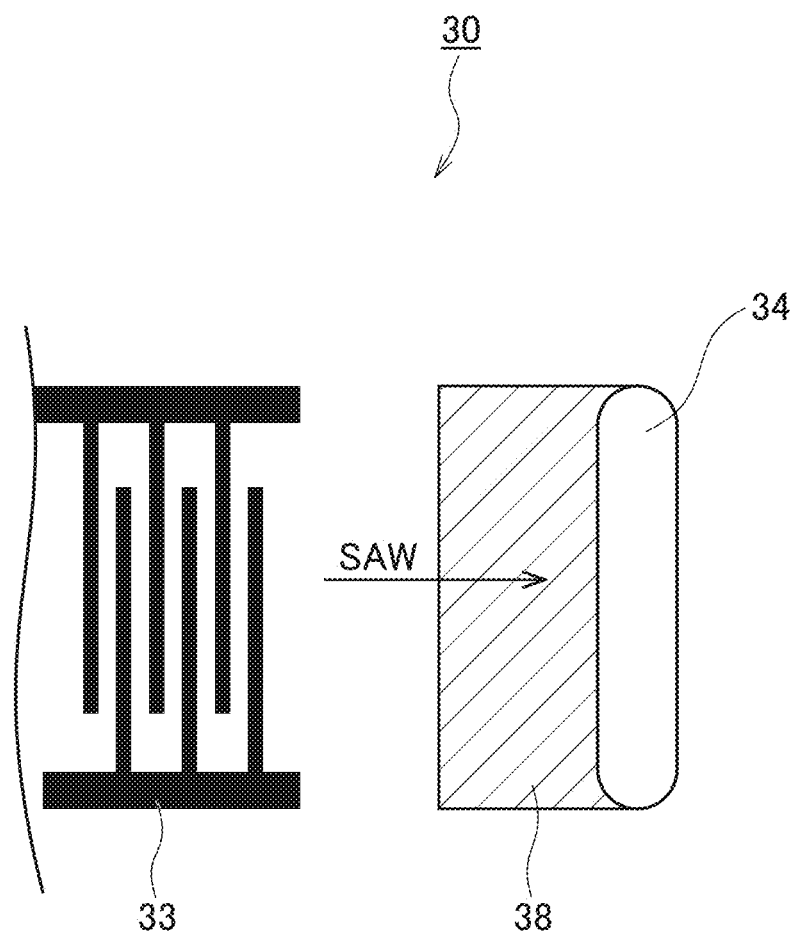

In the first modification, similarly to the embodiment, the penetrated aperture 34 has a shape in which the maximum length $L_{MAX}$ is greater than the maximum width $W_{MAX}$. Under such premise, as illustrated in FIG. 6, the penetrated aperture 34 is provided so as to reduce interference between a reflected wave of the SAW reflected by the penetrated aperture 34 and the SAW generated by the pairs of interlocking comb-shaped metallic electrodes 33. Specifically, it is preferable that the longitudinal axis of the penetrated aperture 34 has an inclination with respect to the orthogonal direction B. The longitudinal axis of the penetrated aperture 34 may have an inclination 30° or more and 45° or less with respect to the orthogonal direction B. It is noted that the shape of the penetrated aperture 34 is not limited to the elliptical shape illustrated in FIG. 6 and may be a rectangular shape.

Further, the penetrated aperture 34 may have a shape other than the elliptical shape and the rectangular shape. Even in such a case, the penetrated aperture 34 is provided so as to reduce the interference between the reflected wave of the SAW reflected by the penetrated aperture 34 and the SAW generated by the pairs of interlocking comb-shaped metallic electrodes 33. For example, at least a part of the penetrated aperture 34 is defined by an edge line where the penetrated aperture 34 comes in contact with the SAW. The edge line has an inclination with respect to the orthogonal direction B to the travel direction A of the SAW. Here, the edge line may have a portion parallel to the orthogonal direction B. However, it is preferable that the portion of at least a half or more of the edge line has an inclination with respect to the orthogonal direction B. It is preferable that the portion of at least a half or more of the edge line has an inclination of 30° or more and 45° or less with respect to the orthogonal direction B. If the penetrated aperture 34 is an elliptical shape or a rectangular shape, the longitudinal axis of the penetrated aperture 34 may have an inclination of 30° or more and 45° or less with respect to the orthogonal direction B.

According to such a configuration, the SAW generated by applying a voltage to the pairs of interlocking comb-shaped metallic electrodes 33 at a high frequency (resonant frequency) is not easily interfered by the reflected wave of the SAW reflected at the penetrated aperture 34. Therefore, the tolerance of the piezoelectric element substrate 31 improves and the atomizing efficiency of the aerosol also improves.

Second Modification

A second modification of the embodiment will be described below. A difference from the embodiment will be mainly described below.

In the second modification, the SAW module 30 has a separation wall 37 separating the liquid exposed from the penetrated aperture 34 and the disposition portion 30A. It is preferable that the separation wall 37 entirely covers the disposition portion 30A. Further, the separation wall 37 may be configured to separate the air flow path extending from the inlet 51 to the outlet 52 and the disposition portion 30A. According to such a configuration, it is possible to suppress the deterioration of the pairs of interlocking comb-shaped metallic electrodes 33 caused due to adherence of the liquid and collision of air introduced from the inlet 51.

As illustrated in FIG. 7, the separation wall 37 may be provided on the front surface 31F so as to come in contact with the front surface 31F of the piezoelectric element substrate 31 between the disposition portion 30A and the penetrated aperture 34. The separation wall 37 may not cover the entire piezoelectric element substrate 31. Typically, the separation wall 37 may be positioned at a minimum of 0.5 mm far from the edge (correspond to the typical thin film width). According to such a configuration, it is possible to ensure the suppression of the deterioration of the pairs of interlocking comb-shaped metallic electrodes 33 caused due to adherence or the like of the liquid.

In such a case, the separation wall 37 may be provided on the front surface 31F so as to come in contact with the front surface 31F of the piezoelectric element substrate 31 between the disposition portion 30A and a atomization zone when the atomization zone is provided at a side of the pairs of interlocking comb-shaped metallic electrodes 33 relative to the penetrated aperture 34.

As illustrated in FIG. 8, the separation wall 37 may be provided on the front surface 31F so as not to come in contact with the front surface 31F of the piezoelectric element substrate 31 between the disposition portion 30A and the penetrated aperture 34. It is possible to suppress, if not eliminate, the deterioration of the pairs of interlocking comb-shaped metallic electrodes 33 caused due to adherence or the like of the liquid while avoiding a situation where propagation of the SAW is blocked by the separation wall 37. Further, a gap between the separation wall 37 and the front surface 31F provided for the propagation of the SAW may be approximately several microns. Such a gap can sufficiently suppress the deterioration of the pairs of interlocking comb-shaped metallic electrodes 33.

In such a case, the separation wall 37 may be provided on the front surface 31F so as not to come in contact with the front surface 31F of the piezoelectric element substrate 31 between the disposition portion 30A and a atomization zone when the atomization zone is provided at a side of the pairs of interlocking comb-shaped metallic electrodes 33 relative to the penetrated aperture 34.

Third Modification

A third modification of the embodiment will be described below. A difference from the embodiment will be mainly described below.

In the third modification, as illustrated in FIG. 9, a hydrophilic layer 38 continuous from the penetrated aperture 34 is provided on the front surface 31F of the piezoelectric element substrate 31 between the pairs of interlocking comb-shaped metallic electrodes 33 and the penetrated aperture 34. For example, the hydrophilic layer 38 is configured by a material such as Teflon (trademark) resin, glass fiber, and the like. The hydrophilic layer 38 can be formed by a generally known hydrophilic treatment technology. For example, the hydrophilic treatment technology may be a formation of a hydrophilic polymer film such as acetate, a diamond-like carbon film forming treatment, plasma treatment, surface roughening treatment, or a combination thereof. According to such a configuration, the liquid exposed from the penetrated aperture 34 easily moves to the hydrophilic layer 38 and a thin film of the liquid is easily formed on the hydrophilic layer 38. Accordingly, it is possible to generate an aerosol having a small particle size from the thin film formed on the hydrophilic layer 38. For example, if the desired particle size is a comparatively small particle size (for example, 0.2 μm to 1.0 μm), it is preferable that the hydrophilic layer 38 is provided.

Fourth Modification

A fourth modification of the embodiment will be described below. A difference from the embodiment will be mainly described below.

In the fourth modification, a display device configured to display a state of the flavor inhaler 1 is provided. The display device may be provided on an exterior surface of the housing 1X of the flavor inhaler 1, or may be separately provided from the flavor inhaler 1. If the display device is separated from the flavor inhaler 1, the display device has a function of performing communication with the flavor inhaler 1. The display device includes a display such as a liquid crystal or an organic EL. The display device may display the remaining amount of the liquid stored in the liquid storage unit 200, and may display a count of puff actions executed by the user.

Experiment Result

First Experiment

Figure 10:
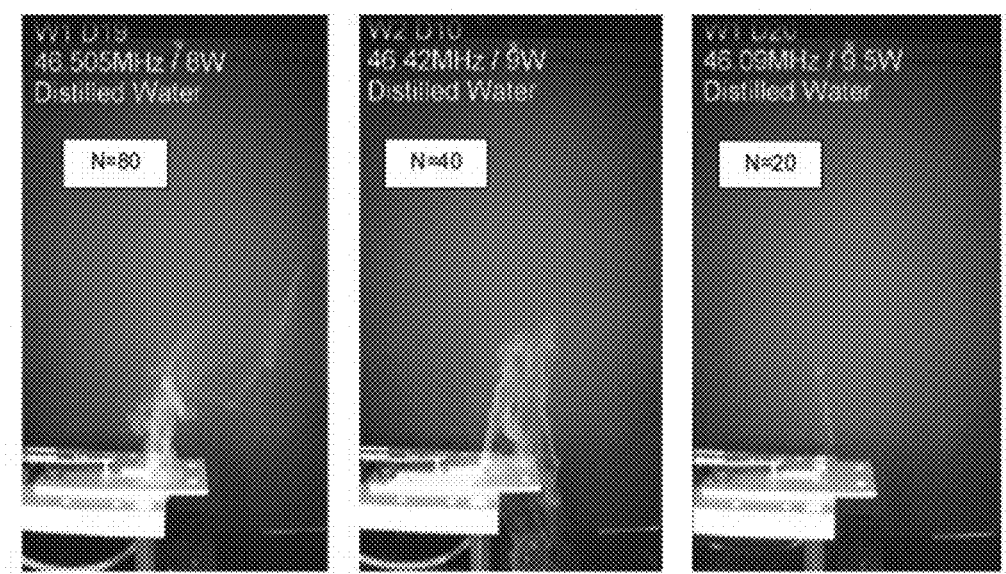

A first experiment will be described below. In the first experiment, the atomization state of the aerosol was visually confirmed by modifying the number of pairs of interlocking comb-shaped metallic electrodes 33. FIG. 10 is a diagram illustrating a result of the first experiment.

In a sample of N=20, the number of pairs of interlocking comb-shaped metallic electrodes 33 was 20 and the power of 9.5 W was applied to the pairs of interlocking comb-shaped metallic electrodes 33 at a frequency of 46.09 MHz. In a sample of N=40, the number of pairs of interlocking comb-shaped metallic electrodes 33 was 40 and the power of 9.0 W was applied to the pairs of interlocking comb-shaped metallic electrodes 33 at a frequency of 46.42 MHz. In a sample of N=80, the number of pairs of interlocking comb-shaped metallic electrodes 33 was 80 and the power of 8.0 W was applied to the pairs of interlocking comb-shaped metallic electrodes 33 at a frequency of 46.505 MHz.

As illustrated in FIG. 10, it was confirmed that an aerosol amount of the sample of N=40 is larger than an aerosol amount of the sample of N=20, and an aerosol amount of the sample of N=80 is larger than the aerosol amount of the sample of N=40. From such experimental results, it was visually confirmed that the atomizing efficiency increases as the number of pairs of interlocking comb-shaped metallic electrodes 33 increases.

It is noted that an experiment was also performed on a sample where the number of pairs of interlocking comb-shaped metallic electrodes 33 was 160, and it was confirmed that the atomization did not occur in such a sample at similar power. Such a result is considered to be caused because a frequency that can be used became too narrow due to an NBW becoming too narrow, and thus, appropriate atomization did not occur due to the technical difficulty to drive the device at the most efficient frequency at all times, as described in a second experiment.

Second Experiment

A second experiment will be described below. In the second experiment, an NBW was confirmed by modifying the number of pairs of interlocking comb-shaped metallic electrodes 33. FIG. 11 is a table showing a result of the second experiment. In FIG. 11, "N" is the number of pairs of interlocking comb-shaped metallic electrodes 33. "Frequency" is a frequency of the AC voltage applied to the pairs of interlocking comb-shaped metallic electrodes 33. "NBW" is the frequency bandwidth centered around the SAW resonant frequency in which a magnitude of the power reflection coefficient of the SAW is smaller than a threshold value. A smaller magnitude of the power reflection coefficient of the SAW means more electrical energy is converted to mechanical energy. That is, the maximum energy conversion is achieved in the NBW which is the frequency bandwidth centered around the SAW resonant frequency.

As shown in FIG. 11, it was confirmed that the NBW (Null Bandwidth) becomes narrower as the number of pairs of interlocking comb-shaped metallic electrodes 33 increases. As described above, for the sample of N=160, it was confirmed that the frequency that can be used became too narrow due to the NBW becoming too narrow, and thus, appropriate atomization did not occur.

As explained above, it was confirmed, from the result of the first experiment, that the atomizing efficiency improves as the number of pairs of interlocking comb-shaped metallic electrodes 33 increases; however, it was confirmed, from the result of the second experiment, that the atomizing efficiency rather decreases if the number of pairs of interlocking comb-shaped metallic electrodes 33 is too large. That is, from the results of the first experiment and the second experiment, it was confirmed that it is preferable to determine the number of pairs of interlocking comb-shaped metallic electrodes 33, based on the atomizing efficiency of the aerosol. In other words, it was confirmed that it is preferable that the number of pairs of interlocking comb-shaped metallic electrodes 33 is determined so as to satisfy a condition in which the NBW does not fall below a predetermined width and the amount of aerosol is equal to or more than the threshold value.

Third Experiment

Figure 12:
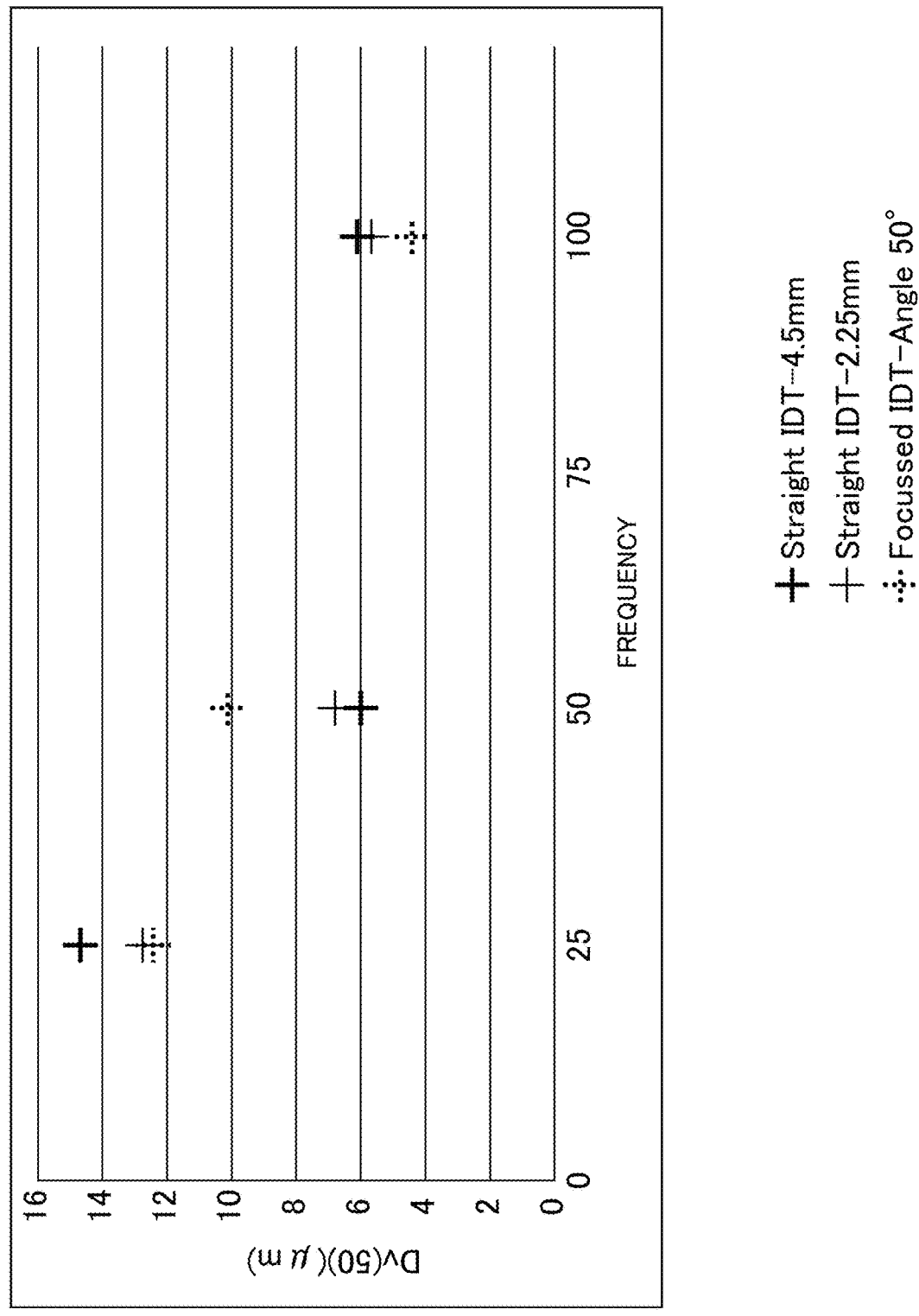

A third experiment will be described below. The effect of the frequency on the particle diameter (median volume based Dv50) was confirmed for three samples. FIG. 12 is a diagram illustrating a result of a third experiment.

"Straight IDT-2.25 mm" refers to a sample including the pairs of interlocking comb-shaped metallic electrodes 33 of a linear shape having a length of 2.25 mm. "Straight IDT-4.5 mm" refers to a sample including the pairs of interlocking comb-shaped metallic electrodes 33 of a linear shape having a length of 4.5 mm. "Focussed IDT-50°" refers to a sample including the pairs of interlocking comb-shaped metallic electrodes 33 of a fan shape having a length of 2.25 mm and a central angle of 50°.

As illustrated in FIG. 12, it was confirmed that the average volume size (Dv 50) becomes smaller as the frequency increases, regardless of the design of the pairs of interlocking comb-shaped metallic electrodes 33. According to such a result, it was confirmed that it might be sufficient that the interval (that is, frequencies) of the electrodes and the width of the electrodes are determined based on a desired particle size of the aerosol.

Fifth Modification

A fifth modification of the embodiment will be described below. A difference from the embodiment will be mainly described below.

In the fifth modification, an amplitude of a high-frequency voltage applied to the pairs of interlocking comb-shaped electrodes 33 will be described.

Specifically, in the fifth modification, the controller 400 periodically changes the amplitude of the high frequency voltage applied to the pairs of interlocking comb-shaped electrodes 33. According to such a configuration, it is possible to suppress droplets from scattering from the liquid guided to the front surface 31F of the piezoelectric element substrate 31. Accordingly, the liquid can be effectively used and stable aerosol atomization can be realized. In detail, the aerosol is atomized from the liquid (the thin film portion) at near-side of the pairs of interlocking comb-shaped electrodes 33 upon the application of the high voltage, and the supply of the liquid decreased by the atomization is promoted upon the application of the low voltage. A generation of coarse particles can be suppressed and the atomizing amount of fine particles can be decreased by repeating such operations. Note that the high voltage and the low voltage are repeated around 100 Hz.

For example, as illustrated in FIG. 13, the periodic amplitude of the high frequency voltage may draw a sinusoidal wave shape, draw a rectangular wave shape, draw a triangular wave shape, and draw a sawtooth wave shape. In particular, it is preferable to apply a high frequency voltage so that the periodic amplitude of the high frequency voltage draws a rectangular wave shape.

Sixth Modification

A sixth modification of the embodiment will be described below. A difference from the embodiment will be mainly described below.

In the sixth modification, a profile of the optimum frequency of the voltage applied to the pairs of interlocking comb-shaped electrodes 33 will be described. The optimum frequency is a resonance frequency of the SAW (for example, the center frequency of the NBW described above) in which the magnitude of the power reflection coefficient of the SAW is smaller than a threshold value.

Figure 14:
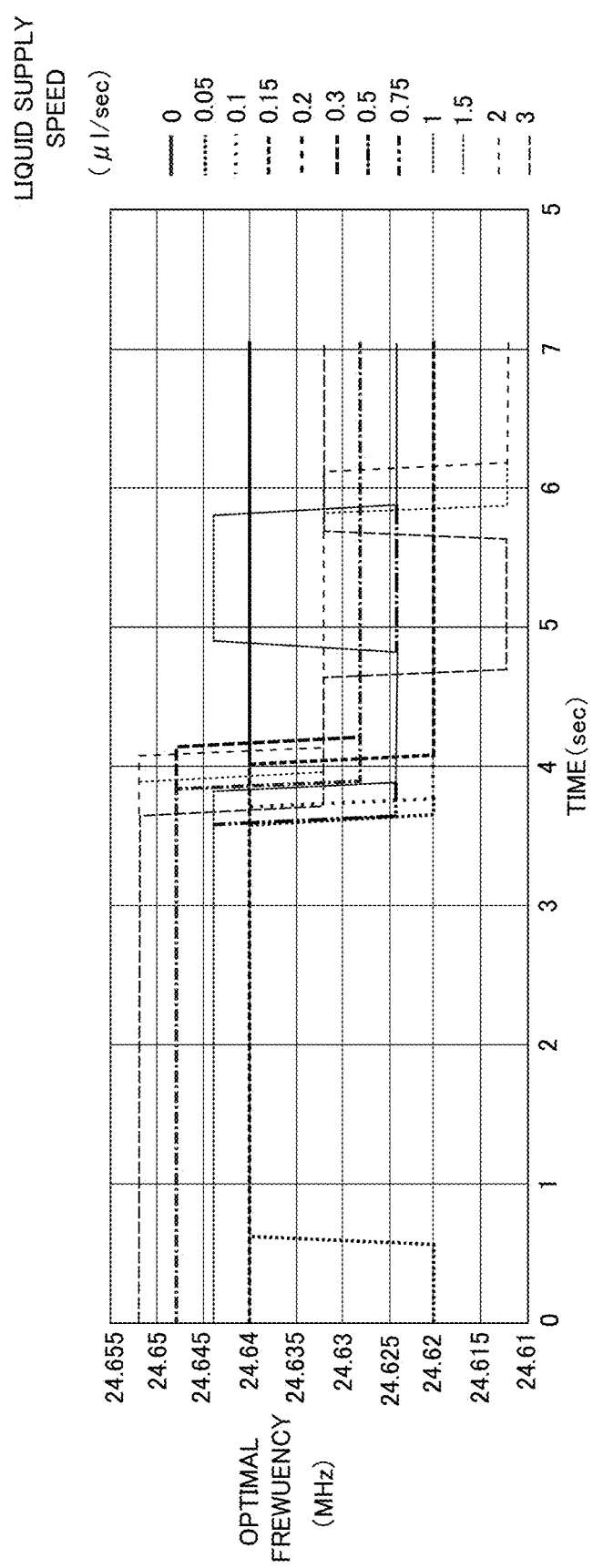

Firstly, a characteristic where the optimum frequency varies according to a relationship between a liquid supply speed (μl/sec) of the liquid guided to the front surface 31F of the piezoelectric element substrate 31 and a time will be described. Specifically, as illustrated in FIG. 14, samples (12 samples in FIG. 14) different in liquid supply speed were prepared and the relationship between a time for applying a voltage to the pairs of interlocking comb-shaped electrodes 33 and the optimum frequency was confirmed. Note that the width of the pairs of interlocking comb-shaped electrodes 33 is constant. According to such a confirmation result, it can be seen that the optimum frequency varies with a lapse of time, and it can also be seen that such a variance is different depending on each liquid supply speed. Therefore, the controller 400 can improve the atomizing efficiency of the aerosol by monitoring the optimum frequency, which varies according to the liquid supply speed and the time, and supplying the liquid at the monitored optimum frequency.

Figure 15:
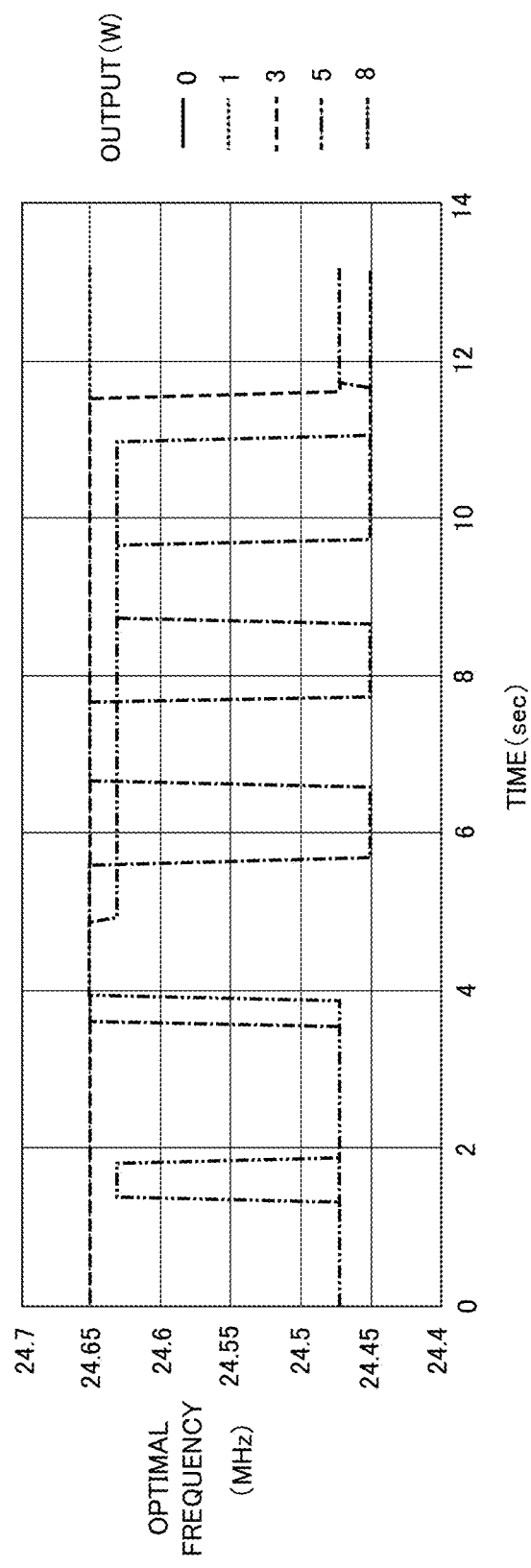

Secondly, a characteristic where the optimum frequency varies according to a relationship between an output (W) of the SAW generated by applying a high frequency voltage to the pairs of interlocking comb-shaped electrodes 33 and a time will be described. Specifically, as illustrated in FIG. 15, samples (5 samples in FIG. 15) different in SAW output were prepared, and the relationship between the time for applying a voltage to the pairs of interlocking comb-shaped electrodes 33 and the optimum frequency was confirmed. Note that the width of the pairs of interlocking comb-shaped electrodes 33 is constant. According to such a confirmation result, it can be seen that the optimum frequency varies with a lapse of time, and it can also be seen that such a variance is different depending on each output of the SAW. Therefore, the controller 400 can improve the atomizing efficiency of the aerosol by monitoring the optimum frequency, which varies according to the output of the SAW and the time, and supplying the liquid at the monitored optimum frequency.

Seventh Modification

A seventh modification of the embodiment will be described below. A difference from the embodiment will be mainly described below.

In the seventh modification, a relationship between the liquid supply speed (μl/sec) of the liquid guided to the front surface 31F of the piezoelectric element substrate 31 and the output (W) of the SAW generated by applying a high frequency voltage to the pairs of interlocking comb-shaped electrodes 33 will be described.

Figure 16:
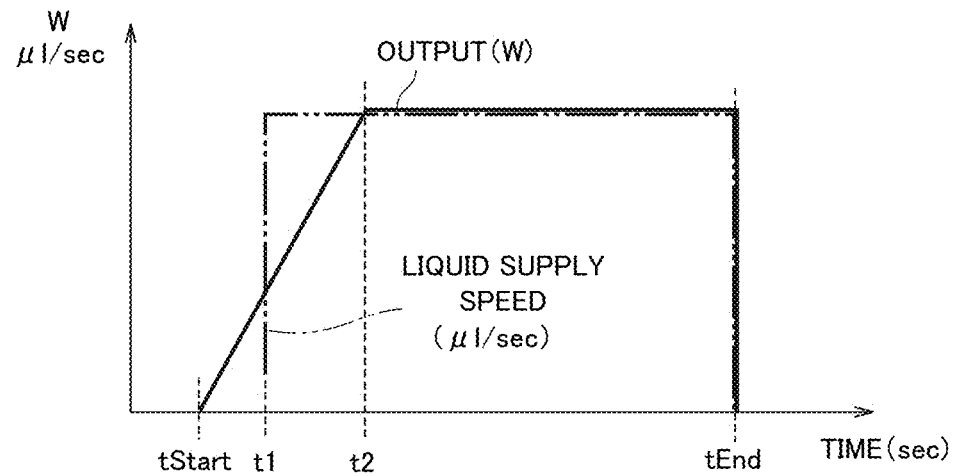

Firstly, as illustrated in FIG. 16, the controller 400 gradually increases the output of the SAW from a time tStart so that the output of the SAW reaches a desired level at a time t2. The controller 400 sets the output of the SAW to zero at a time tEnd. On the other hand, the controller 400 increases the liquid supply speed to a desired level at a time t1. The controller 400 sets the liquid supply speed to zero at the time tEnd. The time t1 may be between the time tStart and the time t2.

Figure 17:
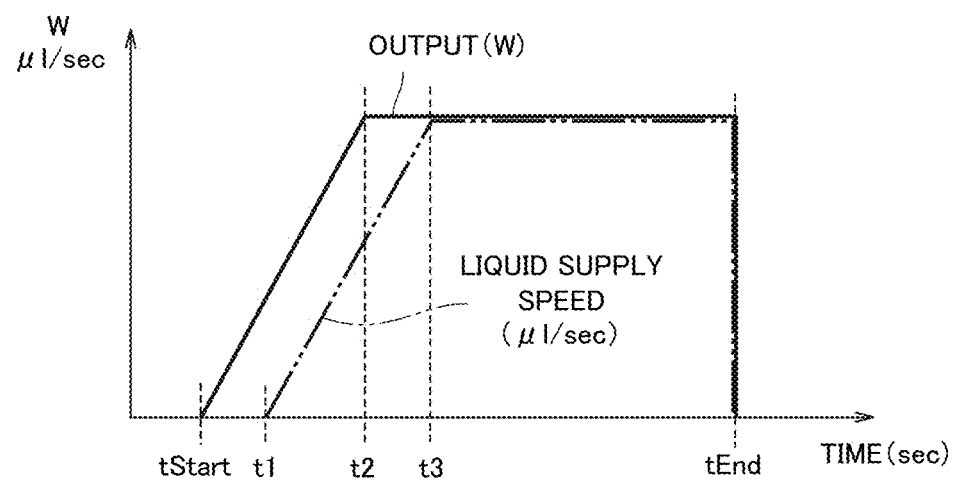

Secondly, as illustrated in FIG. 17, the controller 400 gradually increases the output of the SAW from the time tStart so that the output of the SAW reaches the desired level at the time t2. The controller 400 sets the output of the SAW to zero at the time tEnd. On the other hand, the controller 400 gradually increases the liquid supply speed from the time t1 so that the liquid supply speed reaches a desired level at a time t3. The controller 400 sets the liquid supply speed to zero at the time tEnd. The time t1 may be between the time tStart and the time t2. The time t3 may be after the time t2.

Note that the time tStart may be a timing at which the start of the puff action is detected by the sensor 300 or a timing at which a button for performing the puff action is pressed. The time tEnd may be a timing at which the end of the puff action is detected by the sensor 300 or a timing at which the button for performing the puff action is no longer pressed.

As illustrated in FIG. 16 and FIG. 17, the output of the SAW gradually increases from the time tStart and the liquid supply speed starts increasing at the time t1 after the time tStart, and thus, it is possible to suppress scattering of droplets having a large diameter from the liquid guided to the front surface 31F of the piezoelectric element substrate 31 in an initial phase during which the output (W) of the SAW increases. Further, as illustrated in FIG. 17, scattering of droplets having a large diameter can be suppressed by gradually increasing the liquid supply speed.

Eighth Modification

An eighth modification of the embodiment will be described below. A difference from the embodiment will be mainly described below.

In the eighth modification, a detector configured to detect a state of the aerosol is provided. For example, the controller 400 may feedback an error such as a poor aerosol generation, based on a detection result of the detector. The detector may be a microphone sensor configured to detect a weak noise caused by the aerosol generation.

Figure 18:
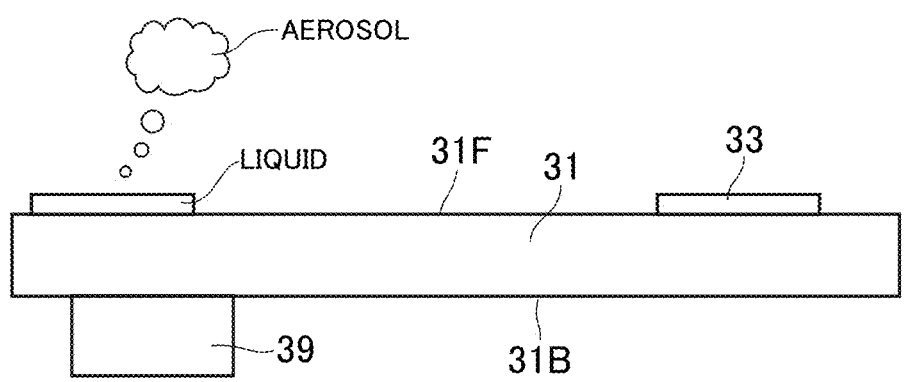

As illustrated in FIG. 18, a detector 39 may be provided on the rear surface 31B of the piezoelectric element substrate 31. The detector 39 is preferably provided on an opposite side of the liquid with the piezoelectric element substrate 31 interposed therebetween.

Figure 19:
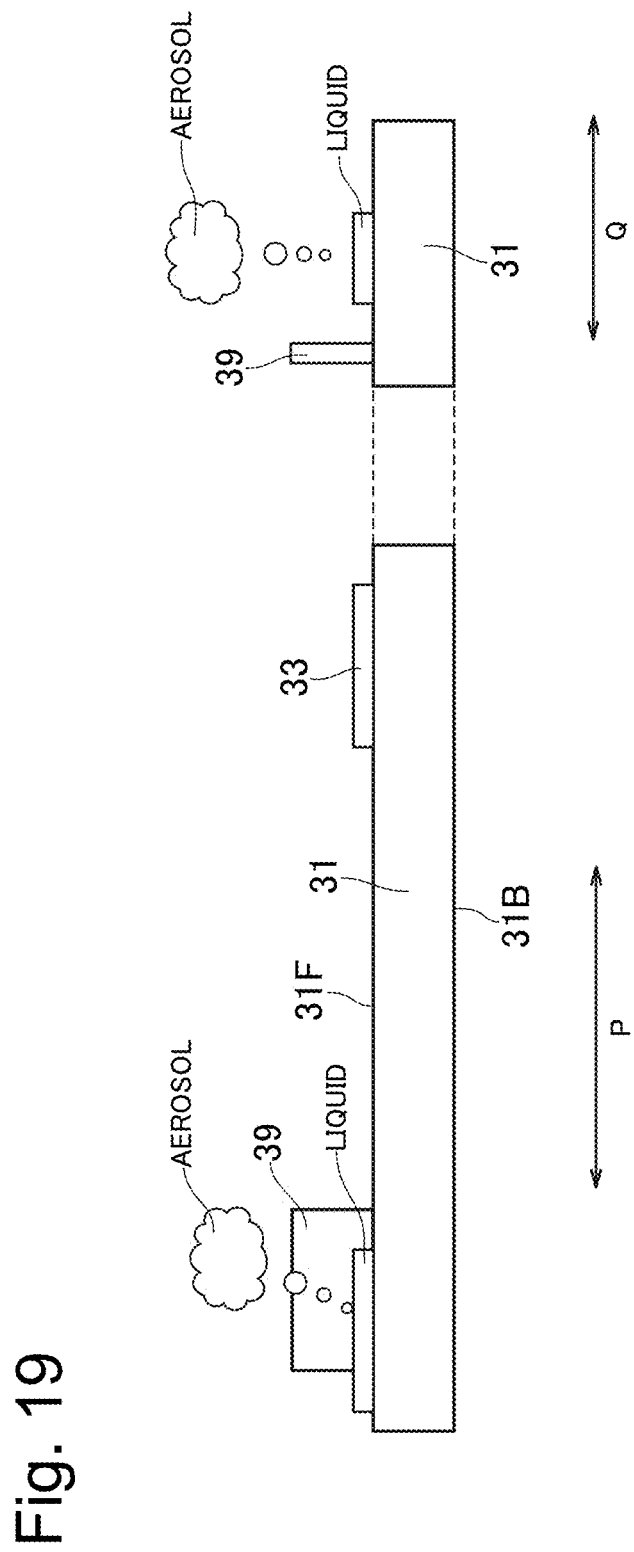

As illustrated in FIG. 19, the detector 39 may be provided on the front surface 31F of the piezoelectric element substrate 31. If the travel direction of the SAW is a direction P, the detector 39 may be provided next to the liquid in a direction Q orthogonal to the direction P. The detector 39 is preferably not in contact with the liquid.

Figure 20:
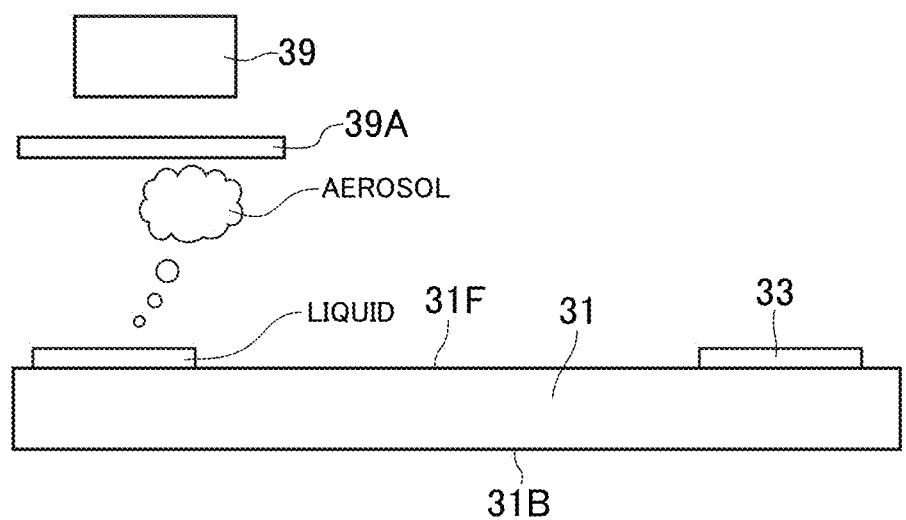

As illustrated in FIG. 20, the detector 39 may be provided above the front surface 31F of the piezoelectric element substrate 31, at a position apart from the front surface 31F of the piezoelectric element substrate 31. In order to suppress a contact between the detector 39 and the aerosol, it is preferable that a shield 39A is provided between the detector 39 and the aerosol.

Ninth Modification

A ninth modification of the embodiment will be described below. A difference from the embodiment will be mainly described below.

In the ninth modification, a sensor configured to detect the liquid exposed from the penetrated aperture 34 is provided. For example, the controller 400 may control the liquid supplier 60 (liquid supply speed, and the like), based on a detection result of the sensor. According to such a configuration, it is possible to suppress an excessive supply of the liquid to the atomizer as well as drying up of the liquid at the atomizer by accurate pump control, and the stability of aerosol atomization is improved.

As illustrated in FIG. 21, a sensor 71 may be an electric conductivity sensor including a pair of tip ends (for example, tip ends 71A, 71B). The pair of tip ends are adjacent to the penetrated aperture 34 and are electrically connected by the liquid exposed from the penetrated aperture 34. The sensor 71 detects a presence of the liquid based on the conductivity of the electric signal between the pair of tip ends.

As illustrated in FIG. 22, a sensor 72 may be an electric conductivity sensor including two or more pairs of tip ends (for example, tip ends 72A, 72B, and the like). The two or more pairs of tip ends are adjacent to the penetrated aperture 34 and are electrically connected by the liquid exposed from the penetrated aperture 34. However, the positions where the pairs of tip ends are provided are different from each other. Based on the conductivity of the electrical signal between the pair of tip ends, the uniformity of the thin film can be monitored and the presence of the liquid at the position where the pair of tip ends can be detected by use of the sensor 72.

As illustrated in FIG. 23, a sensor 73 may be a sensor including an emitter (for example, an emitter 73A) configured to output a predetermined signal and a receiver (for example, a receiver 73B) configured to receive the predetermined signal. The emitter 73A and the receiver 73B are disposed with the penetrated aperture 34 interposed therebetween, and the sensor 73 detects the presence of the liquid based on a transmission magnitude of the predetermined signal. The emitter 73A and the receiver 73B may be configured of a thin film solid pad.

As illustrated in FIG. 24, a sensor 74 may be a SAW sensor including an emitter (for example, an emitter 74A) configured to output the SAW and a receiver (for example, a receiver 74B) configured to receive the SAW. The emitter 74A and the receiver 74B are disposed with the penetrated aperture 34 interposed therebetween, and the sensor 74 detects the presence of the liquid based on the transmission magnitude of the SAW. The emitter 74A and the receiver 74B may be configured of a thin film IDT.

As illustrated in FIGS. 25 (*a*) and 25 (*b*), a sensor 75 may be a capacitive sensor including one or more pairs of electrodes (for example, tip ends 75A, 75B and the like). In such a case, the one or more pairs of electrodes are disposed across the liquid disposed on the atomization zone. The sensor 75 detects the presence or non-presence of the liquid based on a difference of capacitance caused by the presence or non-presence of the liquid. In such a case, the penetrated aperture 34 can be omitted.

Tenth Modification

A tenth modification of the embodiment will be described, below. A difference from the embodiment will be mainly described below.

In the tenth modification, an example of a combination of the eighth modification and the ninth modification will be described. As illustrated in FIG. 26, the SAW module 30 includes a detector 81, a sensor 82, and a depth sensor 83.

Similar to the detector 39 described in the eighth modification, the detector 81 detects the state of the aerosol. Similar to the electric conductivity sensor or the SAW sensor described in the ninth modification, the sensor 82 detects the liquid exposed from the penetrated aperture 34. The depth sensor 83 detects a depth of the liquid (a surface water level of the liquid) in the penetrated aperture 34. The depth sensor 83 may be an electric conductivity sensor configured to detect the presence of the liquid based on the conductivity of the electric signal.

In such a configuration, before and after the atomization of the aerosol, the controller 400 controls the liquid supplier 60 (the liquid supply speed and the like), based on a detection result of the depth sensor 83, as illustrated in an upper part of FIG. 26. For example, the controller 400 controls the liquid supplier 60 so that the liquid is maintained at a desired depth. According to such a configuration, a responsiveness of the aerosol atomization improves.

During the atomization of the aerosol, the controller 400 feeds back an error such as a poor aerosol generation, based on a detection result of the detector 81, as illustrated in a lower part of FIG. 26. The controller 400 may notify the user of the error and may stop an operation of the flavor inhaler 1 (for example, the atomizing unit 100). Further, the controller 400 controls the liquid supplier 60 (liquid supply speed, and the like) based on a detection result of the sensor 82. According to such a configuration, the stability of the aerosol atomization is improved.

Moreover, the liquid amount during the atomization can be controlled using the depth sensor 83. The controller 400 controls the liquid supplier 60 (the liquid supply speed and the like) based on the detection result of the depth sensor 83 when the depth sensor 83 detects a decrease of the liquid. According to such a configuration, the liquid amount can be kept at a desired level during the atomization and the stability of the aerosol atomization is improved.

Further, although not shown, two or more depth sensors, each having different detection depths, can be provided as the depth sensor 83. In such a case, it is easy to appropriately control the liquid amount in a range of the depth sensors having the different detection depths. For example, when the first depth sensor, which detects the first depth of the liquid, detects the liquid and the second sensor, which detects the second depth shallower than the first depth, does not detects the liquid, it is possible to detect the depth of liquid is between the first depth and the second depth.

Eleventh Modification

An eleventh modification of the embodiment will be described below. A difference from the embodiment will be mainly described below.

Figure 27:
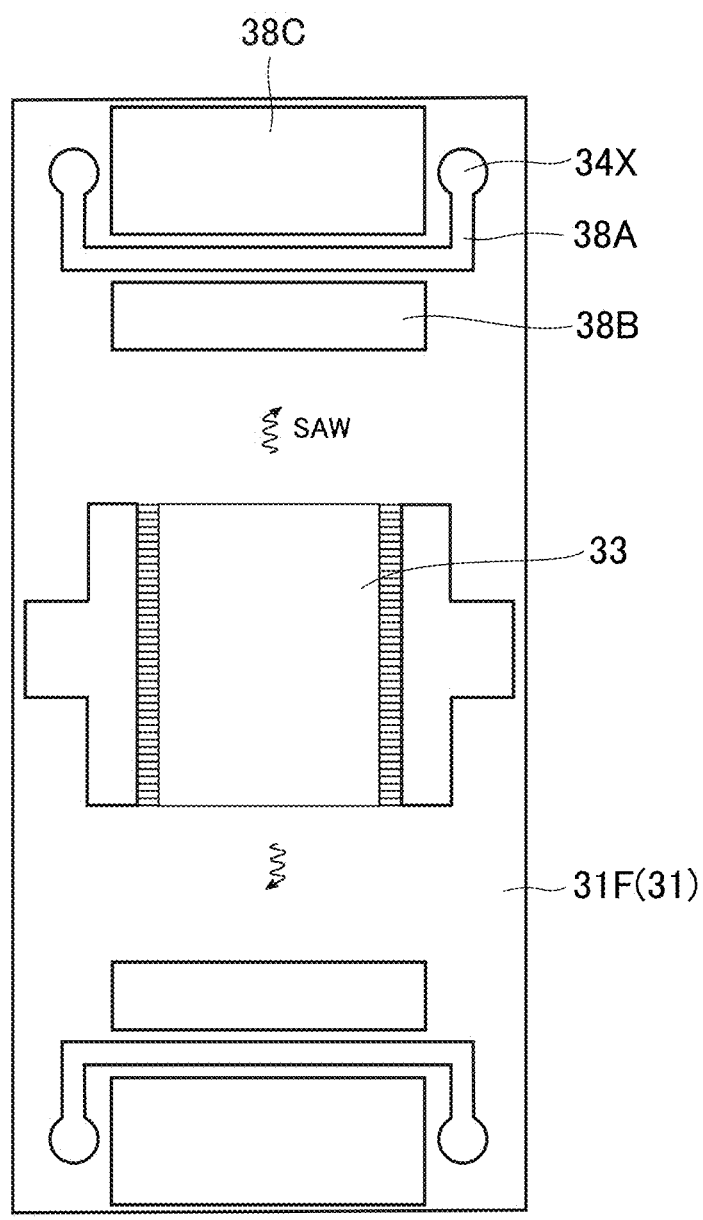

In the eleventh modification, a method of guiding the liquid on the front surface 31F of the piezoelectric element substrate 31 will be described. Specifically, as illustrated in FIG. 27, a supply port 34X, a hydrophilic layer 38A, a hydrophobic layer 38B, and a hydrophobic layer 38C are provided on the front surface 31F of the piezoelectric element substrate 31.

The supply port 34X is a point to which liquid is supplied. The supply port 34X is provided outside a path of the SAW. Therefore, the supply port 34X does not need to be the above-described penetrated aperture 34, and may be a point at which the liquid is supplied from a side of the front surface 31F of the piezoelectric element substrate 31.

The hydrophilic layer 38A is continuous to the supply port 34X and has a pattern for leading the liquid into the path of the SAW. The hydrophobic layer 38B is provided on a near side to the pairs of interlocking comb-shaped electrodes 33 than the hydrophilic layer 38A, and is provided apart from the hydrophilic layer 38A. The hydrophobic layer 38C is provided on a far side from the pairs of interlocking comb-shaped electrodes 33 than the hydrophilic layer 38A, and is provided apart from the hydrophilic layer 38A. The movement of the liquid from hydrophilic layer 38A can be restricted by the hydrophobic layers 38B and 38C, the contact angle of SAW to the liquid can be reduced, and the efficiency of the aerosol atomization is improved.

According to such a configuration, the penetrated aperture 34 does not need to be provided and thus, the coating layer 36 coating the piezoelectric element substrate 31 can easily be provided.

Twelfth Modification

A twelfth modification of the embodiment will be described below. A difference from the embodiment will be mainly described below.

Figure 28:
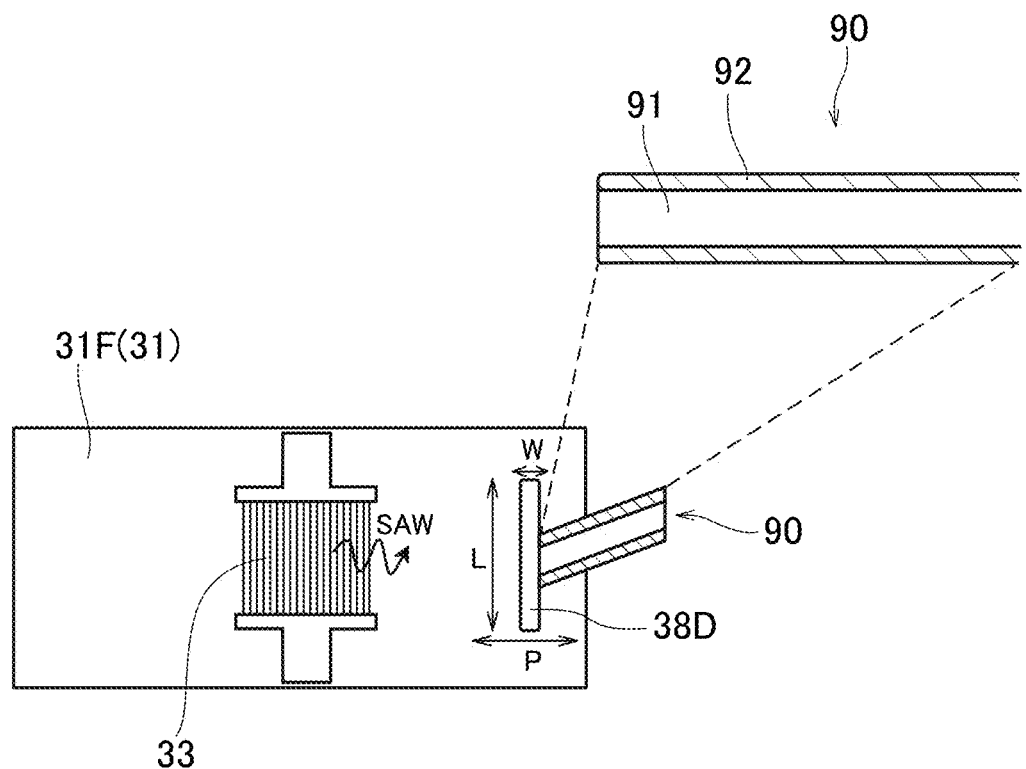

In the twelfth modification, a method of supplying the liquid to the front surface 31F of the piezoelectric element substrate 31 will be described. Specifically, as illustrated in FIG. 28, a hydrophilic layer 38D and a wick 90 are provided on the front surface 31F of the piezoelectric element substrate 31.

The hydrophilic layer 38D is provided on the path of the SAW. The hydrophilic layer 38D has a length L and a width W and configures an atomization zone for atomizing the aerosol. The wick 90 is continuous to the hydrophilic layer 38D and supplies the liquid to the hydrophilic layer 38D. The wick 90 may have a wick core 91 which keeps a shape of the wick 90, and a holding layer 92 which holds the liquid. The wick core 91 contacts with the front surface 31F of the piezoelectric element substrate 31 preferably formed of a metal or a plastic having a hardness which can reflect the SAW transmitted on the piezoelectric element substrate 31. The holding layer 92 may be configured of a capillary member configured to supply the liquid by a capillary phenomenon.

According to such a configuration, the penetrated aperture 34 does not need to be provided and thus, the coating layer 36 coating the piezoelectric element substrate 31 can easily be provided.

Thirteenth Modification

A thirteenth modification of the embodiment will be described below. A difference from the embodiment will be mainly described below.

Figure 29:
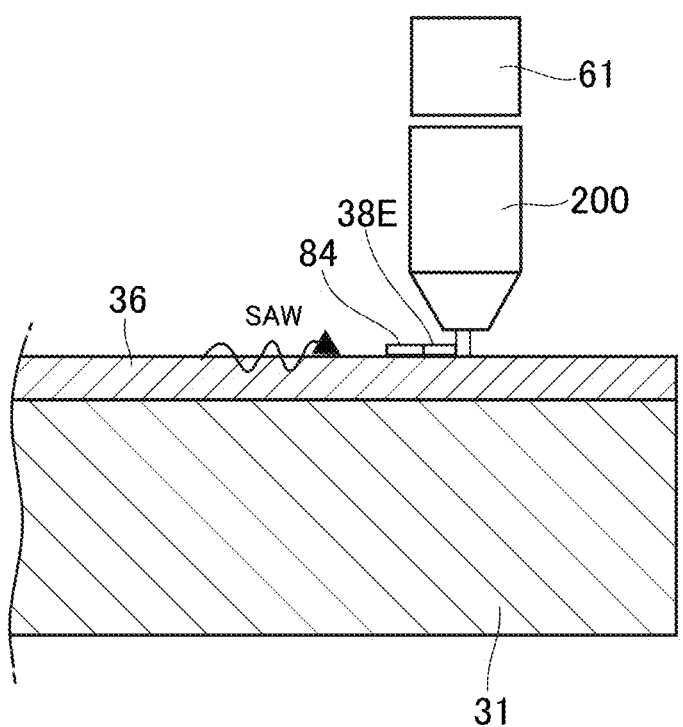

In the thirteenth modification, a method of supplying the liquid to the front surface 31F of the piezoelectric element substrate 31 will be described. Specifically, as illustrated in FIG. 29, a hydrophilic layer 38E and a member 84 are provided on the front surface 31F of the piezoelectric element substrate 31. Further, a liquid storage unit 200 and a driving unit 61 are provided on the front surface 31F of the piezoelectric element substrate 31.

The hydrophilic layer 38E is provided on the path of the SAW and configures an atomization zone for atomizing the aerosol. The member 84 may be a sensor configured to detect the presence of the liquid or a detector configured to detect the state of the aerosol.

The liquid storage unit 200 and a driving unit 61 configure a device configured to drop the liquid in the vicinity of the hydrophilic layer 38E. For example, the liquid storage unit 200 may include a nozzle configured to store the liquid and drop the liquid. The driving unit 61 may be a member (for example, a motor) configured to generate a drive force for dropping the liquid from the nozzle.

According to such a configuration, the penetrated aperture 34 does not need to be provided and thus, the coating layer 36 coating the piezoelectric element substrate 31 can easily be provided.

Fourteenth Modification

A fourteenth modification of the embodiment will be described below. A difference from the embodiment will be mainly described below.

Figure 30:
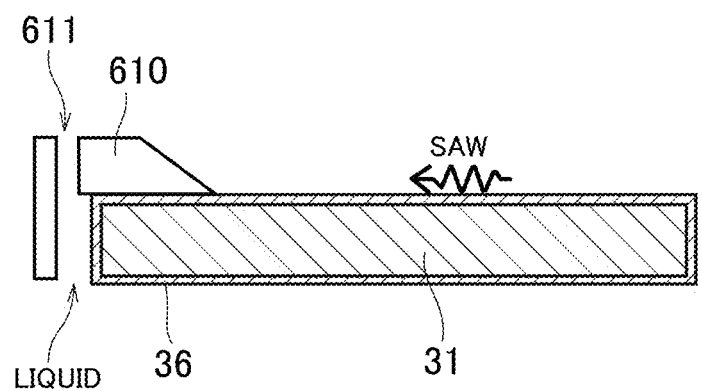
Figure 31:
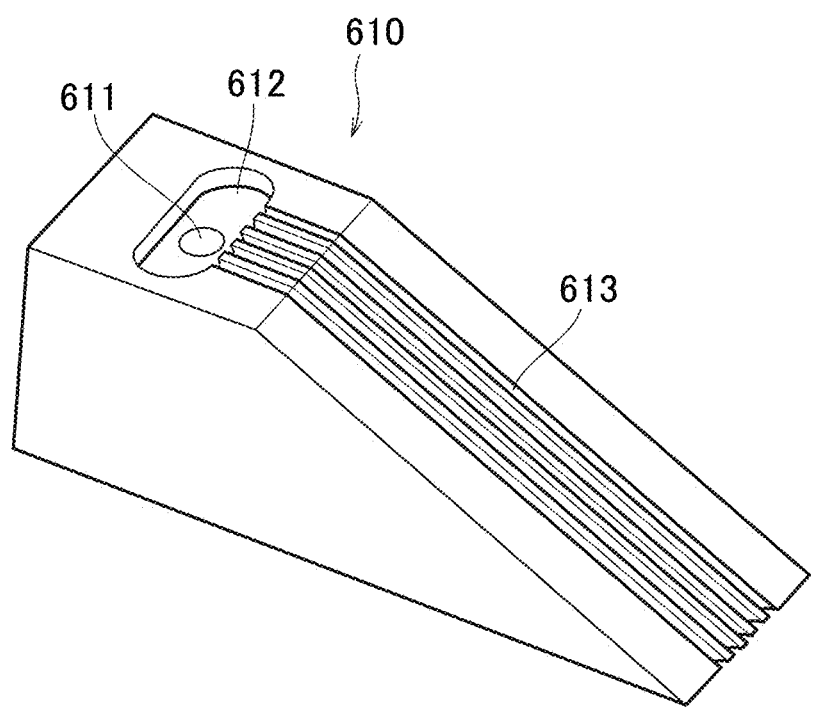

In the fourteenth modification, a method of supplying the liquid to the front surface 31F of the piezoelectric element substrate 31 will be described. Specifically, as illustrated in FIG. 30 and FIG. 31, the SAW module 30 has a guide member 610 configured to guide the liquid. The piezoelectric element substrate 31 is coated with the coating layer 36.

The guide member 610 is provided on the front surface 31F of the piezoelectric element substrate 31 at an edge portion of the piezoelectric element substrate 31. The guide member 610 has a shape having a predetermined height from the front surface 31F of the piezoelectric element substrate 31. The guide member 610 may be made in a material with high thermal conductivity (metal or ceramic, for example). The guide member 610 includes a flow path 611, a temporary storage unit 612, and a guide slit 613. The flow path 611 configures a flow path of the liquid. The temporary storage unit 612 temporarily stores the liquid supplied via the flow path 611. The guide slit 613 has an inclination with respect to the front surface 31F of the piezoelectric element substrate 31. The guide slit 613 guides the liquid overflowing from the temporary storage unit 612 to the front surface 31F of the piezoelectric element substrate 31 by the weight of the liquid and/or capillary force. Two or more guide slits may be provided as the guide slit 613.

According to such a configuration, the atomization zone can be disposed at a position apart from the edge portion of the piezoelectric element substrate 31 by the guide member 610 provided at the edge portion of the piezoelectric element substrate 31, and a detachment of the coating layer 36 can be suppressed at the edge portion. Further, the penetrated aperture 34 does not need to be provided and thus, the coating layer 36 coating the piezoelectric element substrate 31 can easily be provided.

In the fourteenth modification, a case of supplying the liquid from the rear surface 31B of the piezoelectric element substrate 31 is exemplified, however, the fourteenth modification is not limited thereto. The liquid may be supplied from the side of the guide member 610 or may be supplied from above the guide member 610. If the liquid is supplied from above the guide member 610, the above-described flow path 611 may not be provided.

Alternatively, the liquid may be supplied via the penetrated aperture 34. In such a case, the guide member 610 is provided so that the flow path 611 communicates with the penetrated aperture 34, the atomization zone can be disposed at a position apart from the edge portion of the penetrated aperture 34, and the detachment of the coating layer 36 at the edge portion can be suppressed.

Figure 32:
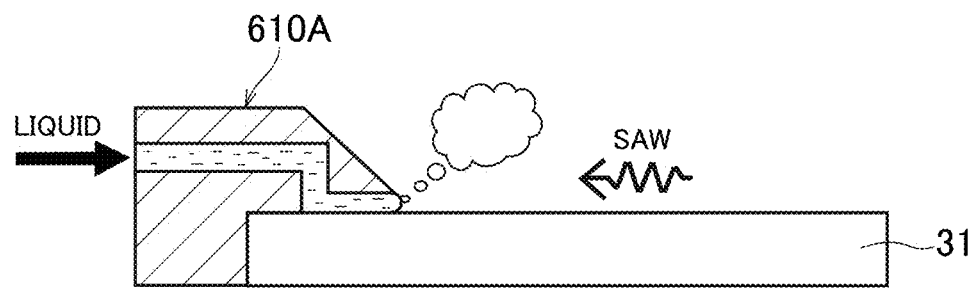

Alternatively, as shown in FIG. 32, the SAW module 30 may have a guide member 610A configured to guide the liquid. The guide member 610A is formed of a member such as a plastic or metal having a fine flow path inside and provided on the front surface 31F of the piezoelectric element substrate 31. The guide member 610A guides the liquid impregnated in the guide member 610A to the fine space between the front surface 31F of the piezoelectric element substrate 31 and the guide member 610A. The guide member 610A guides the liquid on the front surface 31F of the piezoelectric element substrate 31 from the fine space.

Figure 33:
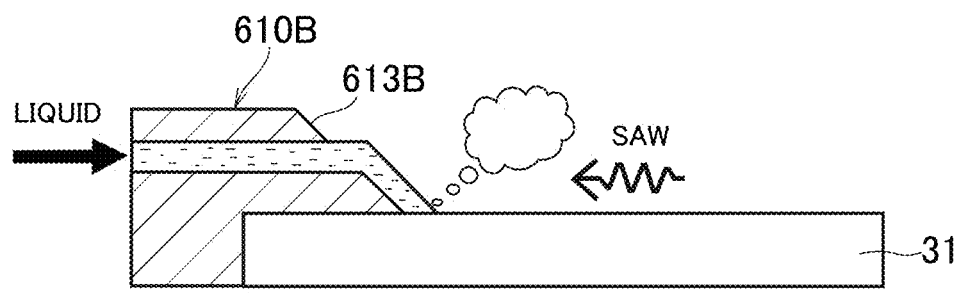

Alternatively, as shown in FIG. 33, the SAW module 30 may have a guide member 610B configured to guide the liquid. The guide member 610B is formed of a member such as a plastic or metal having a fine flow path inside and provided on the front surface 31F of the piezoelectric element substrate 31. The guide member 610B guides the liquid impregnated in the guide member 610B to the front surface 31F of the piezoelectric element substrate 31 along a slant surface 613B of the guide member 610B.

According to the configurations shown if FIGS. 32 and 33, as same as the configuration shown in FIGS. 30 and 32, the atomization zone can be disposed at a position apart from the edge portion of the piezoelectric element substrate 31 and a detachment of the coating layer 36 can be suppressed at the edge portion.

Fifteenth Modification

A fifteenth modification of the embodiment will be described below. A difference from the embodiment will be mainly described below.

Figure 34:
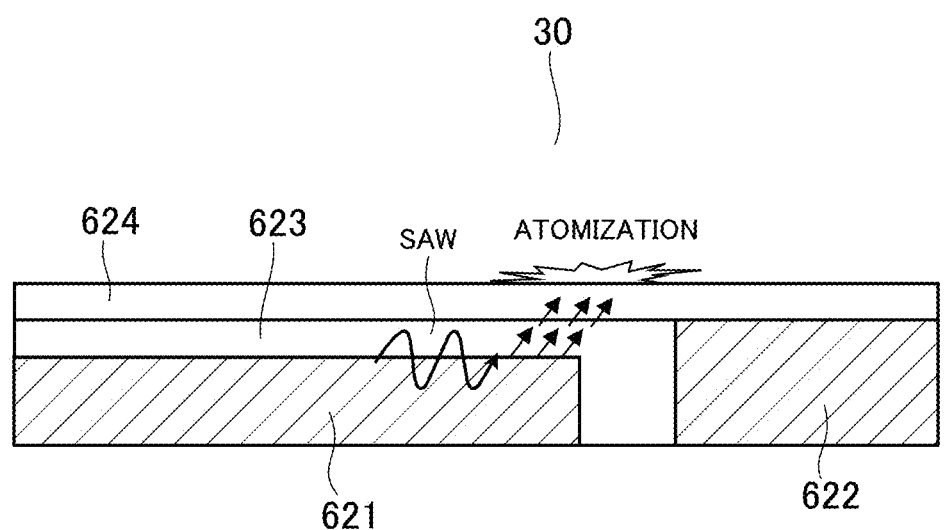

In the fifteenth modification, a variation of a substrate configuration of the SAW module 30 will be described. Specifically, as illustrated in FIG. 34, the SAW module 30 includes a piezoelectric element substrate 621, a plate 622, a buffer 623, and an atomization surface layer 624. In FIG. 34, a configuration other than the substrate configuration (for example, the pairs of interlocking comb-shaped electrodes 33) is omitted.

Figure 35:
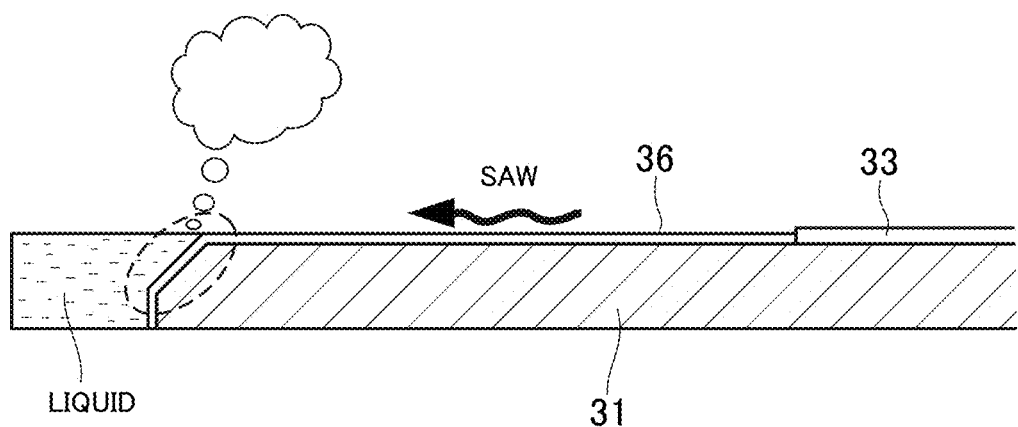
Figure 36:
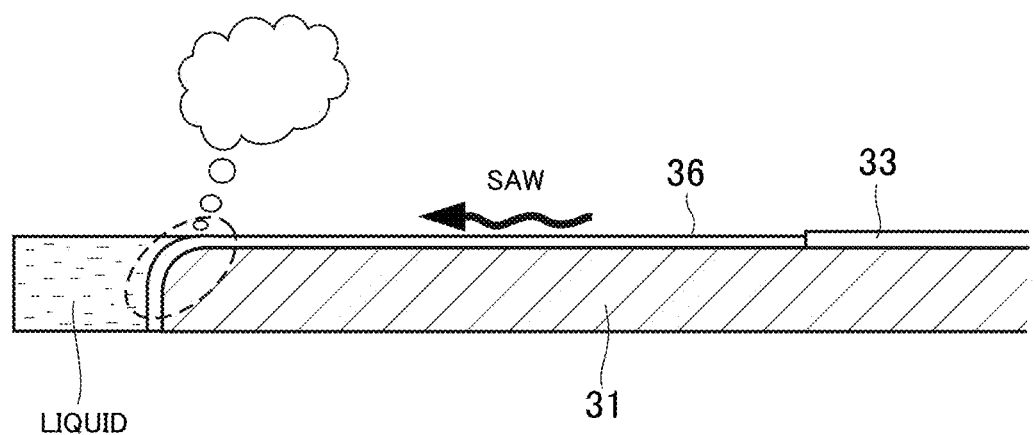
Figure 37:
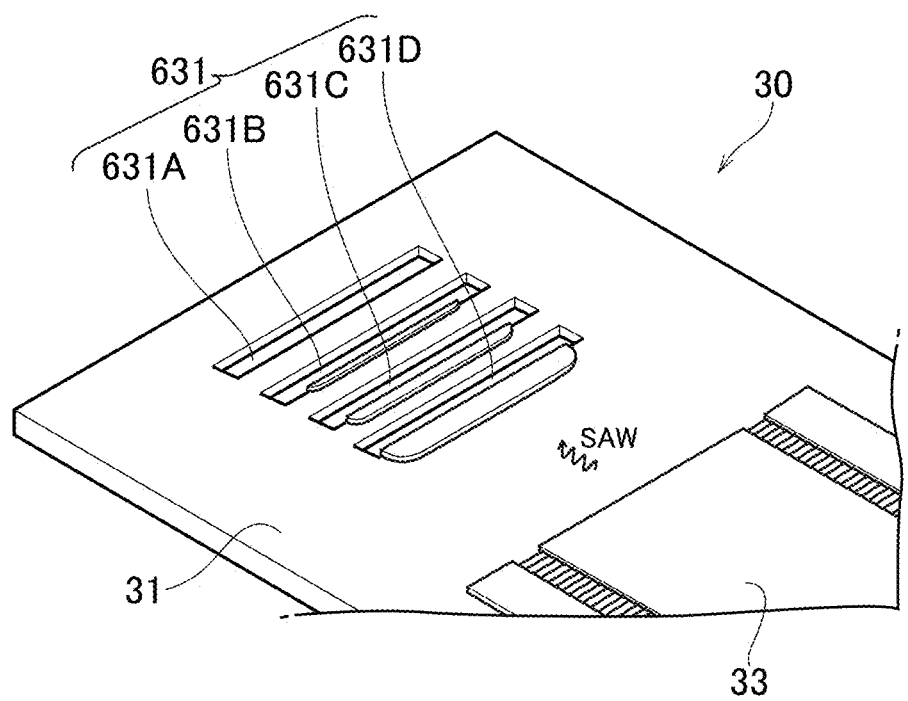
Figure 38:
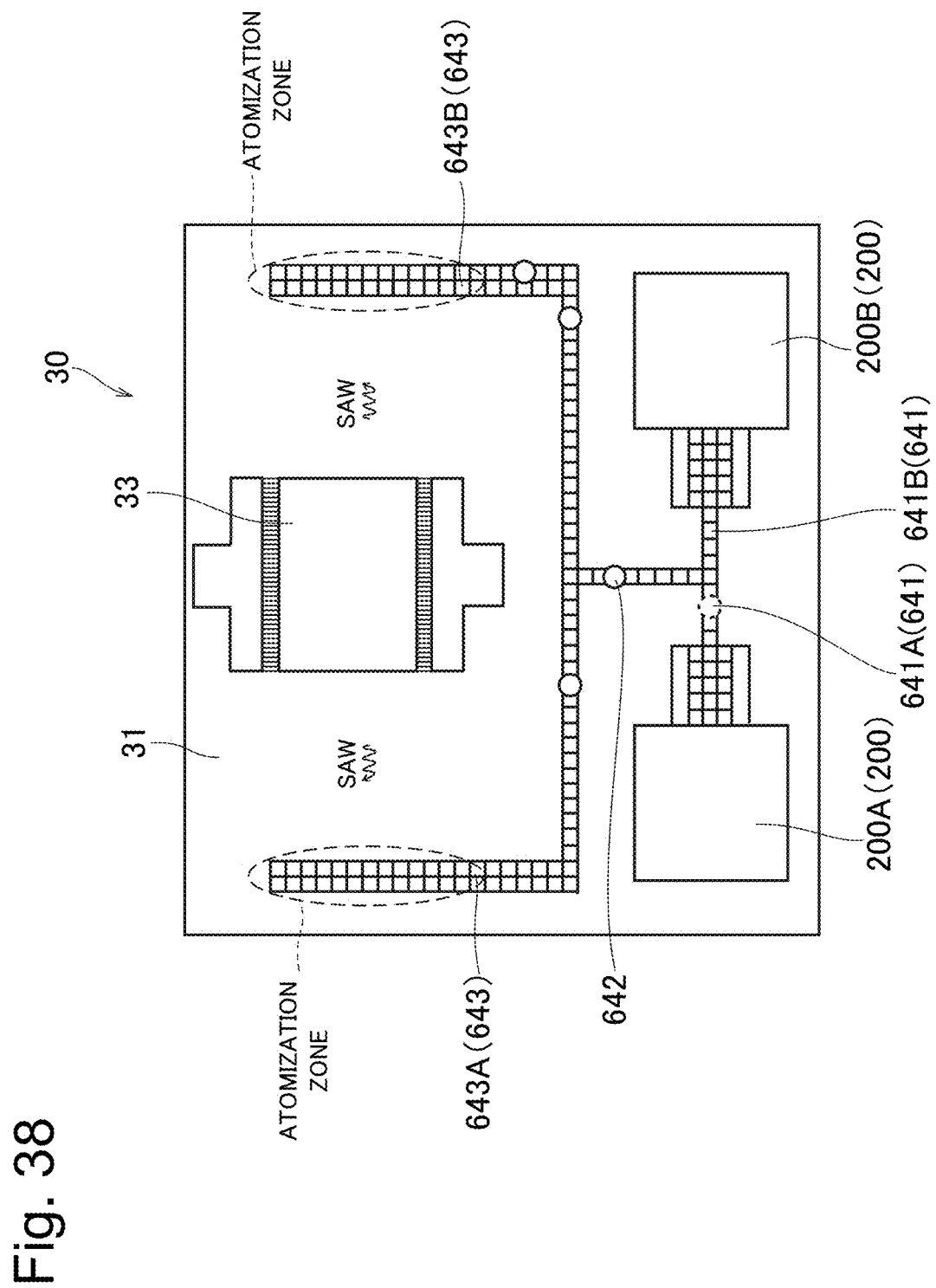
FIG. 38 is a diagram for describing an eighteenth modification.

The piezoelectric element substrate 621 is similar to the piezoelectric element substrate 31 described above. The plate 622 is a substrate different from the piezoelectric element substrate 31, and is an aluminum plate, for example. The buffer 623 is located on a front surface and a side surface of the piezoelectric element substrate 621 and is configured by a buffer liquid that transmits the SAW generated from the piezoelectric element substrate 621 to the atomization surface layer 624. For example, the buffer liquid is Glycerin. The atomization surface layer 624 is provided on the buffer 623 and the plate 622 and is provided with an atomization zone for atomizing the aerosol. For example, the atomization surface layer 624 is configured of a stainless plate. In such a case, the liquid may be supplied from a front surface side of the atomization surface layer 624.

According to such a configuration, the SAW can be transmitted to the atomization surface layer 624 that is different from the piezoelectric element substrate 621, and a contact of the liquid (a flavor liquid) with the piezoelectric element substrate 621 can be avoided. For example, a penetrated aperture corresponding to the penetrated aperture 34 described above may be provided in the plate 622.

Sixteenth Modification

A sixteenth modification of the embodiment will be described below. A difference from the embodiment will be mainly described below.

In the sixteenth modification, a variation of a shape of the edge portion of the piezoelectric element substrate 31 will be described in a case where the liquid is supplied from the rear surface 31B of the piezoelectric element substrate 31. The edge portion is a portion adjacent to the atomization zone. The edge portion is subjected to a filleting and chamfering process. According to such a configuration, the detachment of the coating layer 36 at the edge portion can be suppressed by reducing the energy density at the atomization zone.

Here, the chamfering process of the edge portion may be a linear chamfering process, as illustrated in FIG. 35, or a round chamfering process, as illustrated in FIG. 36. The edge portion may be an edge portion of the penetrated aperture 34.

Seventeenth Modification

A seventeenth modification of the embodiment will be described below. A difference from the embodiment will be mainly described below.

In the seventeenth modification, a variation of the atomization zone will be described. Specifically, as illustrated in FIG. 37, the SAW module 30 includes two or more shallow grooves 631 (here, grooves 631A to 631D) as the atomization zone. Each of the grooves 631 has a shape extending in a direction orthogonal to the travel direction of the SAW. The liquid is supplied to each of the grooves 631. An amount of liquid supplied to each of the grooves 631 may be larger for a groove closer to the pairs of interlocking comb-shaped electrodes 33. Although not illustrated in FIG. 34, the piezoelectric element substrate 31 is coated by the coating layer 36.

According to such a configuration, the energy of the SAW is dispersed by two or more grooves and thus, a detachment of the coating layer 36 in the atomization zone is suppressed, and the robustness of the conformal coating in the edge portion would be increased.

Eighteenth Modification

An eighteenth modification of the embodiment will be described, below. A difference from the embodiment will be mainly described, below.

In the eighteenth modification, a method of guiding the liquid on the front surface 31F of the piezoelectric element substrate 31 will be described. Specifically, as illustrated in FIG. 35, the SAW module 30 has a printed electrode 641 to a printed electrode 643. Two liquid storage units 200 (a liquid storage unit 200A and a liquid storage unit 200B) are provided. A liquid stored in the liquid storage unit 200A may be different from a liquid stored in the liquid storage unit 200B.

The printed electrode 641 to the printed electrode 643 transport the liquid by utilizing a voltage difference between printed electrodes adjacent to each other. For example, the printed electrode 641A transports the liquid stored in the liquid storage unit 200A, and the printed electrode 641B transports the liquid stored in the liquid storage unit 200B. The printed electrode 642 transports a mixture of liquids supplied from the printed electrode 641A and the printed electrode 641B. The printed electrode 643A and the printed electrode 643B transport a mixture of liquids supplied from the printed electrode 642. Each of a part of the printed electrode 643A and a part of the printed electrode 643B configures the atomization zone.

A width of the printed electrode configuring the atomization zone may be larger than a width of the printed electrode (for example, the printed electrode 642) not configuring the atomization zone and may be actuated in a specific manner to attract the bulk of liquid in two or more different directions at the same time. According to such a configuration, the width of the printed electrode not configuring the atomization zone is small and thus, it is possible to save a space of the printed electrode not configuring the atomization zone. The bulk of liquid is attracted in two or more different directions at the same time and thus, the liquid in the atomization zone can be flattened and the contact angle of the SAW to the liquid can be reduced.

Nineteenth Modification

A nineteenth modification of the embodiment will be described, below. A difference from the embodiment will be mainly described, below.

Figure 39:
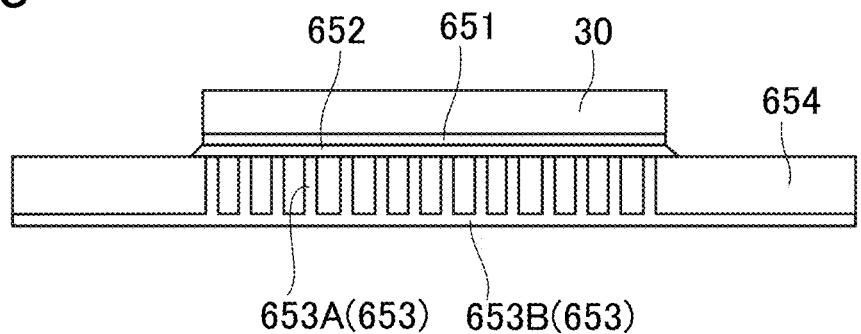
FIG. 39 is a diagram for describing a nineteenth modification.
Figure 40:
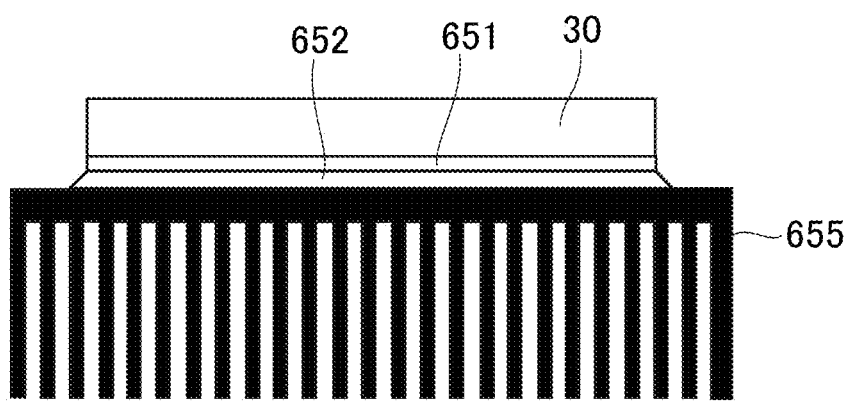
FIG. 40 is a diagram for describing the nineteenth modification.
Figure 41:
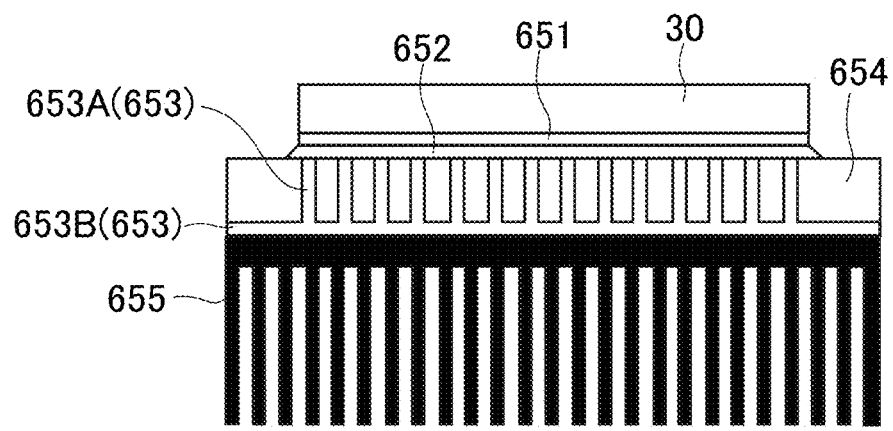
FIG. 41 is a diagram for describing the nineteenth modification.

In the nineteenth modification, a variation of the heat radiation mechanism will be described. Specifically, as illustrated in FIG. 39 to FIG. 41, a coating layer 651 and an adhesive layer 652 are provided on the rear surface of the SAW module 30. The coating layer 651 may include metal. The adhesive layer 652 may include solder.

Under such premise, as illustrated in FIG. 39, the SAW module 30 is adhered to a heat conductive member 653 and a circuit board 654 via the adhesive layer 652. The heat conductive member 653 includes a heat conductive member such as metal, and has a columnar portion 653A and a plate portion 653B. The columnar portion 653A penetrates the circuit board 654, and the plate portion 653 B is disposed on the rear surface of the circuit board 654. The circuit board 654 is configured of a member easily adherable to the adhesive layer 652, and includes a penetrated aperture passing through the columnar portion 653A.

Alternatively, as illustrated in FIG. 40, the SAW module 30 is adhered to a heat sink 655 via the adhesive layer 652. The heat sink 655 is configured of a heat conductive member such as metal.

Alternatively, as illustrated in FIG. 41, the SAW module 30 may be adhered to the heat conductive member 653 and the circuit board 654 via the adhesive layer 652, and the heat sink 655 may be adhered to the plate portion 653B (combination of FIG. 39 and FIG. 40).

Twentieth Modification

A twentieth modification of the embodiment will be described below. A difference from the embodiment will be mainly described below.

In the twentieth modification, a variation of the liquid supplier will be described. Here, a case where the liquid supplier has a liquid storage unit will be exemplified.

Figure 42:
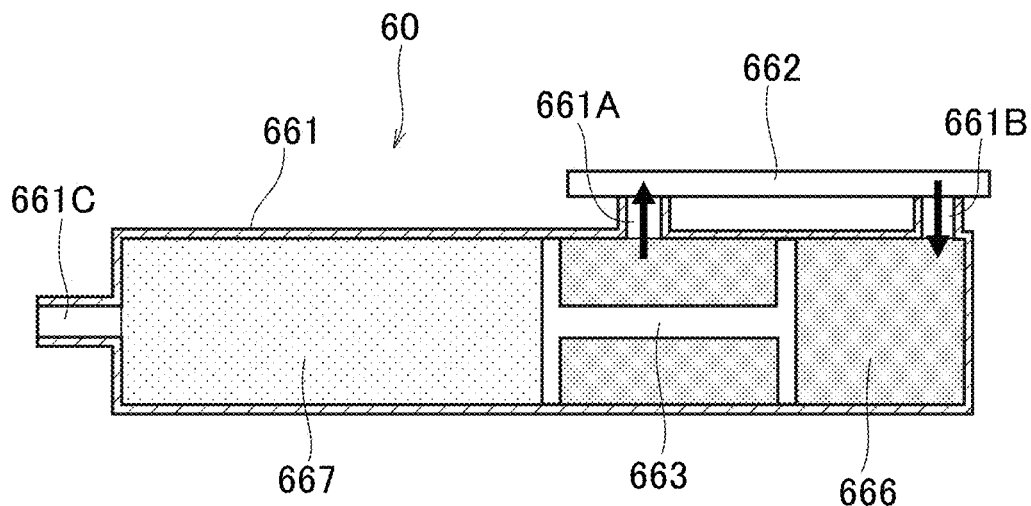
FIG. 42 is a diagram for describing a twentieth modification.

Firstly, as illustrated in FIG. 42, the liquid supplier 60 may include a housing 661, a pump 662, and a piston 663. The housing 661 includes a liquid 666 for driving the piston 663 and a liquid 667 for generating an aerosol. The liquid 666 and the liquid 667 are partitioned by the piston 663. The housing 661 includes a flow path 661A for communicating the housing 661 and the pump 662, and a flow path 661B for communicating the housing 661 and the pump 662. The housing 661 includes a discharge port 661C configured to discharge the liquid 667.

Here, the pump 662 moves the piston 663 by a reflux of the liquid 666. For example, the pump 662 advances the piston 663 by sucking up the liquid 666 via the flow path 661A and returning the liquid 666 to the housing 661 via the flow path 661B. Thus, the pump 662 can discharge the liquid 667 from the discharge port 661C. The pump 662 may be a piezo pump.

According to such a configuration, the liquid 666 used for discharging the liquid 667 does not mix with the liquid 667 and thus, the possibility that an impurity is mixed into the liquid 667 can be reduced. Further, the liquid 667 that generates the aerosol does not pass through the pump 662 and thus, a deterioration of the liquid 667 can be suppressed. Further, an amount of movement of the piston 663 can be specified by the amount of reflux of the liquid 666, and a remaining amount of the liquid 667 can be specified by the amount of movement of the piston 663.

In FIG. 42, the liquid 666 is exemplified as a medium for driving the piston 663, however, a gas may be used instead of the liquid 666.

Figure 43:
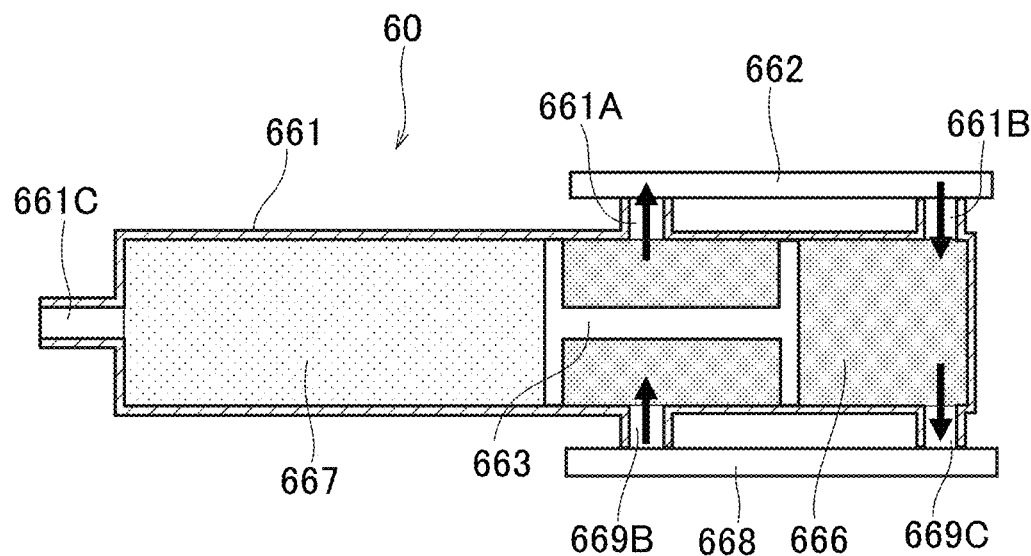
FIG. 43 is a diagram for describing the twentieth modification.

Here, as shown in FIG. 43, the liquid supplier 60 may include the pump 668 in addition to the configuration shown in FIG. 42. The pump 668 moves the piston 663 by a reflux of the liquid 666. The pump 668 retracts the piston 663 by sucking up liquid 666 via the flow path 669A and returning the liquid 666 to the housing 661 via the flow path 669B. The pump 668 may be a piezo pump.

Figure 44:
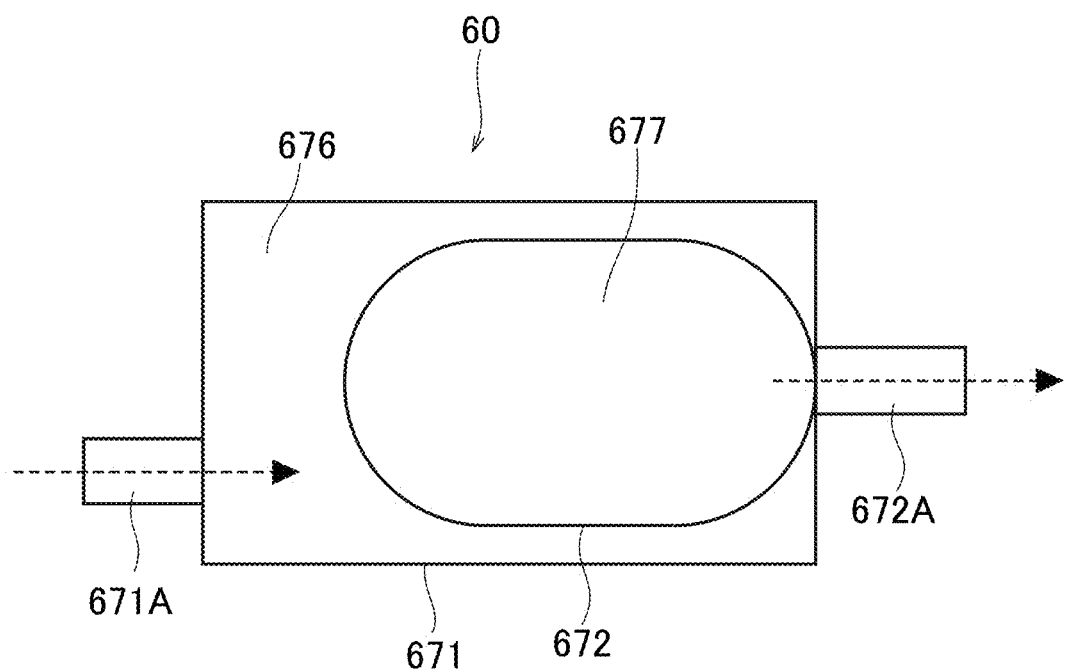
FIG. 44 is a diagram for describing the twentieth modification.

Secondly, as illustrated in FIG. 44, the liquid supplier 60 includes a housing 671 and a bag 672. The housing 671 houses the bag 672 and an air 676 and includes an inlet 671A configured to supply the air 676 into the housing 671. The bag 672 houses the liquid 677 for generating the aerosol and includes a discharge port 672A configured to discharge the liquid 677. A discharge port 672A may be integrally formed with the housing 671.

Here, the bag 672 is configured of a flexible member. Thus, when the air 676 is supplied into the housing 671 from the inlet 671A, the bag 672 can discharge the liquid 677 by a pressure of the air 676.

According to such a configuration, the air 676 used for ejecting the liquid 677 does not mix with the liquid 677 and thus, the possibility that an impurity is mixed into the liquid 677 can be reduced.

In FIG. 44, the air 676 is exemplified as a medium for pressurizing the bag 672, however, a liquid may be used instead of the air 676.

Twenty First Modification

A twenty first modification of the embodiment will be described below. A difference from the embodiment will be mainly described below.

Although not particularly mentioned in the embodiment, the piezoelectric element substrate 31 may be cut out by laser cutting. According to such a configuration, since the edge portion of the piezoelectric element substrate 31 becomes smooth, the durability of the piezoelectric element substrate 31 and the adhesion of the coating layer 36 are improved.

Twenty Second Modification

A twenty second modification of the embodiment will be described below. A difference from the embodiment will be mainly described below.

Figure 45:
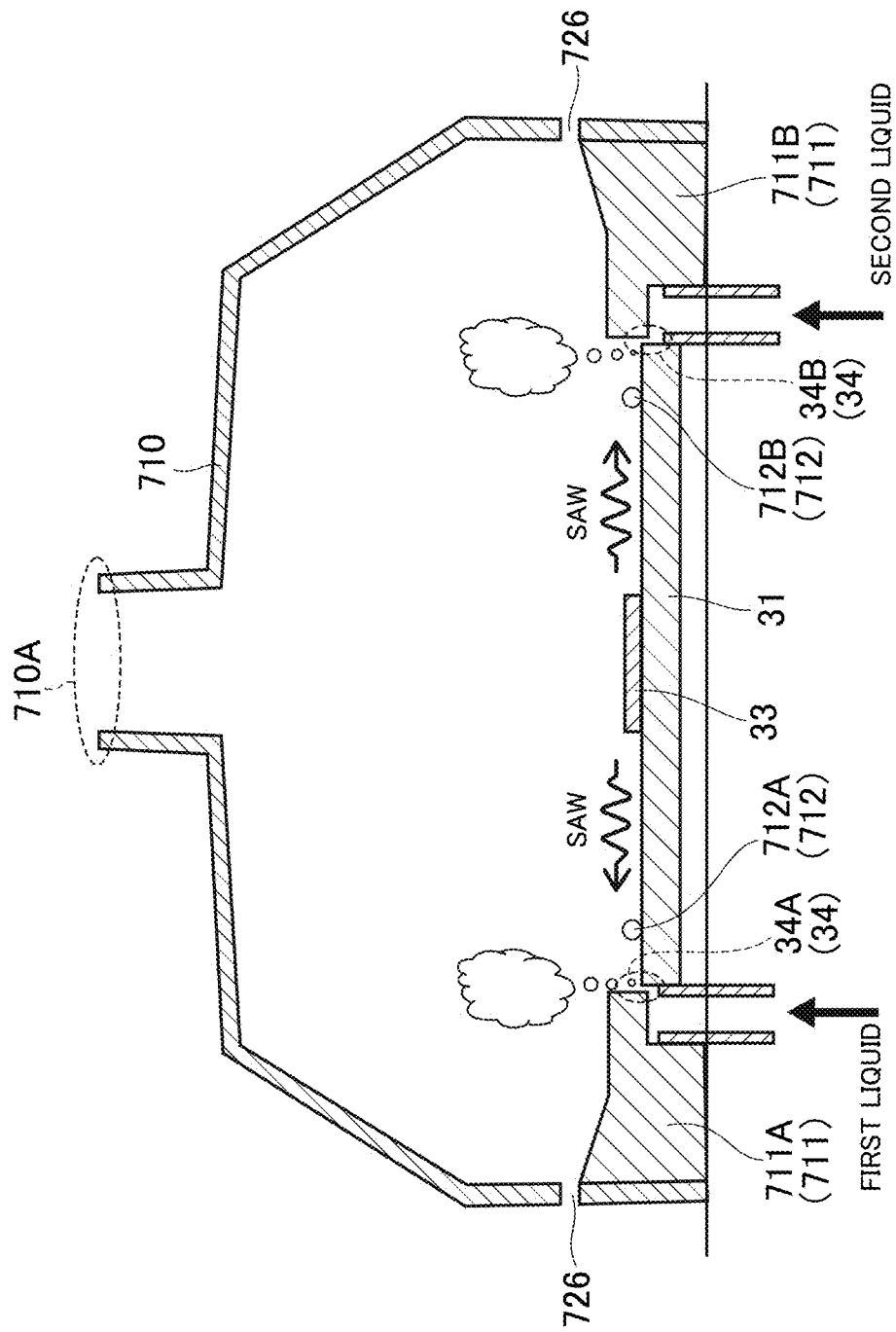
FIG. 45 is a diagram for describing a twenty second modification.

In the twenty second modification, as illustrated in FIG. 45, the atomizing unit 100 includes a top cover 710, a guide wall 711, and a sensor 712. The atomizing unit 100 includes the piezoelectric element substrate 31 and the pairs of interlocking comb-shaped metallic electrodes 33 as described in the embodiment.

The top cover 710 is provided to cover a lateral and upper side of the aerosol atomized by SAW. An opening 710A is provided at an upper end of the top cover 710 to lead out the aerosol.

The guide wall 711 is provided to contact with an inner wall of the top cover 710 not allowing a space with the inner wall of the top cover 710. The guide wall 711 is positioned away from the piezoelectric element substrate 31, the penetrated aperture 34 is provided between the piezoelectric element substrate 31 and the guide wall 711. In FIG. 45, guide walls 711A and 711B are provided as the guide wall 711.

The first liquid is provided to the penetrated aperture 34A provided between the piezoelectric element substrate 31 and the guide wall 711A from the liquid supplier (a syringe pump, for example). Similarly, the second liquid is provided to the penetrated aperture 34B provided between the piezoelectric element substrate 31 and the guide wall 711B from the liquid supplier (a syringe pump, for example). The first liquid and the second liquid may be the same kind of liquid or the different kind of the liquid.

The sensor 72 detects the liquid exposed from the penetrated aperture 34 as same as the ninth modification or the like. The liquid supplier 60 (supplying speed of the liquid) can be controlled based on the detection result of the sensor 72. In FIG. 45, a sensor 72A detects the first liquid exposed from the penetrated aperture 34A and a sensor 72B detects the second liquid exposed from the penetrated aperture 34B as the sensor 72.

Although not shown in FIG. 45, a sealing member such as O-ring or packing may be provided to suppress a leakage of the first liquid and the second liquid.

Twenty Third Modification

A twenty third modification of the embodiment will be described below. A difference from the embodiment will be mainly described below.

Figure 46:
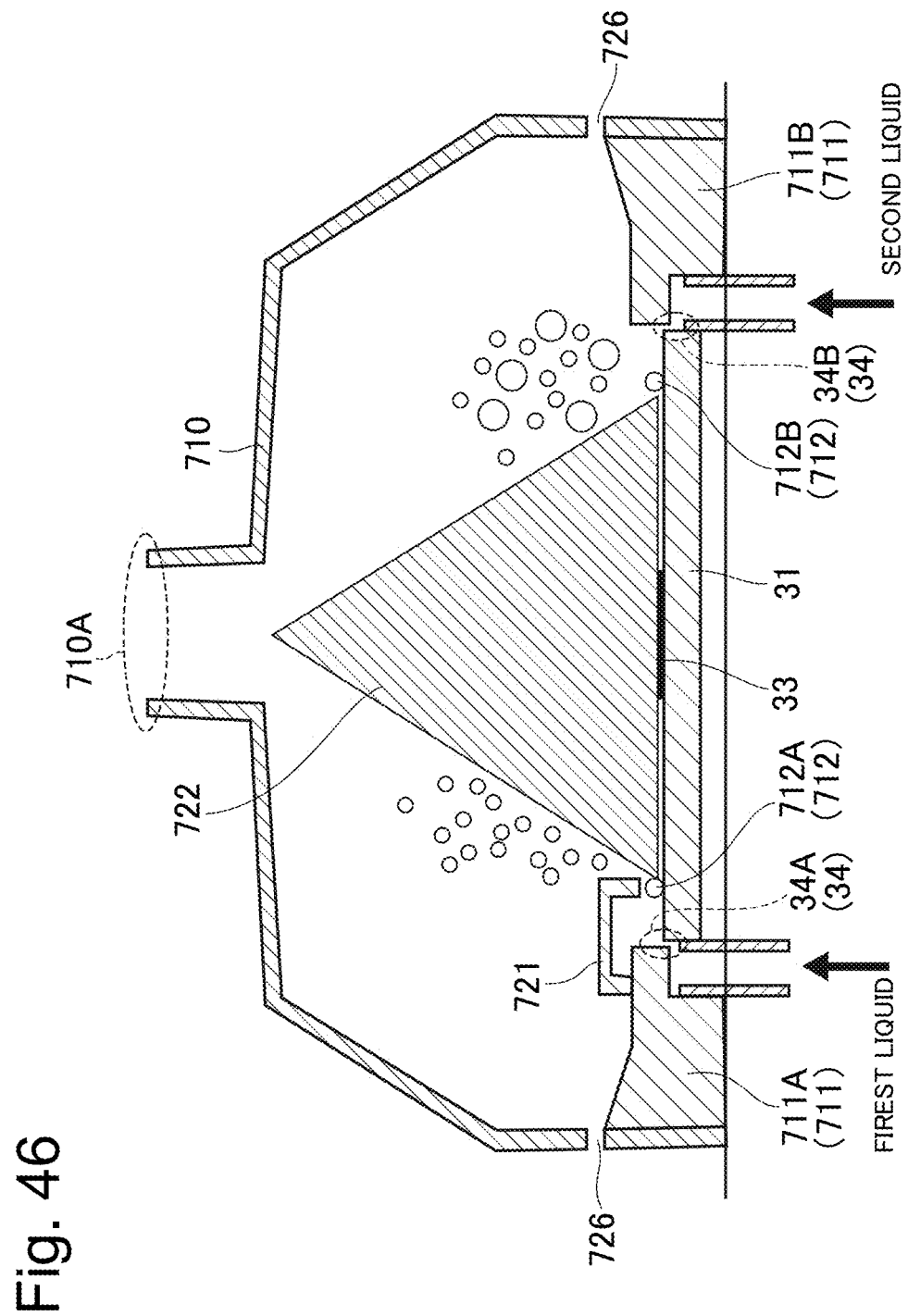
FIG. 46 is a diagram for describing a twenty third modification.

In the twenty third modification, as illustrated in FIG. 46, the atomizing unit 100 includes an impactor 721 and a separation wall 722 in addition to the configuration in FIG. 45.

The impactor 721 is positioned to cover the atomization zone of the first liquid. The impactor 721 has a function to trap the coarse particles (about 10 microns, for example) included in the aerosol generated from the first liquid by inertial impaction. The fine particles are guided to the opening 710A (that is the mouth of user) from a void between the impactor 721 and the piezoelectric element substrate 31 without trapped by the impactor 721.

The coarse particles trapped by the impactor 721 may be returned to the atomization zone. The coarse particles returned to the atomization zone may be re-atomized. Alternately, the coarse particles trapped by the impactor 721 can be collected by a collecting member such as a porous absorber or a reservoir without re-used for the atomization.

In FIG. 46, although a impactor is not provided which covers the atomization zone of the second liquid, the impactor may be provided which covers the atomization zone of the second liquid. The first liquid and the second liquid may be the same kind of liquid or the different kind of the liquid. The aerosol including the particles of the desired size can be supplied by providing the impactor or not.

Although FIG. 46 shows an example that the first liquid and the second liquid are atomized independently, the first liquid and the second liquid may be atomized after mixed. The impactor 721 may be positioned to cover the atomization zone of the mixed liquid or positioned at the mouthpiece.

The separation wall 722 is provided between the atomization zone of the first liquid and the atomization zone of the second liquid. The separation wall 722 suppress the mix of the aerosol generated from the first liquid and the aerosol generated from the second liquid until the aerosol is led out from the opening 710A. According to such a configuration, the mixing of the aerosol generated from the different kind of liquids can be suppressed when the first liquid and the second liquid are the different kind. Specifically, it is preferable to suppress the mixing of the aerosol generated from the different kind of liquids, when the coarse particles generated from respective liquids are re-used.

Further, the separation wall 722 can trap the extra-large particles (about 100 micron, for example) larger than the coarse particles trapped by the impactor 721. Moreover, the separation wall 722 can trap the extra-large particles about 100 micron when the impactor 712 is not provided.

The extra-large particles trapped by the separation wall 722 may be returned to the atomization zone. The extra-large particles returned to the atomization zone may be re-atomized. Alternately, the extra-large particles trapped by the separation wall 722 can be collected by a collecting member such as a porous absorber or a reservoir without re-used for the atomization.

Figure 47:
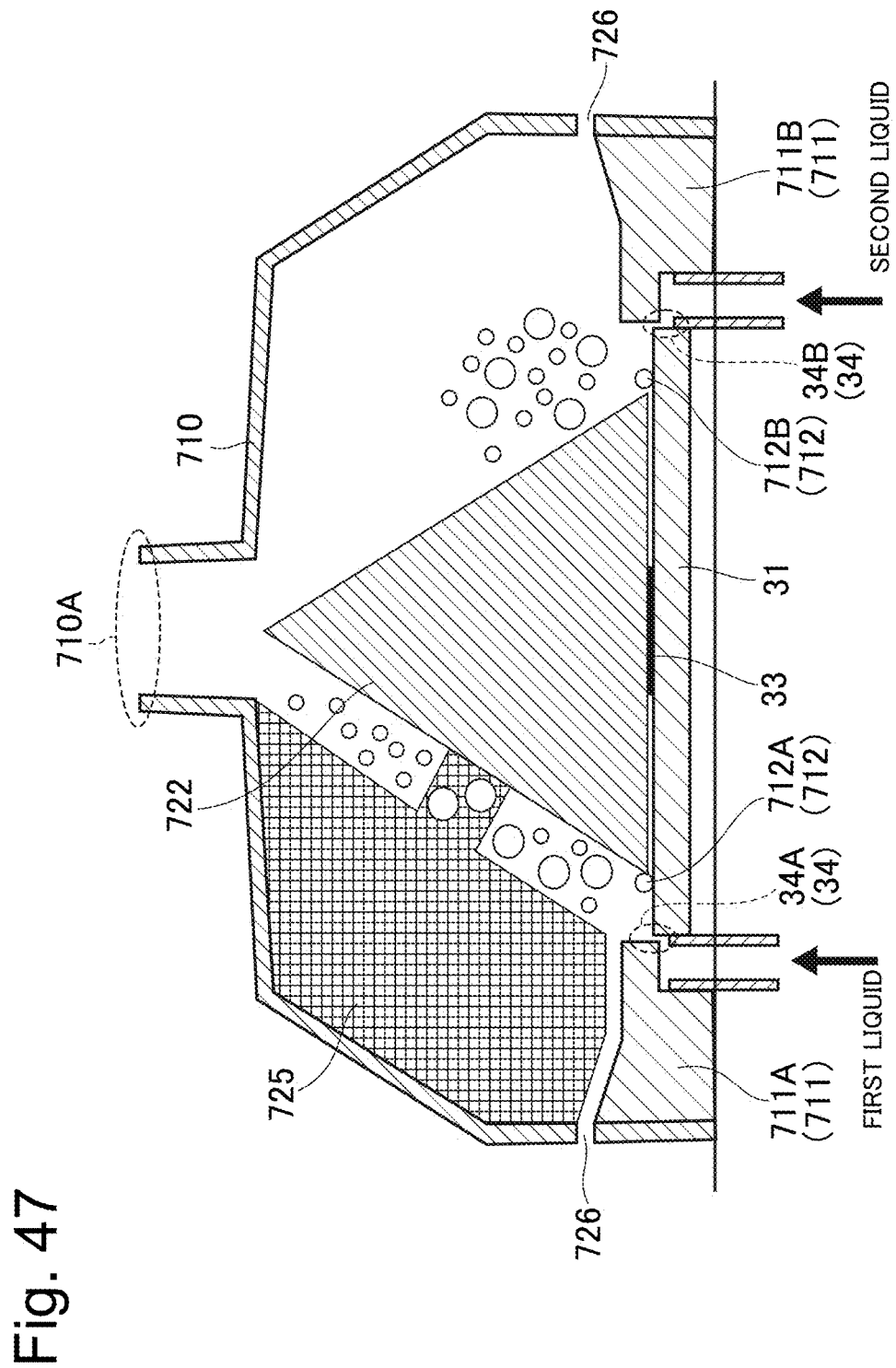
FIG. 47 is a diagram for describing the twenty third modification.

Although the impactor 721 is provided in FIG. 46, a filter 725 may be provided instead of the impactor 721 as shown in FIG. 47. The filter 725 may be a fibrous layer filter or a granular packed layer provided at an arbitrary position within the top cover 710. It is possible to design the trap efficiency of the coarse particles appropriately by changing a fiber diameter, a grain size, a filling ratio, and a filling length of the filter 721.

The top cover 710 may include an inlet 726. The flow path of air or aerosol from the inlet 726 to the opening 710A is formed in the top cover 710. According to such a configuration, it is possible to suppress a retention of aerosol in the top cover 710 and to optimize an amount of the aerosol delivered to the mouth. The top cover 710 in FIGS. 45 and 46 may include the inlet 726.

[Experiment Result]

Figure 48:
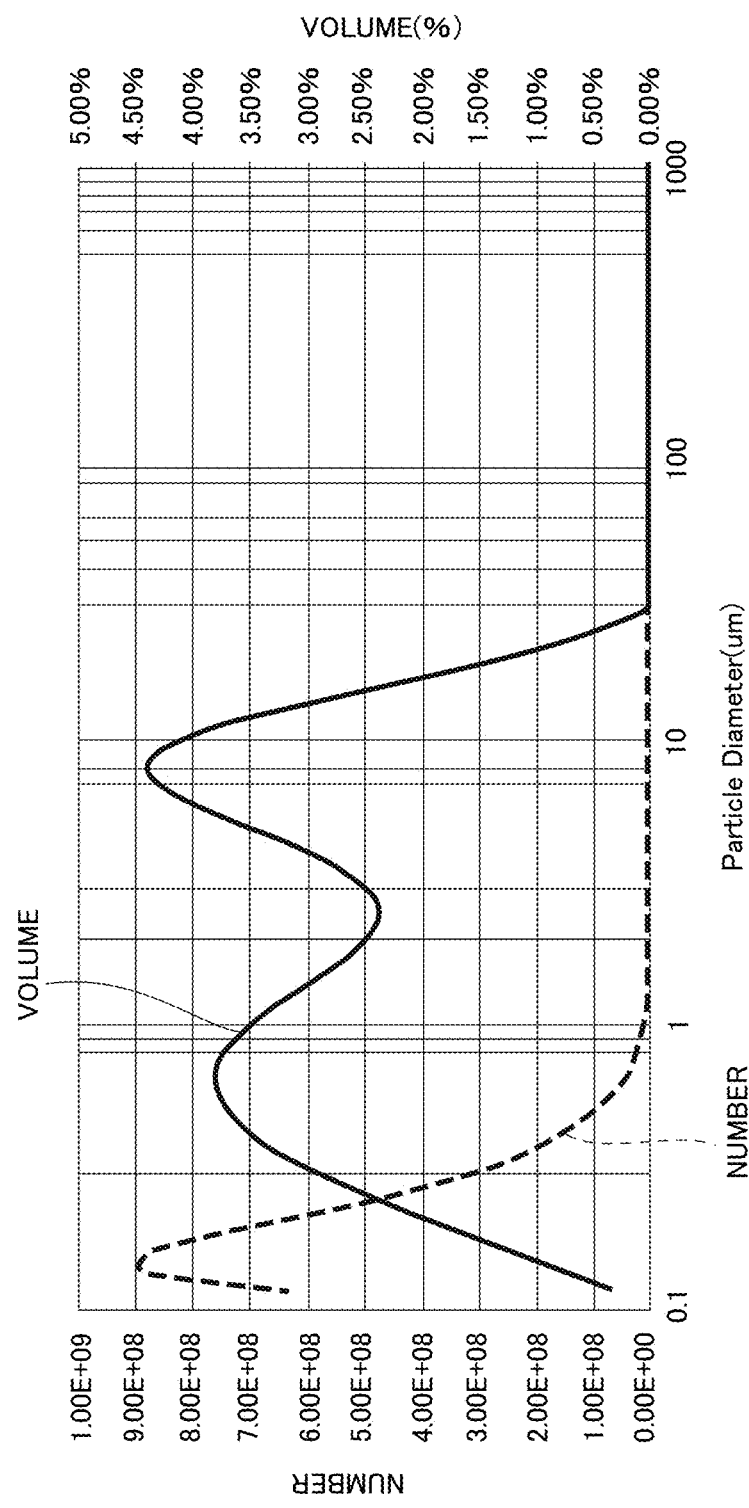
FIG. 48 is a diagram for describing a result of an experiment.

The experiment result would be described below. In the experiment, a distilled water is used as the liquid and 50 MHz is used as the frequency of the voltage applied to the pairs of interlocking comb-shaped metallic electrodes. In the experiment, a diameter distribution of particles included in aerosol. FIG. 48 shows the experiment result.

Figure 52:
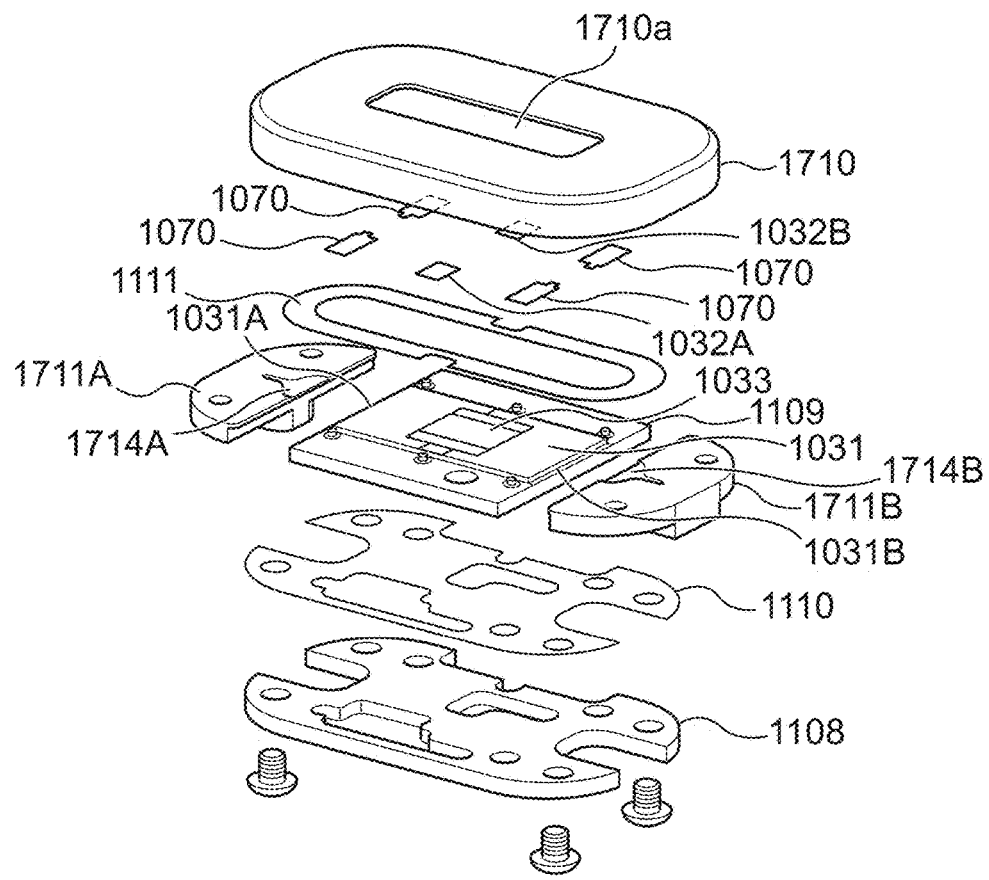
FIG. 52 is an exploded perspective view of the atomizing unit from which the first cover and the second cover have been removed.
Figure 53:
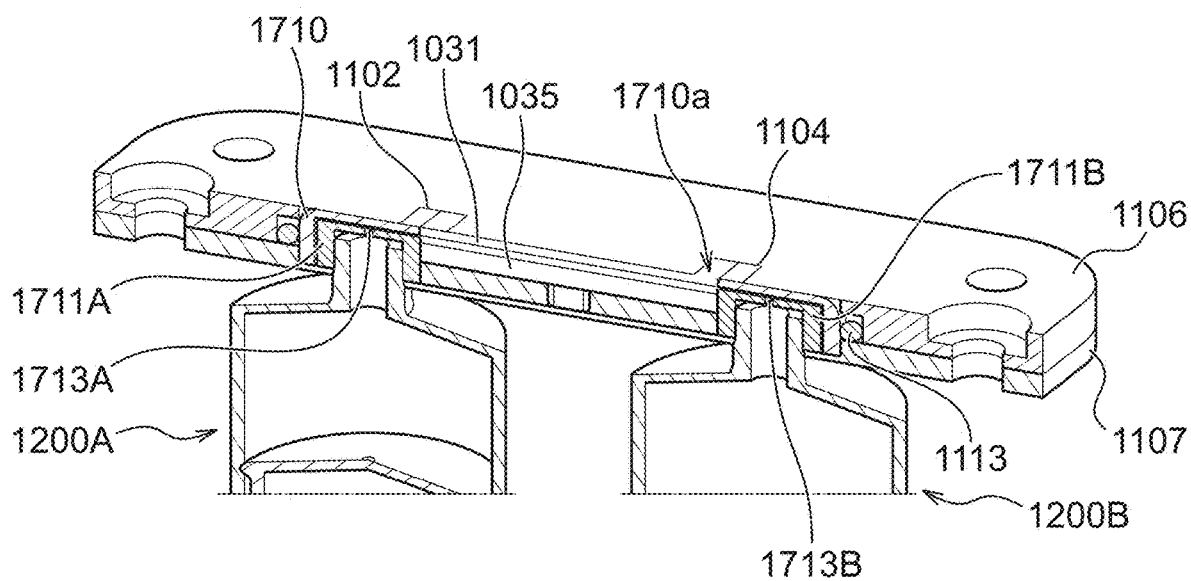
FIG. 53 is a cross-section view of the atomizing unit.

FIG. 48 shows the diameter distributions observed based on the number of particles and the volume of the particles. Regarding the number of particles, it is observed that the diameter distribution has the single peak. However, regarding the volume of particles, it is observed that the diameter distribution has two peaks (about 0.6 micron and about 8 micron).

In such a case, it is possible to adjust the diameter distribution based on the volume of particles to have the single peak (about 0.6 micron) by selectively trapping the particles of 8 micron by use of the impactor 721 or the filter 725 described in the twenty third modification (see FIG. 46 or 47).

[Twenty-Fourth Modification]

FIG. 49 is a perspective view showing an example of an exterior of the unit excluding the sensor 300, the controller 400, and the power source 500 of the flavor inhaler 1 shown in FIG. 1. FIG. 50 is a longitudinal section of the unit shown in FIG. 49. FIG. 51 is an exploded perspective view of the unit shown in FIG. 49. As shown in FIG. 49 to FIG. 51, a unit 1000 comprises a mouthpiece 1001D, an atomizing unit 1100, a first liquid storage unit 1200A, and a second liquid storage unit 1200B. Note that, in the following description, the "flavor inhaler" may simply be referred to as an "inhaler." In addition to the flavor components, any components, which can be inhaled, can be inhaled by use of the "inhaler."

The first liquid storage unit 1200A and the second liquid storage unit 1200B are housed in a housing 1202 which is a component of the housing 1X shown in FIG. 1. In the present modified example, the first liquid storage unit 1200A comprises a cylinder 1204A and a piston 1206A, and first liquid is stored in a space defined by the cylinder 1204A and the piston 1206A. Similarly, the second liquid storage unit 1200B comprises a cylinder 1204B and a piston 1206B, and second liquid is stored in a space defined by the cylinder 1204B and the piston 1206B. The first liquid storage unit 1200A and the second liquid storage unit 1200B may be integrally constructed as a cartridge for making them to be attachable/detachable in a simultaneous manner.

In the present modified example, the first liquid and the second liquid may be the same liquid. Alternatively, the first liquid and the second liquid may be different from each other. The first liquid may comprise at least nicotine. In addition, the first liquid may comprise an acid such as malic acid, citric acid, tartaric acid, or the like, for forming a salt with nicotine, for example. Further, the first liquid may comprise at least one of erythritol, a salt, an inosinic acid, a glutamic acid, a succinic acid, sodium salts of these, potassium salts of these, isohumulone, cucurbitacin, curcumine, falcarindiol, naringin, quassin, quinine, riboflavin, thiamine, and catechin, as a taste component. Also, the first liquid may comprise at least one of capsaicin, piperine, eugenol, allicin, allyl isothiocyanate, gingerol, cinnamic aldehyde, and glycosides of these, as a component (a somatosensory component) for making somatic sense to be expressed in a user who inhaled the component.

The second liquid may comprise a flavor component which includes at least one of menthol, limonene, citral, linalool, vanillin, carvone, and glycosides of these. The second liquid may comprise an emulsifier, and may be in an emulsified state. Regarding the emulsifier, it may be possible to use emulsifiers such as glycerine fatty acid ester, sorbitan fatty acid ester, propylene glycol fatty acid ester, sucrose fatty acid ester, lecithin, saponin, sodium caseinate, oxyethylene fatty acid alcohol, sodium oleate, a morpholine fatty acid salt, polyoxyethylene higher fatty acid alcohol, calcium stearoyl lactate, monoglyceride ammonium phosphate, and so on. The second liquid may comprise a solvent such as glycerin, propylene glycol, ethanol, or the like. In the case that a hydrophobic flavor component is to be used in the second liquid, it can be made to have the form of a solution by dissolving the flavor component in the solvent. Further, the second liquid may comprise at least one of erythritol, a salt, an inosinic acid, a glutamic acid, a succinic acid, sodium salts of these, potassium salts of these, isohumulone, cucurbitacin, curcumine, falcarindiol, naringin, quassin, quinine, riboflavin, thiamine, and catechin, as a taste component. Also, the second liquid may comprise at least one of capsaicin, piperine, eugenol, allicin, allyl isothiocyanate, gingerol, cinnamic aldehyde, and glycosides of these, as a component (a somatosensory component) for making somatic sense to be expressed in a user who inhaled the component. At least one of the first liquid and the second liquid may be the same as liquid stored in the liquid storage unit 200 which has been explained in relation to FIG. 1.

As shown in FIG. 50, the housing 1202 houses a motor 1208A and a gear box 1210A. Electric power is supplied from the power source 500 shown in FIG. 1 to the motor 1208A. The gear box 1210A can convert driving force in the direction of rotation of the motor 1208 A to driving force in the direction of an axis of the piston 1206A. Also, the gear box 1210A can change the speed of rotation of the motor 1208A. Similarly, the housing 1202 houses a motor 1208B and a gear box 1210B, and a piston 1206B is driven by the motor 1208B and the gear box 1210B. Electric power is supplied from the power source 500 shown in FIG. 1 to the motor 1208B. That is, in the present modified example, a liquid supplier for supplying liquid from the first liquid storage unit 1200A and the second liquid storage unit 1200B is constructed by using, as components thereof, the motors 1208A and 1208B and the gear boxes 1210A and 1210B. Note that it may be possible to drive both the pistons 1206A and 1206B by use of a single motor and a single gear box.

As shown in FIG. 50, the atomizing unit 1100 is arranged at a position above the first liquid storage unit 1200A and the second liquid storage unit 1200B, and fixed to an upper part of the housing 1202 by a fixture 1002 such as a screw and so on. Also, the mouthpiece 1001D is fixed to an upper part of the atomizing unit 1100 by a fixture 1004 such as a screw and so on.

As shown in FIG. 51, the atomizing unit 1100 is covered by a first cover 1106 and a second cover 1107. The first cover 1106 comprises, on its upper surface, a first opening part 1102 and a second opening part 1104. The first opening part 1102 is constructed in such a manner that first aerosol, which is generated by atomizing the first liquid, passes through it, as will be explained later. The second opening part 1104 is constructed in such a manner that second aerosol, which is generated by atomizing the second liquid, passes through it, as will be explained later.

Next, the atomizing unit 1100 shown in FIG. 49 to FIG. 51 will be explained. FIG. 52 is an exploded perspective view of the atomizing unit 1100 from which the first cover 1106 and the second cover 1107 have been removed. FIG. 53 is a cross-section view of the atomizing unit 1100. In FIG. 53, for convenience of explanation, the first liquid storage unit 1200A and the second liquid storage unit 1200B are shown. As shown in FIG. 52, the atomizing unit 1100 comprises a base member 1108, a PCB board 1109, a piezoelectric element substrate 1031 comprising a pair of interlocking comb-shaped metallic electrodes 1033, a pair of guide walls 1711A and 1711B, and a top cover 1710. An adhesive sheet 1110 is positioned between the base member 1108 and the PCB board 1109, so that the position of the PCB board 1109 relative to the base member 1108 is fixed, and leaking of the first liquid and the second liquid is suppressed.

As shown in FIG. 53, the piezoelectric element substrate 1031 is positioned on a top surface of the PCB board 1109. A heat sink structure 1035 similar to the heat sink structure 35 shown in FIG. 3 and FIG. 4 is positioned on a rear surface of the piezoelectric element substrate 1031. Note that it is possible to adopt the heat sink structure shown in FIGS. 39-41 in place of the heat sink structure 1035.

Further, the piezoelectric element substrate 1031 comprises a pair of edges 1031A and 1031B which are opposite to each other. The guide wall 1711A is positioned at the edge 1031A side, and the guide wall 1711B is positioned at the edge 1031B side. The guide walls 1711A and 1711B comprise penetrated apertures 1713A and 1713B, which extend between the top surface and the bottom surface, respectively. Further, the guide walls 1711A and 1711B comprise concave parts 1714A and 1714B communicating with the penetrated apertures 1713A and 1713B, respectively. As shown in FIG. 53, the first liquid storage unit 1200A and the second liquid storage unit 1200B are connected to the bottom surfaces of the guide walls 1711A and 1711B, respectively. The liquids (a first liquid and a second liquid) supplied by syringe pumps from the first liquid storage unit 1200A and the second liquid storage unit 1200B pass through the penetrated apertures 1713A and 1713B from a lower side to an upper side and arrive at the concave parts 1714A and 1714B, respectively. The liquids, which have arrived at the concave parts 1714A and 1714B, arrive at the edges 1031A and 1031B, and are atomized by energy in the pair of interlocking comb-shaped metallic electrodes 1033. That is, the syringe pumps are constructed to supply the first liquid and the second liquid to the edges 1031A and 1031B of the piezoelectric element substrate 1031, respectively.

Further, the atomizing unit 1100 comprises a seal member 1111. The seal member 1111 as a whole has an approximately ring shape, and is in contact with the top surfaces of the guide walls 1711A and 1711B and the top surface of the piezoelectric element substrate 1031. As a result, the liquids that arrived at the concave parts 1714A and 1714B is controlled in such a manner that liquids do not flow to the outside of the guide walls 1711A and 1711B and the piezoelectric element substrate 1031.

Figure 21:
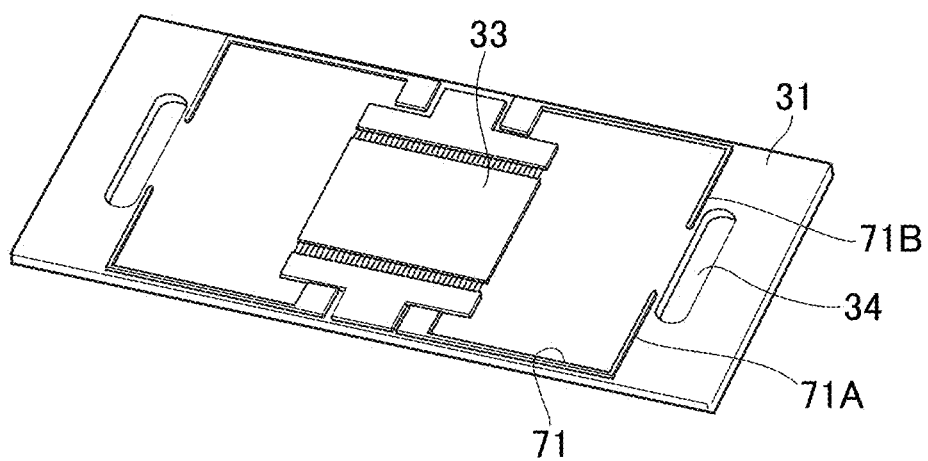
Figure 22:
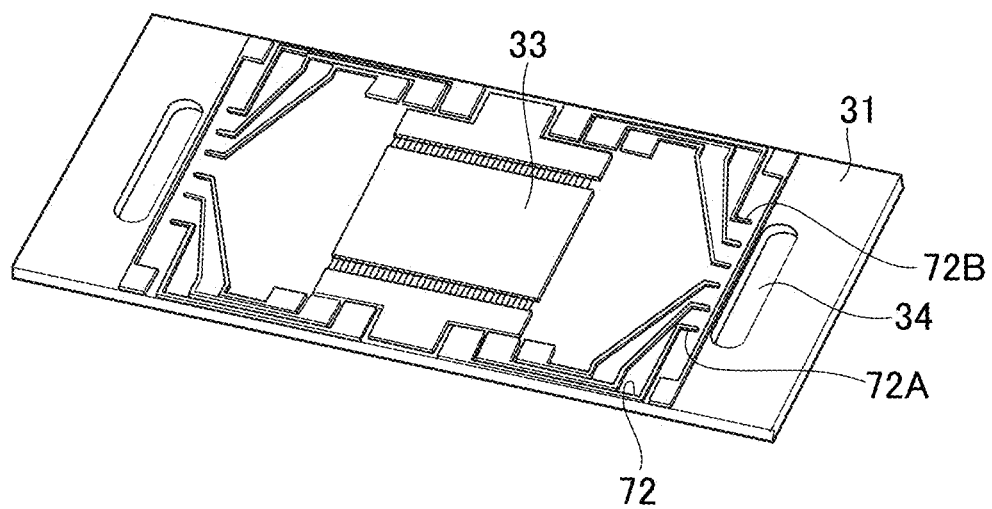
Figure 23:
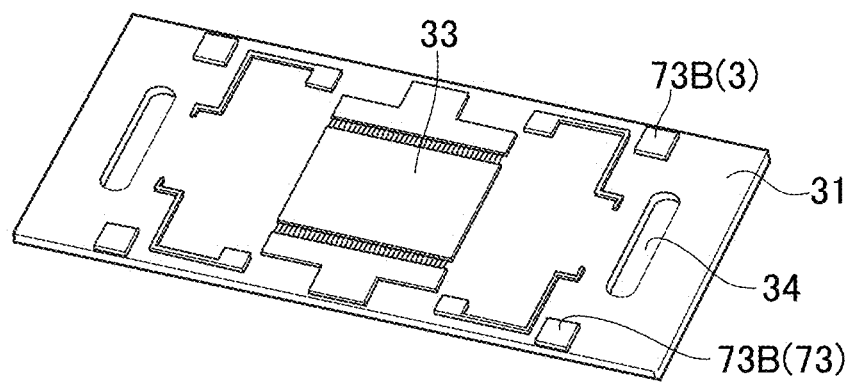
Figure 24:
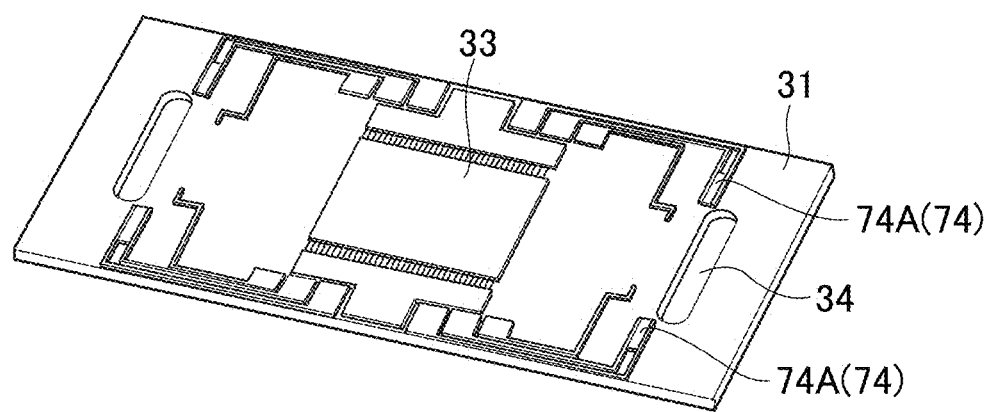
Figure 26:
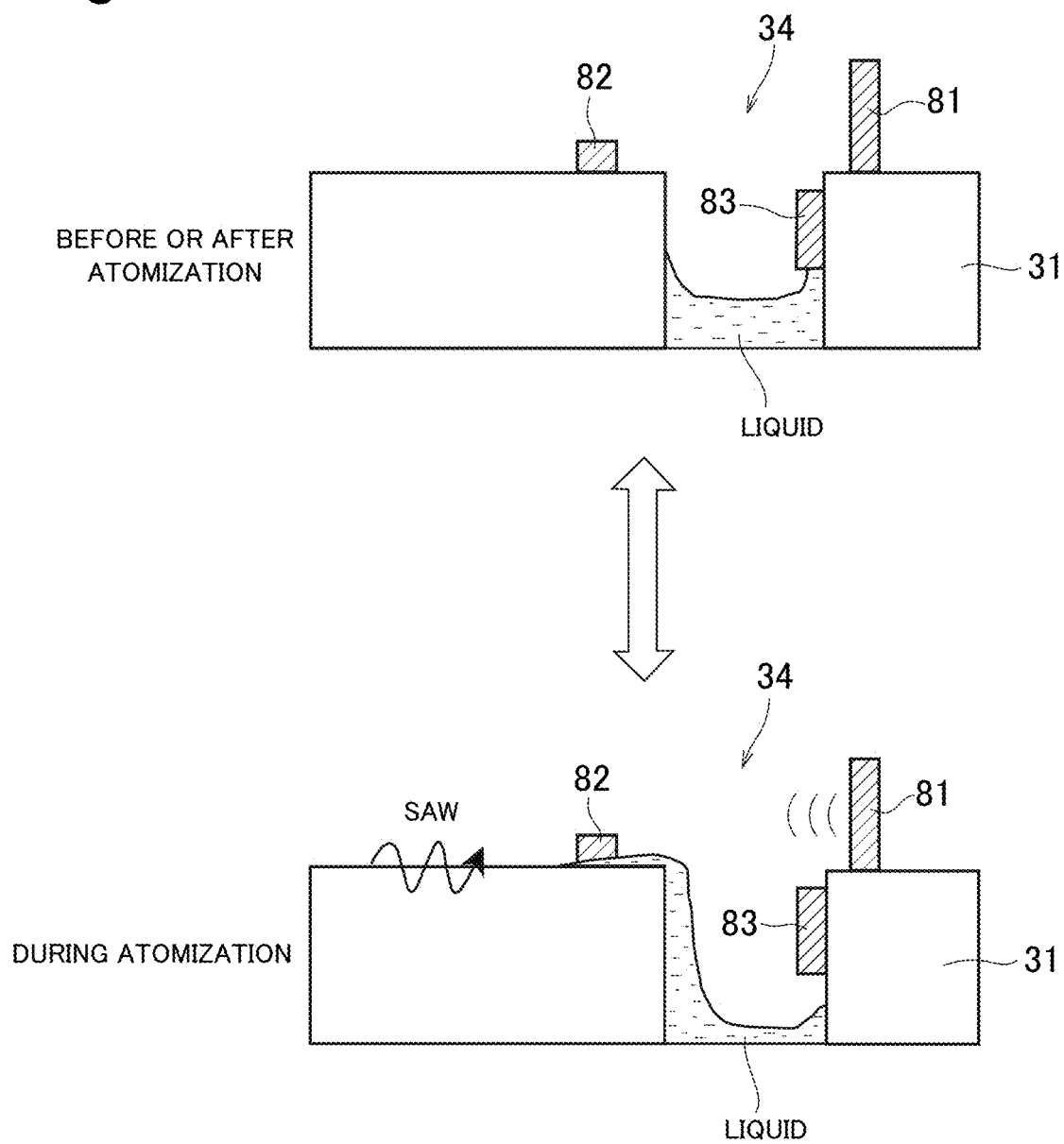

The atomizing unit 1100 comprises a pair of electric contacts 1032A and 1032B which electrically connect contacts formed on the PCB board 1109 with the pair of interlocking comb-shaped metallic electrodes 1033. Further, the atomizing unit 1100 comprises sensors 1070 for detecting liquid. In the example shown in FIG. 52, the sensor 1070 is an electric conductivity sensor. The function of the sensor 1070 is similar to the function of sensor 71 shown in FIG. 21. Also, the sensor for detecting the liquid is not limited to the above, and it is possible to adopt the emitter/receiver sensor or the capacitive sensor shown in FIGS. 22-25.

As shown in FIG. 52 and FIG. 53, the top cover 1710 comprises, at a center part thereof, an opening part 1710a through which aerosol passes, and is arranged to cover the guide walls 1711A and 1711B, the PCB board 1109, and the piezoelectric element substrate 1031, from above. Also, an O-ring 1113 is arranged between a periphery at the side part of the top cover 1710 and the first cover 1106.

Further, as shown in FIG. 53, the opening part 1710a of the top cover 1710 is positioned above the pair of interlocking comb-shaped metallic electrodes 1033 and the pair of edges 1031A and 1031B of the piezoelectric element substrate 1031. Thus, the aerosol from the first liquid and the aerosol from the second liquid, which are generated by the pair of edges 1031A and 1031B, can flow to the outside of the top cover 1710. Also, as shown in the figure, the first cover 1106 is arranged to cover the front surface side of the piezoelectric element substrate 1031. The first opening part 1102 and the second opening part 1104 of the first cover 1106 are positioned right above the edges 1031A and 1031B of the piezoelectric element substrate 1031, respectively. Thus, the aerosol from the first liquid and the aerosol from the second liquid, which are generated by the edges 1031A and 1031B, respectively, can pass through the first opening part 1102 and the second opening part 1104, respectively. Accordingly, the first opening part 1102 of the first cover 1106 can emit the aerosol from the first liquid mainly, and the second opening part 1104 can emit the aerosol from the second liquid mainly.

Further, as shown in FIG. 53, the first cover 1106 is arranged in such a manner that it covers the part right above the disposition portion, where the pair of interlocking comb-shaped metallic electrodes 1033 is positioned, and is not to be in contact with the pair of interlocking comb-shaped metallic electrodes 1033. Thus, the aerosol generated by the edges 1031A and 1031B is made to be in contact with the pair of interlocking comb-shaped metallic electrodes 1033, so that degradation of the pair of interlocking comb-shaped metallic electrodes 1033 can be suppressed, and propagation of a SAW by the pair of interlocking comb-shaped metallic electrodes 1033 cannot be prevented. A gap between the first cover 1106 and the piezoelectric element substrate 1031 may be approximately several microns, for example. If the gap is that explained above, degradation of the pair of interlocking comb-shaped metallic electrodes 33 can be suppressed sufficiently.

Figure 49:
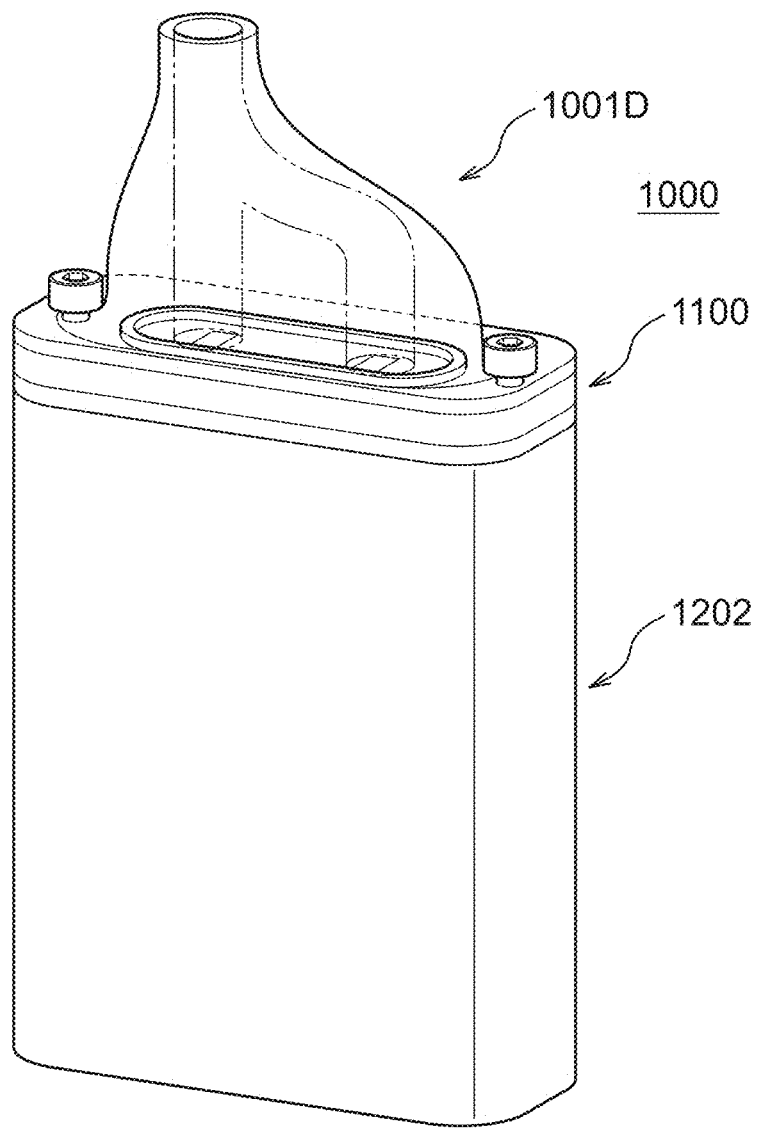
FIG. 49 is a perspective view showing an example of an exterior of the unit which is that from which the sensor, the controller, and the power source of the flavor inhaler 1 shown in FIG. 1 have been removed.
Figure 50:
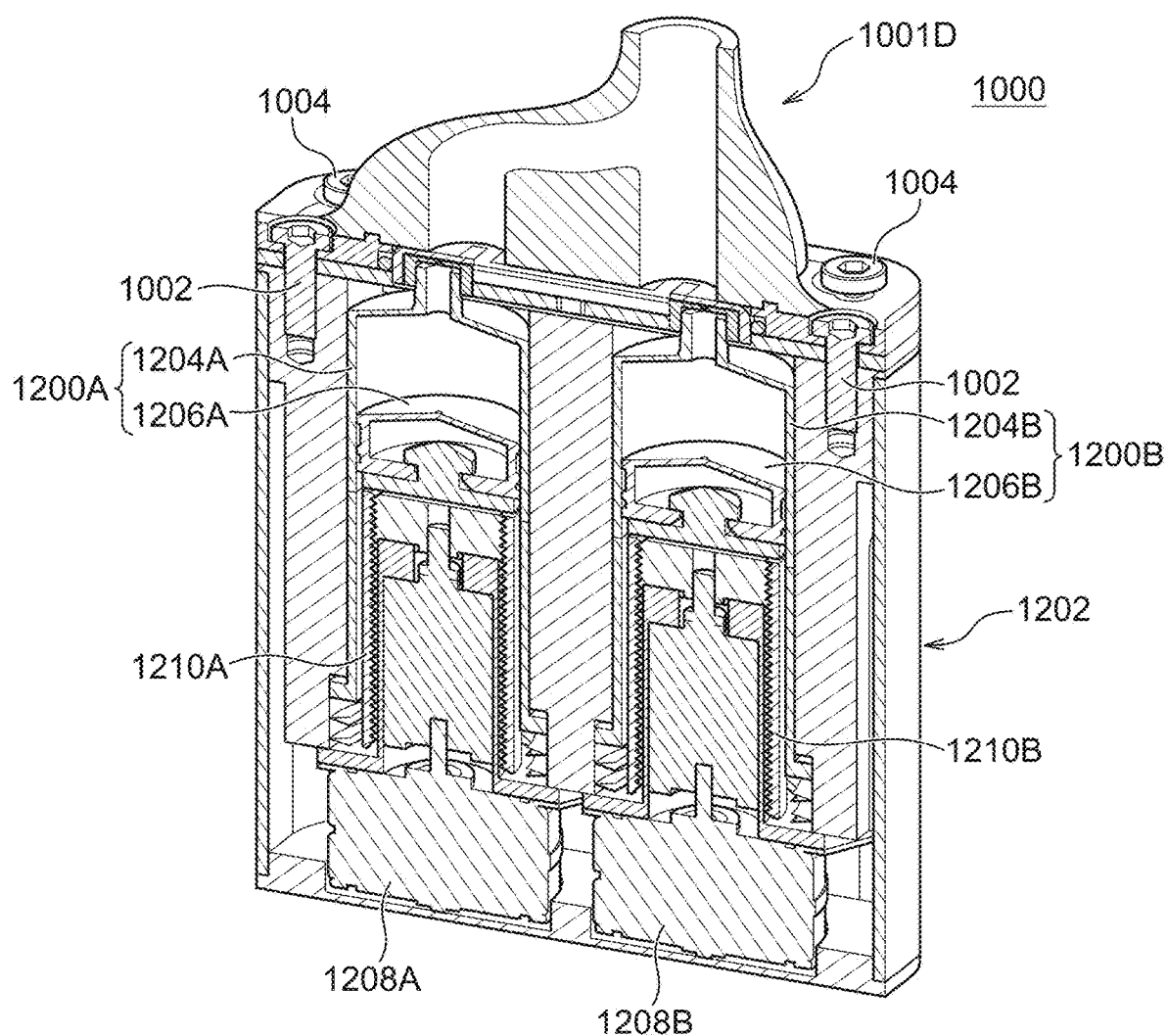
FIG. 50 is a longitudinal section of the unit shown in FIG. 49.
Figure 54:
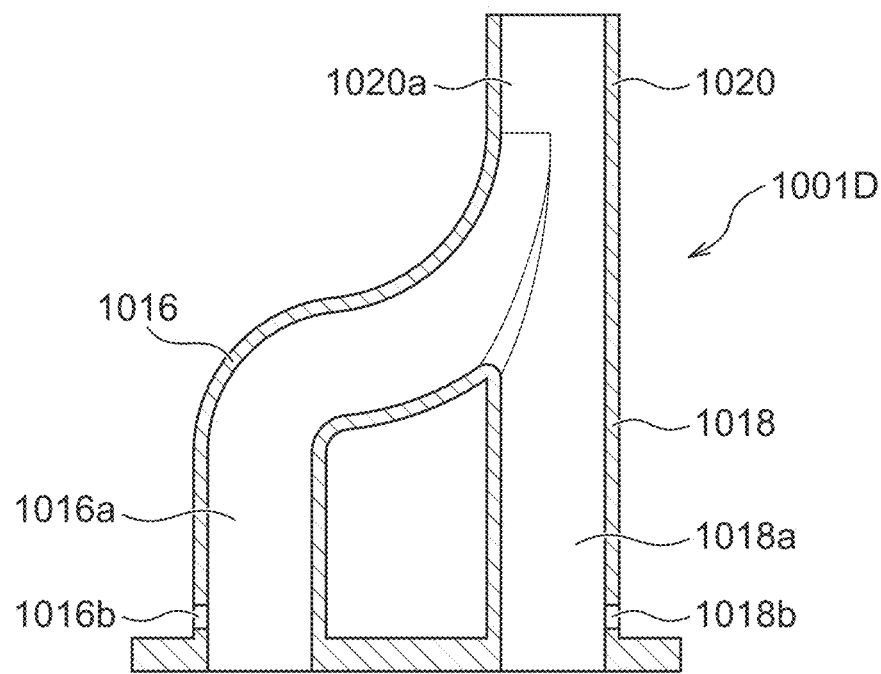
FIG. 54 is a side cross-section view of the mouthpiece.

Next, the mouthpiece 1001D shown in FIG. 49 to FIG. 51 will be explained. FIG. 54 is a cross-section view of the mouthpiece 1001D. The mouthpiece 1001D comprises a first pipeline 1016 which comprises at least a part which is curved, a second pipeline 1018 which is approximately straight, and a third pipe line 1020. As would be understood based on FIG. 50, the first pipeline 1016 communicates with the first opening part 1102 of the first cover 1106, and the second pipeline 1018 communicates with the second opening part 1104. That is, the first pipe line 1016 defines a first flow path 1016a through which the first aerosol, which is generated by atomizing the first liquid, passes mainly. Also, the second pipe line 1018 defines a second flow path 1018a through which the second aerosol, which is generated by atomizing the second liquid, passes mainly. Also, regarding a third flow path 1020a which is defined by the third pipe line 1020, the first aerosol and the second aerosol flow into each other in it and pass through it. A first air inlet 1016b is formed on a side surface of the first pipe line 1016, and a second air inlet 1018b is formed on a side surface of the second pipe line 1018. As a result of inhaling action by a user, air flows into the first flow path 1016*a* and the second flow path 1018*a* from the first air inlet 1016*b* and the second air inlet.

Regarding the case that the first liquid includes nicotine and water, and that the first liquid is atomized by the SAW generated by the pair of interlocking comb-shaped metallic electrodes 1033, it has been known that peaks in diameter distribution of particles included in the aerosol appear at a point near 10 microns (hereinafter, coarse particles) and a point in submicron (hereinafter, submicron particles), as shown by the experimental result shown in FIG. 48. According to the mouthpiece 1001D shown in FIG. 54, the aerosol including coarse particles, in the aerosol passing through the first flow path 1016*a*, collides with a wall surface of the first pipe line 1016 and is trapped thereby. Thus, the aerosol including coarse particles is eliminated from the aerosol passing through the first flow path 1016*a*, so that the aerosol including particles having desired particle sizes can be supplied to the mouth of the user. For holding the collided particles in the aerosol, it is preferable that the wall surface of the first pipe line 1016 is provided with porous material such as a fibrous packed bed, a granular packed bed, a sponge, a sintered body, and so on, or the wall surface itself is formed by use of porous material.

Also, regarding the case that the second liquid includes flavor components, and that the second liquid is atomized by the SAW generated by the pair of interlocking comb-shaped metallic electrodes 1033, it has been known that a peak in diameter distribution of particles included in the aerosol appears at a point near 10 microns. According to the mouthpiece 1001D shown in FIG. 54, each of the second pipe line 1018 defining the second flow path 1018*a* and the third pipe line 1020 defining the third flow path 1020*a* is formed to have an approximately straight shape. Thus, even if the particles of the aerosol generated from the second liquid are coarse particles, trapping of aerosol by each of wall surfaces of the second pipe line 1018 and the third pipe line 1020 can be suppressed.

Figure 55:
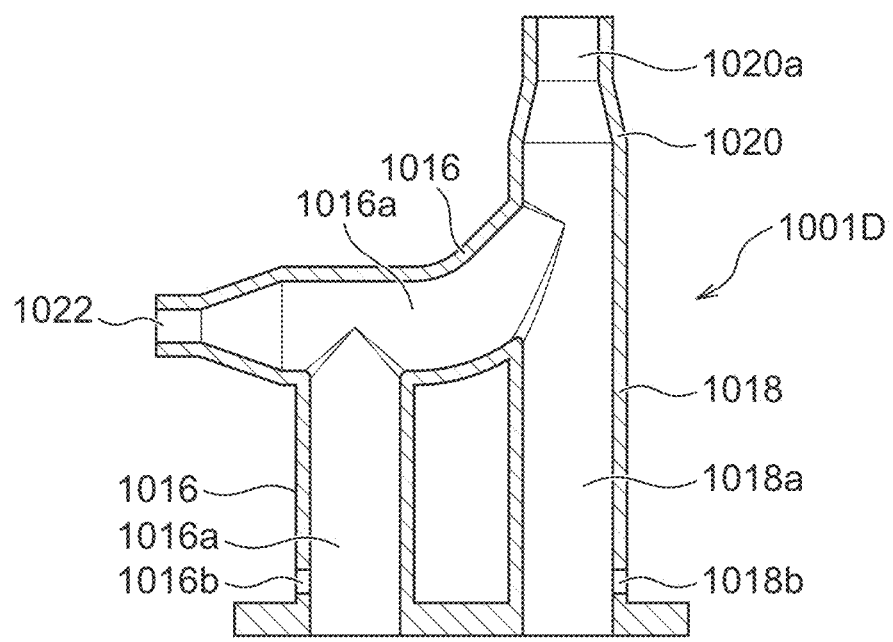
FIG. 55 is a side cross-section view showing another example of the mouthpiece.

FIG. 55 is a side cross-section view showing another example of the mouthpiece 1001D. The mouthpiece 1001D shown in FIG. 55 is different, when compared with the mouthpiece 1001D shown in FIG. 54, in the point that it comprises an air inlet 1022 communicating with the first flow path 1016*a*. In the mouthpiece 1001D shown in FIG. 55, the first pipeline 1016 also comprises at least a part which is curved, and the second pipeline 1018 is also formed to have an approximately straight shape. Thus, the aerosol including coarse particles, in the aerosol passing through the first flow path 1016*a*, collides with a wall surface of the first pipe line 1016 and is trapped thereby. Also, even if the particles of the aerosol generated from the second liquid are coarse particles, trapping of aerosol by each of wall surfaces of the second pipe line 1018 and the third pipe line 1020 can be suppressed. For holding the collided particles in the aerosol, it is preferable that the wall surface of the first pipe line 1016 is provided with porous material such as a fibrous packed bed, a granular packed bed, a sponge, a sintered body, and so on, or the wall surface itself is formed by use of porous material.

Figure 56:
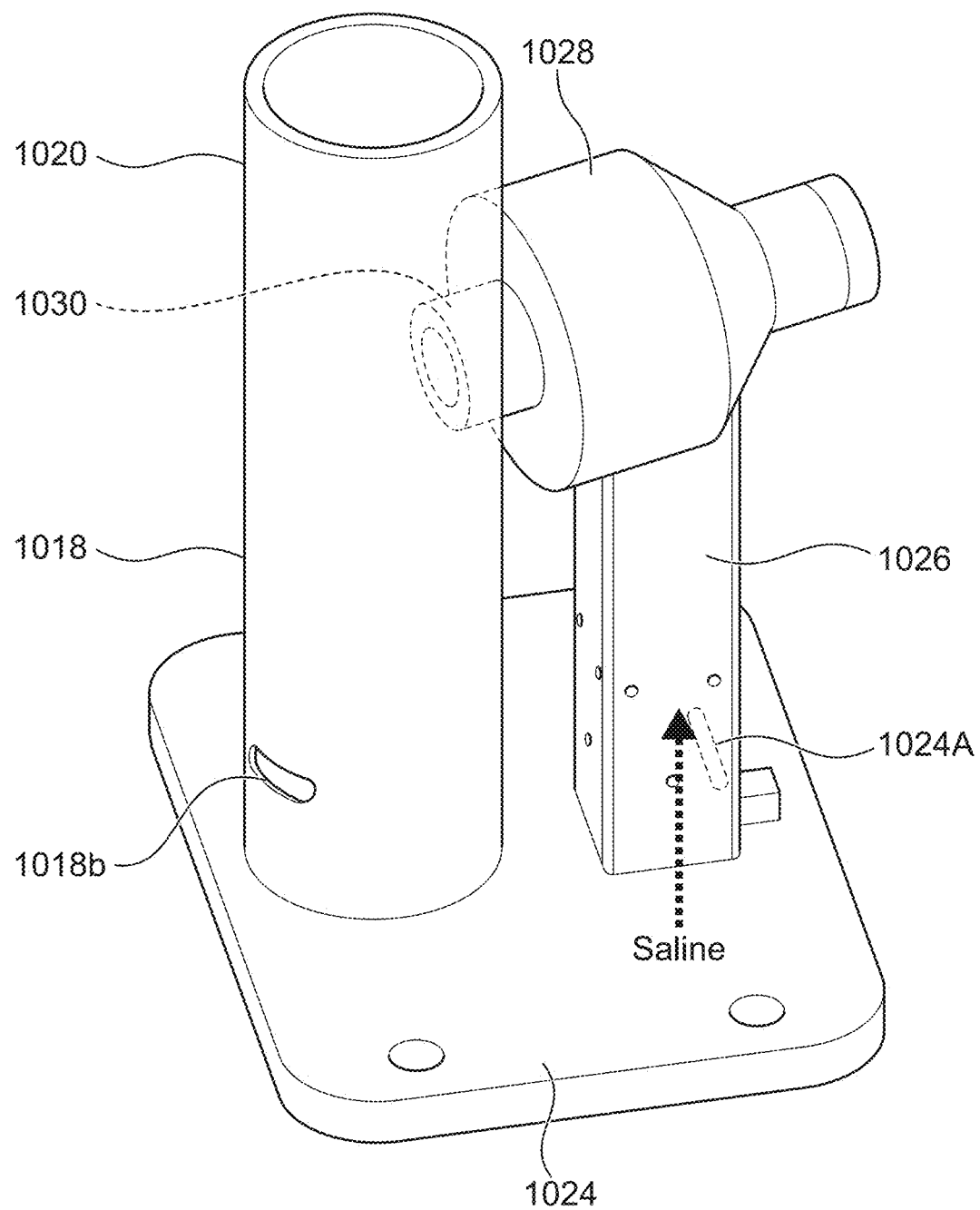
FIG. 56 is a perspective view showing a further example of the mouthpiece.

FIG. 56 is a perspective view showing a further example of the mouthpiece 1001D. As shown in FIG. 56, the mouthpiece 1001D comprises a base part 1024 which is connected to the atomizing unit 1100 shown in FIG. 51 and so on, an air flow path part 1026 extending upwardly from the base part 1024, a separation part 1028 connected to the air flow path part 1026, and an air outlet 1030. In the air flow path part 1026, an air inlet 1024A is formed for supplying air to an air flow path, which is not shown in the figure, of the air flow path part 1026.

The mouthpiece 1001D shown in FIG. 56 comprises a flow path in which the aerosol flown into the mouthpiece 1001D as a result of inhaling action performed by a user swirls while the aerosol passes through the flow path, and is guided to the air outlet 1030. Specifically, air flowing in from the air inlet 1024A during inhaling action performed by a user takes therein the aerosol generated in the atomizing unit 1100, and arrives at the separation part 1028 via an air flow path, which is not shown in the figure, in the air flow path part 1026. Note that the first aerosol, which is generated in the atomizing unit 1100 from the first liquid may pass through the air flow path, which is not shown in the figure, in the air flow path part 1026. In the separation part 1028, aerosol including coarse particles is trapped by swirling the aerosol, and aerosol including submicron particles flows out of the air outlet 1030.

Further, the mouthpiece 1001D shown in FIG. 56 comprises the second pipe line 1018 through which the second aerosol, which is generated in the atomizing unit 1100 from the second liquid, may pass through. In the present modified example, the second pipe line 1018 extends, in an orthogonal direction, from the base part 1024. The second pipe line 1018 is in fluid communication with the air outlet 1030, and aerosol including submicron particles, in the first aerosol, flows into the second pipe line 1018 from the air outlet 1030. The third pipe line 1020 is that extending from the second pipe line 1018, and aerosol including submicron particles, in the first aerosol, and the second aerosol pass through the third pipe line 1020.

Figure 57:
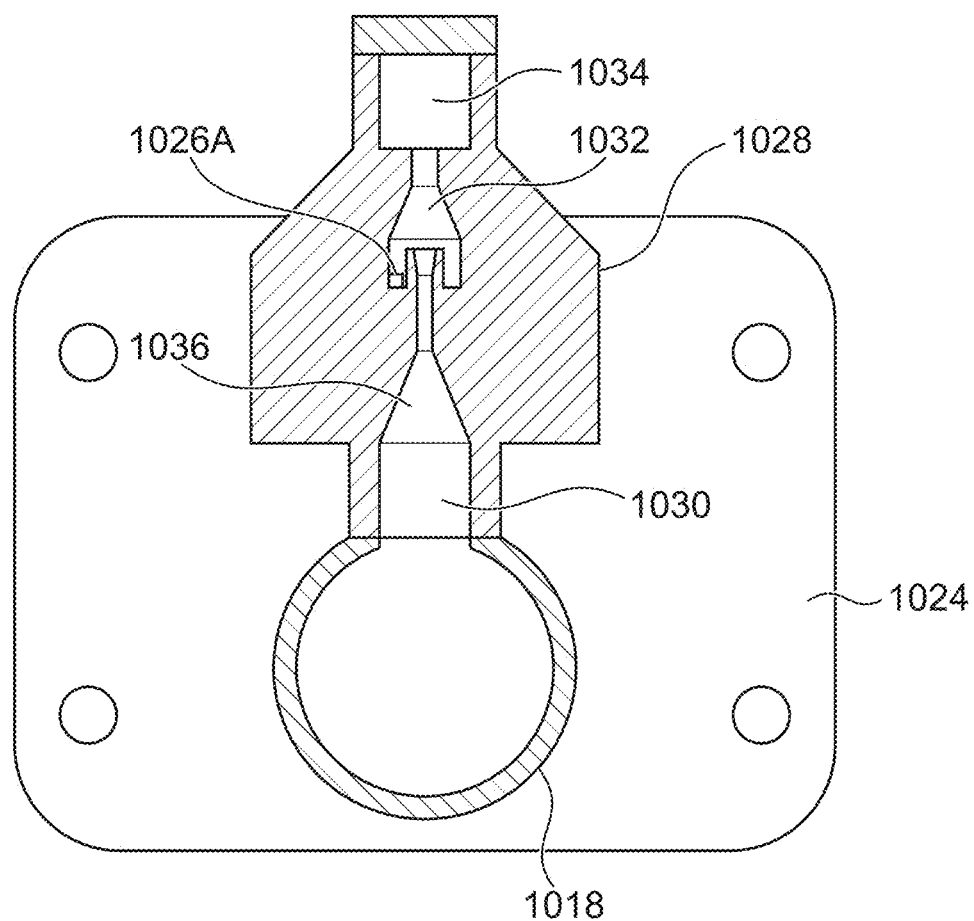
FIG. 57 is a schematic drawing of the mouthpiece wherein cross sections of the separation part and the air outlet shown in FIG. 56 are shown.

FIG. 57 is a schematic drawing of the mouthpiece 1001D wherein cross sections of the separation part 1028 and the air outlet 1030 shown in FIG. 56 are shown. The separation part 1028 comprises a cone part 1032 which communicates with an air flow path 1026A of an air flow path part 1026, a trap part 1034 which communicates with a tip part (a smaller-diameter side) of the cone part 1032, and an outflow part 1036 which communicates with a rear end part (a larger-diameter side) of the cone part 1032. Aerosol flowing into the separation part 1028 from the air flow path 1026A swirls in the cone part 1032. At that time, aerosol including coarse particles is separated from the flow of air, trapped by a wall surface of the cone part 1032, and the trapped liquid is finally dropped into the trap part 1034 and held therein. On the other hand, aerosol including submicron particles does not adhere to the wall surface of the cone part 1032 even if the aerosol is made to swirl, and flows into the second pipe line 1018 from the air outlet 1030 along with the flow of air.

The mouthpiece 1001D shown in each of FIG. 54 to FIG. 56 may be provided with at least one of the impactor 721 explained in relation to FIG. 46 and the filter 725 explained in relation to FIG. 47 (each of which corresponds to an example of a trap member), in an appropriate manner. Then, coarse particles can be trapped in a more appropriate manner. It is preferable that the impactor 721 is formed by use of porous material such as a fibrous packed bed, a granular packed bed, a sponge, a sintered body, and so on, for holding collided particles of aerosol.

Figure 58:
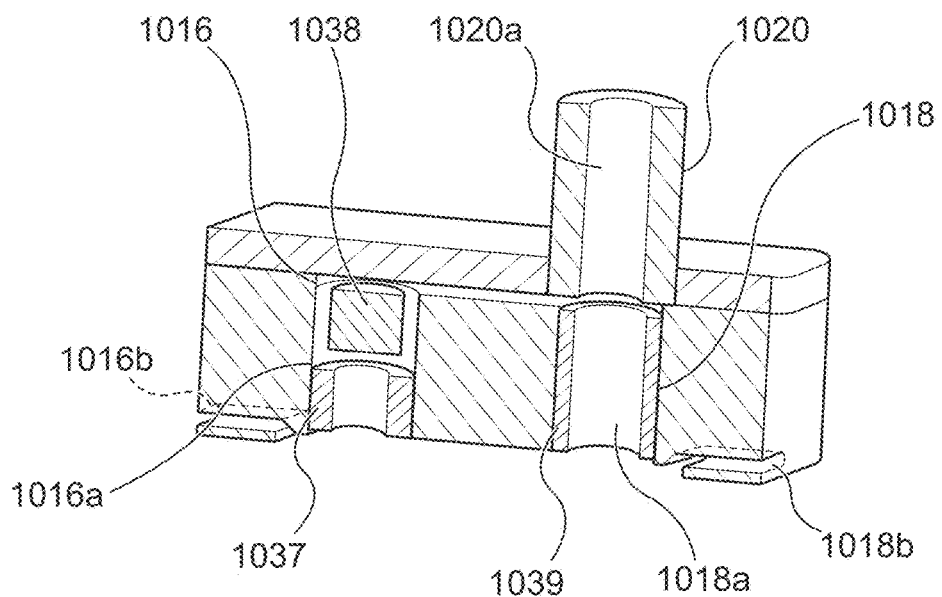
FIG. 58 is a side cross-section view showing a still further example of the mouthpiece.
Figure 59:
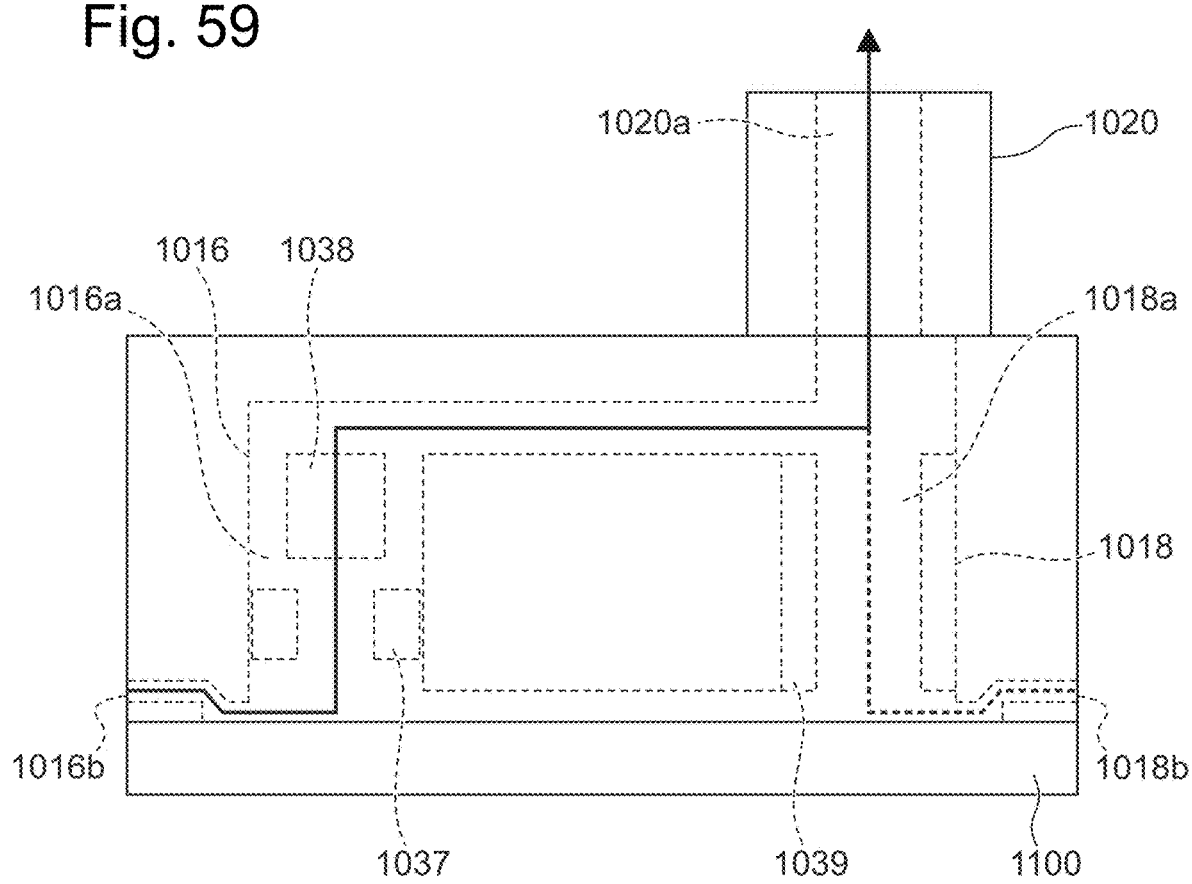
FIG. 59 is a schematic side view showing the flow of air passing through the mouthpiece shown in FIG. 58.

FIG. 58 is a side cross-section view showing a still further example of the mouthpiece 1001D. FIG. 59 is a schematic side view showing the flow of air passing through the mouthpiece 1001D shown in FIG. 58. In FIG. 59, the flow of air flowing in form a first air inlet 1016*b* and a second air inlet 1018*b* is shown by use of an arrow. Similarly to the mouthpiece 1001D shown in FIG. 54, the mouthpiece 1001D shown in FIG. 58 and FIG. 59 comprises a first pipeline 1016 which comprises at least a part which is curved, a second pipeline 1018 which is approximately straight, and a third pipe line 1020. The first pipeline 1016 communicates with the first opening part 1102 of the first cover 1106 shown in FIG. 51, and the second pipeline 1018 communicates with the second opening part 1104. That is, the first pipe line 1016 defines a first flow path 1016a through which the first aerosol, which is generated by atomizing the first liquid, passes mainly. Also, the second pipe line 1018 defines a second flow path 1018a through which the second aerosol, which is generated by atomizing the second liquid, passes mainly. Also, regarding a third flow path 1020a which is defined by the third pipe line 1020, the first aerosol and the second aerosol flow into each other in it and pass through it.

Further, the first flow path 1016a in the mouthpiece 1001D shown in FIG. 58 and FIG. 59 is provided with an air flow accelerating member 1037 and a trap member 1038 positioned at a downstream side of the air flow accelerating member 1037. The air flow accelerating member 1037 can reduce the flow path of the first flow path 1016a, so that the flow velocity of the first aerosol flowing toward the trap member 1038 can be increased. The trap member 1038 is arranged at position whereat the first aerosol passed through the air flow accelerating member 1037 collides, and to have a gap in terms of a cross section of the first flow path 1016a. In the example shown in the figure, the air flow accelerating member 1037 is formed by use of a porous fibrous layer filter having a through hole at the center thereof (a center hall filter) or the like, and the trap member 1038 is formed by use of a solid porous fibrous layer filter (a super slim filter) or the like.

The second flow path 1018a is provided with an air flow accelerating member 1039 which has a hole at the center part thereof. For example, the air flow accelerating member 1039 lies along the whole length of the second flow path 1018a, and has an inner diameter larger than that of the air flow accelerating member 1037.

Figure 51:
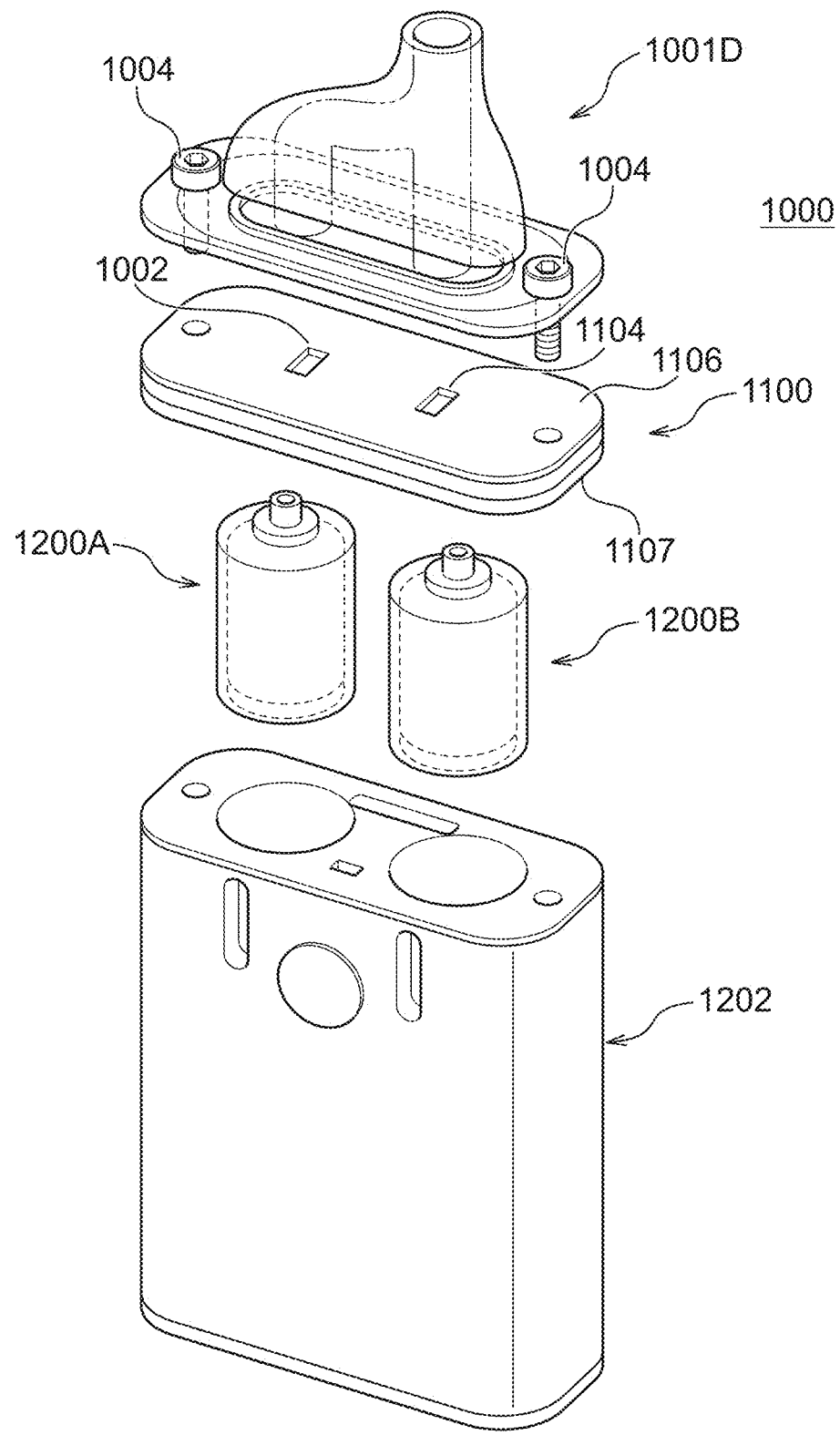
FIG. 51 is an exploded perspective view of the unit shown in FIG. 49.

As shown by use of the arrow in FIG. 59, the air flowing in from the first air inlet 1016b (not shown in FIG. 58) takes therein the first aerosol from the first opening part 1102 shown in FIG. 51, and flows into the first flow path 1016a. The air flowing in from the second air inlet 1018b takes therein the second aerosol from the second opening part 1104 shown in FIG. 51, and flows into the second flow path 1018a.

A part of aerosol including coarse particles, in the first aerosol flown into the first flow path 1016a, is trapped by an inner surface of the air flow accelerating member 1037 when the aerosol passes through the air flow accelerating member 1037 which is formed by use of a filter. Also, the flow velocity of the first aerosol passed through the air flow accelerating member 1037 is increased by the air flow accelerating member 1037, and the first aerosol collides with the trap member 1038. As a result, aerosol including coarse particles, in the first aerosol, is trapped by the trap member 1038, and, on the other hand, aerosol including submicron particles is not trapped by the trap member 1038, so that it passes through the gap between the trap member 1038 and the wall surface of the first pipe line 1016, and arrives at the third flow path 1020a. By increasing the flow velocity of the first aerosol by use of the air flow accelerating member 1037, efficiency of inertial trapping of aerosol, which includes coarse particles, in the trap member 1038 can be improved.

As shown in the figure, since the second pipe line 1018 is formed to have an approximately straight shape, trapping of the second aerosol, which includes coarse particles and flows into the second flow path 1018a, at a wall surface of the second pipeline 1018 (inner wall of the air flow accelerating member 1039) is suppressed, so that the second aerosol can arrive at the third pipe line 1020. Note that the air flow accelerating member 1037, the trap member 1038, and the air flow accelerating member 1039 may be formed by use of porous material such as a fibrous packed bed, a granular packed bed, a sponge, a sintered body, and so on.

Figure 60:
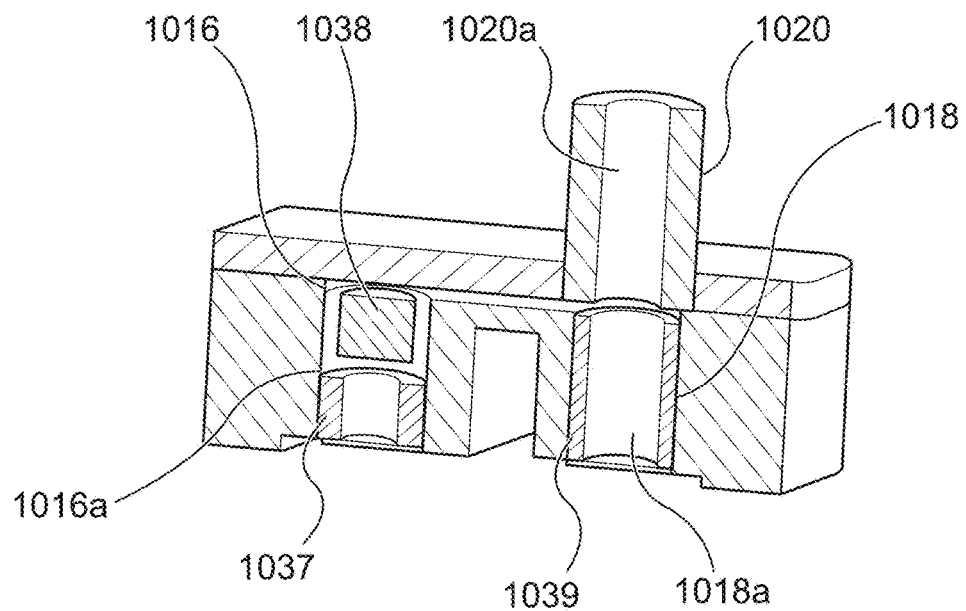
FIG. 60 is a side cross-section view showing a still further example of the mouthpiece.
Figure 61:
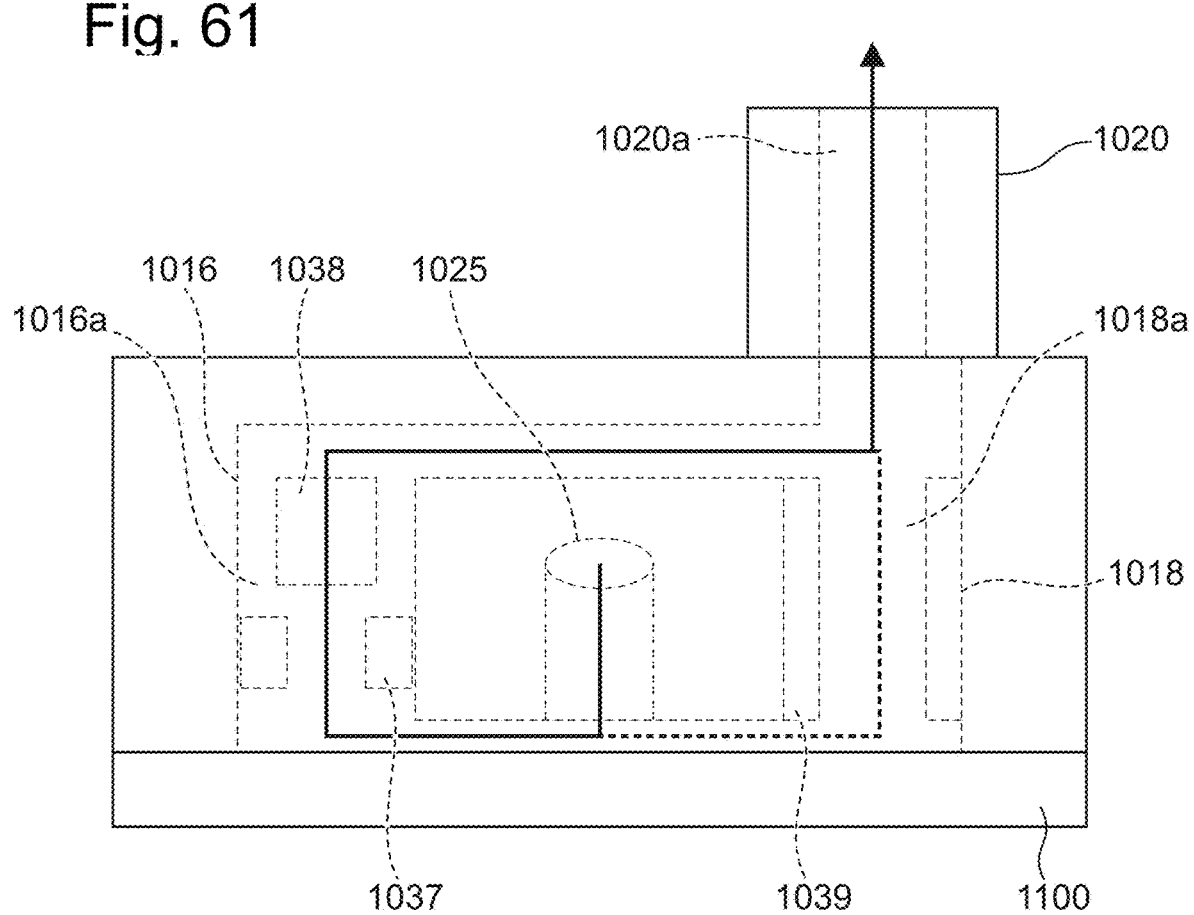
FIG. 61 is a schematic side view showing the flow of air passing through the mouthpiece shown in FIG. 60.

FIG. 60 is a side cross-section view showing a still further example of the mouthpiece 1101D. FIG. 61 is a schematic side view showing the flow of air passing through the mouthpiece shown in FIG. 60. The mouthpiece 1001D shown in FIG. 60 and FIG. 61 is different, when compared with the mouthpiece 1001D shown in FIG. 58 and FIG. 59, in the point that the air inlet for supplying air to the mouthpiece 1001D of the former is different from that of the latter. Specifically, the mouthpiece 1001D shown in FIG. 60 and FIG. 61 comprises an air inlet 1025 positioned between a first pipe line 1016 and a second pipe line 1018, instead of the first air inlet 1016b and the second air inlet 1018b.

The air inlet 1025 goes through the mouthpiece 1001D from a surface at a front side to a surface at a rear side of the mouthpiece 1001D, when the sheet showing FIG. 61 is viewed from the front. Also, as shown in FIG. 61, the air inlet 1025 communicates with the first flow path 1016a of the first pile line 1016 and the second flow path 1018a of the second flow path 1018. A part of the air flowing in from the air inlet 1025 takes therein the first aerosol from the first opening part 1102 shown in FIG. 51, and flows into the first flow path 1016a. Also, the remaining part of the air flowing in from the air inlet 1025 takes therein the second aerosol from the second opening part 1104 shown in FIG. 51, and flows into the second flow path 1018a. Further, in the case of the present example, an opening which is different from the first opening part 1102 and the second opening part 1104 may be formed on the first cover 1106 shown in FIG. 51 and FIG. 53, and air taken from the air inlet 1025 may be made to be flown into the inside of the first cover 1106, made to pass on the surface of the IDT (the pair of interlocking comb-shaped metallic electrodes 1033), and, thereafter, made to flow through the first opening part 1102 and the second opening part 1104. By causing the air to flow as explained above, adhesion of the aerosol, which is generated by the edge 1031A and the edge 1031B, to the IDT can be more reliably prevented. Note that, the flow of air explained above is not limited to that in the case of the mouthpiece 1001D shown in FIG. 61, and it may be adopted in other mouthpieces 1001D.

The mouthpieces 1001D shown in FIG. 54 to FIG. 61 are explained as those having the third pipe lines 1020; however, the constructions thereof are not limited to those explained above. That is, each of the mouthpieces 1001D shown in FIG. 54 to FIG. 61 may be constructed in such a manner that it does not comprise the third pipe line 1020, and the first aerosol passing through the first pipe line 1016 and the second aerosol passing through the second pipe line 1018 arrive at the mouth of a user independently from each other. Further, regarding the twenty-fourth modification, although it is explained that the second liquid is atomized by use of energy of a surface acoustic wave in the IDT, the construction is not limited to the above, and the second liquid may be atomized by use of another appropriate method such as that using an existing mesh nebulizer or the like. Further, the first cover 1106 and the second cover 1107 shown in FIG. 51 to FIG. 53 may be formed by use of metal, for suppressing emission of EMC.

<Experiment 1>

An experiment for measuring diameter distribution with respect to aerosol passed through the first flow path 1016a and the third flow path 1020a in the mouthpiece 1001D shown in FIG. 58 and FIG. 59 was conducted. In the experiment, the flow rate of the aerosol was set to 55 ml/3 s, and a solution including 96 wt % of water, 2 wt % of malic acid, and 2 wt % of nicotine was adopted as the aerosol source. Spraytech which is available from Malvern corporation was used as the measurement device. Further, an experiment in which the air flow accelerating member 1037 and the trap member 1038 are not used, an experiment in which the air flow accelerating member 1037 having an inner diameter of 2.0 mm is used, and an experiment in which the air flow accelerating member 1037 having an inner diameter of 3.2 mm is used, in the mouthpiece 1001, were conducted.

Figure 62:
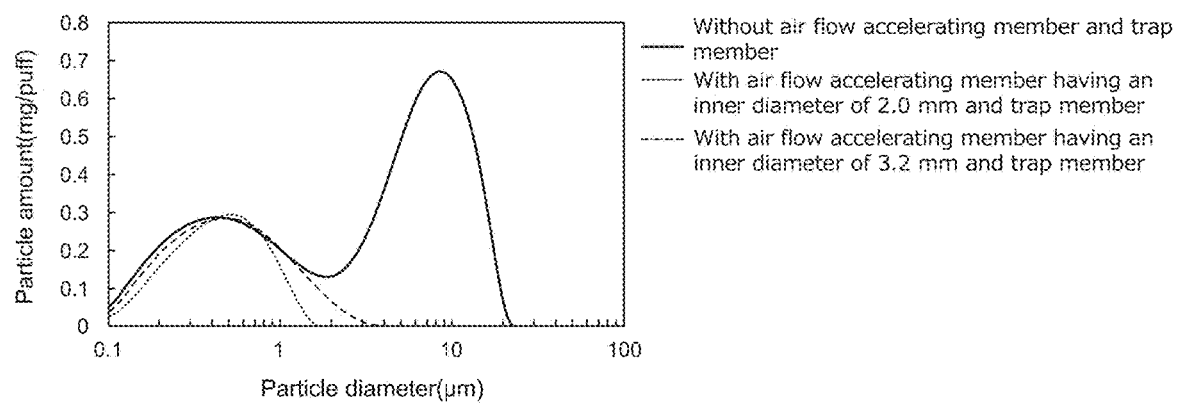
FIG. 62 is a graph showing a result of measurement of diameter distribution with respect to aerosol in experiment 1.

FIG. 62 is a graph showing a result of measurement of diameter distribution with respect to aerosol in experiment 1. Note that the vertical axis in FIG. 62 shows weight distribution, that is a result of transformation from volume distribution, when it is assumed that an integrated value of volume distribution of all aerosol particle diameters corresponds to weight of the aerosol inhaled by a single inhaling action. Note that the weight of the aerosol inhaled by a single inhaling action was evaluated by trapping, by a filter, aerosol outputted when the inhaling action is performed in such a manner that a quantity of 55 ml is inhaled during a period of 3 seconds with constant inhaling velocity, and calculating a difference between the weight before the inhaling action and the weight after the inhaling action. As shown in FIG. 62, in the case that the air flow accelerating member 1037 and the trap member 1038 are not used in the mouthpiece 1001D, a peak of the diameter distribution appeared at a point near 10 microns. On the other hand, in each of the case that the trap member 1038 and the air flow accelerating member 1037 having an inner diameter of 2.0 mm is used and the case that the trap member 1038 and the air flow accelerating member 1037 having an inner diameter of 3.2 mm is used, distribution of particle diameters around 10 microns disappeared. More specifically, in the case that the trap member 1038 and the air flow accelerating member 1037 having an inner diameter of 2.0 mm is used, almost all diameter distribution of 2 microns or more disappeared; and in the case that the trap member 1038 and the air flow accelerating member 1037 having an inner diameter of 3.2 mm is used, almost all diameter distribution of 5 microns or more disappeared. On the other hand, diameter distribution of submicron particles in each case is not very different from those of other cases. Based on the above result of the experiment, it can be understood that aerosol including coarse particles is trapped, and submicron particles are allowed to arrive at the third flow path 1020a, in the case that the trap member 1038 and the air flow accelerating member 1037 are used.

<Experiment 2>

An experiment for verifying degrees of discomfort in a throat, when aerosol passed through the first flow path 1016a and the third flow path 2010a in the mouthpiece 1001D shown in FIG. 58 and FIG. 59 was inhaled, was conducted. In the experiment, a solution including 96 wt % of water, 2 wt % of malic acid, and 2 wt % of nicotine was adopted as the aerosol source; and degrees of discomfort in a throat with respect to each person on a panel including five people, when the person performed inhaling action by use of the mouthpiece 1001D, were verified. Also, similarly to the case of experiment 1, an experiment in which the air flow accelerating member 1037 and the trap member 1038 are not used, an experiment in which the air flow accelerating member 1037 having an inner diameter of 2.0 mm is used, and an experiment in which the air flow accelerating member 1037 having an inner diameter of 3.2 mm is used, in the mouthpiece 1001, were conducted.

FIG. 63 shows a graph and an evaluation sheet showing degrees of discomfort in the throat. Regarding discomfort in the throat, the strength of discomfort in the throat, that was felt by each person on the panel when the person inhaled aerosol, was evaluated by use of the evaluation sheet shown in FIG. 63. Specifically, discomfort in the throat in the case that each of the five people on the panel inhaled aerosol by use of the mouthpiece 1101D which uses neither the air flow accelerating member 1037 nor the trap member 1038 was evaluated, and discomfort in the throat with respect to each of the other examples was also evaluated. In addition to the positions on the evaluation sheet where numbers are written, each person on the panel can enter a recording mark on any position, such as a position between the numbers 2 and 3, for example. In analysis of the result, positions of recorded marks are measured by use of a ruler, and are converted to numerical values. Each error bar in the graph in FIG. 63 shows a confidence interval with respect to a population mean when the confidence level is 95%.

Note that, in the experiment, a solution including 2 wt % of nicotine, 2 wt % of malic acid, and 96 wt % of water was used, and it was atomized by supplying electric power of 11 W with a resonant frequency of 23.9 MHz. The parts shown in FIGS. 60 and 61 were used in the mouthpiece 1101D. The quantity of the solution to be supplied during atomization was set to 5 mg/sec, and each subject inhaled the atomized aerosol for arbitrary length of time, and performed evaluation with respect to the degree of discomfort felt during the time.

As shown by the graph in FIG. 63, in each of the case that the air flow accelerating member 1037 having an inner diameter of 2.0 mm is used and the case that the air flow accelerating member 1037 having an inner diameter of 3.2 mm is used, the degree of discomfort in the throat was significantly lowered, compared with the case that air flow accelerating member 1037 and the trap member 1038 were not used in the mouthpiece 1101D; thus, it can be stated that the above two cases are preferable in terms of feeling of fragrance inhaling taste.

Regarding the case of FIG. 63, note that, in the case that the air flow accelerating member 1037 and the trap member 1038 are used, the quantity of nicotine inhaled per unit time is reduced, compared with the case that the air flow accelerating member 1037 and the trap member 1038 are not used. For evaluating the effect due to the above matter, concentration of nicotine in the solution, which was used, was adjusted in such a manner that the quantity of nicotine inhaled per unit time was set to be the same, and evaluation was performed; however, as a result, the tendency shown in FIG. 63 was not changed (not shown in the figure). That is, the size of the particle mainly contributes mainly to the degree of discomfort in the throat, and the degree of discomfort in the throat can be lowered by reducing coarse particles.

As explained above, according to experiment 1, aerosol including coarse particles is trapped, and submicron particles are allowed to arrive at the third flow path 1020a, in the case that air flow accelerating member 1037 and the trap member 1038 are used. Accordingly, in experiment 2, it can be understood that, in the case that air flow accelerating member 1037 and the trap member 1038 are used, aerosol including coarse particles is trapped, and submicron particles are allowed to arrive at the third flow path 1020*a*, thus, arrive at the mouth of a user. Also, in experiment 2, in the case that air flow accelerating member 1037 and the trap member 1038 are used, discomfort in the throat can be remarkably reduced, and desirable fragrance inhaling taste can be obtained. That is, it can be stated that, by using the flow accelerating member 1037 and the trap member 1038 in the mouthpiece 1001D, aerosol including coarse particles is trapped, and, as a result, discomfort in the throat is remarkably reduced.

In general, it has been known that the size of a particle emitted from a cigarette when it is burned is approximately 0.2 microns. On the other hand, as explained above, the aerosol generated by the atomizing unit 1100 relating to the twenty-fourth modification includes coarse particles, each having the size of approximately 10 microns, in addition to submicron particles. Thus, by adopting the mouthpiece 1001D shown in FIG. 58 in the unit 1000 relating to the twenty-fourth modification, submicron particles are allowed to arrive at the mouth of a user while the coarse particles are remarkably reduced. As a result, fragrance inhaling taste similar to that obtainable from a burned cigarette can be obtained. Note that since the mouthpieces 1001D shown in FIG. 54 to FIG. 57 can also deliver submicron particles into the mouth of a user while reducing the coarse particles, the mouthpieces can provide fragrance inhaling taste similar to that provided by the mouthpiece 1001D shown in FIG. 58.

Twenty-Fifth Modification

Regarding the twenty-fifth modification, a sensor 1070 for detecting a liquid supplied to the edges 1031A and 1031B in the piezoelectric element substrate 1031 shown in FIG. 52 will be explained. For example, based on result of detection by the sensor 1070, the controller 400 shown in FIG. 1 may drive the motors 1208A and 1208B which are liquid suppliers and are shown in FIG. 50, and control the supply speeds of the liquids and the supply quantities of the liquids that are supplied from the first liquid storage unit 1200A and the second liquid storage unit 1200B to the edges 1031A and 1031B, respectively. A sufficient atomizing amount cannot be obtained in the case that the quantities of liquids supplied to the edges 1031A and 1031B are small; and the particle diameters in atomized aerosol become large in the case that the quantities of liquids supplied to the edges 1031A and 1031B are large. Specifically, at that time, aerosol which includes extra-large particles, each of which is larger than a coarse particle and has a diameter of approximately 100 microns, and particles, each of which has a diameter larger than that of an extra-large particle, is generated. Thus, by controlling operation of the liquid suppliers by the controller 400 based on result of detection by the sensor 1070, certain quantities of liquids can be supplied to the edges 1031A and 1031B in the piezoelectric element substrate 1031. As a result, a sufficient atomizing amount can be realized, and generation of aerosol having a particle diameter larger than that of a coarse particle can be prevented.

Figure 64:
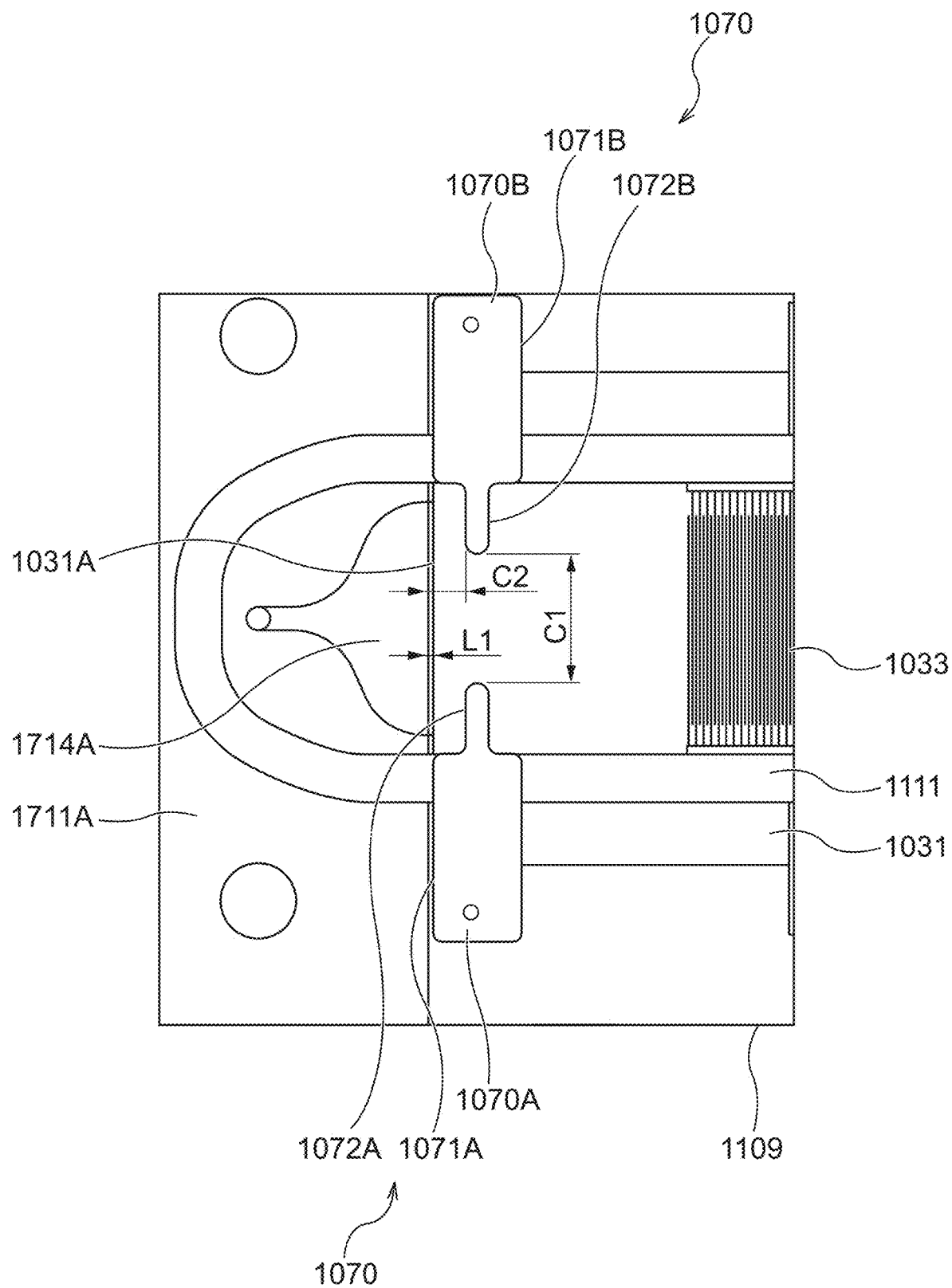
FIG. 64 is an enlarged view of a part extracted from the atomizing unit shown in FIG. 52.

FIG. 64 is an enlarged view of a part extracted from the atomizing unit 1100 shown in FIG. 52. Specifically, FIG. 64 illustrates the PCB board 1109, the piezoelectric element substrate 1031 comprising the pair of interlocking comb-shaped metallic electrodes 1033, the guide wall 1711A, the seal member 1111, and the sensor 1070 in the atomizing unit 1100 shown in FIG. 52.

In FIG. 64, the sensor 1070 comprises a pair of sensor electrodes (detection part) 1070A and 1070B which are opposite to each other. The sensor electrodes 1070A and 1070B are constructed by use of a metal such as gold-plated copper, for example. Also, the sensor electrodes 1070A and 1070B are attached to the PCB board 1109, and electrically connected to contacts formed on the PCB board 1109. In this regard, the sensor electrodes 1070A and 1070B are positioned above the piezoelectric element substrate 1031, with the seal member 1111 positioned between the sensor electrodes 1070A and 1070B and the piezoelectric element substrate 1031. For example, the sensor electrodes 1070A and 1070B are positioned in such a manner that they are separated by 0.1 mm (±0.05 mm) from the surface of the piezoelectric element substrate 1031. In the case that the sensor electrodes 1070A and 1070B are positioned on the surface of the piezoelectric element substrate 1031, there are risks that the sensor electrodes 1070A and 1070B may peel off, and relative positions of the sensor electrodes 1070A and 1070B may shift, due to vibration caused by a SAW that propagates through the piezoelectric element substrate 1031. Thus, by separating the sensor electrodes 1070A and 1070B from the surface of the piezoelectric element substrate 1031, peeling off of the sensor electrodes 1070A and 1070B and shifting of relative positions of the sensor electrodes 1070A and 1070B can be prevented, and accurate result of detection can be obtained.

The sensor electrode 1070A comprises a base part 1071A which has a rectangular shape and has one end side electrically connected to a contact formed on the PCB board 1109, and a convex part 1072A which projects toward the sensor electrode 1070B from the other end side of the base part 1071A. On the other hand, the sensor electrode 1070B comprises a base part 1071B which has a rectangular shape and has one end side electrically connected to a contact formed on the PCB board 1109, and a convex part 1072B which projects toward the sensor electrode 1070A from the other end side of the base part 1071B. Note that each of the base parts 1071A and 1071B may have a shape other than a rectangular shape. The convex parts 1072A and 1072B are positioned adjacent to the edge 1031A to which liquid is supplied, and are electrically connected by the liquid supplied from the edge 1031A. The sensor 1070 outputs, as detection result, the conductivity of the electric signal corresponding to the quantity of the liquid between the convex part 1072A and the convex part 1072B. The conductivity of the electric signal outputted from the sensor 1070 becomes large as the quantity of the liquid supplied to the edge 1031A becomes large. Thus, it is possible to judge, based on the magnitude of the conductivity of the electric signal, the state that an appropriate quantity of the liquid is supplied to the edge 1031A, the state that an excessive quantity of the liquid is supplied to the edge 1031A, and the state that the quantity of the liquid supplied to the edge 1031A is insufficient.

In the case that the controller 400 has judged, based on the conductivity of the electric signal outputted from the sensor 1070, that an excessive quantity of the liquid has been supplied to the edge 1031A, it drives the motor 1208A to reduce the liquid supply speed and/or the liquid supply quantity of the liquid supplied from the first liquid storage unit 1200A to the edge 1031A. Further, in the case that the controller 400 has judged, based on the conductivity of the electric signal outputted from the sensor 1070, that the quantity of the liquid supplied to the edge 1031A is insufficient, it drives the motor 1208A to increase the liquid supply speed and/or the liquid supply quantity of the liquid supplied from the first liquid storage unit 1200A to the edge 1031A. As a result, a certain appropriate quantity of the liquid can be supplied to the edge 1031A, so that a sufficient atomizing amount can be realized, and generation of aerosol having particle diameters larger than those of coarse particles can be prevented. Note that, although the edge 1031A side is extracted and shown in FIG. 64, the edge 1031B side also has a construction similar to that of the edge 1031A side, and the controller 400 drives, based on detection result from the sensor 1070, the motor 1208B in a manner similar to that in the case of the edge 1031A side.

Next, positional relationship between the piezoelectric element substrate 1031 and the sensor electrodes 1070A and 1070B and positional relationship between the piezoelectric element substrate 1031 and the guide wall 1711A will be explained with reference to result of experiments. As shown in FIG. 64, it is defined herein that the space between the top end of the convex part 1072A and the top end of the convex part 1072B is C1; the space between the edge 1031A and the side, at the edge 1031A side, of each of the convex part 1072A and the convex part 1072B is C2; and the space between the edge 1031A and the end surface, at the edge 1031A side, of the guide wall 1711A is L1.

Figure 65:
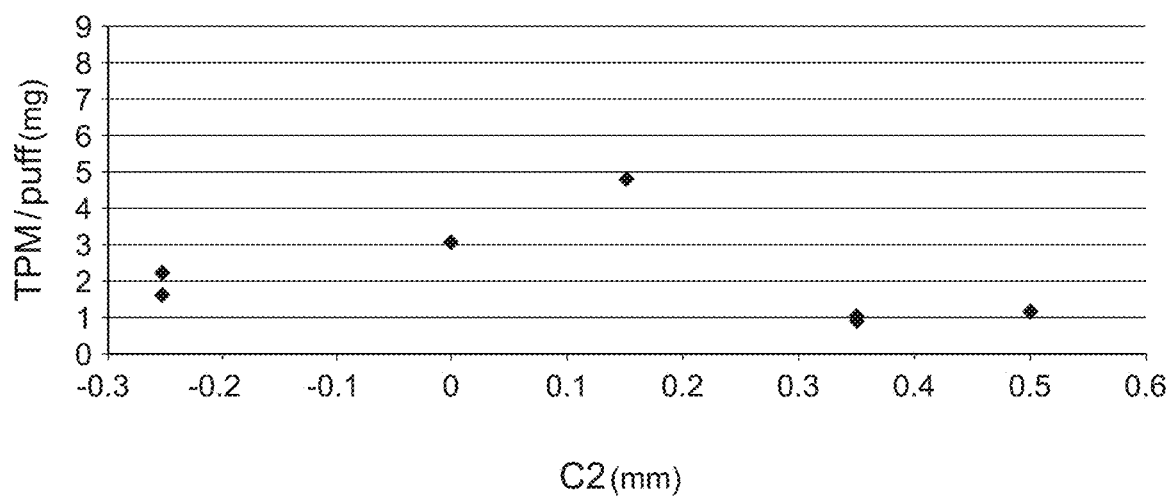
FIG. 65 is a graph showing relationship between the spaces C2 shown in FIG. 64 and the atomizing amounts.

First, the atomizing amounts of aerosol generated in the atomizing unit 1100 were measured, under a condition that the space C1 is set to 4 mm, the space L1 is set to 0.4 mm, and the space C2 is varied. Note that the space C1 may be set in accordance with the output width of the SAW, i.e., the width that the aerosol is generated, to correspond to the overlap length of the pair of interlocking comb-shaped metallic electrodes 1033. In the measurement, electric power of 10 W was supplied to the pair of interlocking comb-shaped metallic electrodes 1033, and the atomizing amounts, when liquid for testing was atomized, were measured, under the state that the top cover 1710 has been removed. FIG. 65 is a graph showing relationship between the space C2 and the atomizing amount. In FIG. 65, the horizontal axis represents the space C2 (mm), and the vertical axis represents an atomizing amount per a single puff TPM/puff (mg). Note that, in the case that the space C2 is a negative value, it means that the convex part 1072A and the convex part 1072B are positioned, across the edge 1031A, on the guide wall 1711A. It can be understood from FIG. 65 that the atomizing amount becomes the maximum at a point where the space C2 is around 0.15 mm. Thus, it is desirable that the space C2 be set to 0.15 mm (±0.05 mm).

Figure 66:
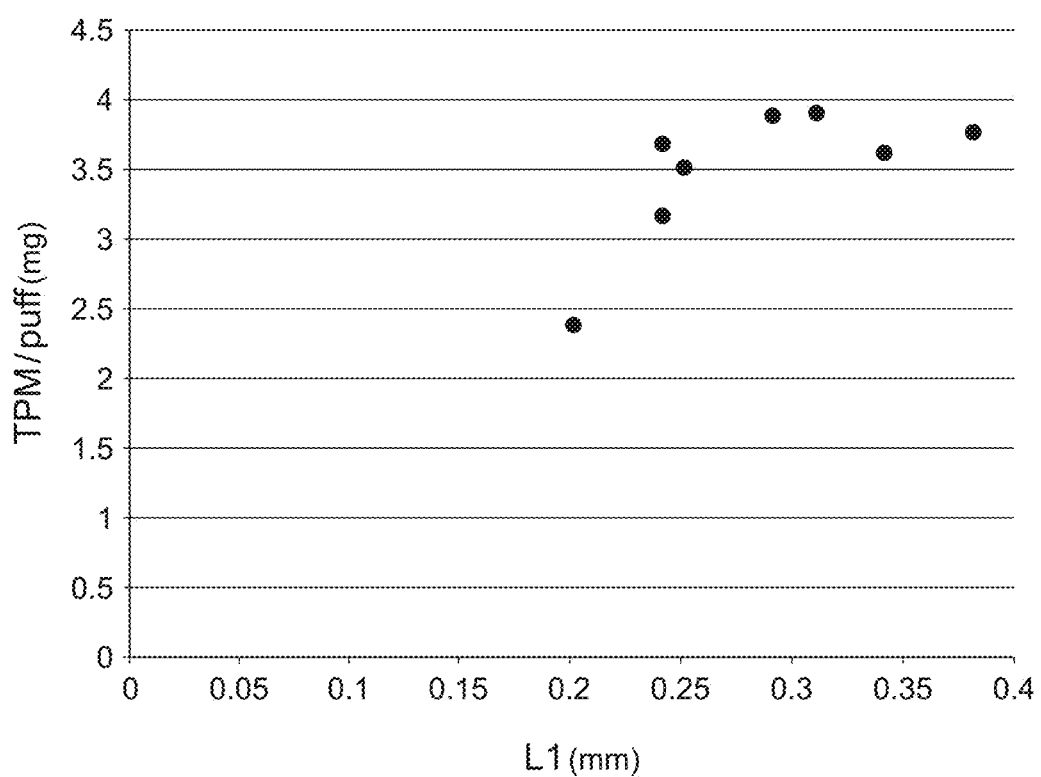
FIG. 66 is a graph showing relationship between the spaces L1 shown in FIG. 64 and the atomizing amounts.

Next, the atomizing amounts of aerosol generated in the atomizing unit 1100 were measured, under a condition that the space C1 is set to 4 mm, the space C2 is set to 0.15 mm, and the space L1 is varied. In the measurement, electric power of 10 W was supplied to the pair of interlocking comb-shaped metallic electrodes 1033, and the atomizing amounts when liquid for testing was atomized were measured, under the state that the top cover 1710 has been removed. FIG. 66 is a graph showing relationship between the space L1 and the atomizing amount. In FIG. 66, the horizontal axis represents the space L1 (mm), and the vertical axis represents an atomizing amount TPM/puff (mg). It can be understood from FIG. 66 that the atomizing amount becomes the maximum in the region where the space L1 is equal to or larger than 0.25 mm. Thus, it is desirable that the space L1 be set to equal to or larger than 0.25 mm.

Note that, although the case that the sensor 1070 is an electric conductivity sensor has been explained with respect to the present modified example, the sensor is not limited to the above, and the emitter-receiver sensor or the capacitive sensor shown in FIGS. 22-25 may be adopted as a sensor for detecting liquid.

Twenty-Sixth Modification A

In the following, a modified example 26A of the embodiment will be explained. In the following, differences between embodiments will be explained mainly.

Regarding the modified example 26A, amplitude of a voltage having a high frequency (this is also referred to as a "high-frequency voltage" in the following explanation of the modified example 26A) applied to the pairs of interlocking comb-shaped metallic electrodes 33 will be explained.

Figure 67:
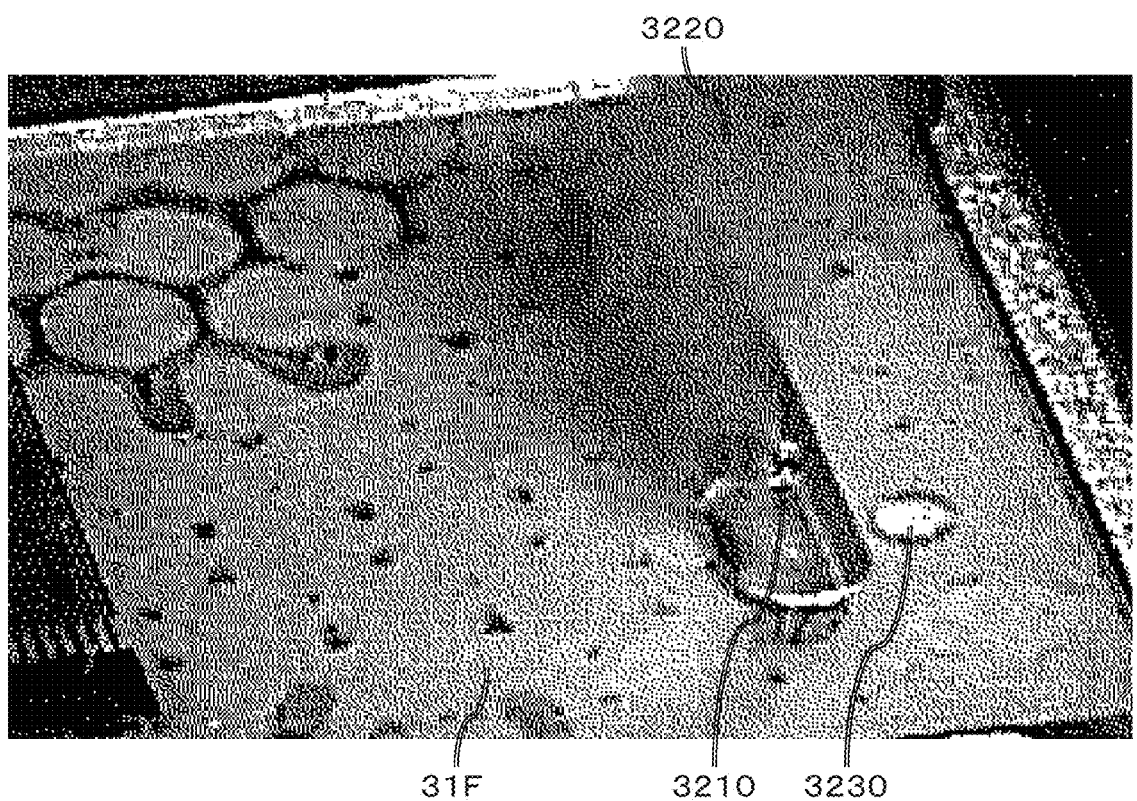
FIG. 67 is figure for explaining twenty-sixth modification A.

Specifically, in the modified example 26A, the controller 400 periodically changes amplitude of a high-frequency voltage applied to the pairs of interlocking comb-shaped metallic electrodes 33. In the case that the amplitude of the high-frequency voltage is set to be constant and is applied, power consumption becomes large, and, due thereto, the piezoelectric element substrate 31 may be overheated; thus, if a configuration for periodically changing the amplitude is adopted, power consumption can be reduced, and damage to the piezoelectric element substrate 31, due to high temperature, can be avoided. Further, according the above configuration, it is possible to suppress scattering by receiving a SAW of a droplet, as a bulk droplet, from liquid, which is guided to the front surface 31F of the piezoelectric element substrate 31. FIG. 67 is an example picture in which a droplet 3210 scattered as a bulk droplet is photographed. Note that 3220 denotes minute particles, and 3230 denotes a droplet adhered to the front surface 31F of the piezoelectric element substrate 31 after it is scattered. By suppressing scattering of a bulk droplet, the liquid can be used effectively, and stable atomization of aerosol can be realized. In detail, when a high voltage is being applied, aerosol is atomized by use of a liquid at a side close to the pairs of interlocking comb-shaped metallic electrodes 33 (the thin film part); and, when a low voltage is being applied, supply of the liquid to the thin film part, that is reduced as a result of atomization, is accelerated. As a result that the above phenomena are repeated in a periodic manner, generation of particles having sizes larger than a predetermined size can be suppressed, and the quantity of atomization of minute particles can be increased (Refer to FIG. 5 and explanations relating thereto, also). Note that it is preferable to repeat application of a high voltage and a low voltage, i.e., it is preferable to repeat increasing and decreasing of amplitude of the high-frequency voltage at a frequency between approximately 50 Hz-500 Hz, more preferably, at a frequency of approximately 100 Hz.

Periodic changing in the amplitude of the high-frequency voltage can be realized by defining the high-frequency voltage applied to the pairs of interlocking comb-shaped metallic electrodes 33 as a wave which is to be modulated, and performing amplitude modulation based on a modulating signal having a predetermined waveform. The controller 400 may comprise a modulating signal generating circuit, a modulation circuit, and so on.

Alternatively, it is possible to realize periodic changing of the amplitude of the high-frequency voltage by use of the controller 400 in such a manner that the amplitude of the high-frequency voltage applied to the pairs of interlocking comb-shaped metallic electrodes 33 is made to be a wave having a predetermined waveform. In such a case, it is not necessary to include a modulating signal generating circuit, a modulation circuit, or the like in the controller 400.

For example, as shown in FIG. 68, the periodic amplitude of the high-frequency voltage, and the above modulating signal which is causes of such a periodic amplitude may draw a sine wave shape, may draw a rectangular wave shape, may draw a triangular wave shape, or may draw a saw tooth wave shape. Especially, it is preferable that a high-frequency voltage be applied in such a manner that the periodic amplitude of the high-frequency voltage draws a rectangular wave shape. The controller 400 can change the amplitude of the high-frequency voltage applied to the pair of interlocking comb-shaped metallic electrodes 33 in such a manner that the change in the amplitude over time corresponds to the shape of a rectangular wave, by providing with, in an alternative manner, a period during which the high-frequency voltage is applied and a period during which the high-frequency voltage is not applied.

In the case that a sine wave is used, the period of the sine wave may be set, by performing numerical calculation or performing an experiment, such that damage to the piezoelectric element substrate 31 due to overheat at the time that the high-frequency voltage is applied to the pair of interlocking comb-shaped metallic electrodes 33 is prevented. In addition or alternatively, the period of the sine wave may be set, by performing numerical calculation or performing an experiment, such that generation of particles having sizes larger than a predetermined size in atomization is suppressed.

In the case that a rectangular wave is used, a duty ratio of the rectangular wave may be set, by performing numerical calculation or performing an experiment, such that damage to the piezoelectric element substrate 31 due to high temperature is prevented, and/or generation, by atomization, of particles having particle sizes larger than a predetermined size is suppressed, when the high-frequency voltage is applied to the pairs of interlocking comb-shaped metallic electrodes 33.

In the case that a triangular wave is used, a slope during an increasing state and a slope during a decreasing state in the triangular wave may be set, by performing numerical calculation or performing an experiment, such that damage to the piezoelectric element substrate 31 due to high temperature is prevented, and/or generation, by atomization, of particles having particle sizes larger than a predetermined size is suppressed, when the high-frequency voltage is applied to the pairs of interlocking comb-shaped metallic electrodes 33.

Note that, in more general, the "slope during an increasing state" can be specified by a ratio between amplitude and a length of a period (this corresponds to p Sin+ in FIG. 68), during which a change occurs in a first direction which is parallel the amplitude (for example, D1 in FIG. 68), in a single period of the triangular wave. Also, in more general, the "slope during a decreasing state" can be specified by a ratio between the amplitude and a length of a period (this corresponds to p Sin– in FIG. 68), during which a change occurs in a second direction opposite to the first direction, in a single period of the triangular wave.

In the case that a saw tooth wave is used, a slope of the saw tooth wave may be set, by performing numerical calculation or performing an experiment, such that damage to the piezoelectric element substrate 31 due to high temperature is prevented, and/or generation, by atomization, of particles having particle sizes larger than a predetermined size is suppressed, when the high-frequency voltage is applied to the pairs of interlocking comb-shaped metallic electrodes 33.

Note that, in more general, a "slope" of a saw tooth wave can be specified by a ratio between a length of a single period of the saw tooth wave and amplitude thereof.

Note that, although the "droplet" scattered as a bulk droplet, which is explained above, includes an extra-large particle having a particle diameter of approximately 100 microns which is larger than that of a coarse particle, and a particle having a particle diameter larger than that of an extra-large particle, the "droplet" is not limited to those explained above. Accordingly, the "predetermine size" with respect to the above explained "particle larger than a predetermined size" may be 100 microns, for example.

At least a part of the controller 400 according to the modified example 26A may be realized by a processor. For example, the controller 400 may comprise a processor and a memory which stores a program, and the program may be that causing the processor to function as at least a part of the controller 400 according to the modified example 26A.

Twenty-Sixth Modification B

In the following, a modified example 26B of the embodiment will be explained. The modified example 26B is a modified version of the modified example 26A; and, in the following, differences from the modified example 26A will be explained mainly.

In the modified example 26A, the amplitude of the high-frequency voltage applied to the pairs of interlocking comb-shaped metallic electrodes 33 is periodically changed; on the other hand, in the modified example 26B, the frequency of the high-frequency voltage applied to the pairs of interlocking comb-shaped metallic electrodes 33 is periodically changed. According to the above configuration, it is possible to suppress scattering by receiving a SAW of a droplet, as a bulk droplet, from liquid, which is guided to the front surface 31F of the piezoelectric element substrate 31. By the above configuration, the liquid can be used effectively, and stable atomization of aerosol can be realized. In detail, when a high-frequency voltage having a frequency relatively close to a resonant frequency is being applied, aerosol is atomized by use of a liquid at a side close to the pairs of interlocking comb-shaped metallic electrodes 33 (the thin film part); and, when a high-frequency voltage having a frequency relatively far from the resonant frequency is being applied, supply of the liquid to the thin film part, that is reduced as a result of atomization, is accelerated. As a result that the above phenomena are repeated in a periodic manner, generation of particles having sizes larger than a predetermined size can be suppressed, and the quantity of atomization of minute particles can be increased (Refer to FIG. 5 and explanations relating thereto, also). Note that it is preferable to repeat frequency changing of the high-frequency voltage at a frequency between approximately 50 Hz-500 Hz, more preferably, at a frequency of approximately 100 Hz.

Periodic changing in the frequency of the high-frequency voltage can be realized by defining the high-frequency voltage applied to the pairs of interlocking comb-shaped metallic electrodes 33 as a wave which is to be modulated, and performing frequency modulation based on a modulating signal having a predetermined waveform. The controller 400 may comprise a modulating signal generating circuit, a modulation circuit, and so on. The modulating signal may draw a sine wave shape, may draw a rectangular wave shape, may draw a triangular wave shape, or may draw a saw tooth wave shape.

In the case that a sine wave is used, the period of the sine wave may be set, by performing numerical calculation or performing an experiment, such that generation, by atomization, of particles having sizes larger than the above predetermined size is suppressed.

In the case that a rectangular wave is used, a duty ratio of the rectangular wave may be set, by performing numerical calculation or performing an experiment, such that generation, by atomization, of particles having sizes larger than the above predetermined size is suppressed.

In the case that a triangular wave is used, a slope during an increasing state and a slope during a decreasing state in the triangular wave may be set, by performing numerical calculation or performing an experiment, such that generation, by atomization, of particles having sizes larger than the above predetermined size is suppressed.

In the case that a saw tooth wave is used, a slope of the saw tooth wave may be set, by performing numerical calculation or performing an experiment, such that generation, by atomization, of particles having sizes larger than the above predetermined size is suppressed.

At least a part of the controller 400 according to the modified example 26B may be realized by a processor. For example, the controller 400 may comprise a processor and a memory which stores a program, and the program may be that causing the processor to function as at least a part of the controller 400 according to the modified example 26B.

Twenty-Sixth Modification C

A modified example 26C is a combination of the modified example 26A and the modified example 26B. That is, in the modified example 26C, the amplitude and the frequency of the high-frequency voltage applied to the pairs of interlocking comb-shaped metallic electrodes 33 are periodically changed. The period for changing the amplitude and the period for changing the frequency may be the same or different.

At least a part of the controller 400 according to the modified example 26C may be realized by a processor. For example, the controller 400 may comprise a processor and a memory which stores a program, and the program may be that causing the processor to function as at least a part of the controller 400 according to the modified example 26C.

Twenty-Sixth Modification D

In the following, a modified example 26D of the embodiment will be explained. In the following, differences between embodiments will be explained mainly.

Regarding the modified example 26D, relationship between a liquid supply speed (µl/sec) of liquid guided to the front surface 31F of the piezoelectric element substrate 31 and output (W) of a SAW generated as a result of application of a high-frequency voltage to the pairs of interlocking comb-shaped metallic electrodes 33 will be explained.

Figure 69:
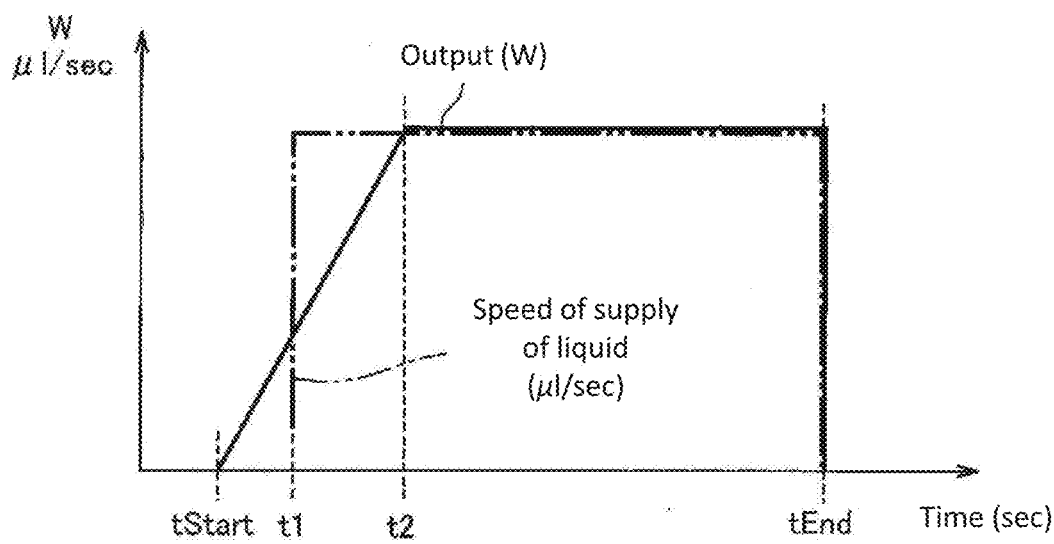
FIG. 69 is figure for explaining twenty-sixth modification D.

First, as shown in FIG. 69, the controller 400 makes the output of the SAW gradually increase from time tStart, such that the output of the SAW reaches a desired level at time t2. The controller 400 makes the output of the SAW be zero at time tEnd. On the other hand, the controller 400 makes the liquid supply speed increase to a desired level at time t1. The controller 400 makes the liquid supply speed be zero at time tEnd. The time t1 may be that between the time tStart and the time t2.

Figure 70:
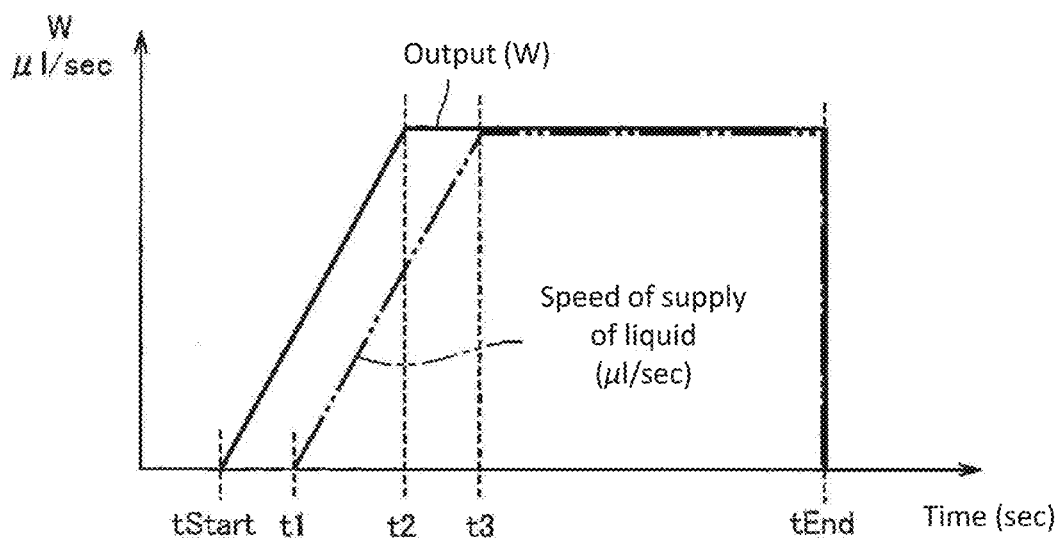
FIG. 70 is figure for explaining twenty-sixth modification D.
Figure 71:
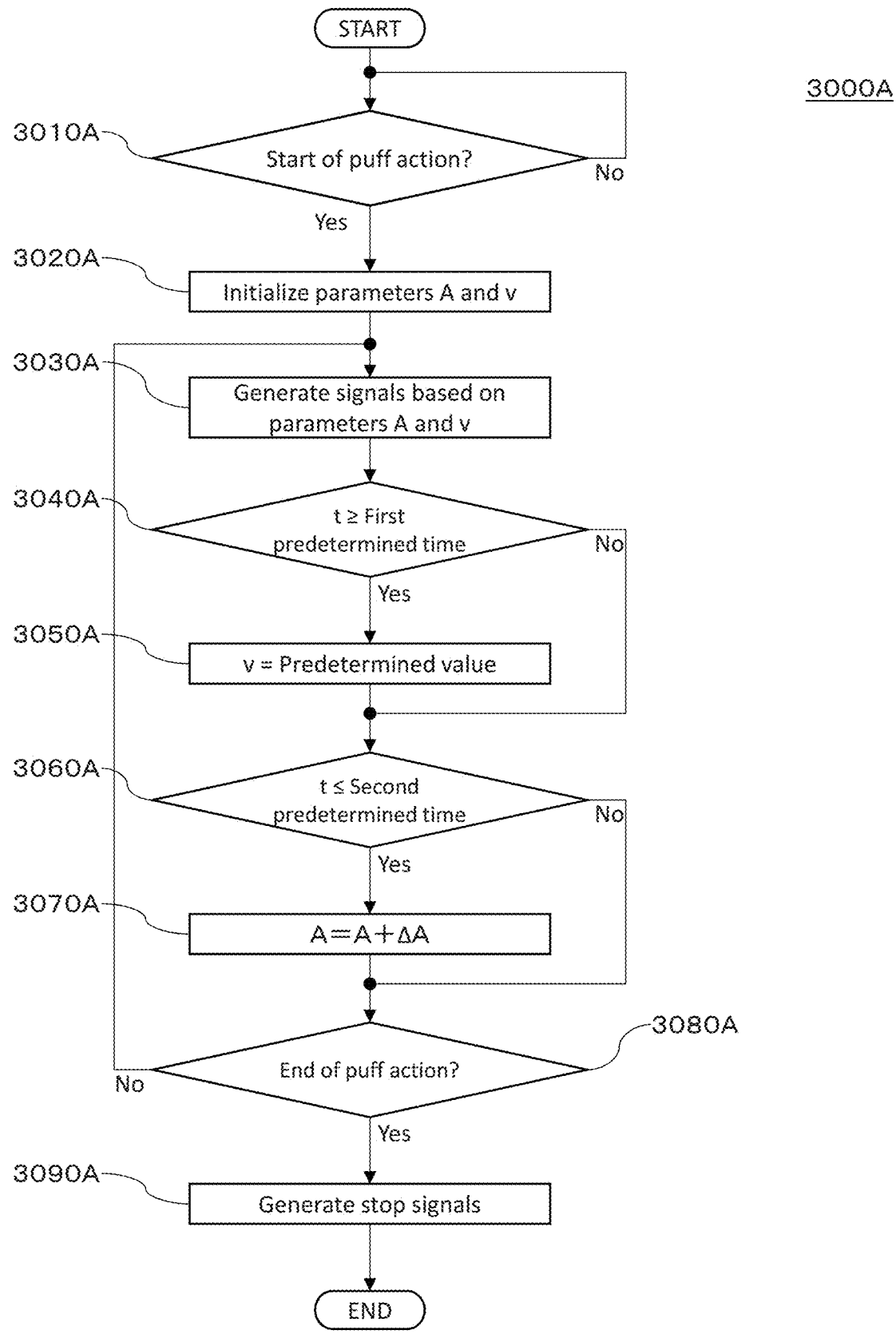
FIG. 71 is figure for explaining twenty-sixth modification D.

Second, as shown in FIG. 70, the controller 400 makes the output of the SAW gradually increase, from time tStart, such that the output of the SAW reaches a desired level at time t2. The controller 400 makes the output of the SAW be zero at time tEnd. On the other hand, the controller 400 makes the liquid supply speed gradually increase, from time t1, such that the liquid supply speed reaches a desired level at time t3. The controller 400 makes the liquid supply speed be zero at time tEnd. The time t1 may be that between the time tStart and the time t2. The time t3 may be that after the time t2.

Note that the time tStart may be the timing when the start of a puff action is detected by the sensor 300, or the timing when a button for performing a puff action is pressed. The time tEnd may be the timing when the end of a puff action is detected by the sensor 300, or timing when a button for performing a puff action, which has been pressed, is released.

As shown in FIG. 69 and FIG. 70, the output of the SAW gradually increases form the time tStart, and increasing of the liquid supply speed is started at the time t1 that is after the time tStart; thus, in an initial stage for increasing the output (W) of the SAW, it is possible to suppress scattering by receiving the SAW of a droplet having a large diameter, i.e., a bulk droplet, from the liquid, which is guided to the front surface 31F of the piezoelectric element substrate 31. Further, as shown in FIG. 70, by gradually increasing the liquid supply speed, scattering of a droplet having a large diameter, i.e., a bulk droplet, can be suppressed.

Note that the modified example 26D deals with the problem that power consumption becomes large in the case that the amplitude of the high-frequency voltage is set to be constant. That is, in the modified example 26D, the SAW output is zero at the time tStart, and it gradually increases to a desired level. This can be realized by changing the amplitude of the high-frequency voltage applied to the pairs of interlocking comb-shaped metallic electrodes 33 to that by which desired SAW output is obtained. Thus, according to the modified example 26D, power consumption becomes smaller, compared with the case that a high-frequency voltage having constant amplitude is applied, such that SAW output having a predetermined level is obtained from the point in time at the time tStart.

FIG. 71 is an example flow chart 3000A for realizing the above-explained process. The respective steps included in the flow chart may be those executed by the controller 400.

Note that the flow chart 3000A corresponds to a single suction (puff) action, and a similar process may be performed with respect to each suction action. Accordingly, after completion of the process shown by the flow chart 3000A, the process may be repeated immediately; thus, in the flow chart 3000A, right after the process has reached "END," the process may proceed to "START." In such a case, the process shown by the flow chart 3000A forms a loop; and the loop is commenced from "START" when a predetermined signal (for example, a signal representing a power ON state) is received by the controller 400, and terminated when another predetermined signal (for example, a signal representing a power OFF state) is received by the controller 400.

3010A denotes a step for determining whether the start of a puff action is detected. In the case that the start of a puff action is detected, the process proceeds to step 3020A, and, if not, step 3010A is repeated. Note that the above-explained time tStart may be a point of time when the start of a puff action is detected in the step.

3020A denotes a step for initializing parameters A and v, which represent the amplitude of a high-frequency voltage applied to the pairs of interlocking comb-shaped metallic electrodes 33 and speed of supply of liquid to the SAW module, more specifically, to the piezoelectric element substrate 31, to have values of zeros, respectively.

3030A denotes a step for generating signals for applying a high-frequency voltage having amplitude of magnitude A to the pairs of interlocking comb-shaped metallic electrodes 33 and supplying liquid with a liquid supply speed of magnitude v to the piezoelectric element substrate 31. The above signals may be that which is to be sent to the atomizing unit 100.

3040A denotes a step for determining whether time t that has elapsed since the start of the puff action has detected in step 3010A is equal to or longer than a first predetermined time, in other words, whether the first predetermined time has elapsed since the start of the puff action has detected. If it is determined that the first predetermined time has elapsed, the process proceeds to step 3050A, and, if not, the process proceeds to step 3060A. The first predetermined time corresponds to the above-explained time t1 minus the time tStart.

3050A denotes a step for setting the parameter v to a predetermined value. The predetermined value is a value corresponding to a desired level of the liquid supply speed.

3060A denotes a step for determining whether the elapsed time t is equal to or less than a second predetermined time, in other words, whether the second predetermined time has not yet elapsed since the start of the puff action has detected. If it is determined that the second predetermined time has not yet elapsed, the process proceeds to step 3070A, and, if it is not determined so, the process proceeds to step 3080A. The second predetermined time corresponds to the above-explained time t2 minus the time tStart.

3070A denotes a step for adding a predetermined value ΔA to the parameter A. The predetermined value ΔA corresponds to a value which is calculated by multiplying a value by a value, wherein the former value is obtained by dividing a value corresponding to a desired level of amplitude of the high-frequency voltage by a value obtained by subtracting the above explained time tStart from the time t2, and the latter value is a value obtained by subtracting the time when step 3070A was executed last time from the time at when step 3070A is executed this time. In the case that the interval between executions of steps 3070A is constant, ΔA can be regarded as a constant. Note that, ΔA may be zero when step 3070A is executed for the first time.

3080A denotes a step for determining whether the end of the puff action is detected. In the case that the end of the puff action is detected, the process proceeds to step 3090A, and, if not, the process returns to step 3030A.

3090A denotes a step for generating signals for stopping application of the high-frequency voltage to the pairs of interlocking comb-shaped metallic electrodes 33 and stopping supply of the liquid to the piezoelectric element substrate 31. The above signals may be that which is to be sent to the atomizing unit 100. Also, the above-explained time tEnd may be a point of time when this step is executed.

Figure 72:
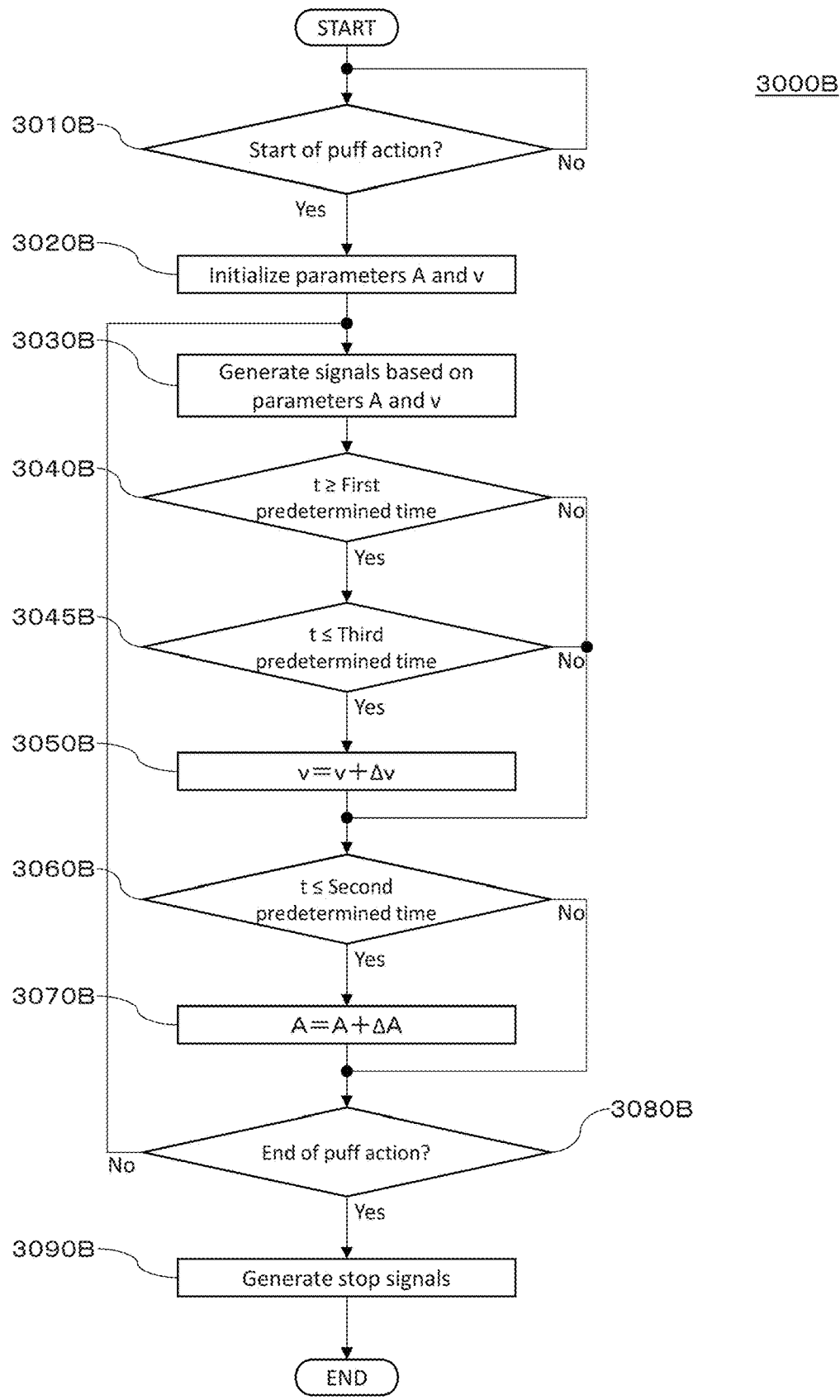
FIG. 72 is figure for explaining twenty-sixth modification D.

FIG. 72 is another example flow chart 3000B for realizing the above-explained process. The respective steps included in the flow chart 3000B may be those executed by the controller 400. Note that, similarly to the case of the flow chart 3000A, the flow chart 3000B corresponds to a single suction (puff) action, and a similar process may be performed with respect to each suction action.

3010B, 3020B, 3030B, 3060B, 3070B, 3080B, and 3090B denote steps similar to steps 3010A, 3020A, 3030A, 3060A, 3070A, 3080A, and 3090A included in the flow chart 3000A.

3040B denotes a step which is similar to step 3040A included in the flow chart 3000A in the point that determination regarding whether the first predetermined time has elapsed is performed; however, there is a point of difference which is that the process proceeds to step 3045B if it is determined that the first predetermined time has elapsed, wherein a step similar to step 3045B is not included in the flow chart 3000A.

3045B denotes a step for determining whether the elapsed time t is equal to or less than a third predetermined time, in other words, whether the third predetermined time has not yet elapsed since the start of the puff action has detected. If it is determined that the third predetermined time has not yet elapsed, the process proceeds to step 3050B, and, if it is not determined so, the process proceeds to step 3060B. The third predetermined time corresponds to the above-explained time t3 minus the time tStart.

3050B denotes a step for adding a predetermined value Δv to the parameter v. The predetermined value Δv corresponds to a value which is calculated by multiplying a value by a value, wherein the former value is obtained by dividing a value corresponding to a desired level of the liquid supply speed by a value obtained by subtracting the above explained time t1 from the time t3, and the latter value is a value obtained by subtracting the time when step 3050B was executed last time from the time when step 3050B is executed this time. In the case that the interval between executions of steps 3050B is constant, Δv can be regarded as a constant. Note that, Δv may be zero when step 3050B is executed for the first time.

Each of lengths of the first predetermined time, the second predetermined time, and the third predetermined time in the above-explained flow chart may be set, by performing numerical calculation or performing an experiment, such that generation of particles having sizes larger than a predetermined size in atomization is suppressed.

Note that, although the "droplet having a large diameter," which is scattered as a bulk droplet and is explained above, includes an extra-large particle having a particle diameter of approximately 100 microns which is larger than that of a coarse particle, and a particle having a particle diameter larger than that of the extra-large particle, the "droplet" is not limited to that explained above. Accordingly, the "predetermine size" with respect to the above explained "particle larger than a predetermined size" may be 100 microns, for example.

Note that at least a part of the controller 400 according to the modified example 26D may be realized by a processor. For example, the controller 400 may comprise a processor and a memory which stores a program, and the program may be that causing the processor to function as at least a part of the controller 400 according to the modified example 26D.

Twenty-Sixth Modification E

In the following, a modified example 26E of the embodiment will be explained. In the following, differences between embodiments will be explained mainly.

In the modified example 26E, the quantity of the liquid, which is to be atomized and exists on the piezoelectric element substrate 31, is obtained by use of a sensor, for example, the above-explained sensor 1070, for detecting the quantity of the liquid, which is to be atomized and exists on the piezoelectric element substrate 31; and based on the quantity, supply of the liquid, which is to be atomized, to the piezoelectric element substrate 31 is controlled; and, by the above control, scattering by receiving a SAW of a droplet, as a bulk droplet having a large diameter, from liquid, which is guided to the front surface 31F of the piezoelectric element substrate 31, is suppressed.

Figure 73:
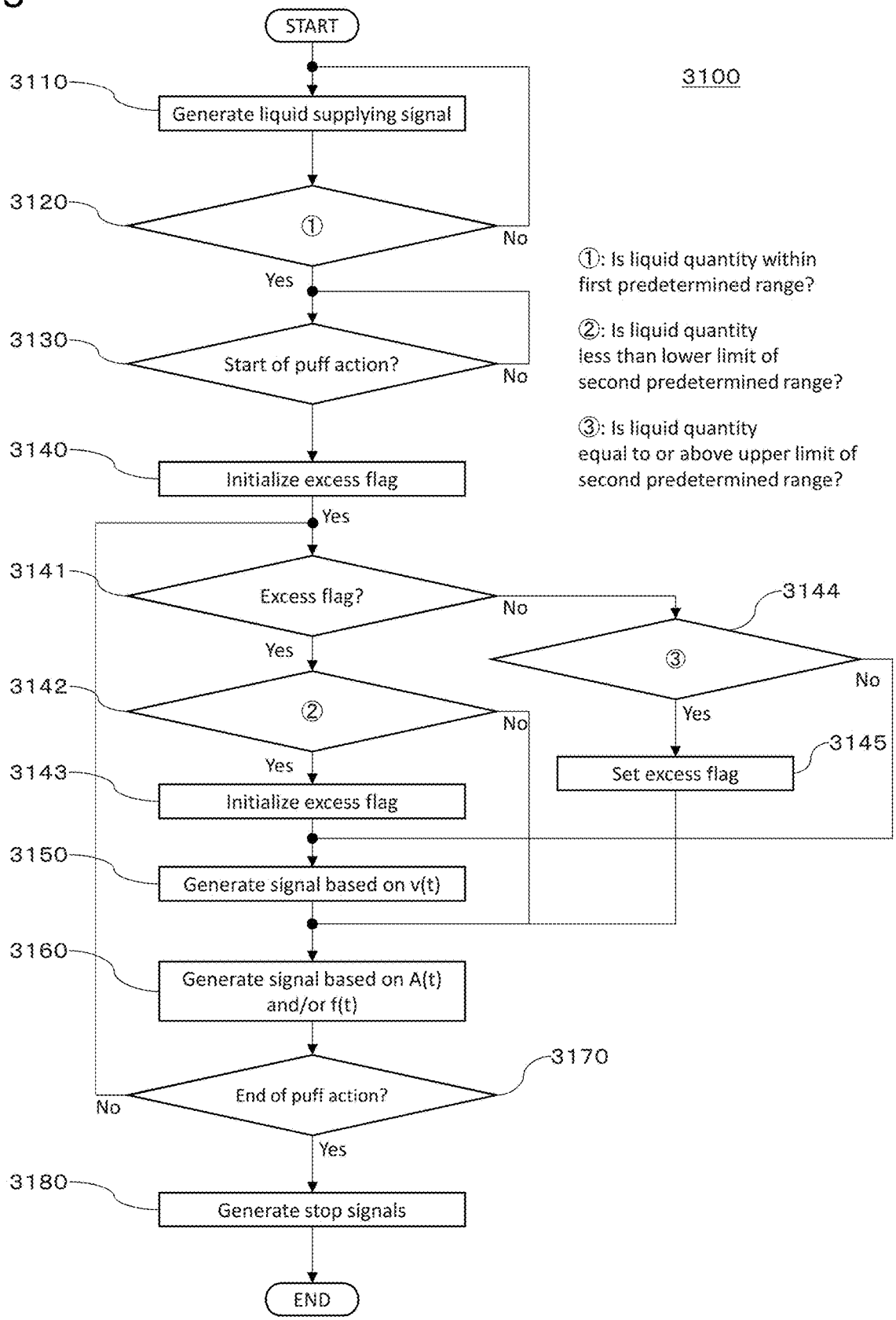
FIG. 73 is figure for explaining twenty-sixth modification E.

FIG. 73 is an example flow chart 3100 for realizing a process relating to the modified example 26E. The respective steps included in the flow chart may be those executed by the controller 400. Note that, similarly to the case of the flow chart 3000A, the flow chart 3100 corresponds to a single suction (puff) action, and a similar process may be performed with respect to each suction action.

3110 denotes a step for generating a signal for supplying liquid, which is to be atomized, to the piezoelectric element substrate 31. The above signal may be that which is to be sent to the atomizing unit 100.

3120 denotes a step for determining whether the quantity of the liquid, which is to be atomized and exists on the piezoelectric element substrate 31 (more specifically, on the front surface of the piezoelectric element substrate 31; this also applies to the following), is in a first predetermined range. In the case that the quantity of the liquid, which is to be atomized, is in the first predetermined range, the process proceeds to step 3130, and, if not, the process returns to step 3110.

According to the steps 3110 and 3120, the quantity of the liquid, which is to be atomized and is in the first predetermined range of quantities, would be supplied to the piezoelectric element substrate 31. Note that the first predetermined range of quantities may be set, by performing numerical calculation or performing an experiment, such that generation of particles having sizes larger than a predetermined size is suppressed, when application of the high-frequency voltage to the pairs of interlocking comb-shaped metallic electrodes 33 is started via step 3160 which will be explained later.

3130 denotes a step for determining whether the start of a puff action is detected. In the case that the start of a puff action is detected, the process proceeds to step 3140, and, if not, the process repeats step 3130.

3140 denotes a step for initializing an excess flag which will be used in a later step, that is, a step for making a state in which the flag has not been set. The excess flag can be realized by use of a memory included in the controller 400.

3141 denotes a step for determining whether an excess flag has been set. In the case that an excess flag has been set, the process proceeds to step 3142, and, if not, the process proceeds to step 3144.

3142 denotes a step for determining whether the quantity of the liquid, which is to be atomized and exists on the piezoelectric element substrate 31, is less than a lower limit of a second predetermined range. In the case that the quantity of the liquid, which is to be atomized, is less than the lower limit of the second predetermined range, the process proceeds to step 3143, and, if not, the process proceeds to step 3160.

3143 denotes a step for initializing the excess flag. Step 3143 is a step similar to step 3140.

3144 denotes a step for determining whether the quantity of the liquid, which is to be atomized and exists on the piezoelectric element substrate 31, is equal to or more than an upper limit of the second predetermined range. In the case that the quantity of the liquid, which is to be atomized, is equal to or more than the upper limit of the second predetermined range, the process proceeds to step 3145, and, if not, the process proceeds to step 3150.

3145 denotes a step for setting the excess flag.

3150 denotes a step for generating a signal for supplying the liquid, with liquid supply speed having magnitude of the parameter v(t), to the piezoelectric element substrate 31. The above signal may be that which is to be sent to the atomizing unit 100.

The parameter v(t) may exhibit predetermined change that is a function of time t elapsed since detection of the start of a puff action in step 3130. After at least certain time has elapsed since the start of a puff action has detected, the value of v(t) or an average value of v(t) over predetermined time must be larger than speed of consumption of the liquid, which exists on the piezoelectric element substrate 31, by atomization through step 3160 which will be explained later. However, the predetermined change may be a change that is zero for a while since the start of a puff action has detected, and, thereafter, become larger than zero. Also, the parameter v(t) may take a predetermined constant value over time.

According to steps 3140-3150, in the case that the quantity of the liquid, which is to be atomized and exists on the piezoelectric element substrate 31, becomes equal to or more than the upper limit of the second predetermined range, step 3150 is not executed, and supplying of the liquid, which is to be atomized, to the piezoelectric element substrate 31 is stopped. Further, according to steps 3140-3150, after supplying of the liquid, which is to be atomized, to the piezoelectric element substrate 31 is stopped, if the quantity of the liquid, which is to be atomized and exists on the piezoelectric element substrate 31, becomes less than the lower limit of the second predetermined range, step 3150 is executed and supply is restarted. Thus, according to steps 3140-3150, the quantity of the liquid, which is to be atomized and exists on the piezoelectric element substrate 31, can be within the second predetermined range.

Note that the second predetermined range of quantities may be set, by performing numerical calculation or performing an experiment, such that generation of particles having sizes larger than a predetermined size, when the high-frequency voltage to the pairs of interlocking comb-shaped metallic electrodes 33 is applied through step 3160 which will be explained later. In this regard, the upper limit and the lower limit of the second predetermined range of quantities may be equal to or larger than upper limit and the lower limit of the first predetermined range of quantities, respectively. Thus, the second predetermined range of quantities may be equal to the first predetermined range of quantities.

3160 denotes a step for generating a signal for applying, to the pairs of interlocking comb-shaped metallic electrodes 33, a high-frequency voltage having amplitude having magnitude corresponding to the parameter A(t) and a frequency corresponding to the parameter f(t). The above signal may be that which is to be sent to the atomizing unit 100.

The parameters A(t) and f(t) may exhibit predetermined change that is a function of time t elapsed since detection of the start of a puff action in step 3130. Also, the parameters A(t) and/or f(t) may take a predetermined constant value/values over time.

3170 denotes a step for determining whether the end of the puff action is detected. In the case that the end of the puff action is detected, the process proceeds to step 3180, and, if not, the process returns to step 3141.

3180 denotes a step for generating signals for stopping application of the high-frequency voltage to the pairs of interlocking comb-shaped metallic electrodes 33 and stopping supply of the liquid to the piezoelectric element substrate 31. The above signals may be that which is to be sent to the atomizing unit 100.

Note that, although the "droplet having a large diameter," which is scattered as bulk a droplet and is explained above, includes an extra-large particle having a particle diameter of approximately 100 microns which is larger than that of a coarse particle, and a particle having a particle diameter larger than that of the extra-large particle, the "droplet" is not limited to that explained above. Accordingly, the "pre-determine size" with respect to the above explained "particle larger than a predetermined size" may be 100 microns, for example.

Note that at least a part of the controller 400 according to the modified example 26E may be realized by a processor. For example, the controller 400 may comprise a processor and a memory which stores a program, and the program may be that causing the processor to function as at least a part of the controller 400 according to the modified example 26E.

Twenty Seventh Modification

The inhaler 1 of the present invention may be configured to apply a consistently appropriate frequency to a pair of interlocking comb-shaped electrodes 33 of an interdigital transducer (IDT).

Figure 74:
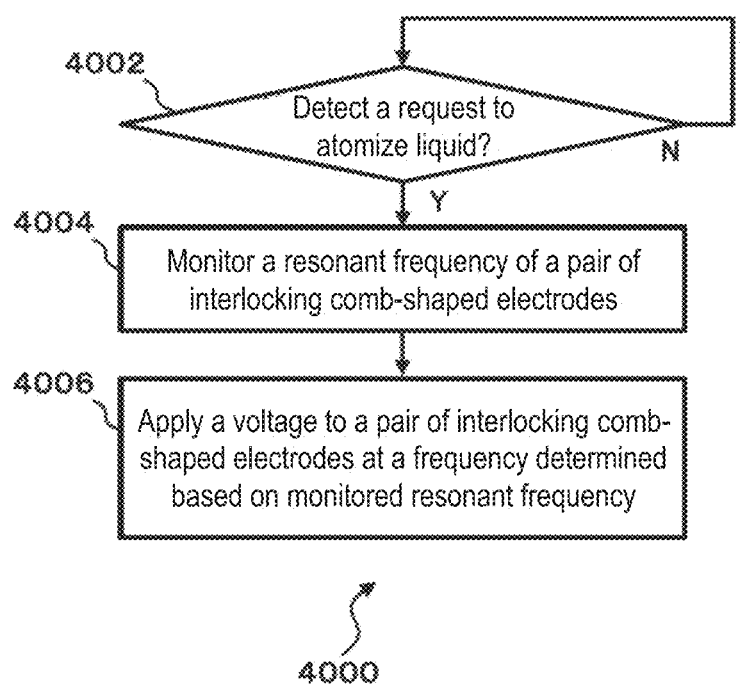
FIG. 74 is a flow chart illustrating a method of operating the inhaler according to the twenty seventh modification.
Figure 75:
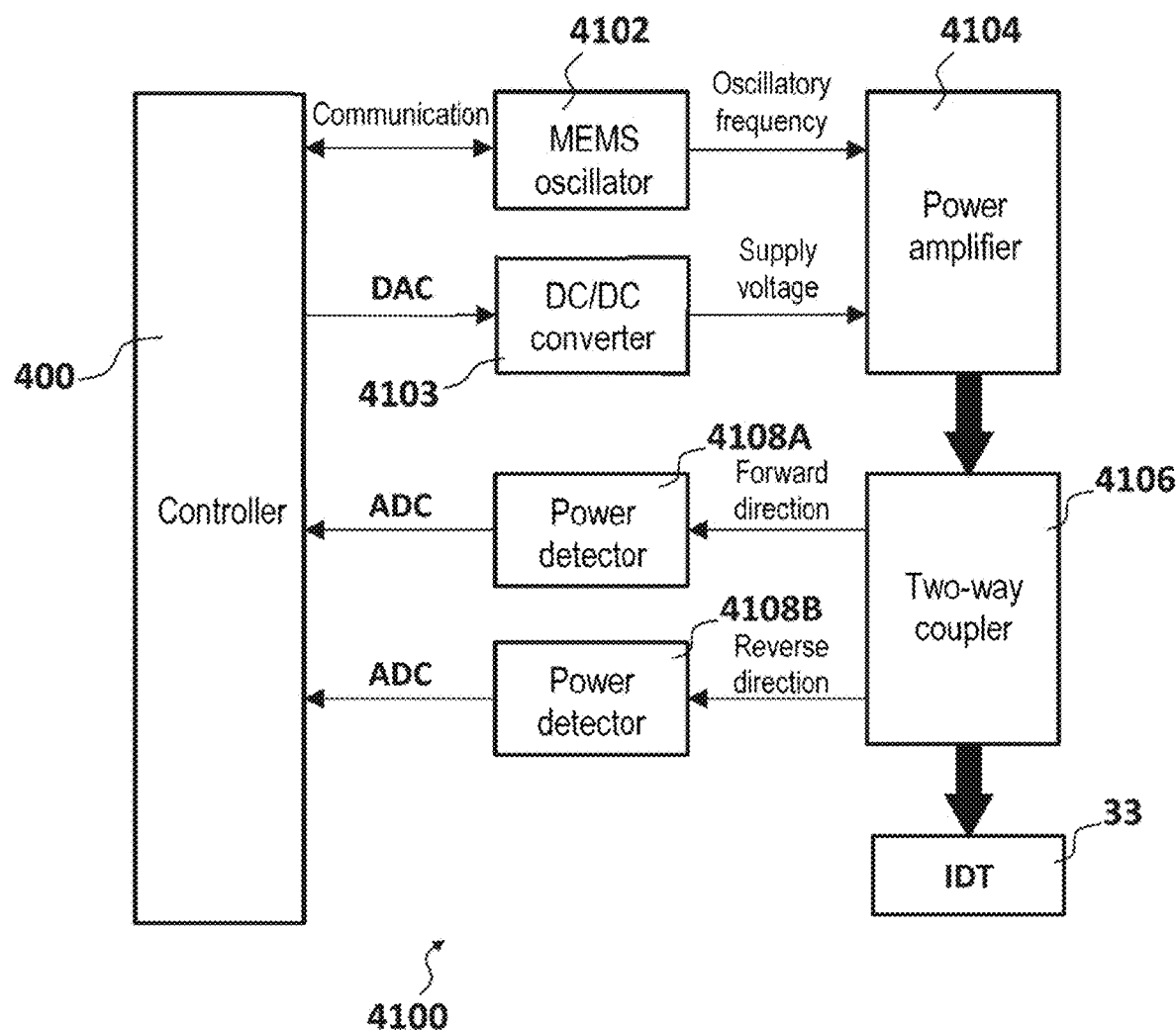
FIG. 75 illustrates an example of a control circuit of the inhaler.
Figure 76:
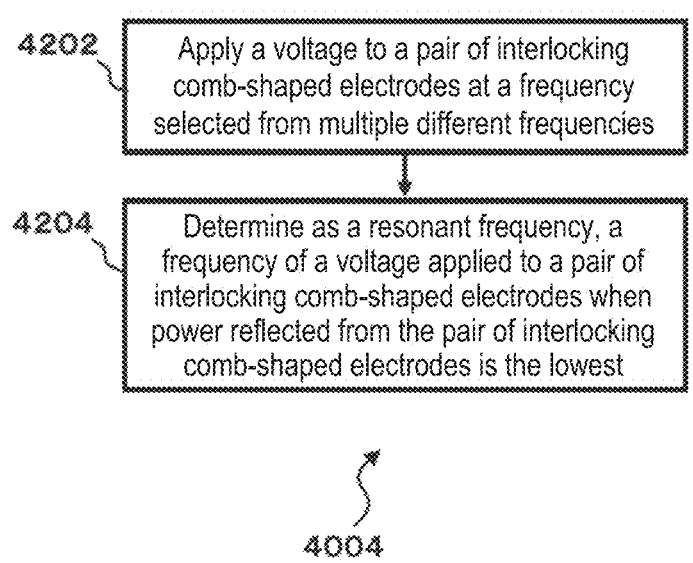
FIG. 76 is a flow chart illustrating a specific example of a process performed at step 4004 in FIG. 74.

FIG. 74 is a flow chart illustrating a method of operating the inhaler 1 according to the present modification. Hereafter, the method will be explained on the assumption that all the steps illustrated in FIG. 74 are carried out by the controller 400 of the inhaler 1. It should be noted, however, that at least some of the steps may be carried out by one or more of the other components of the inhaler 1. Further, it should be apparent that when the present modification is carried out by a processor such as the controller 400 or the like, the present modification can be implemented as a program for causing the processor to carry out a method or as a computer readable storage medium in which the program is stored. The same could be said of the flow charts shown in FIGS. 76, 79, 80A, 80B, 80C, 81A, 81B, 81C, 82 and 83.

Figure 77:
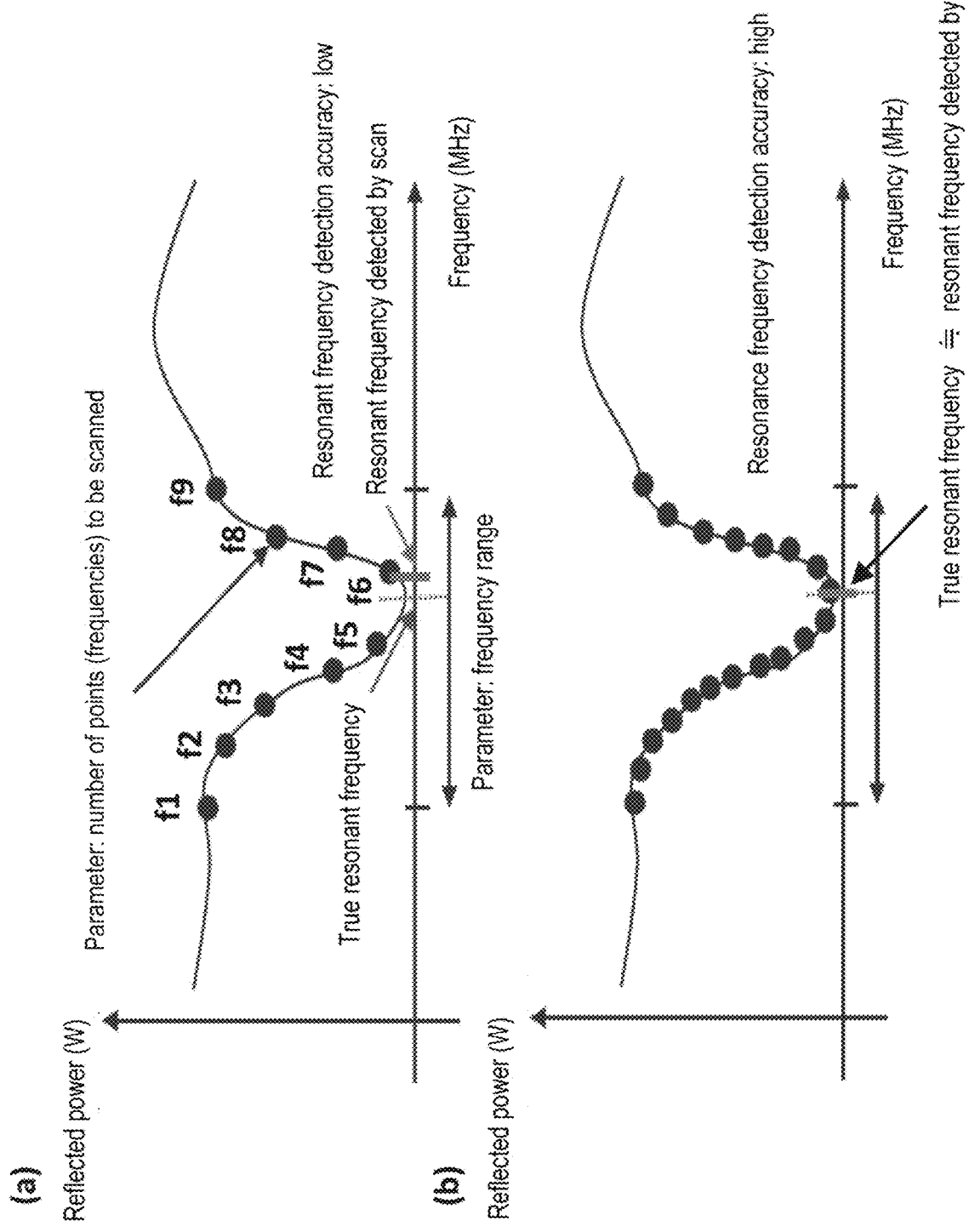
FIG. 77 shows graphs for explaining an example of a method of determining a resonant frequency during the process illustrated in FIG. 76.

At step 4002, the controller 400 determines whether a request to atomize liquid to be stored in the liquid storage unit 200 is detected. The inhaler 1 may comprise a power source switch and a drive switch for liquid atomization. The power source switch and the drive switch may be separate switches. Alternatively, one switch may have the functions of both a power source switch and a drive switch. Further, when the power source switch and the drive switch are separate switches, the power source switch may be a dip switch. The power source switch may be designed such that when the power source switch is turned on, a predetermined amount of liquid is supplied to be inhalable. The drive switch may be in the form of a button, so that when a user depresses the drive switch, power is supplied. In one example, the controller 400 may be configured to determine that a request to atomize liquid is detected when the drive switch is depressed. In another example, the controller 400 may be configured to determine that a request to atomize liquid is detected when inhalation by a user is detected. For example, the inhaler 1 may comprise a pressure sensor and the controller 400 may be configured to detect inhalation by a user based on the variation in pressure detected by the pressure sensor, etc.

When a request to atomize liquid is not detected ("N" at step 4002), the process returns to the step preceding step 4002. In contrast, when a request to atomize liquid is detected ("Y" at step 4002), the process proceeds to step 4004.

At step 4004, the controller 400 monitors a resonant frequency of the pair of interlocking comb-shaped electrodes 33. A specific configuration for carrying out step 4004 will be described below.

FIG. 75 illustrates an example of the control circuit 4100 of the inhaler 1. The control circuit 4100 is configured to control the frequency of the voltage applied to the pair of interlocking comb-shaped electrodes 33 and monitor a resonant frequency of the pair of interlocking comb-shaped electrodes 33. In this example, the control circuit 4100 comprises a MEMS oscillator 4102, DC/DC converter 4103, power amplifier 4104, two-way coupler 4106, power detector 4108A and power detector 4108B in addition to the controller 400. The controller 400 communicates with the MEMS oscillator 4102 to thereby control an oscillatory frequency of the MEMS oscillator 4102. The MEMS oscillator 4102 outputs an indicated oscillatory frequency. The DC/DC converter 4103 supplies to the power amplifier 4104 a voltage indicated by the controller 400. The power amplifier 4101 is connected to the power source 500 and amplifies a voltage supplied from the power source 500 with a voltage supplied from the DC/DC converter. The power amplifier 4101 may be configured to modulate the voltage with an oscillatory frequency received from the MEMS oscillator 4102. The controller 400 can amplitude-modulate a voltage output from the power amplifier 4101 by changing a supply voltage from the DC/DC converter 4103. In one example, a modulation frequency for the amplitude-modulation may be 100 Hz.

The two-way coupler 4106 receives an output from the power amplifier 4104, supplies a portion of the received output to the pair of interlocking comb-shaped electrodes 33 of the IDT and outputs another portion of the received output to the power detector 4108A. In other words, the power detector 4108A detects power (or voltage) supplied to the pair of interlocking comb-shaped electrodes 33 in the forward direction. The analog-digital conversion is performed on a power value detected by the power detector 4108A and the converted value is supplied to the controller 400. The two-way coupler 4106 receives power (or voltage) reflected from the pair of interlocking comb-shaped electrodes 33 and supplies at least a portion of the received power to the power detector 4108B. In other words, the power detector 4108B detects reverse power reflected from the pair of interlocking comb-shaped electrodes 33. The analog-digital conversion is performed on a power value detected by the power detector 4108B and the converted value is supplied to the controller 400.

FIG. 76 is a flow chart illustrating a specific example of a process performed at step 4004 in FIG. 74. At step 4202, the controller 400 applies a voltage to the pair of interlocking comb-shaped electrodes 33 at a frequency selected from multiple different frequencies. Next, at step 4204, the controller 400 determines as a resonant frequency, the frequency of the voltage applied to the pair of interlocking comb-shaped electrodes 33 when power reflected from the pair of interlocking comb-shaped electrodes 33 is the lowest.

FIG. 77 illustrates a specific example of a method of determining a resonant frequency in the process illustrated in FIG. 76. FIG. 77(*a*) will be described below. The controller 400 determines multiple different frequencies (f1-f9) used to determine a resonant frequency. The controller 400 first selects a frequency f1 from the multiple different frequencies and controls the MEMS oscillator 4102 so as to output a signal of the oscillatory frequency f1. Based on a signal received from the MEMS oscillator 4102, the power amplifier 4104 outputs a voltage that fluctuates at frequency f1. The thus output voltage is applied to the pair of interlocking comb-shaped electrodes 33 of IDT via the two-way coupler 4106. If the frequency f1 and the resonant frequency of the pair of interlocking comb-shaped electrodes 33 do not completely match, a portion of power supplied to the pair of interlocking comb-shaped electrodes 33 is reflected to be input to the power detector 4108B via the two-way coupler 4106. Thus, the controller 400 obtains a value of reflected power. FIG. 77(*a*) is a plot showing the relationship between reflected power and frequencies f1-f9. When the frequency is f6, power reflected from the pair of interlocking comb-shaped electrodes 33 is the lowest. Thus, the controller 400 determines f6 as a resonant frequency.

Parameters to be set in advance with respect to the method described in FIG. 77 can be the number of points (frequencies) to be scanned, a frequency range to be scanned, an interval between adjacent frequencies, etc. In FIG. 77(*a*), frequencies are scanned at nine points f1-f9. Since the intervals between the respective adjacent frequencies are relatively large, there can be some gap between the resonant frequency f6 detected by scanning and the true resonant frequency. On the other hand, if there are more frequencies to be scanned in the same frequency range, the intervals between the respective adjacent frequencies naturally become smaller, which enables more accurate determination of a resonant frequency. As described above, the controller 400 is able to flexibly provide for a variety of accuracies demanded for resonant frequency detection, by changing configurable parameters.

In one example, the controller 400 may be configured to detect first power reflected from the pair of interlocking comb-shaped electrodes 33 when a voltage is applied to the pair of interlocking comb-shaped electrodes 33 at a first frequency (for example, f1). The controller 400 may be configured to detect second power reflected from the pair of comb-shaped electrodes 33 when a voltage is subsequently applied to the pair of interlocking comb-shaped electrodes 33 at a second frequency (for example, f2) separated from the first frequency by a first value. When the second power is lower than the first power, the controller 400 may next apply a voltage to the pair of interlocking comb-shaped electrodes 33 at a third frequency (for example, f3) separated from the second frequency by a second value that is smaller than the first value, in which case a frequency interval between f2 and f3 may be set to be smaller than the frequency interval between f1 and f2. According to this example, when a frequency of a voltage applied to the pair of interlocking comb-shaped electrodes 33 is greatly separated from a resonant frequency, a frequency scanning operation is conducted with wide intervals between the respective adjacent frequencies, whereas as the frequency of the voltage to be applied approaches a resonant frequency, a frequency scanning operation is conducted with narrow intervals between the respective adjacent frequencies. Thus, a less detailed scan is carried out where the frequency intervals are large and a detailed scan does not have to be carried out over the entire frequency range, which advantageously reduces time required for monitoring a resonant frequency.

In one example, the controller 400 may be configured to monitor reflected power from the pair of interlocking comb-shaped electrodes 33 while discretely increasing or decreasing the frequency of the voltage applied to the pair of interlocking comb-shaped electrodes 33. The controller 400 may be configured to end a scan when the trend of the value indicating reflected power shifts from a decreasing trend to an increasing trend and determine as a resonant frequency, the frequency of the voltage applied to the pair of interlocking comb-shaped electrodes 33 when reflected power becomes the lowest. According to this example, the range of frequencies to be scanned can be decreased, which advantageously reduces time required for monitoring a resonant frequency.

In one example, the controller 400 may be configured to monitor reflected power from the pair of interlocking comb-shaped electrodes 33 while discretely increasing the frequency of the voltage applied to the pair of interlocking comb-shaped electrodes 33. The controller 400 may be configured to reduce the range of variation in the frequency of the voltage applied to the pair of interlocking comb-shaped electrodes 33 and discretely decrease the frequency when the trend of the value indicating reflected power shifts from a decreasing trend to an increasing trend. According to this example, a less detailed scan is carried out where the frequency intervals are large and a detailed scan does not have to be carried out over the entire frequency range, which advantageously reduces time required for monitoring a resonant frequency.

In one example, the controller 400 may be configured to monitor reflected power from the pair of interlocking comb-shaped electrodes 33 while discretely decreasing the frequency of the voltage applied to the pair of interlocking comb-shaped electrodes 33. The controller 400 may be configured to reduce the range of variation in the frequency of the voltage applied to the pair of interlocking comb-shaped electrodes 33 and discretely increase the frequency when the trend of the value indicating reflected power shifts from a decreasing trend to an increasing trend. According to this example, a less detailed scan is carried out where the frequency intervals are large and a detailed scan does not have to be carried out over the entire frequency range, which advantageously reduces time required for monitoring a resonant frequency.

In one example, the controller 400 may be configured to determine a resonant frequency monitored before the start of atomization of liquid by the atomizing unit 100, a resonant frequency estimated from the temperature of the piezoelectric element substrate 31 or a frequency closest to the resonant frequency at the time of the previous inhalation as a frequency to be selected first from the multiple different frequencies.

Figure 78A:
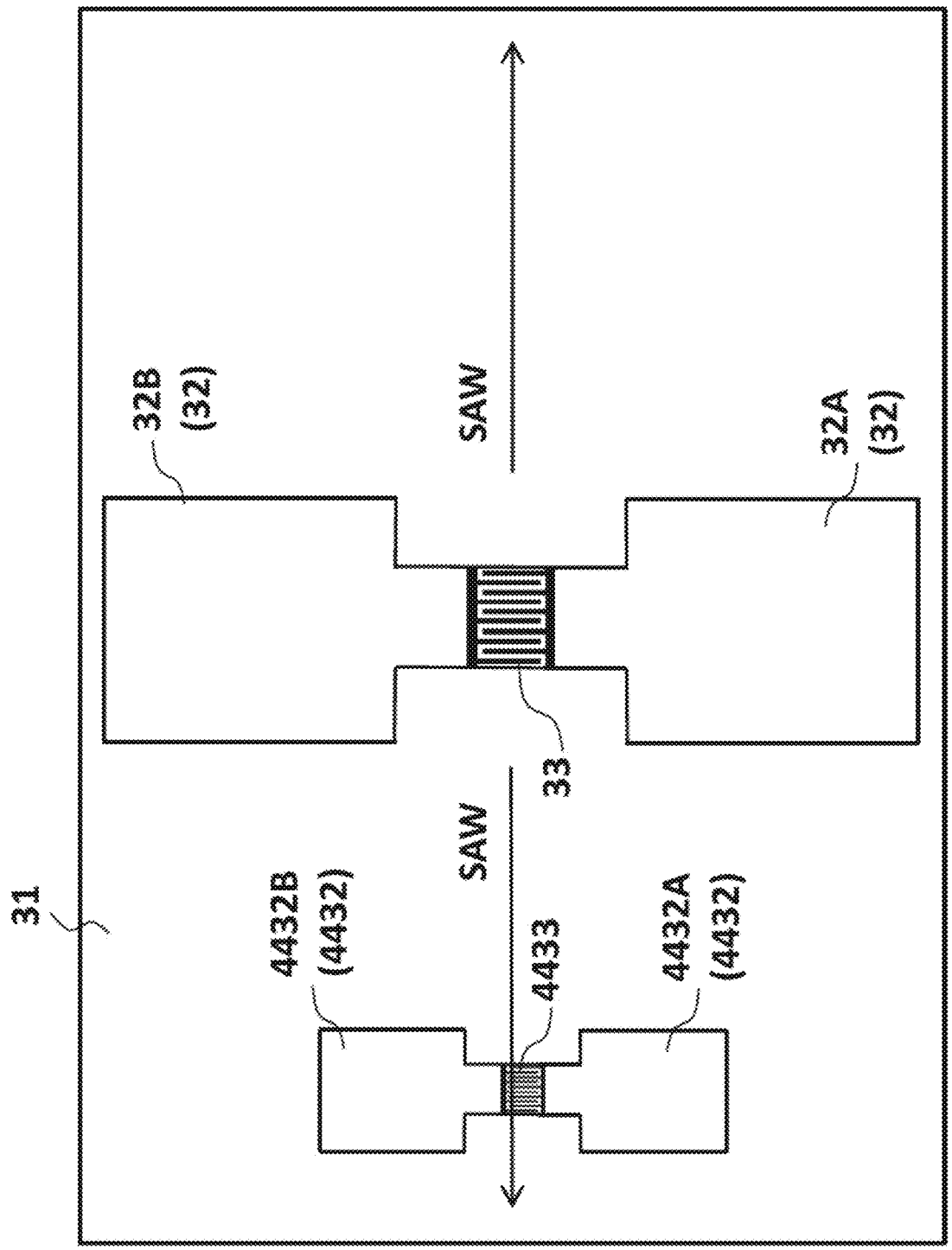
FIG. 78A illustrates an example of a configuration of the inhaler according to the twenty seventh modification for determining a resonant frequency by a method that differs from the method explained in FIG. 77.

FIG. 78A illustrates an example of a configuration of the inhaler 1 according to the present modification for determining a resonant frequency by a method different from the method explained with reference to FIG. 77. In addition to the IDT (hereafter referred to as a first IDT) comprising the main body portion 32 and pair of interlocking comb-shaped electrodes 33, a second IDT comprising the main body portion 4432 and pair of interlocking comb-shaped electrodes 4433 is disposed on the piezoelectric element substrate 31. The second IDT may have a similar configuration to the first IDT. The second IDT is provided at a position where a SAW (surface acoustic wave) output from the first IDT passes. As is illustrated in FIG. 78A, the second IDT is disposed such that the intersection of the second IDT and the intersection of the first IDT at least partially overlap one another along the direction of propagation of a SAW. The second IDT may be smaller than the first IDT or as large as the first IDT. When the second IDT is smaller than the first IDT, the second IDT may be disposed only on one side of the first IDT as illustrated in FIG. 78A or at least one second IDT may be disposed on each side of the first IDT. Since a SAW is partially converted to a voltage or heat by the second IDT, a SAW decreases as it is output from the first IDT and passes through the second IDT. Thus, when the second IDT is as large as the first IDT, it should be disposed only on one side of the first IDT for the sake of efficiency.

If the second IDT is provided at a position where a SAW (surface acoustic wave) passes as is described in the foregoing example, such a configuration presents a problem that the electrodes of the second IDT could come off due to surface acoustic wave vibration. With a view to solving the problem, the first IDT and the second IDT in the present modification may be first disposed on the piezoelectric element substrate 31 and then, a coating layer may be provided on the piezoelectric element substrate 31, which could prevent vibration-induced detachment of the electrodes of the IDT.

Figure 78B:
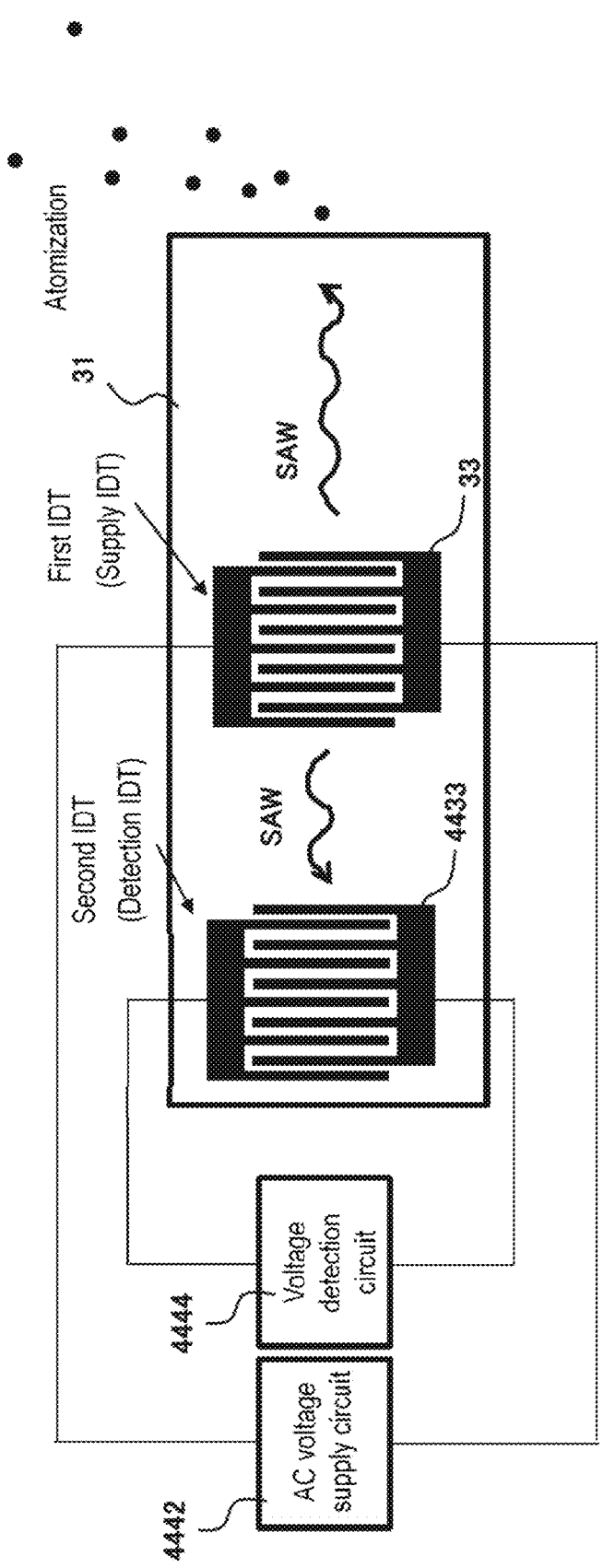
FIG. 78B illustrates an example of the arrangement of the first and second IDTs.

FIG. 78B illustrates an example of the placement of the first and second IDTs. The first IDT (supply IDT) for supplying AC voltage and the second IDT (detection IDT) for detecting the frequency of the supplied voltage are disposed on the piezoelectric element substrate 31. The AC voltage supply circuit 4442 is connected to the first IDT. The voltage detection circuit 4444 is connected to the second IDT. When a voltage is supplied by the AC voltage supply circuit 4442 to the first IDT, a SAW is generated on either side of the first IDT. As was explained in connection with FIG. 78A, the second IDT could assume various sizes. In the example illustrated in FIG. 78B, the second IDT and the first IDT are the same size. In FIG. 78B, a SAW on one side of the first IDT that propagates rightward from the first IDT, is used to atomize liquid, whereas a SAW on the other side of the first IDT that propagates leftward from the first IDT, is used by the second IDT to detect a voltage.

Figure 78C:
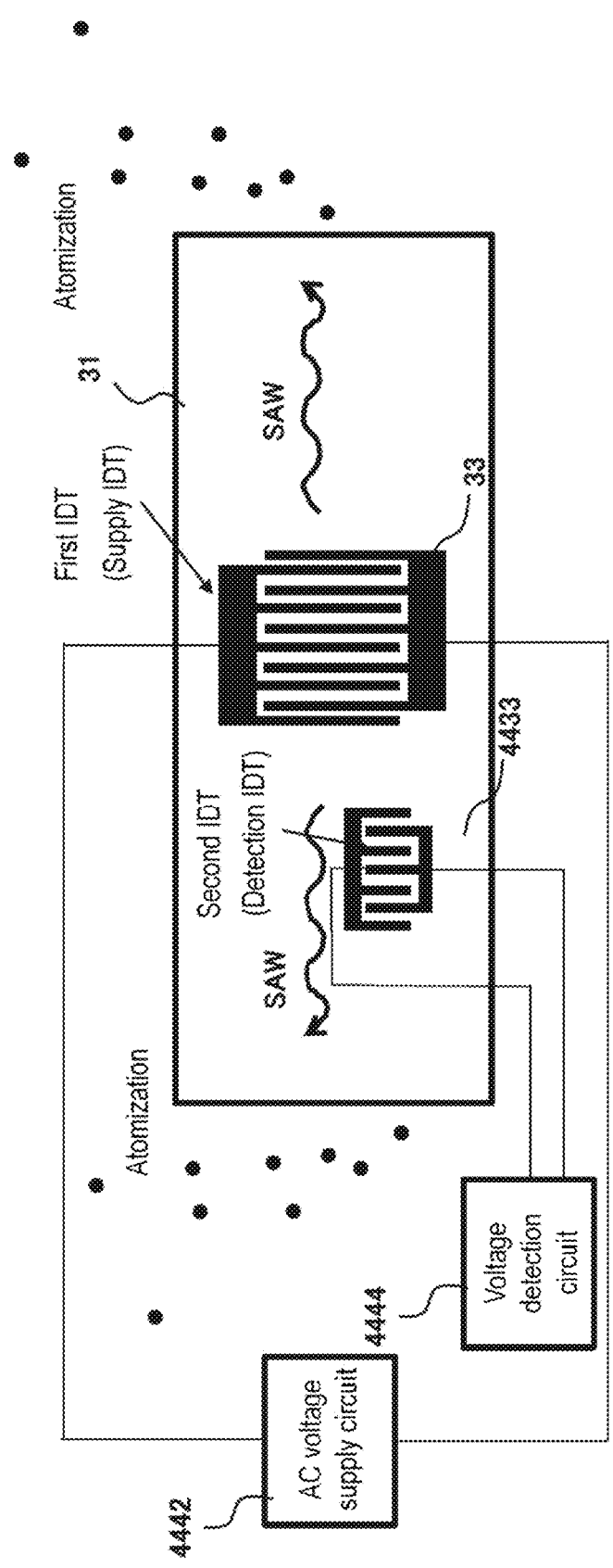
FIG. 78C illustrates an example of the arrangement of the first and second IDTs.

FIG. 78C illustrates an example of the arrangement of the first and second IDTs. In the example illustrated in FIG. 78C, the second IDT is smaller than the first IDT. The second IDT uses a portion of a SAW that propagates leftward from the first IDT to pick up power (voltage.) In this example, a SAW generated on either side of the first IDT can be used to atomize liquid.

Figure 78D:
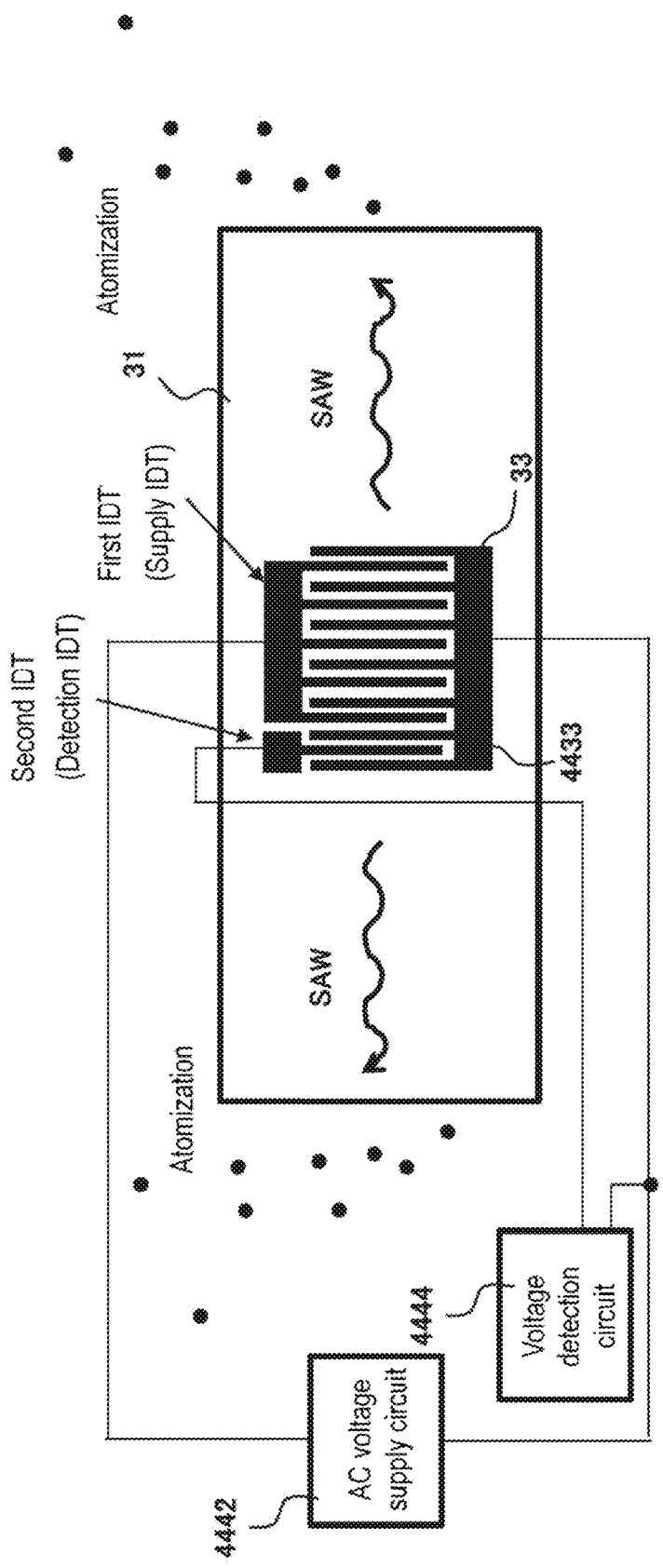
FIG. 78D illustrates an example of the arrangement of the first and second IDTs.

FIG. 78D illustrates an example of the arrangement of the first and second IDTs. In this example, the first and second IDTs are disposed to have a common reference voltage. Since the number of a pair of interlocking comb-shaped electrodes of the second IDT is smaller than the number of pair of interlocking comb-shaped electrodes of the first IDT in this example, SAW reduction is prevented and power (voltage) can be picked up.

A device that generates a SAW such as the first IDT illustrated in FIGS. 78A-78D tends to generate heat when high power is supplied to the device. Since such a device as described above usually has a narrow range of frequencies at which impedance matching is achieved, a frequency, at which impedance matching is achieved, sometimes changes with temperature variations. Considering that low power consumption is required when such a device is used in portable equipment, it is desirable to be able to detect a matching frequency with low power consumption. Therefore, when monitoring a resonant frequency of the pair of interlocking comb-shaped electrodes 33 of the first IDT, electric power lower than necessary for atomizing liquid may be supplied to the first IDT, and after determining the frequency of the voltage to be applied to the pair of interlocking comb-shaped electrodes 33, higher electric power necessary for atomization may be supplied to the first IDT. Thereby, power consumption in monitoring a resonant frequency can be reduced.

Figure 79:
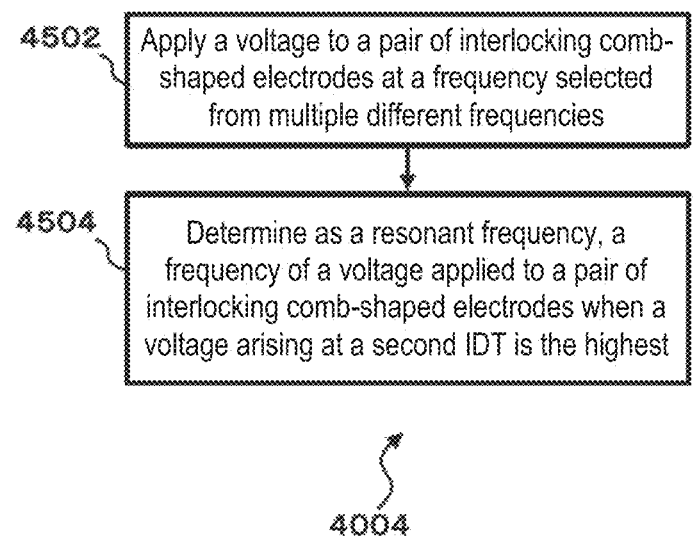
FIG. 79 is a flow chart illustrating a specific example of a process performed at step 4004 in FIG. 74.
Figure 80A:
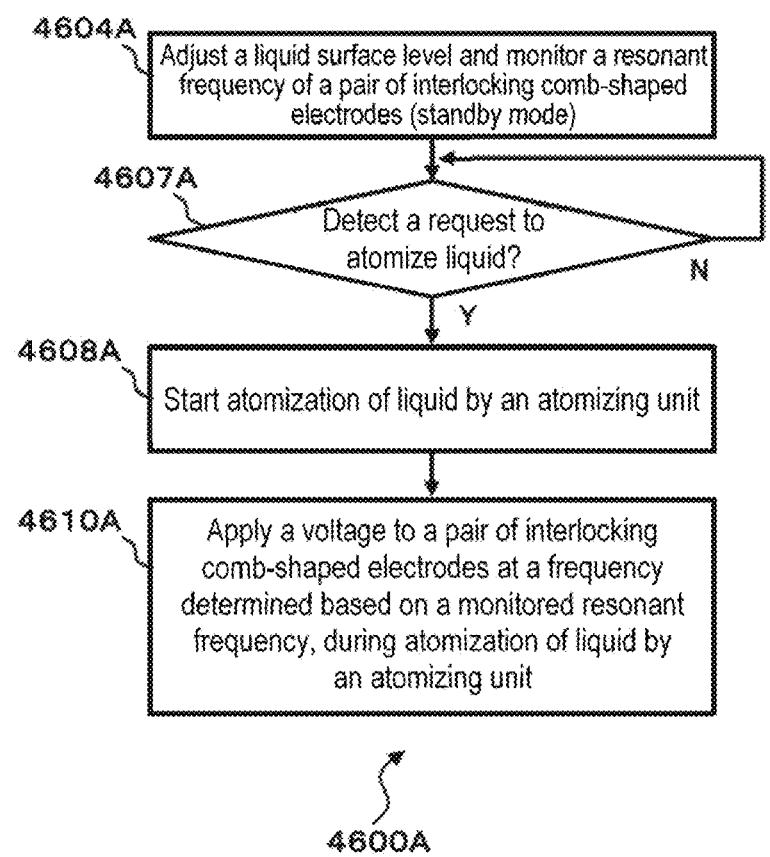
FIG. 80A is a flow chart illustrating a method of operating the inhaler according to the twenty seventh modification.

FIG. 79 is a flow chart illustrating a specific example of a process performed at step 4004 in FIG. 74. The process illustrated in FIG. 79 can be implemented by applying the configurations shown in FIGS. 78A to 78D to the inhaler 1. At step 4502, the controller 400 applies a voltage to the pair of interlocking comb-shaped electrodes 33 at a frequency selected from multiple different frequencies (for example, f1-f9.) Next, at step 4504 the controller 400 determines as a resonant frequency, the frequency of the voltage applied to the pair of interlocking comb-shaped electrodes 33 when a voltage generated at the second IDT is the highest.

In one example, the controller 400 may detect a first voltage arising at the second IDT when a voltage is applied to the interlocking comb-shaped electrodes 33 at a first frequency (for example, f1). Next, the controller 400 may detect a second voltage arising at the second IDT when a voltage is applied to the interlocking comb-shaped electrodes 33 at a second frequency (for example, f2) separated from the first frequency by a first value. When the second voltage is higher than the first voltage, the controller 400 may apply a voltage to the pair of interlocking comb-shaped electrodes 33 at a third frequency (for example, f3) separated from the second frequency by a second value that is smaller than the first value.

In one example, the controller 400 may monitor a voltage that arises at the second IDT while discretely increasing or decreasing the frequency of the voltage applied to the pair of interlocking comb-shaped electrodes 33. The controller 400 may be configured to end a scan when the trend of the value of a voltage arising at the second IDT shifts from an increasing trend to a decreasing trend and determine as a resonant frequency, the frequency of the voltage applied to the pair of interlocking comb-shaped electrodes 33 when the voltage becomes the highest.

In one example, the controller 400 may be configured to monitor a voltage arising at the second IDT while discretely increasing the frequency of the voltage applied to the pair of interlocking comb-shaped electrodes 33. The controller 400 may be configured to reduce the range of variation in the frequency of the voltage applied to the pair of interlocking comb-shaped electrodes 33 and discretely decrease the frequency when the trend of the value of a voltage arising at the second IDT shifts from an increasing trend to a decreasing trend.

In one example, the controller 400 may be configured to monitor a voltage arising at the second IDT while discretely decreasing the frequency of the voltage applied to the pair of interlocking comb-shaped electrodes 33. The controller 400 may be configured to reduce the range of variation in the frequency of the voltage applied to the pair of interlocking comb-shaped electrodes 33 when the trend of the value of a voltage arising at the second IDT shifts from an increasing trend to a decreasing trend.

In one example, the controller 400 may be configured to determine a resonant frequency monitored before the start of atomization of liquid by the atomizing unit 100, a resonant frequency estimated from the temperature of the piezoelectric element substrate 31 or a frequency closest to the resonant frequency at the time of the previous inhalation as a frequency to be selected first from multiple different frequencies.

Returning to FIG. 74, at step 4004 a resonant frequency of the pair of interlocking comb-shaped electrodes 33 is monitored and a frequency of a voltage applied to the pair of interlocking comb-shaped electrodes 33 is determined based on the monitored resonant frequency by use of the configuration and process described in FIGS. 75 to 79. Next, at step 4006 the controller 400 applies a voltage to the pair of interlocking comb-shaped electrodes 33 at the determined frequency.

Manufacturing variations in terms of inter-electrode distance and the like can occur in an IDT for an inhaler. Further, a resonant frequency of a pair of interlocking comb-shaped electrodes of an IDT varies depending on the usage temperature of an inhaler, etc. Accordingly, a conventional inhaler cannot attain a sufficient amount of atomized liquid under various circumstances. According to the present modification, a resonant frequency of a pair of interlocking comb-shaped electrodes can be monitored and a frequency of a voltage to be applied to the pair of interlocking comb-shaped electrodes can be dynamically controlled. Thus, an inhaler according to the present modification can apply a voltage at a frequency appropriate for a pair of interlocking comb-shaped electrodes and provide a sufficient amount of atomized liquid under various circumstances even monitored to dynamically control a frequency of a voltage to be applied to the pair of interlocking comb-shaped electrodes. Thus, an inhaler according to the present modification can apply a voltage at a frequency appropriate for a pair of interlocking comb-shaped electrodes and provide a sufficient amount of atomized liquid under various circumstances even if a resonant frequency of the pair of interlocking comb-shaped electrodes differs from a design value due to manufacturing variations, etc.

According to the present modification, a resonant frequency is determined only once before the start of atomization of liquid, which simplifies a process performed by a controller. A controller monitors a resonant frequency at the time of performing a process for entering a standby mode, determines a frequency for atomization based on the thus obtained resonant frequency before atomization and applies the determined frequency for atomization. In other words, the controller 400 does not monitor a resonant frequency each time inhalation occurs, which enables the controller 400 to use the time in which a user is inhaling to atomize liquid. Thus, the present modification can secure a sufficient amount of atomized liquid, compared to a case when a resonant frequency is monitored every time a user inhales.

Figure 81A:
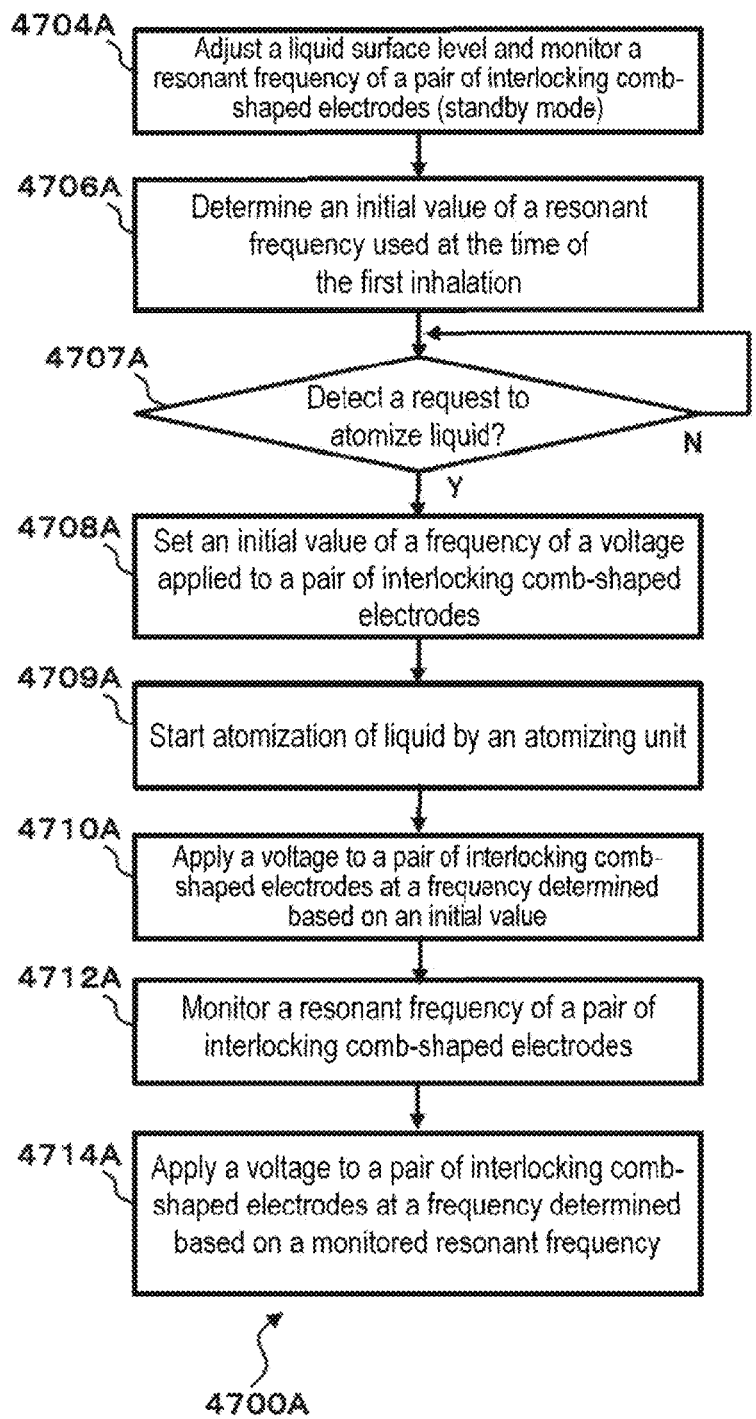
FIG. 81A is a flow chart illustrating a method of operating the inhaler according to the twenty seventh modification.

FIG. 81A is a flow chart illustrating a method of operating the inhaler 1 according to the present modification. Since the process at step 4704A is similar to the process at step 4604A, an explanation for step 4704 is omitted here.

At step 4706A the controller 400 determines based on the values monitored at step 4704A, an initial value of a resonant frequency for the pair of interlocking comb-shaped electrodes 33 used at the time of the first inhalation.

The process proceeds to step 4707A, where the controller 400 determines whether a request to atomize liquid is detected (whether the drive switch of the inhaler 1 is depressed, whether inhalation by a user is detected, etc.) If it transpires that a request to atomize liquid is not detected ("N" at step 4707A), the process returns to the step preceding step 4707A.

In contrast, if it transpires that a request to atomize liquid is detected ("Y" at step 4707A), the process proceeds to step 4708A and the controller 400 sets an initial value of a frequency of a voltage applied to the pair of interlocking comb-shaped electrodes 33. At the time of the first inhalation, the initial value is a value determined at step 4706A. At the time of inhalation from the second time onward, the initial value set at step 4708A may be a resonant frequency monitored at the time of the previous inhalation. At step 4709A the controller 400 starts atomization of liquid by the atomizing unit 100. Next, at step 4710A the controller 400 applies a voltage to the pair of interlocking comb-shaped electrodes 33 at a frequency (fixed value) determined based on the initial value.

At step 4712A the controller 400 monitors a resonant frequency of the pair of interlocking comb-shaped electrodes 33, during atomization of liquid by the atomizing unit 100.

At step 4714A the controller 400 applies a voltage to the pair of interlocking comb-shaped electrodes 33 at a frequency determined based on the monitored resonant frequency, which enables fine adjustments in the frequency for the current or next inhalation. From that time onwards, the process at step 4710A to step 4714A may be repeated during atomization of liquid.

FIG. 81B is a flow chart illustrating a method of operating the inhaler according to the present modification. Since the process at step 4704B to step 4709B is similar to the process at step 4704A to step 4709A, an explanation for the process at step 4704B to step 4709B is omitted here.

At step 4710B the controller 400 is configured to control a voltage applied to the pair of interlocking comb-shaped electrodes 33 so as to vary within a predetermined range of frequencies including a frequency determined based on the initial value. For example, the controller 400 may be configured to vary a frequency of a voltage applied to the pair of interlocking comb-shaped electrodes 33 within a narrow range of frequencies including the initial value (for example, initial value+/−0.1 MHz).

At step 4712B, the controller 400 monitors a resonant frequency of the pair of interlocking comb-shaped electrodes 33, during atomization of liquid by the atomizing unit 100. In the example shown in FIG. 81B, a voltage applied to the pair of interlocking comb-shaped electrodes 33 is controlled so as to vary within a predetermined range of frequencies, at step 4710B. Thus, a resonant frequency can be monitored at the same time as liquid is atomized. On the other hand, in the example shown in FIG. 81A, atomization of liquid must be stopped during the process of monitoring a resonant frequency. Thus, compared to the example illustrated in FIG. 81A, the example shown in FIG. 81B comprises the foregoing additional feature.

At step 4714B the controller 400 adjusts a predetermined range of frequencies used at step 4710B so as to include the resonant frequency monitored at step 4712B, which enables fine adjustments in the frequency for the current inhalation. From that time onwards, the process at step 4710B to step 4714B may be repeated during atomization of liquid.

Figure 81C:
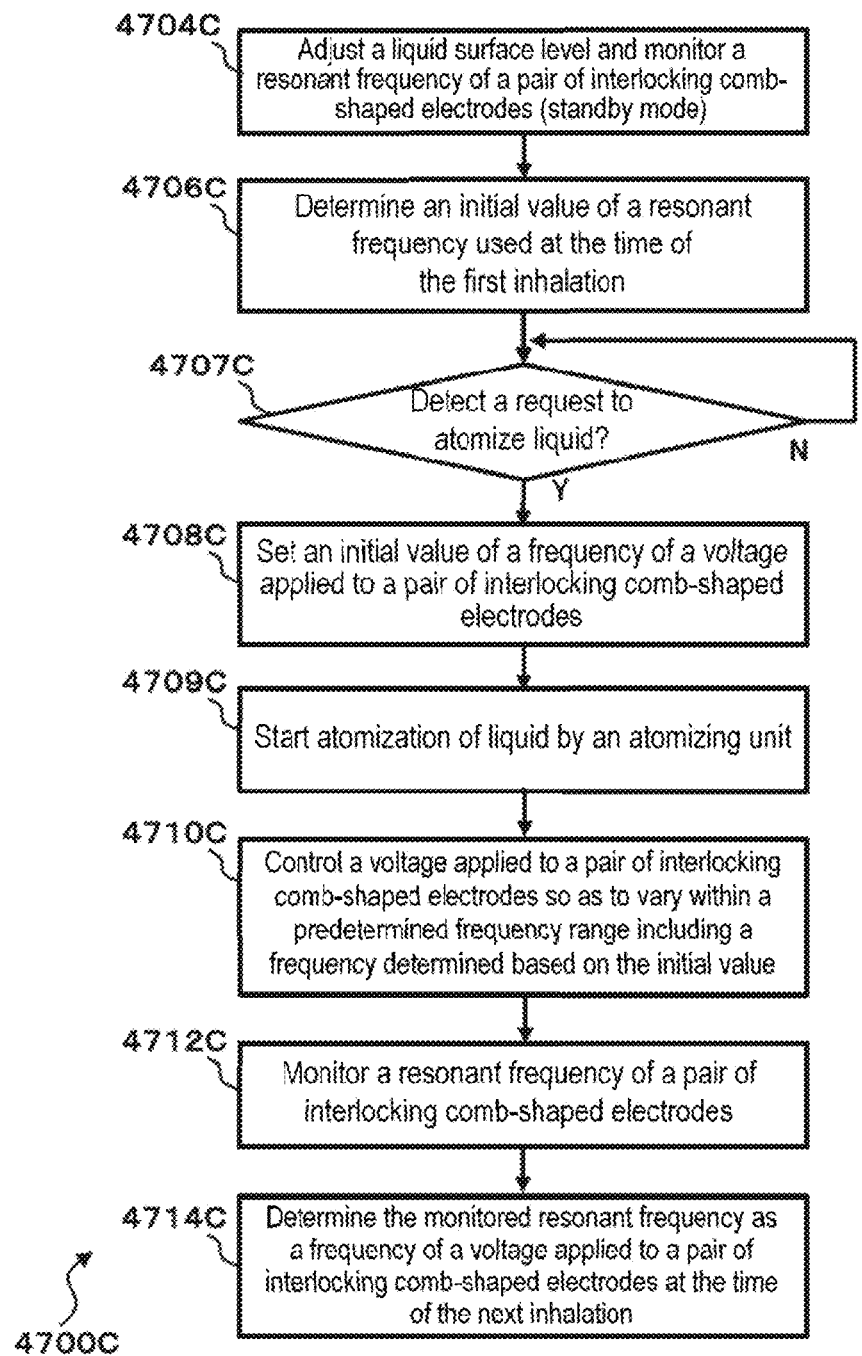
FIG. 81C is a flow chart illustrating a method of operating the inhaler according to the twenty seventh modification.

FIG. 81C is a flow chart illustrating a method of operating the inhaler 1 according to the present modification. Since the process at step 4704C to step 4712C is similar to the process at step 4704B to step 4712B, an explanation for the process at step 4704C to step 4712C is omitted here.

At step 4714C the controller 400 determines the resonant frequency monitored at the step 4712C as a frequency of a voltage applied to the pair of interlocking comb-shaped electrodes 33 at the time of the next inhalation. The thus determined frequency may be stored in a memory unit. When the inhalation action occurs next time, the controller 400 applies a voltage to the pair of interlocking comb-shaped electrodes 33 at a frequency determined at step 4714C.

According to the present modification, a frequency of a voltage applied to a pair of interlocking comb-shaped electrodes can be appropriately set while a user is using an inhaler and liquid is atomized. Thus, the present modification can provide detailed control suited for the condition of an inhaler, which changes from moment to moment, thereby to optimize the liquid atomization amount.

Figure 82:
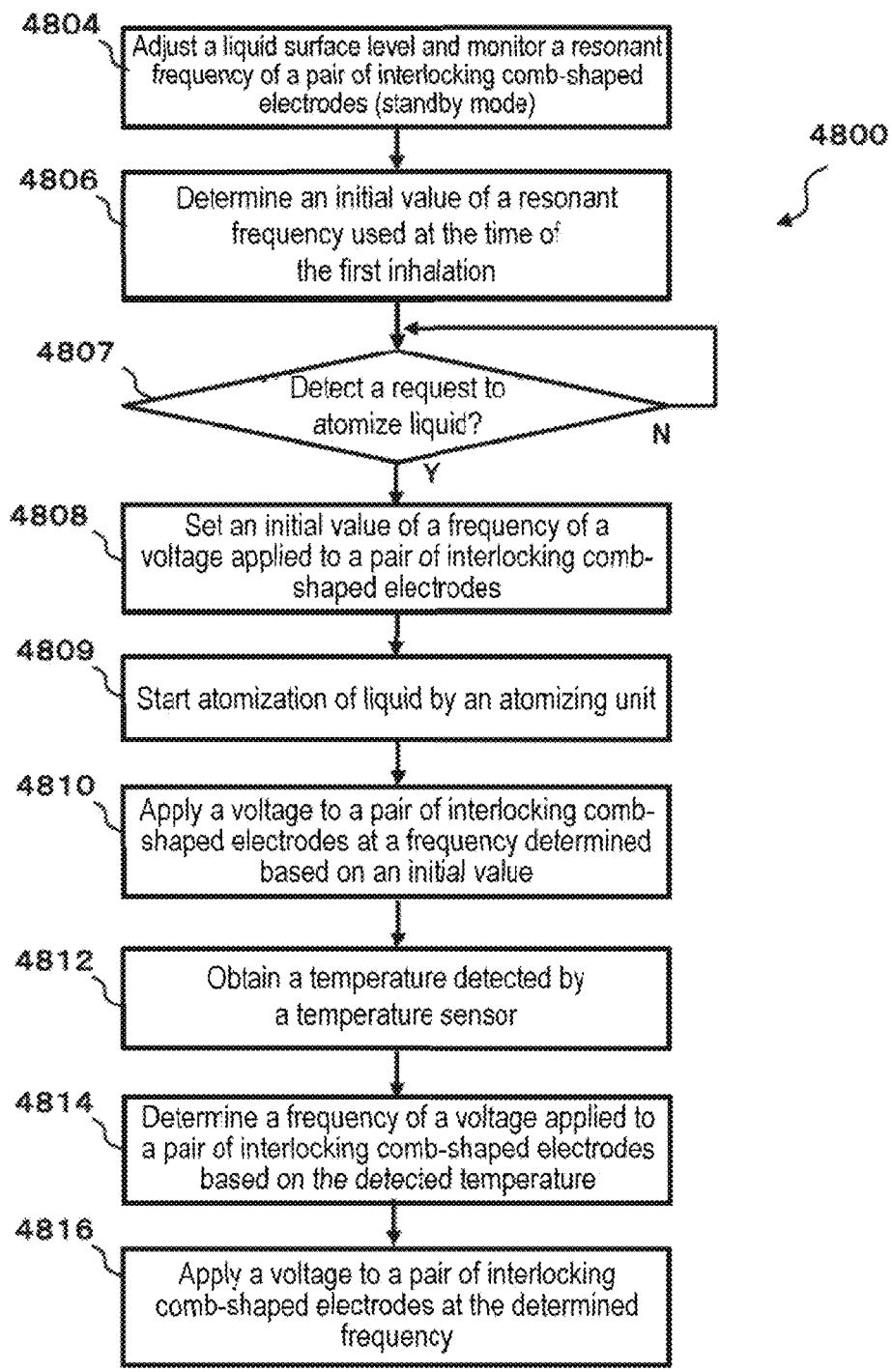
FIG. 82 is a flow chart illustrating a method of operating the inhaler according to the twenty seventh modification.

FIG. 82 is a flow chart illustrating a method of operating the inhaler 1 according to the present modification. Since the process at step 4804 to step 4810 is similar to the process at step 4704A to step 4710A, an explanation for the process at step 4804 to step 4810 is omitted here.

The inhaler 1 may comprise a temperature sensor configured to detect the temperature of the piezoelectric element substrate 31 that contributes to the phase and amplification of a SAW. The temperature sensor may be configured to detect the temperature of the appropriate component of the inhaler 1 other than the piezoelectric element substrate 31. The temperature sensor may be provided at any appropriate position in the inhaler 1. Alternatively, the temperature may be measured by having thermocouples, thermistors or the like contact the components, in which case the temperature of the substrate surface in the neighborhood of the pair of interlocking comb-shaped electrodes 33 may be measured to prevent short circuits. Alternatively, a non-contact temperature measuring system such as a radiation thermometer using infrared may be employed, in which case the temperature of the pair of interlocking comb-shaped electrodes 33 may be measured.

At step 4812 the controller 400 obtains the temperature detected by the temperature sensor, during atomization of liquid by the atomizing unit 100. The process proceeds to step 4814, where the controller 400 determines a frequency of a voltage applied to the pair of interlocking comb-shaped electrodes 33 based on the temperature detected at step 4812.

Figure 83:
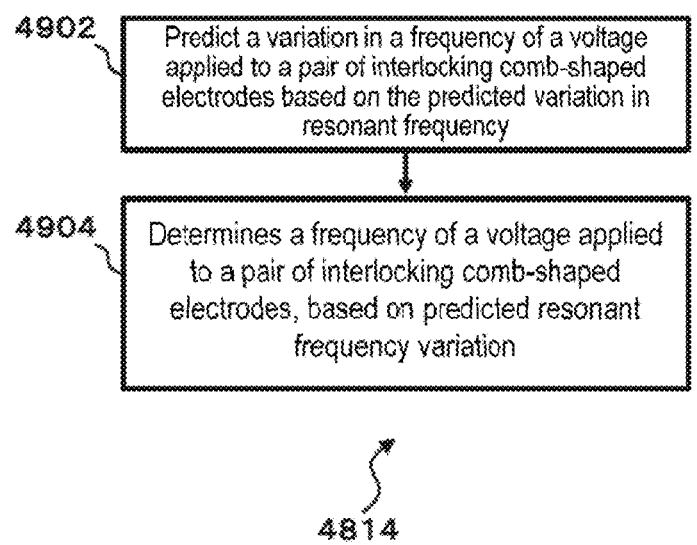
FIG. 83 is a flow chart illustrating a specific example of a process performed at step 4814.

FIG. 83 is a flow chart illustrating a specific example of a process performed at step 4814. At step 4902 the controller 400 predicts a resonant frequency variation during atomization of liquid by the atomizing unit 100, based on the temperature detected at step 4812. Since the velocity of propagation of a SAW increases as the temperature rises, the resonant frequency tends to increase. Thus, the controller 400 may predict a resonant frequency variation by utilizing such tendency. Alternatively, the inhaler 1 may comprise a memory unit and the memory unit may store information regarding correspondence between the temperature of the piezoelectric element substrate 31 (or other appropriate component) and the resonant frequency. The controller 400 may be configured to predict a variation in the resonant frequency of the pair of interlocking comb-shaped electrode 33 (or other appropriate component) based on the measured temperature of the piezoelectric element substrate 31 (or other appropriate component) and the foregoing information.

The process proceeds to step 4904 and the controller 400 determines a frequency of a voltage applied to the pair of interlocking comb-shaped electrodes 33 based on resonant frequency variation predicted at step 4902.

Referring back to FIG. 82, at step 4816 the controller 400 applies a voltage to the pair of interlocking comb-shaped electrodes 33 at a frequency determined at step 4814.

According to the present modification, a resonant frequency of a pair of interlocking comb-shaped electrodes can be monitored to dynamically control a frequency of a voltage that is applied to the pair of interlocking comb-shaped electrodes. Further, a variation in a resonant frequency of the pair of interlocking comb-shaped electrodes during atomization of liquid can be predicted by also using the temperature detected by a temperature sensor. Thus, the present modification can apply a voltage at a frequency appropriate for a pair of interlocking comb-shaped electrodes and provide a sufficient amount of atomized liquid under various circumstances even if a resonant frequency of the pair of interlocking comb-shaped electrodes varies due to manufacturing variations, usage temperature, etc. Further, the present modification can provide detailed control suited for the condition of an inhaler, which changes from moment to moment, thereby to optimize the liquid atomization amount.

In another example, the controller 400 may be configured to detect the temperature before the start of atomization of liquid by the atomizing unit 100 and determine a frequency of a voltage applied to the pair of interlocking comb-shaped electrodes 33 based on the thus detected temperature. According to the foregoing configuration, the temperature is detected only once before the start of atomization of liquid, which enables precise control of a resonant frequency by a relatively simple process.

Other Embodiments

The present invention has been described in terms of the embodiment set forth above; however, the invention should not be understood to be limited by the statements and the drawings constituting a part of this disclosure. From this disclosure, various alternative embodiments, examples, and operational technologies will become apparent to those skilled in the art.

In the embodiment, the liquid supplier 60 is provided on the side of the rear surface 31B of the piezoelectric element substrate 31. However, the embodiment is not limited thereto. For example, the liquid supplier 60 may be provided on the side of the front surface 31F of the piezoelectric element substrate 31. In such a case, the liquid supplier 60 may drop the liquid onto the front surface 31F of the piezoelectric element substrate 31. Further, the piezoelectric element substrate 31 may not need to have the penetrated aperture 34.

In the embodiment, the pairs of interlocking comb-shaped metallic electrodes 33 have a linear shape. However, the embodiment is not limited thereto. For example, the pairs of interlocking comb-shaped metallic electrodes 33 may have a fan shape.

In the embodiment, the number of pairs of interlocking comb-shaped metallic electrodes 33 is determined based on the atomizing efficiency of the aerosol atomized by use of the SAW. However, the embodiment is not limited thereto. For example, the number of pairs of interlocking comb-shaped metallic electrodes 33 may be determined based on a magnitude of power that can be supplied to the pairs of interlocking comb-shaped metallic electrodes 33. The number of pairs of interlocking comb-shaped metallic electrodes 33 may be determined based on the type of solute or solvent configuring the liquid. the number of pairs of interlocking comb-shaped metallic electrodes 33 may be determined based on a supplying method and a supplying speed of the liquid supplied to the SAW module.

In the embodiment, the flavor inhaler 1 has the inlet 1A. However, the embodiment is not limited thereto. The flavor inhaler 1 may not need to have the inlet 1A. In such a case, a user inhales the aerosol flowing out from the mouthpiece 1D together with outside air without holding the mouthpiece 1D with a mouth.

Although not particularly mentioned in the embodiment, the amount of aerosol inhaled by a user may be settable by the user. The flavor inhaler 1 may adjust, based on the amount of aerosol set by the user, the voltage applied to the SAW module 30, and may adjust the amount of liquid supplied to the SAW module 30 from the liquid supplier 60.

In the embodiment, a case has been exemplified in which the flavor inhaler 1 has one SAW module 30. However, the embodiment is not limited thereto. The flavor inhaler 1 may have two or more SAW modules 30.

Although not particularly mentioned in the embodiment, the flavor inhaler 1 may have a power source switch. The flavor inhaler 1 may operate in a drive mode in response to turning on the power source. The drive mode is a mode in which the power is supplied to each configuration provided in the flavor inhaler 1, and for example, is a mode in which the atomization action of the atomizing unit 100 can be started. The flavor inhaler 1 may operate in a standby mode in a state where the power source switch is turned off. The standby mode is a mode operating at standby power that can detect whether the power source switch is turned on.

Although not particularly mentioned in the embodiment, the flavor inhaler 1 may have a temperature sensor configured to detect a temperature (for example, atmospheric temperature) of the flavor inhaler 1. If the temperature of the flavor inhaler 1 falls below a lower limit temperature, the flavor inhaler 1 may have a function of not performing the atomization action of the liquid. If the temperature of the flavor inhaler 1 exceeds a higher limit temperature, the flavor inhaler 1 may have a function of not performing the atomization action of the liquid.

Although not particularly mentioned in the embodiment, the flavor inhaler 1 may have a remaining amount sensor configured to detect the remaining amount of the liquid. The remaining amount sensor may be provided within the penetrated aperture 34 and may detect a liquid surface level of the liquid within the penetrated aperture 34. The surface water level of the liquid may be controlled by a detection result of the remaining amount sensor. If at least any one of the atomizing unit 100 and the liquid storage unit 200 is a cartridge, the flavor inhaler 1 may have a detecting sensor configured to detect a presence or an absence of the cartridge. If there is no cartridge, the flavor inhaler 1 may have a function of not performing the atomization action of the liquid.

In the embodiment, the flavor inhaler 1 has the sensor 300. However, the embodiment is not limited thereto. The flavor inhaler 1 may have, instead of the sensor 300, a drive switch used to drive the atomizing unit 100. The flavor inhaler 1 may start the atomization action of the atomizing unit 100 in response to the drive switch being turned on. The flavor inhaler 1 may stop the atomization action of the atomizing unit 100 in response to the drive switch being turned off. If a certain period has passed from a switch-on of the drive switch, the flavor inhaler 1 may stop the atomization action of the atomizing unit 100.

Although not particularly mentioned in the embodiment, a switch provided on the flavor inhaler 1 may be a switch other than the above-described power source switch and drive switch. For example, the switch may be the one configured to switch two or more operation modes of the flavor inhaler 1. The switch provided on the flavor inhaler 1 may be a mechanical switch or a touch panel.

Although not particularly mentioned in the embodiment, the flavor inhaler 1 may have a function of returning, to the liquid storage unit 200, an unused liquid within a pipe for supplying the liquid from the liquid storage unit 200 to the atomizing unit 100. The flavor inhaler 1 may have a structure of preventing the unused liquid from flowing out through the mouthpiece 1D, such as a liquid reservoir structure configured to reserve and recycle the unused liquid.

INDUSTRIAL APPLICABILITY

According to the embodiment, it is possible to provide an atomizing unit by which atomizing efficiency of liquid can be improved.

The invention claimed is:

1. A controller for controlling an atomizing unit, wherein:
the atomizing unit comprises
a piezoelectric element substrate comprising an IDT comprising a pair of interlocking comb-shaped metallic electrodes, and
a liquid supplier configured to supply liquid, which is to be atomized, to the piezoelectric element substrate;
wherein the piezoelectric element substrate is configured to atomize the liquid by use of a surface acoustic wave generated by applying a high-frequency voltage to the pair of interlocking comb-shaped metallic electrodes; and
wherein the controller is configured to periodically change amplitude and/or a frequency of the high-frequency voltage applied to the pair of interlocking comb-shaped metallic electrodes in such a manner that generation, by atomization, of particles having particle sizes larger than a predetermined size is suppressed.

2. The controller according to claim 1, wherein the controller is configured to modulate the high-frequency voltage applied to the pair of interlocking comb-shaped metallic electrodes based on a sine wave, a rectangular wave, a triangular wave, or a saw tooth wave; and the modulation is amplitude modulation and/or frequency modulation.

3. The controller according to claim 1, wherein the controller is configured to modify the amplitude of the high-frequency voltage applied to the pair of interlocking comb-shaped metallic electrodes to have the form of a sine wave, a rectangular wave, a triangular wave, or a saw tooth wave.

4. The controller according to claim 3, wherein the controller is configured to modify the amplitude of the high-frequency voltage applied to the pair of interlocking comb-shaped metallic electrodes by providing with, in an alternating manner, a period during which the high-frequency voltage is applied and a period during which the high-frequency voltage is not applied.

5. The controller according to claim 2, wherein a duty ratio of the rectangular wave is set in such a manner that damage to the piezoelectric element substrate due to high temperature is avoided, and/or in such a manner that generation, by atomization, of particles having particle sizes larger than a predetermined size is suppressed, when the high-frequency voltage is applied to the pair of interlocking comb-shaped metallic electrodes.

6. The controller according to claim 2, wherein, in a single period of the triangular wave, a ratio between amplitude and a length of a period during which a change occurs in a first direction which is parallel to the amplitude and a ratio between the amplitude and a length of a period during which a change occurs in a second direction which is opposite to the first direction are set in such a manner that damage to the piezoelectric element substrate due to high temperature is avoided, and/or in such a manner that generation, by atomization, of particles having particle sizes larger than a predetermined size is suppressed, when the high-frequency voltage is applied to the pair of interlocking comb-shaped metallic electrodes.

7. The controller according to claim 2, wherein a ratio between a length of a single period and amplitude of the saw tooth wave is set in such a manner that damage to the piezoelectric element substrate due to high temperature is avoided, and/or in such a manner that generation, by atomization, of particles having particle sizes larger than a predetermined size is suppressed, when the high-frequency voltage is applied to the pair of interlocking comb-shaped metallic electrodes.

8. The controller according to claim 1, wherein a frequency of the periodical changing is equal to or higher than 50 Hz and equal to or lower than 500 Hz.

9. A controller for controlling an atomizing unit, wherein:
the atomizing unit comprises
a piezoelectric element substrate comprising an IDT comprising a pair of interlocking comb-shaped metallic electrodes, and
a liquid supplier configured to supply liquid, which is to be atomized, to the piezoelectric element substrate;

wherein the piezoelectric element substrate is configured to atomize the liquid by use of a surface acoustic wave generated by applying a high-frequency voltage to the pair of interlocking comb-shaped metallic electrodes;

wherein the controller is configured to start supply of the liquid, which is to be atomized, to the piezoelectric element substrate after predetermined time has elapsed since application of the high-frequency voltage to the pair of interlocking comb-shaped metallic electrodes has started, and wherein a length of the predetermined time is set in such a manner that generation, by atomization, of particles having particle sizes larger than a predetermined size is suppressed.

10. The controller according to claim 9, wherein the controller is configured to set a speed to supply the liquid, which is to be atomized, to the piezoelectric element substrate to a predetermined value, right after supplying is started.

11. The controller according to claim 9, wherein the controller is configured to set a speed to supply the liquid, which is to be atomized, to the piezoelectric element substrate to zero right after supplying is started, and gradually increase the supply speed to a predetermined value.

12. The controller according to claim 11, wherein a length of time during which the supply speed increases from zero to the predetermined value is set in such a manner that generation, by atomization, of particles having particle sizes larger than a predetermined size is suppressed.

13. A controller for controlling an atomizing unit, wherein:
the atomizing unit comprises:
a piezoelectric element substrate comprising an IDT comprising a pair of interlocking comb-shaped metallic electrodes,
a liquid supplier configured to supply liquid, which is to be atomized, to the piezoelectric element substrate, and
a sensor for detecting a quantity of liquid, which is to be atomized, which exists on the piezoelectric element substrate;
wherein the piezoelectric element substrate is configured to atomize the liquid by use of a surface acoustic wave generated by applying a high-frequency voltage to the pair of interlocking comb-shaped metallic electrodes;
wherein the controller is configured to control supply of the liquid, which is to be atomized, to the piezoelectric element substrate based on the quantity of the liquid existing on the piezoelectric element substrate,
wherein the controller is configured to control supply of the liquid, which is to be atomized, to the piezoelectric element substrate in such a manner that a quantity, that is in a first predetermined range of quantities, of the liquid, which is to be atomized, exists on the piezoelectric element substrate, before application of the high-frequency voltage to the pair of interlocking comb-shaped metallic electrodes is started, and wherein the first predetermined range of quantities is set in such a manner that generation, by atomization, of particles having particle sizes larger than a predetermined size is suppressed.

14. The controller according to claim 13, wherein the controller is configured to start, at the same time, application of the high-frequency voltage to the pair of interlocking comb-shaped metallic electrodes, and supply of the liquid, which is to be atomized, to the piezoelectric element substrate.

15. The controller according to claim 13, wherein the controller is configured to start supply of the liquid, which is to be atomized, to the piezoelectric element substrate, after starting application of the high-frequency voltage to the pair of interlocking comb-shaped metallic electrodes.

16. The controller according to claim 13, wherein the controller is configured to control supply of the liquid, which is to be atomized, to the piezoelectric element substrate in such a manner that the speed to supply the liquid, which is to be atomized, to the piezoelectric element substrate is made to have a predetermined value or predetermined change, after application of the high-frequency voltage to the pair of interlocking comb-shaped metallic electrodes is started.

17. The controller according to claim 13, wherein the controller is configured to stop supply of the liquid, which is to be atomized, to the piezoelectric element substrate, in the case that the quantity of the liquid, which is to be atomized, existing on the piezoelectric element substrate is equal to or above an upper limit in a second predetermined range of quantities, when supplying the liquid, which is to be atomized, to the piezoelectric element substrate; and the upper limit and a lower limit of the second predetermined range of quantities are equal to or larger than an upper limit and a lower limit of the first predetermined range of quantities, respectively.

18. The controller according to claim 17, wherein the controller is configured to restart supply of the liquid, which is to be atomized, to the piezoelectric element substrate, in the case that the quantity of the liquid, which is to be atomized, existing on the piezoelectric element substrate is less than the lower limit of the second predetermined range of quantities, when supply of the liquid, which is to be atomized, to the piezoelectric element substrate is being stopped.

19. The controller according to claim 17, wherein the second predetermined range of quantities is set in such a manner that generation, by atomization, of particles having particle sizes larger than a predetermined size is suppressed.

20. A non-transitory computer readable medium storing a program causing a processor to function as at least a part of the controller recited in claim 1.

* * * * *